US009260727B2

(12) United States Patent
Cervin et al.

(10) Patent No.: US 9,260,727 B2
(45) Date of Patent: Feb. 16, 2016

(54) COMPOSITIONS AND METHODS FOR PRODUCING ISOPRENE

(75) Inventors: Marguerite A. Cervin, Redwood City, CA (US); Gopal K. Chotani, Cupertino, CA (US); Frank J. Feher, Copley, OH (US); Richard La Duca, Pleasanton, CA (US); Joseph C. McAuliffe, Sunnyvale, CA (US); Andrei Miasnikov, Mountain View, CA (US); Caroline M. Peres, Palo Alto, CA (US); Aaron S. Puhala, Kent, OH (US); Karl J. Sanford, Cupertino, CA (US); Fernando Valle, Burlingame, CA (US); Gregory M. Whited, Belmont, CA (US)

(73) Assignees: DANISCO US INC., Palo Alto, CA (US); THE GOODYEAR TIRE & RUBBER COMPANY, Akron, OH (US)

(*) Notice: Subject to any disclaimer, the term of this patent is extended or adjusted under 35 U.S.C. 154(b) by 639 days.

(21) Appl. No.: 13/600,132

(22) Filed: Aug. 30, 2012

(65) Prior Publication Data
US 2013/0078699 A1 Mar. 28, 2013

Related U.S. Application Data

(62) Division of application No. 12/335,071, filed on Dec. 15, 2008, now Pat. No. 8,288,148.

(60) Provisional application No. 61/013,574, filed on Dec. 13, 2007.

(51) Int. Cl.
| | | |
|---|---|---|
| *C12N 1/20* | (2006.01) | |
| *C12P 7/42* | (2006.01) | |
| *C12P 5/02* | (2006.01) | |
| *C12N 15/00* | (2006.01) | |
| *C12N 15/74* | (2006.01) | |
| *C07H 21/04* | (2006.01) | |
| *C12P 5/00* | (2006.01) | |
| *C12N 9/10* | (2006.01) | |
| *C12N 9/12* | (2006.01) | |
| *C12N 9/88* | (2006.01) | |
| *C12N 9/90* | (2006.01) | |

(52) U.S. Cl.
CPC .............. *C12P 5/007* (2013.01); *C12N 9/1022* (2013.01); *C12N 9/1205* (2013.01); *C12N 9/88* (2013.01); *C12N 9/90* (2013.01); *Y02E 50/343* (2013.01)

(58) Field of Classification Search
None
See application file for complete search history.

(56) References Cited

U.S. PATENT DOCUMENTS

| | | |
|---|---|---|
| 1,344,713 A | 6/1920 | Peters |
| 3,686,349 A | 8/1972 | Schliebs et al. |
| 4,570,029 A | 2/1986 | Kulprathipanja et al. |
| 4,647,344 A | 3/1987 | Lindner et al. |
| 4,683,195 A | 7/1987 | Mullis et al. |
| 4,683,202 A | 7/1987 | Mullis |
| 4,703,007 A | 10/1987 | Mulholland et al. |
| 4,846,872 A | 7/1989 | Kamuro et al. |
| 4,965,188 A | 10/1990 | Mullis et al. |
| 5,322,770 A | 6/1994 | Gelfand |
| 5,349,126 A | 9/1994 | Chappell et al. |
| 5,380,831 A | 1/1995 | Adang et al. |
| 5,436,391 A | 7/1995 | Fujimoto et al. |
| 5,545,816 A | 8/1996 | Ausich et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,270,739 B1 | 8/2001 | Barnicki et al. |
| 6,294,653 B1 | 9/2001 | Mayfield |
| 6,582,914 B1 | 6/2003 | Caldwell et al. |
| 6,806,076 B1 | 10/2004 | Miyake et al. |
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 * | 2/2007 | Keasling et al. .............. 435/167 |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |

(Continued)

FOREIGN PATENT DOCUMENTS

| | | |
|---|---|---|
| DE | 196 29 568 C1 | 1/1998 |
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |

(Continued)

OTHER PUBLICATIONS

Miller et al. First isolation of an isoprene synthase gene from poplar and successful expression of the gene in *Escherichia coli*. Planta, Jul. 2001;213(3):483-7.*

(Continued)

*Primary Examiner* — Iqbal H Chowdhury
(74) *Attorney, Agent, or Firm* — Mintz, Levin, Cohn, Ferris, Glovsky and Popeo, P.C.

(57) ABSTRACT

The invention features methods for producing isoprene from cultured cells. The invention also provides compositions that include these cultured cells.

33 Claims, 171 Drawing Sheets

(56) References Cited

U.S. PATENT DOCUMENTS

| | | |
|---|---|---|
| 7,531,333 B2 | 5/2009 | Miyake et al. |
| 8,173,410 B2 | 5/2012 | Bott et al. |
| 8,288,148 B2 | 10/2012 | Cervin et al. |
| 2002/0095818 A1 | 7/2002 | Jain et al. |
| 2003/0033626 A1 | 2/2003 | Hahn et al. |
| 2004/0005678 A1 | 1/2004 | Kleasling et al. |
| 2004/0219629 A1 | 11/2004 | Cheng et al. |
| 2005/0287655 A1 | 12/2005 | Tabata et al. |
| 2006/0009647 A1 | 1/2006 | Yeates et al. |
| 2006/0020095 A1 | 1/2006 | Gandon-Pain |
| 2008/0038805 A1 | 2/2008 | Melis |
| 2008/0178354 A1* | 7/2008 | Chappell et al. ............. 800/298 |
| 2009/0155874 A1 | 6/2009 | Clark et al. |
| 2009/0203102 A1 | 8/2009 | Cervin et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0196982 A1* | 8/2010 | Anderson ..................... 435/167 |
| 2011/0045563 A1 | 2/2011 | Melis |
| 2011/0076743 A1 | 3/2011 | Beck et al. |

FOREIGN PATENT DOCUMENTS

| | | |
|---|---|---|
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-182950 A | 8/2008 |
| JP | 2009-207402 A | 9/2009 |
| KR | 2001-0084864 A | 9/2001 |
| RU | 2 197 461 C2 | 1/2003 |
| WO | WO-95/04134 | 2/1995 |
| WO | WO-96/35796 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 | 6/2006 |
| WO | WO-2006/085899 A2 | 8/2006 |
| WO | WO-2006/085899 A3 | 8/2006 |
| WO | WO-2007/018062 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 | 1/2010 |
| WO | WO-2010/031062 | 3/2010 |
| WO | WO-2010/031068 | 3/2010 |
| WO | WO-2010/031076 A2 | 3/2010 |
| WO | WO-2010/031076 A3 | 3/2010 |
| WO | WO-2010/031077 | 3/2010 |
| WO | WO-2010/031079 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |

OTHER PUBLICATIONS

Sharkey et al. Evolution of the isoprene biosynthetic pathway in Kudzu, Plant Physiol. 2005, 137:700-712.*

Kaneda et al. PNAS, 98(3), 932-937, 2001.*

Albrecht, M. et al. (Aug. 2000). "Novel Hydroxycarotenoids with Improved Antioxidative Properties Produced by Gene Combination in *Escherichia coli*," *Nature Biotechnology* 18:843-846.

Alexopoulos, C.J. (1962). Introductory Mycology, Wiley: New York, NY, pp. ix-x, (Table of Contents Only).

Allison, R. et al. (1986). "The Nucleotide Sequence of the Coding Region of Tobacco Etch Virus Genomic RNA: Evidence for the Synthesis of a Single Polyprotein," *Virology* 154:9-20.

Alper, H. et al. (2008). "Uncovering the Gene Knockout Landscape for Improved Lycopene Production in *E. coli*," *AppL Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol. Biol.* 215:403-410.

Altschul, S.F. et al. (1996). "Local Alignment Statistics," Chapter 27 in Multiple Alignment and Phylogenetic Trees, American Press, Inc. 266:460-480.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces cerevisiae*," *J. Biol. Chem.* 264(32):19169-19175.

Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.

Arai, Y. et al. (2004). "Production of Polyhydroxybutyrate by Polycistronic Expression of Bacterial Genes in Tobacco Plastid," *Plant Cell Physiol.* 45(9):1176-1184.

Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.

(56) References Cited

OTHER PUBLICATIONS

Ausubel, F.M. et al. eds. (1987). Current Protocols in Molecular Biology, John Wiley and Sons, Inc., pp. 1-13, (Table of Contents Only).

Baba, T. et al. (Feb. 21, 2006). "Construction of *Escherichia coli* K-12 In-Frame, Single-Gene Knockout Mutants: The Keio Collection," *Molecular Systems Biology* pp. 1-11.

Ballas, N. et al. (1989). "Efficient Functioning of Plant Promoters and Poly(A) Sites in *Xenopus* Oocytes," *Nucleic Acids Research* 17(19):7891-7903.

Barkovich, R. et al. (2001, e-pub. Dec. 1, 2000). "Metabolic Engineering of Isoprenoids," *Metabolic Engineering* 3:27-29.

Beaucage, S.L. et al. (1981). "Deoxynucleoside Phosphoramidites—A New Class of Key Intermediates for Deoxypolynucleotide Synthesis," *Tetrahedron Letters* 22(20):1859-1862.

Bellion, E. et al. (1993). "Methylamine Utilization in Yeast and Bacteria: Studies Using in vivo NMR," Chapter 32 in Microbial Growth C$_1$ Compounds, Muerrell, J.C. et al. eds, Intercept Ltd: Andover, UK, pp. 415-432.

Bennett, J.W. et al. eds. (1991). "Gene Cloning and Analysis," Chapter 3 in More Gene Manipulations in Fungi, Academic Press, San Diego, CA pp. 70-76.

Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.

Beytia, E. et al. (Oct. 25, 1970). "Purification and Mechanism of Action of Hog Liver Mevalonic Kinase," *The Journal of Biological Chemistry* 245(20):5450-5458.

Bock, R. et al. (2000). "Extranuclear Inheritance: Plastid Genetic: Manipulation of Plastid Genomes and Biotechnological Application," *Progress in Botany* 61:76-90.

Bock, R. (2001). "Transgenic Plastids in Basic Research and Plant Biotechnology," *J. Mol. Biol.* 312:425-438.

Bock, R. et al. (Jun. 2004). "Taming Plastids for a Green Future," *Trends in Biotechnology* 22(6):311-318.

Boel, E. et al. (1984). "Two Different Types of Intervening Sequences in the Glucoamylase Gene from *Aspergillus niger*," *The EMBO Journal* 3(7):1581-1585.

Bouvier, F. et al. (2005). "Biogenesis, Molecular Regulation and Function of Plant Isoprenoids," *Progress in Lipid Res.* 44:357-429.

Boynton, J.E. et al. (1993). "Chloroplast Transformation in *Chlamydomonas*," *Methods in Enzymology* 217(37):510.536.

Broun, P. et al. (Nov. 13, 1998). "Catalytic Plasticity of Fatty Acid Modification Enzymes Underlying Chemical Diversity of Plant Lipids," *Science* 282:1315-1317.

Brunger, A.T. et al. (1998). "Crystallography& NMF? System: A New Software Suite for Macromolecular Structure Determination," *Acta Cryst.* D54:905-921.

Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.

Campbell, E.I. et al. (1989). "Improved Transformation Efficiency of *Aspergillus niger* Using the Homologous niaD Gene for Nitrate Reductase," *Curr. Genet.* 16:53-56.

Campbell, J.W. et al. (Oct. 2001). "*Escherichia coli* FadR Positively Regulates Transcription of the *fabB* Fatty Acid Biosynthetic Gene," *J. Bacteriol.* 183(20):5982-5990.

Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.

Cao, Q-N. et al. (2000). "Penicillopepsin-JT2, a Recombinant Enzyme from *Penicillium janthinellum* and the Contribution of a Hydrogen Bond in Subsite S3 to kcat," *Protein Science* 9:991-1001.

Chamberlin, M. et al. (Oct. 17, 1970). "New RNA Polymerase from *Escherichia coli* Infected with Bacteriophage T7," *Nature* 228:227-231.

Champenoy, S. et al. (1998). "Expression of the Yeast Mevalonate Kinase Gene in Transgenic Tobacco," *Molecular Breeding* 4:291-300.

Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.

Chappell J. et al. (1995). is the Reaction Catalyzed by 3-Hydroxy-3-Methylglutaryl-Coenzyme A Reductase a Rate-Limiting Step for Isoprenoid Biosynthesis in Plants? *Plant Physiology* (109):1337-1343.

Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.

Chica, R.A. et al. (2005). "Semi-Rational Approaches to Engineering Enzyme Activity: Combining the Benefits of Directed Evolution and Rational Design," *Current Opinion in Biotechnology* 16:378-384.

Cho, H-J. et al. (1995). "Expression Pattern of Bacterial Polycistronic Genes in Tobacco Cells," *Journal of Fermentation and Bioengineering* 80(2):111-117.

Clarke, S. (1992). "Protein Isoprenylation and Methylation at Carboxyl-Terminal Cysteine Residues," *Annu. Rev. Biochem.* 61:355-386.

Clough, S.J. et al. (1998). "Floral Dip: A Simplified Method for *Agrobacterium*-Mediated Transformation of *Arabidopsis thaliana*," *The Plant Journal* 16(6):735-743.

Collaborative Computational Project, No. 4. (1994). "The CCP4 Suite: Programs for Protein Crystallography," *Acta Cryst* D50:760-763.

Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.

Crueger, W. et al. (1989). Biotechnology: A Textbook of Industrial Microbiology, Second Edition, Brock, T.D. ed., Sinauer Associates, Inc.: Sunderland, MA, pp. vii-x, (Table of Contents).

Cunningham, F.X. et al. (1998). "Genes and Enzymes of Carotenoid Biosynthesis in Plants," *Ann. Rev. Plant Physiol. Plant Mol. Biol.* 49:557-583.

Cunningham, F.X. et al. (Oct. 2000). "Evidence of a Role for LytB in the Nonmevalonate Pathway of Isoprenoid Biosynthesis," *Journal of Bacteriology* 182(20):5841-5848.

Dale, P.J. (1992). "Spread of Engineered Genes to Wild Relatives," *Plant PhysioL* 100:13-15.

Dale, G.E. et al. (2003). "The Protein as a Variable in Protein Crystallization," *Journal of Structural Biology* 142:88-97.

Daniell, H. (1997). "Transformation and Foreign Gene Expression in Plants Mediated by Microprojectile Bombardment," Chapter 35 in Methods in Molecular Biology, Recombinant Gene Expression Protocols, Tuan, R S. ed., Humana Press: Totowa, NJ, 62:463-489.

Daniell, H. et al. (Apr. 1998) "Containment of Herbicide Resistance Through Genetic Engineering of the Chloroplast Genome," *Nature Biotechnology* 16:345-348.

Datsenko, K.A. et al. (Jun. 6, 2000). "One-Step Inactivation of Chromosomal Genes in *Escherichia coli* K-12 Using PCR Products," *PNAS* 97(12):6640-6645.

Datta, S. et al. (2006). "A Set of Recombineering Plasmids for Gram-Negative Bacteria," *Gene* 379:109-115.

Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

Davidson, S. (Oct.-Dec. 2003). "Light Factories," located at <http://www.publish.csiro.au/?act-view_file&file_id=EC117p10.pdf>, last visited on Oct. 2, 2008.

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the *Bt* cry2Aa2operon in Chloroplasts Leads to Formation of Insecticidal Crystals," *Nature Biotechnology* 19:71-74.

(56) References Cited

OTHER PUBLICATIONS

Del Campo, E. M. et al. (1997). "Plastid *ndhD* Gene of Barley, Sequence and Transcript Editing (Accesion No. Y12258) (PGR 97-090)," *Plant Physiol.* 114:747-749.

Della-Cioppa, G. et al. (1987). "Protein Trafficking in Plant Cells," *Plant Physiol.* 84:965-968.

Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453461.

Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.

Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.

Devereux, J. et al. (1984). "A Comprehensive Set of Sequence Analysis Programs for the VAX," *Nucleic Acids Research* 12(1):387-395.

Devos, D. et al. (2000). "Practical Limits of Function Prediction," *Proteins: Structure, Function, and Genetics* 41:98-107.

Dewick, P.M. et al. (2002, e-pub. Jan. 22, 2002). "The Biosynthesis of C5-025 Terpenoid Compounds," *Nat. Prod. Rep.* 19:181-222.

Dhe-Paganon, S. et al. (1994). "Mechanism of Mevalonate Pyrophosphate Decarboxylase: Evidence for a Carbocationic Transition State," *Biochemistry* 33(45):13355-13362.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet.* 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, 0. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. AOPFK2, last updated on Mar. 2, 2010, located at <http://srs.ebi.ac.uk/srsbin/cgi-bin/wgetz?-e+[UNIPROT:AOPFK2_POPNI]+-newId>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Aug. 7, 2009, 2 pages.

EMBL-EBI Accession No. AY341431, last updated Apr. 16, 2005, located at <http://www.ebi.ac.uk/cgi-bin/dbfetch?db=embl&id=AY341431∈ . . . >, last visited Nov. 26, 2009, 2 pages.

Emsley, P. et al. (2004). "Coot: Model-Building Tools for Molecular Graphics," *Acta Crystallographica* D60:2126-2132.

Extended European Search Report mailed on Jun. 14, 2011, for EP Patent Application No. 08860589.4, filed on Dec. 15, 2008, 10 pages.

Fall, R. (Sep. 12, 2003). "Final Technical Report: DE-FG03-97ER20274, 'Microbial Production of Isoprene'," located at <http://www.osti.gov/bridge/product.biblio.jsp?query_id=1&page=0&osti_id=814920>, last visited on May 26, 2010, 4 pages.

Farmer, W.R. et al. (May 2000). "Improving Lycopene Production in *Escherichia coli* by Engineering Metabolic Control," *Nature Biotechnology* 18:533-537.

Feng, D-F. et al. (1987). "Progressive Sequence Alignment as a Prerequisite to Correct Phylogenetic Trees," *Journal of Molecular Evolution* 25:351-360.

Finkelstein, D.B. (1992). "Transformation," Chapter 6 in Biotechnology of Filamentous Fungi, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," in Molecular Biology of RNA, Cech, T.R. ed. Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli IpxK* Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ294819.1, last updated Apr. 15, 2005, located at <http://www.ncbi.nlm.nih.gov/nuccore/AJ294819.1>, last visited on Dec. 7, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AM410988.1, last updated Aug. 14, 2008, located at <http://www.ncbi.nlm.nih.gov/nuccore/AM410988.1>, last visited on Dec. 7, 2011, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. EF147555.1, last updated Mar. 24, 2009, located at <http://www.ncbi.nlm.nih.gov/nuccore/EF147555.1>, last visited on Aug. 25, 2015, 2 pages.

GenBank Accession No. EF638224.1, last updated May 3, 2010, located at <http://www.ncbi.nlm.nih.gov/nuccore/EF638224.1>, last visited on Aug. 25, 2015, 2 pages.

GenBank Accession No. EU693027, last updated on May 27, 2008, located at <http://www.ncbi.nlm.nih.gov/nuccore/189017053>, last visited on Jun. 2, 2010, 2 pages.

GenBank Accession No. CAC35696, last updated Apr. 15, 2005, located at <http://www.ncbi.nlm.nih.gov/protein/CAC35696>, last visited on Apr. 6, 2011, 2 pages.

Geneseq Database Accession No. AFB74822, "Monoterpene synthetase protein SEQ ID No. 4." Retrieved from EBI accession No. GSP:AFB74822 (Apr. 19, 2007).

Gerhardt, P. et al. eds. (1994). Manual of Methods for General and Molecular Bacteriology, American Society for Microbiology: Washington, D.C., p. v, (Table of Contents Only).

Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

(56) References Cited

OTHER PUBLICATIONS

Gottschalk, G. (1986). Bacterial Metabolism Second Edition, Springer Verlag: New York, NY, pp. xi-xiii, (Table of Contents Only).
Grawert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.
Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.
Guda, C. et al. (2000). "Stable Expression for a Biodegradable Protein-Based Polymer in Tobacco Chloroplasts," *Plant Cell Reports* 19:257-262.
Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.
Guo, D-A. et al. (1995). "Developmental Regulation of Sterol Biosynthesis in *Zea mays*," *Lipids* 30(3):203-219.
Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.
Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.
Hahn, F.M. et al. (Aug. 1999). "*Escherichia coli* Open Reading Frame 696 Is *idi*, a Nonessential Gene Encoding Isopentenyl Diphosphate Isomerase," *Journal of Bacteriology* 181(15):4499-4504.
Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.
Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.
Hamilton, C.M. et al. (Sep. 1989). "New Method for Generating Deletions and Gene Replacements in *Escherichia coli*," *Journal of Bacteriology* 171(9):4617-4622.
Hale, W.G. et al. (1991). The Harper Collins Dictionary of Biology, Ehrlich, E. ed., Harper Perennial: New York, NY, 2 pages.
Hanai, T. et al. (Dec. 2007). "Engineered Synthetic Pathway for Isopropanol Production in *Escherichia coli*," *Applied and Environmental Microbiology* 73(24):7814-7818.
Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.
Harkki, A. et al. (Jun. 1989). "A Novel Fungal Expression System: Secretion of Active Calf Chymosin from the Filamentous Fungus *Trichoderma reesei*," *Bio. Technol.* 7:596-603.
Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *J. Bacteriol.* 184(8):2116-2122.
Hedl, M. et al. (Apr. 2004). "Class II 3-Hydroxy-3-Methylglutaryl Coenzyme A Reductases," *Journal of Bacteriology* 186(7):1927-1932.
Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.
Herbers, K. et al. (Jun. 1996). "Manipulating Metabolic Partitioning in Transgenic Plants", *TIBTECH* 14:198-205.
Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *Proc. Natl. Acad. Sci. USA* 97(6):2486-2490.
Higgins, D.G. et al. (1989). "Fast and Sensitive Multiple Sequence Alignments on a Microcomputer," *Cabios Communications* 5(2):151-153.
Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.
Hoeffler, J-F. et al. (2002). "Isoprenoid Biosynthesis Via the Methylerythritol Phosphate Pathway. Mechanistic Investigations of the 1-Deoxy-D-Xylulose 5-Phosphate Reductoisomerase," *Eur. J. Biochem.* 269:4446-4457.
Huang, K-X. et al. (1999). "Overexpression, Purification, and Characterization of the Thermostable Mevalonate Kinase from *Methanococcus jannaschii*," *Protein Expression and Purification* 17:33-40.
Hunter, B.K. (1985). "Formaldehyde Metabolism by *Escherichia colL* Carbon and Solvent Deuterium Incorporation into Glycerol, 1,2-Propanediol, and 1,3-Propanediol," *Biochemistry* 24(15):4148-4155.
Hyatt, D.C. et al. (Mar. 27, 2007). "Structure of Limonene Synthase, A Simple Model for Terpenoid Cyclase Catalysis," *PNAS* 104(13):5360-5365.
Ilmen, M. et al. (Apr. 1997). "Regulation of Cellulase Gene Expression in the Filamentous Fungus *Trichoderma reesei*," *AppL Environ. MicrobioL* 63(4):1298-1306.
Innis, M.A. et al. (Apr. 5, 1985). "Expression, Glycosylation, and Secretion of an *Aspergillus* Glucoamylase by *Saccharomyces cerevisiae*," *Science* 228:21-26.
International Search Report mailed on Jun. 18, 2009, for PCT Patent Application No. PCT/US08/86869, filed on Dec. 15, 2008, one page. (2.40).
International Search Report mailed on Dec. 8, 2009, for PCT Application No. PCT/US2009/041581, filed on Apr. 23, 2009, nine pages. (5.40).
International Search Report mailed on Dec. 30, 2010, for PCT Application No. PCT/US2010/032134, filed on Apr. 22, 2010, 15 pages. (15.40).
Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.
Jeong, S.-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.
Jobling, S.A. et al. (Feb. 12, 1987). "Enhanced Translation of Chimaeric Messenger RNAs Containing a Plant Viral Untranslated Leader Sequence," *Nature* 235:622-625.
Jones, K.L. et al. (2000). "Low-Copy Plasmids Can Perform as Well as or Better Than High-Copy Plasmids for Metabolic Engineering of Bacteria," *Metabolic Engineering* 2:238-338.
Jones, E.Y. et al. (1991). "Methodology Employed for the Structure Determination of Tumour Necrosis Factor, a Case of High Non-Crystallographic Symmetry," *Acta Cryst* A47:753-770.
Joshi, C.P. (1987). "Putative Polyadenylation Signals in Nuclear Genes of Higher Plants: A Compilation and Analysis," *Nucleic Acid Research* 15(23):9627-9640.
Julsing, M.K. et al. (2007). "Functional Analysis of Genes Involved in the Biosynthesis of Isoprene in *Bacillus subtilis*," *Applied MicrobioL BiotechnoL* 75:1377-1384.
Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.
Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

(56) References Cited

OTHER PUBLICATIONS

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-295.

Karlin, S. (Jun. 1993). "Applications and Statistics for Multiple High-Scoring Segments in Molecular Sequences," *Proc. Natl. Acad. ScL USA* 90:5873-5787.

Kavanagh, T.A. et al. (Jul. 1999). "Homeologous Plastid DNA Transformation in Tobacco Is Mediated by Multiple Recombination Events," *Genetics* 52:1111-1122.

Keasling, J.D. (Mar. 29, 2004). "Genetic Tools for Metabolic Enzyme Production in *Escherichia coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 in Herbicide Resistant Crops: Agricultural, Environmental, Economic, Regulatory, and Technical Aspects, Duke, S.O. ed., Lewis Publishers: Boca Raton, FL., pp. 303-330.

Kelly, J.M. et al. (1985). "Transformation of *Aspergillus niger* by the *amdS* Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kinghorn, J.R. et al. (1992). Applied Molecular Genetics of Filamentous Fungi, Blackie Academic Professional and Chapman and Hall: London, 3 pages, (Table of Contents Only).

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *Trends in Biotechnology* 25(9):417-424.

Klein-Marcuschamer, D. et al. (Feb. 19, 2008). "Assessing the Potential of Mutational Strategies to Elicit New Phenotypes in Industrial Strains," *Proc. Natl. Acad. Sci.* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Koksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

Kreigler, M. (1990). Gene Transfer and Expression: A Laboratory Manual, W.H. Freeman and Company: New York, NY, pp. Vii-x, (Table of Contents Only.).

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis Via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. et al. (1997). "Biosynthesis of Isoprenoids in Higher Plant Chloroplasts Proceeds Via a Mevalonate-Independent Pathway," *FEBS Letters* 400:271-274.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lin, X-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamaki, M. et al. (Jun. 2007). "Arabidopsis, A Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

(56) References Cited

OTHER PUBLICATIONS

Locker, J. et al. (2002). "Monoterpene Biosynthesis in Lemon (*Citrus limon*). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Lottgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.

Macejak, D.G. et al. (Sep. 5, 1991). "Internal Initiation of Translation Mediated by the 5' Leader of a Cellular mRNA," *Nature* 353:90-94.

Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.

Maldonado-Mendoza, I.E. et al. (1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 134:781-790.

Mann, V. et al. (Aug. 2000). "Metabolic Engineering of Astaxanthin Production in Tobacco Flowers," *Nature Biotechnology* 18:888-892.

Martin, V.J.J. et al. (Dec. 5, 2001). "The In Vivo Synthesis of Plant Sesquiterpenes by *Escherichia coli*," *Biotechnology and Bioengineering* 75(5):497-503.

Martin, V.J.J. et al. (Jul. 2003). "Engineering a Mevalonate Pathway in *Escherichia coli* for Production of Terpenoids," *Nature Biotechnology* 21(7):796-802.

Martin, W. et al. (May 14, 1998). "Gene Transfer to the Nucleus and the Evolution of Chloroplasts," *Nature* 393:162-165.

Mash Ego, M.R. et al. (2007, e-pub. Nov. 8, 2006). "Microbial Metabolomics: Past, Present and Future Methodologies," *Biotechnol. Lett.* 29:1-16.

Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.

Matteucci, M.D. et al. (1981). "Synthesis of Deoxyoligonucleotides on a Polymer Support," *J. American Chemical Society* 103(11):3185-3191.

Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl Microbiol Biotechnol* 53:396-400.

Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.

McPherson, A. (2004). "Introduction to Protein Crystallization," *Methods* 34:254-265.

Meinkoth, J. et al. (1984). "Hybridization of Nucleic Acids Immobilized on Solid Supports," *Analytical Biochemistry* 138:267-284.

Meyer, P. et al. (1996). "Homology-Dependent Gene Silencing in Plants," *Ann. Rev. Plant Physiol. Plant Physiol. Plant Mol. Biol.* 47:23-48.

Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.

Miller, B. (2001). "Erstmalige Isolierung Eines Isoprenysthase-Gens and Heterologe Expression Des Aus Der Pappel Stammenden Gens Sowie Charakterisierung der Eingangsgene des Mevalonat-unabhangigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.

Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.

Mogen, B.D. et al. (Dec. 1990). "Upstream Sequences Other than AAUAAA are Required for Efficient Messenger RNA 3'-End Formation in Plants," *The Plant Cell* 2:1261-1272.

Monson, R.K. et al. (1992). "Relationships Among Isoprene Emission Rate, Photosynthesis, and Isoprene Synthase Activity as Influenced by Temperature," *Plant Physiol.* 98:1175-1180.

Munroe, D. et al. (1990). "Tales of Poly(A): a Review," *Gene* 91:151-158.

Murray, E.E. et al. (1989). "Codon Usage in Plant Genes," *Nucleic Acids Research* 17(2): 477-498.

Nakamura, C.E. et al. (2003). "Metabolic Engineering for the Microbial Production of 1,3-Propanediol," *Current Opinion in Biotechnology* 14:454-459.

Nanchen, A. et al. (Apr. 2008, e-pub. Jan. 25, 2008). "Cyclic AMP-Dependent Catabolite Repression Is the Dominant Control Mechanism of Metabolic Fluxes Under Glucose Limitation in *Escherichia coli*," *Journal of Bacteriology* 190(7):2323-2330.

Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.

Needleman, S. B. et al. (1970). "A General Method Applicable to the Search for Similarities in the Amino Acid Sequence of Two Proteins," *J. Mol Biol.* 48:443-453.

Neidhardt, F.C. et al. (Sep. 1974). "Culture Medium for Enterobacteria," *J. Bacteriology* 119(3):736-747.

Neidhardt, F.C. et al. (1990). "Table 1. Overall Macromolecular Composition of an Average *E. coli* B/r Cell$^a$," in Chapter 1 in Physiology of the Bacterial Cell: A Molecular Approach, Sinauer Associates, Inc.: Sunderland, MA, pp. 4.

Nevalainen, K.M.H. et al. (1992). "The Molecular Biology of *Trichoderma* and Its Application to the Expression of Both Homologous and Heterologous Genes," Chapter 6 in Molecular Industrial Mycology, Systems and Applications for Filamentous Fungi, Leong, S.A. et al. eds., Marcel Dekker Inc.: New York, NY, pp. 129-148.

Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.

Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.

Nielsen, K.M. et al. (1997). "Analysis and Developmental Profile of Carotenoid Pigments in Petals of Three Yellow Petunia Cultivars," *Scientia Horticulturae* 71:257-266.

Niinemets, O. et al. (Nov. 2002). "Stomatal Constraints May Affect Emission of Oxygenated Monoterpenoids from the Foliage of *Pinus pinea*," *Plant Physiology* 130:1371-1385.

Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Oh, M-K. et al. (Apr. 12, 2002). "Global Expression Profiling of Acetate-Grown *Escherichia coli*," *The Journal of Biological Chemistry* 277(15):13175-13183.

Ondrey, G. et al. (Oct. 2008). "Bio-Based Isoprene," *Chemical Engineering, Access Intelligence Association*, Rockville, MA, 115(1):14.

Oulmouden, A. et al. (1991). "Nucleotide Sequence of the ERG12 Gene of *Saccharomyces cerevisiae* Encoding Mevalonate Kinase," *Curr. Genet.* 19:9-14.

Pachuk, C.J. et al. (2000). "Chain Reaction Cloning: A One-Step Method for Directional Ligation of Multiple DNA Fragments," *Gene* 243:19-25.

(56) References Cited

OTHER PUBLICATIONS

Pearson, W.R. et al. (Apr. 1988). "Improved Tools for Biological Sequence Comparison," *Proc. Natl. Acad. Sci. USA* 85:2444-2448.
Pegg, S.C.-H. et al. (2006). "Leveraging Enzyme Structure-Function Relationships for Functional Inference and Experimental Design: The Structure-Function Linkage Database," *Biochemistry* 45:2545-2555.
Penttila, M. et al. (1987). "A Versatile Transformation System for the Cellulolytic Filamentous Fungus *Trichoderma reesei*," *Gene* 61:155-164.
Perego, M. (1993). "Integrational Vectors for Genetic Manipulation in *Bacillus subtilis*," Chapter 42 in *Bacillus subtilis* and Other Gram-Positive Bacteria: Biochemistry, Physiology, and Molecular Genetics, Sonenshein et al. eds., American Society for Microbiology: Washington, D.C., pp. 615-624.
Phan, R.M. et al. (2001, e-pub. Sep. 13, 2001). "Synthesis of (S)-Isoprenoid Thiodiphosphates as Substrates and Inhibitors," *J. Org. Chem.* 66(20):6705-6710.
Phillips, T.A. et al. (Jul. 1984). "Ion Gene Product of *Escherichia coli* Is a Heat-Shock Protein," *Journal of Bacteriology* 159(1):283-287.
Phue, J-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.
Phue, J-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.
Pilloff, D. et al. (Feb. 14, 2003). "The Kinetic Mechanism of Phosphomevalonate Kinase," *The Journal of Biological Chemistry* 278(7):4510-4515.
Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.
Pommer, H. et al. (1975). "Industrial Synthesis of Terpene Compounds," *Pure and Applied Chemistry* 43(3-4):527-551.
Potter, D. et al. (Oct. 10, 1997). "Identification of Catalytic Residues in Human Mevalonate Kinase," *The Journal of Biological Chemistry* 272(41):25449-25454.
Pourquie, J. et al. (1988). "Scale Up of Cellulase Production and Utilization," in Biochemistry and Genetics of Cellulose Degradation, Aubert, J.-P. et al. eds., Academic Press: San Diego, CA, pp. 71-86.
Proudfoot, N. (Feb. 22, 1991). "Poly(A) Signals," *Cell* 64:671-674.
Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.
Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.
Re, E.B. et al. (1995). "Co-Expression of Native and Introduced Genes Reveals Cryptic Regulation of HMG CoA Reductase Expression in *Arabidopsis*," *The Plant Journal* 7(5):771-784.
Reiling, K.K. et al. (Jul. 20, 2004, e-pub. Jun. 18, 2004). "Mono and Diterpene Production in *Escherichia coli*," *Biotechnology and Bioengineering* 87(2):200-212.
Rodr1guez-Concepcion, M. et al. (2000). "Genetic Evidence of Branching in the Isoprenoid Pathway for the Production of Isopentenyl Diphosphate and Dimethylallyl Diphosphate in *Escherichia coli*," *FEBS Letters* 473:328-332.
Rodr1guez-Concepcion, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.
Rodriguez-Villalon, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.
Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.
Rohmer, M. (1998). "Isoprenoid Biosynthesis Via the Mevalonate-Independent Route, a Novel Target for Antibacterial Drugs?" *Progress in Drug Research* 50:137-154.
Rohrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.
Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.
Rosenfeld, J. et al. (1992). "In-Gel Digestion of Proteins for Internal Sequence Analysis After One- or Two-Dimensional Gel Electrophoresis," *Analytical Biochemistry* 203:173-179.
Rost, B. et al. (2004). "The PredictProtein Server," *Nucleic Acids Research* 32:W321-W326.
Sambrook, J. et al. (1989). Molecular Cloning: A Laboratory Manual, 2nd edition, Cold Spring Harbor Laboratory Press: New York, NY, pp. xi-xxxviii (Table of Contents Only).
Sanchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.
Sander, R. (Apr. 8, 1999). Compilation of Henry's Law Constants for Inorganic and Organic Species of Potential Importance in Environmental Chemistry, 3:1-107.
SANFAcON, H. et al. (1991). "A Dissection of the Cauliflower Mosaic Virus Polyadenylation Signal," *Genes & Development* 5:141-149.
Sasaki, K. et al. (2005, e-pub. Apr. 7, 2005). "Gene Expression and Characterization of Isoprene Synthase from *Populus alba*," *FEBS Letters* 579:2514-2518.
Schneider, D. et al. (Jul. 9, 2002). "Genomic Comparisons Among *Escherichia coli* Strains B, K-12, and 0157:H7 Using IS Elements as Molecular Markers," *BMC Microbiology* 2:18, 8 pages.
Schnitzler, J.-P. et al. (2005, e-pub. Jul. 29, 2005). "Biochemical Properties of Isoprene Synthase in Poplar (*Populus* x *canescens*)," *Planta* 222(5):777-786.
Scholler, C. et al. (1997). "Volatile Metabolites from some Gram-Negative Bacteria," *Chemosphere* 35(7):1487-1495.
Scott, E. et al. (2007, e-pub. Mar. 27, 2007). "Biomass in the Manufacture of Industrial Products—The Use of Proteins and Amino Acids," *AppL Microbiol. Biotechnol.* 75:751-762.
Sen, S. et al. (2007). "Developments in Directed Evolution for Improving Enzyme Functions," *AppL Biochem. Biotechnol.* 143:212-223.
Serino, G. et al. (1997). "A Negative Selection Scheme Based on the Expression of Cytosine Deaminase in Plastids," *The Plant Journal* 12(3):697-701.
Sharkey, T.D. et al. (Feb. 1, 2005). "Supplemental data for: Evolution of the Isoprene Biosynthetic Pathway in Kudzu," *Plant Physiology* 137(2):700-712.
Sharkey, T.D. et al. (Feb. 2005). "Evolution of the Isoprene Biosynthetic Pathway in Kudzu," *Plant Physiology* 137:700-712.
Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.
Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.
Shinozaki, K. et al. (1986). "The Complete Nucleotide Sequence of the Tobacco Chloroplast Genome: its Gene Organization and Expression," *The EMBO Journal* 5(9):2043-2049.

(56) References Cited

OTHER PUBLICATIONS

Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, T.L. et al. (2002). "Isoprene Synthase Activity Parallels Fluctuations of Isoprene Release During Growth of *Bacillus subtilis*," *Biochemical and Biophysical Research Communications* 294:71-75.
Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination-Lessons from Structural Genomics," *Protein Science* 16:2472-2482.
Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.
Slater, S. et al. (Oct. 1999). "Metabolic Engineering of *Arabidopsis* and *Brassica* for Poly(3-Hydroxybutyrate-co-3-Hydroxyvalerate) Copolymer Production," *Nature Biotechnology* 17:1011-1016.
Smit, A. et al. (2000). "Biosynthesis of Isoprenoids Via Mevalonate in Archaea: The Lost Pathway," *Genome Research* 10:1468-1484.
Smith, T. et al. (1981). "Comparison of Biosequences." *Advances in Applied Mathematics* 2:482-489.
Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol,"*Proc. Natl. Acad. Sci. USA* 94:12857-12862.
Starks, C.M. et al. (Sep. 19, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric *uidA* Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steinbuchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B.A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.
Takagi, M. et al. (Aug. 2000). "A Gene Cluster for the Mevalonate Pathway from *Streptomyces* sp. Strain CL190," *Journal of Bacteriology* 182(15):4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.
Takara Bio Inc. (Feb. 2008). "Chaperon Plasmid Set," Cat. # 3340, pp. 1-8.
Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.
Thomas, F. et al. (1988). "Expression of the rp123, rp12 and rps19 Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage A Red Recombineering," *Plasmid* 58:148-158.
Thouvenot, B. et al. (2004). "The Strong Efficiency of the *Escherichia coli gapA* P1 Promoter Depends on a Complex Combination of Functional Determinants," *Biochem. J.* 383:371-382.
Timberlake, W.E. (1991). "Gene Cloning and Analysis" in Chapter 3 in More Gene Manipulations in Fungi, Bennett et al. eds., Academic Press: San Diego, CA, pp. 70-76.
Toriyama, K. et al. (1985). "Cell Suspension and Protoplast Culture in Rice," *Plant Science* 41:179-183.
Tsay, Y.H. et al. (Feb. 1991). "Cloning and Characterization of ERG8, an Essential Gene of *Saccharomyces cerevisiae* That Encodes Phosphomevalonate Kinase," *Molecular and Cellular Biology* 11(2):620-631.
Tsudsuki, T. (Apr. 24, 1988) "Direct submission, bases 1-155939", *Data Processing Center*, 1998, Aichi-Gakuin University, Aixhi, Japan, 12 pages.
UniProt Database Accession No. A2XGY9, located at <http://www.uniprot.org/uniprot/A2XGY9.txt>, last visited on Aug. 25, 2015, 2 pages.
UniProt Database Accession No. A5AR04, located at <http://www.uniprot.org/uniprot/A5AR04.txt, last visited on Aug. 25, 2015, 2 pages.
UniProt Database Accession No. A5B7V4, located at <http://www.uniprot.org/uniprot/A5B7V4.txt>, last visited on Aug. 25, 2015, 2 pages.
UniProt Database Accession No. A5BKK1, located at < http://www.uniprot.org/uniprot/A5BKK1.txt>, last visited on Aug. 25, 2015, 2 pages.
UniProt Database Accession No. A5BLS5, located at < http://www.uniprot.org/uniprot/A5BLS5.txt>, last visited on Aug. 25, 2015, 2 pages.
UniProt Database Accession No. A9PGR5, located at <http://www.uniprot.org/uniprot/A9PGR5.txt>, last visited on Aug. 25, 2015 1 page.
UniProt Database Accession No. B1 P189, last updated Jul. 27, 2011, located at <http://www.uniprotorgiobs/201109112CDIFX17BK.txt>, last visited on Sep. 11, 2011, 1 page.
UniProt Database Accession No. B3GEM8, located at <http://www.uniprot.org/uniprot/B3GEM8.txt>, last visited on Aug. 25, 2015, 1 page
UniProt Database Accession No. B3TPQ7, located at < http://www.uniprot.org/uniprot/B3TPQ7.txt>, last visited Aug. 25, 2015, 2 pages.
UniProt Database Accession No. B7FLI6, last updated Jul. 27, 2011, located at <http://www.uniprotorg/jobs/20110911315BAXCRQU.txt>, last visited on Sep. 11, 2011, 1 page.
UniProt Database Accession No. B9HE95, located at <http://www.uniprot.org/uniprot/B9HE95.txt,> last visited on Aug. 25, 2015, 2 pages.
UniProt Database Accession No. B9MXU1, last updated Jul. 27, 2011, located at <http://www.uniprotorg/jobs/201109112CDIFV8DIC.txt>, last visited on Sep. 11, 2011, 2 pages.
UniProt Database Accession No. B9PAP5, last updated Jul. 27, 2011, located at <http://www.uniprotorg/jobs/201109112CDIG1HNFH.txt>, last visited on Sep. 11, 2011, 2 pages.
UniProt Database Accession No. B9RPM0, located at < http://www.uniprot.org/uniprot/B9RPM0.txt>, last visited Aug. 25, 2015, 2 pages.
UniProt Database Accession No. B9T537, last updated Nov. 30, 2010, located at <http://www.uniprotorg/jobs/20110911315BB065GR.txt>, last visited on Sep. 11, 2011, 1 page.

(56) References Cited

OTHER PUBLICATIONS

UniProt Database Accession No. B9T825, located at <http://www.uniprot.org/uniprot/B9T825.txt>, last visited on Aug. 25, 2015, 2 pages.
UniProt Database Accession No. QOPCI3, last updated Jul. 27, 2011, located at <http://www.uniprotorg/jobs/20110911315BAPL92C.txt>, last visited on Sep. 11, 2011, 1 page.
UniProt Database Accession No. QOPCI4, last updated Jul. 27, 2011, located at <http://www.uniprotorg/jobs/20110911315BAQURQ8.txt>, last visited on Sep. 11, 2011, 1 page.
UniProt Database Accession No. Q50L36, located at <http://www.uniprot.org/uniprot/Q50L36.txt>, last visited on Aug. 25, 2015, 2 pages.
UniProt Database Accession No. Q5SBP1, located at <http://www.uniprot.org/uniprot/Q5SBP1.txt>, last visited on Aug. 25, 2015, 2 pages.
UniProt Database Accession No. Q5SBP2, located at <http://www.uniprot.org/uniprot/Q5SBP2.txt>, last visited on Aug. 25, 2015, 2 pages.
UniProt Database Accession No. Q5SBP4, located at < http://www.uniprot.org/uniprot/Q5SBP4.txt>, last visited on Aug. 25, 2015, 2 pages.
UniProt Database Accession No. Q5UB07, located at < http://www.uniprot.org/uniprot/Q5UB07.txt,> last visited on Aug. 25, 2015, 3 pages.
UniProt Database Accession No. Q672F7, located at < http://www.uniprot.org/uniprot/Q672F7.txt>, last visited on Aug. 25, 2015, 2 pages.
UniProt Database Accession No. Q6EJ97, located at < http://www.uniprot.org/uniprot/Q6EJ97.txt>, last visited on Aug. 25, 2015, 2 pages.
UniProt Database Accession No. Q6PWU1, located at < http://www.uniprot.org/uniprot/Q6PWU2.txt>, last visited on Aug. 25, 2015, 2 pages.
UniProt Database Accession No. Q7Y1V1, located at < http://www.uniprot.org/uniprot/Q7Y1V1.txt>, last visited on Aug. 25, 2015, 1 page.
UniProt Database Accession No. Q941 H1, last updated Jul. 27, 2011, located at <http://www.uniprotorg/jobs/201109112CDIG6PW6Y.txt>, last visited on Sep. 11, 2011, 1 page.
UniProt Database Accession No. Q9AR86, located at < http://www.uniprot.org/uniprot/Q9AR86.txt>, last visited on Aug. 25, 2015 2 pages.
UniProt Database Accession No. Q9LIA1; Q84UU7, located at <http://www.uniprot.org/uniprot/Q9LIA1.txt>, last visited on Aug. 25, 2015, 3 pages.
UniProt Database Accession No. Q9LRZ6, located at < http://www.uniprot.org/uniprot/Q9LRZ6.txt>, last visited on Aug. 25, 2015, 3 pages.
UniProt Database Accession No. Q7XAS7, located at <http://www.uniprot.org/uniprot/Q7XAS7.txt>, last visited on Aug. 25, 2015, 2 pages.
UniProt Database Accession No. Q9FQ26, located at <http://www.uniprot.org/uniprot/Q9FQ26.txt>, last visited on Aug. 25, 2015, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21 (5):1558-1561.
Vagin, A. et al. (1997). "MOLREP: An Automated Program for Molecular Replacement," *Journal of Applied Crystallography* 30:1022-1025.
Vandamme, E.J. et al. (2002, e-pub. 2002). "Bioflavours and Fragrances Via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fungi," Chapter 18 in More Gene Manipulations in Fungi, Bennett, J.W. et al. eds., Academic Press, Inc.: San Diego, CA, pp. 396-428.

Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the Strep-tag II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosyntheitc Pathway," *Journal of Bacteriology* 186(1):61-67.
Wagner, W.P. et al. (Aug. 1999). "Three Distinct Phases of Isoprene Formation During Growth and Sporulation of *Bacillus subtilis*," *Journal of Bacteriology* 181(15):4700-4703.
Wagner, W.P. et al. (Jan. 2000, e-pub. Nov. 18, 1999). "Isoprene Biosynthesis in *Bacillus subtilis* Via the Methylerythritol Phosphate Pathway," *J. Nat. Prod.* 63(1):37-40.
Wang, C-W. et al. (Jan. 20, 1999). "Engineered Isoprenoid Pathway Enhances Astaxanthin Production in *Escherichia coli*," *Biotechnology and Bioengineering* 62(2):235-241.
Ward, M. et al. (Aug. 1993). "Use of *Aspergillus* Overproducing Mutants, Cured for Integrated Plasm id, to Overproduce Heterologous Proteins," *Appl. Microbiol. Biotechnol.* 39(6):738-743.
Weissermel, K. et al. (2003). Industrial Organic Chemistry, $4^{th}$, Completely Revised Edition, translated by Lindley, C.R. et al., Wiley-VCH GmbH & Co. KGaA, Weinheim, Germany, pp. 117-222.
Whisstock, J.C. et al. (2003). "Prediction of Protein Function from Protein Sequence and Structure," *Quarterly Reviews of Biophysics* 36(3):307-340.
Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.
Wildermuth, M.C. et al. (1998). "Biochemical Characterization of Stromal and Thylakoid-Bound Isoforms of Isoprene Synthase in Willow Leaves," *Plant Physiology* 116:1111-1123.
Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.
Wilkins, K. (1996). "Volatile Metabolites from Actinomycetes," *Chemosphere* 32(7):1427-1434.
Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.
Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.
Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.
Witkowski, A. et al. (1999, e-pub. Aug. 18, 1999). "Conversion of p-Ketoacyl Synthase to a Malonyl Decarboxylase by Replacement of the Active-Site Cysteine with Glutamine," *Biochemistry* 38(36):11643-11650.
Wolfertz, M. et al. (2003). "Biochemical Regulation of Isoprene Emission," *Plant, Cell and Environment* 26:1357-1364.

(56) References Cited

OTHER PUBLICATIONS

Wolfertz, M. et al. (Aug. 2004). "Rapid Regulation of the Methylerythritol 4-Phosphate Pathway During Isoprene Synthesis," *Plant Physiology* 135:1939-1945.

Wu, D.Y. et al. (1989). "The Ligation Amplification Reaction (LAR)-Amplification of Specific DNA Sequences Using Sequential Rounds of Template-Dependent Ligation," *Genomics* 4:560-569.

Xia, X-X. et al. (2008). "Comparison of the Extracellular Proteomes of *Escherichia coli* B and K-12 Strains During High Cell Density Cultivation," *Proteomics* 8:1-15.

Yamada, K. (1989). "Production of Glycerol from Methanol by a Mutant Strain of *Candida boidinii* No. 2201," *Agric. Biol. Chem.* 53(2):541-543.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A ((3-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *Proc. Natl. Acad. Sci. USA* 81:1470-1474.

Yoon, S-H. et al. (2007, e-pub. May 15, 2007). "Increased /3-Carotene Production in Recombinant *Escherichia coli* Harboring an Engineered Isoprenoid Precursor Pathway with Mevalonate Addition," *Biotechnol. Prog.* 23(3):599-605.

Yoon, S-H. et al. (2009). "Combinatorial Expression of Bacterial Whole Mevalonate Pathway for the Production of I3-Carotene in *E. coli*," *Journal of Biotechnology* 140:218-226.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

\* cited by examiner

Figure 1

1-
atgtgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaagacatcattaaagccctggaaaacatcgtactgctggacgaaaacaaaagaacaaatc
tgacctgcacgcaaccgctctgtctttccgtctgctgcgtcagcacggtttcgaggtttctcag
gatgttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgcctggaactgccatatcaccagcgtctgcaccgtctggaggcac
gttggttcctggataaatacgaaccgaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagaccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttactttcgtatgcagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaagatgaatcgtgaacgcgttagcgactccaccctgctg
cctaaagcgttcatggaaatcgcagttaacatggcacgtgtttcccactgcactaccagtatg
gcgatggtctgggtcgccagactacgcgactgaaaaccgcatcaaactgctgctgattgaccc
tttcccgattaaccagctgatgtatgtc
taactgcag (SEQ ID NO:1)

Figure 3A 1-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgtttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgacggaattatcgattaactttattattaaaaattaaagaggtatatattaat
gtatcgattaaataaggaggaataaaccATGgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacaccagccgctgtccctgctggagctgatcgacgatgtg
cagcgcctgggtctgacctacaaattgaaaaagacatcattaaagccctggaaaacatcgtac
tgctggacgaaaacaaaaagaacaaatctgacctgcacgcaaccgctctgtctttccgtctgct
ggtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttccatcaccacctgaagaacaa
cctgaaagaaggcattaataccaaggttgcagaacaagtgagccacgccctggaactgccatat
caccagcgtctgcacgtctggaggcacgttggttcctggataaatacgaaccgaaagaaccgc
atcaccagctgctgctggagctggcgaagctggatttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagaccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggcttc
tccaagtacctggaaaacgccagcgtttcctcctccggtgtagcgctgctggcgccgtcttact
tttccgtatgcagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggccgcgaagaactgcgtaaactgatcgacgccgaatggaaaagatgaatcg
tgaacgcgttagcgactccaccctgctgcctaaagcgttcatggaaatcgcagttaacatggca
cgtgtttcccactgcacctaccagtatggcgatggtctggtcgccagactacgcgactgaaa
accgcatcaaactgctgctgattgacccttttccggattaaccagctgatgtatgtcTAActgca
gctggtaccatatgggaattcgaagcttctagaacaaaaactcatctcagaagaggatctgaa
tagcgccgtcgaccatcatcatcatcatcattgagtttaaacggtctccagcttggctgtttg
gcggatgagagaagattttcagcctgatacagattaaatcagaacgcagaagcggtctgataaa
acagaatttgcctggcggcagtagcgcggtggtcccacctgacccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcgggcaggacgccgccataaactgccaggcatcaaattaagcagaaggccatcctg
acggatggccttttgcgtttctacaaactctttttgtttattttctaaatacattcaaatat
gtatccgctcatgagacaataacctgataaatgcttcataatattgaaaaggaagagtatg
agtattcaacatttccgtgtcgccttattcctttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcaggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactggtcatggctgcgccccgacaccgcaacacgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaaccctcaagacccgtttagaggccccaagggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatcttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataatttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacatttagtaacagctttgcg
acattcaccaaactcgggtctggcgccataccagtgcccagaaataaacttccatcaggcgg
tcgcgtacaaaatccagtttgctagccaggccatctcggtccaccagcgggacagatcttgca
gctcttctctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctcagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtcttttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
ttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggcccgtggccgggggactgttg
ggcgccatctccttgcatgcaccattccttgcggcggcggtgctcaacggcctcaacctactac
tgggctgcttcctaatgcaggagtcgcataaggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattatttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctcccgcgcg
ttggccgattcattaatgcagctggcacgacaggtttcccgactggaaagcgggcagtgagcgc
aacgcaattaatgtaagttagctcactcattaggcaccgggatctcgaccgatgccccttgagag
ccttcaaccagtcagctccttccggtgggcgcggggcatgactatcgtcgccgcacttatgac
tgtcttctttatcatgcaactcgtaggacaggtgccggcagcgctctggtcatttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgccggcgttgcaggccatgc
tgtccaggcaggtagatgacgaccatcagggacagcttcaaggatcgctcgcggctcttaccag
cctaacttcgatcactggaccgctgatcgtcacggcgatttatgccgctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtaatgcgcaaaccaacccttggc
agaacatatccatcgcgtccgccatctccagcagccgcacgcggcgcatctcggggcagcgttgg
gtcctggccacggtgcgcatgatcgtgctcctgtcgttgaggacccggctaggctggcgggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgatttttctct
ggtcccgccgcatccataccgccagttgttacccctcacaacgttccagtaaccgggcatgttc
atcatcagtaaccgtatcgtgagcatcctctctcgtttcatcggtatcattaccccccatgaac
agaaatccccttacacggaggcatcagtgaccaaacaggaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcggggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcaga

Figure 5C ggtggcgaaacccgacaggactataaagataccaggcgtttccccctggaagctccctcgtgcg
ctctcctgttccgacccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggttttttgttttgcaagcagcagattacg
cgcagaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaatagggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A

1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaagaacaaa
tctgacctgcacgcaaccgctctgtctttccgtctgctgcgtcagcacggtttcgaggttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtaccttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagacctgcaccagaaagagctgcagatctgtccgctggt
ggaccgagatgggcctggctagcaaactggattttgtacgcgaccgcctgatggaagtttatt
ctgggcactgggtatggcgccagaccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttactttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccacctgc
tgcctaaagcgttcatggaaatcgcagttaacatggcacgtgttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatcccgggta
ccgagctcgaattcactggccgtcgttttacaacgtcgtgactgggaaaaccctggcgttaccc
aacttaatcgccttgcagcacatcccccttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

Figure 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacgaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcaccccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgacccggatgaa
gtggttcgcatcctcggtttctggaaggcgagcatcgtttgttcgcccagcttctgtatggaa
agggcatgcggatcagtgagggtttgcaactgcgggtcaaggatctggatttcgatcacggcac
gatcatcgtgcgggagggcaagggctccaaggatcgggcttgatgttaccgagagcttggca
cccagcctgcgcgagcaggggaattaattcccacgggttttgctgccgcaaacgggctgttct
ggtgttgctagtttgttatcagaatcgcagatccggcttcagccggtttgcggctgaaagcgc
tatttcttccagaattgccatgatttttcccacgggaggcgtcactggctccgtgttgtcg
gcagctttgattcgataagcagcatcgcctgtttcaggctgtctatcgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatcttttttacaccgttttcatctgtgca
tatggacagttttcccttgatatgtaacggtgaacagttgttctacttttgtttgttagtctt
gatgcttcactgatagatacaagagccataagaacctcagatccttccgtatttagccagtatg
ttctctagtgtggttcgttgtttttgcgtgagccatgagaacgaaccattgagatcatacttac
tttgcatgtcactcaaaaatttttgcctcaaaactggtgagctgaattttttgcagttaaagcatc
gtgtagtgttttttcttagtccgttatgtaggtaggaatctgatgtaatggttgttggtatttg
tcaccattcattttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagcctttaaactcatgg
tagttatttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaattttttaactggaaaagataaggcaat
atctcttcactaaaaactaattctaattttttcgcttgagaacttggcatagtttgtccactgga
aaatctcaaagcctttaaccaaaggattcctgattccacagttctcgtcatcagctctctggt
tgctttagctaatacaccataagcattttccctactgatgttcatcatctgagcgtattggtta
taagtgaacgataccgtccgttcttccttgtagggttttcaatcgtggggttgagtagtgcca
cacagcataaaattagcttggttcatgctccgttaagtcatagcgactaatcgctagttcatt
tgctttgaaacaactaattcagacatacatctcaattggtctaggtgattttaatcactatac
caattgagatgggctagtcaatgataattactagtccttttcctttgagttgtgggtatctgta

Figure 7C

```
Aattctgctagacctttgctggaaaacttgtaaattctgctagaccctctgtaaattccgctag
accrttgtgtgttttttttgtttatattcaagtggttataatttatagaataaagaaagaataa
aaaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcacctcgcaagctgggcaaatcgctgaatattcctttgtctccgaccatcag
gcacctgagtcgctgtcttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcaccagtaaggcagcggtatcatcaacaggctta
```
(SEQ ID NO:7)

Figure 9
A.
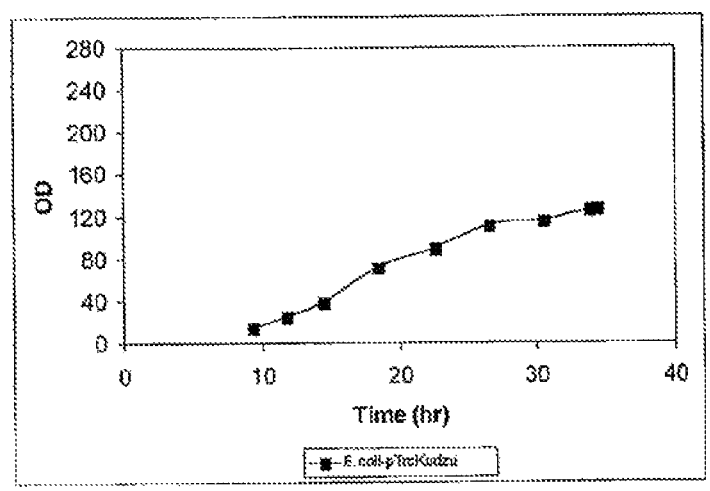
B.
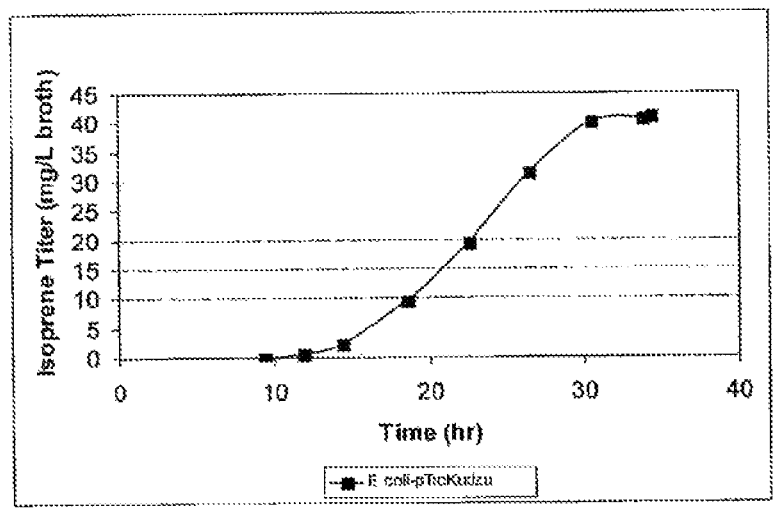

Figure 12A 1-
gaattgctccatttcttctgctatcaaaataacagactcgtgattttccaaacgagctttcaa
aaaagcctctgcccttgcaaatcggatgcctgtctataaaattcccgatattggttaaacagc
ggcgcaatggcggccgcatctgatgtctttgcttggcgaatgttcatcttatttcttcctcct
ctcaataatttttcattctatccttttctgtaaagtttattttcagaatacttttatcatc
atgctttgaaaaaatatcacgataatatccattgttctcacggaagcacacgcaggtcatttga
acgaattttttcgacaggaatttgccgggactcaggagcatttaacctaaaaaagcatgacatt
tcagcataatgaacatttactcatgtctatttcgttcttttctgtatgaaatagttatttcg
agtctctacggaaatagcgagagatgatatacctaaatagagataaaatcatctcaaaaaatg
ggtctactaaaatattattccatctattacaataaattcacagaatagtcttttaagtaagtct
actctgaattttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaagacatcattaaagccctggaaaacat
cgtactgctggacgaaaacaaaaagaacaaatctgacctgcacgcaaccgtctgtctttccgt
ctgctgcgtcagcacggtttcgaggttctcaggatgtttttgagcgtttcaaggataagaag
gtggtttcagcggtgaactgaaaggtgacgtccaaggcctgctgagcctgtatgaagcgtctta
cctgggtttcgagggtgagaacctgctggaggaggcgcgtacctttcatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagaccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgttccctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaagatg
aatcgtgaacgcgttagcgactccaccctgctgcctaaagcgttcatggaaatcgcagttaaca
tggcacgtgtttccactgcacctaccagtatggcgatggtctgggtcgccagactacgcgac
tgaaaaccgcatcaaactgctgctgattgacctttccgattaaccagctgatgtatgtctaa
aaaaaccggcctggcccgccggttttttattattttttcttcctccgcatgttcaatccgct
ccataatcgacggatggctccctctgaaaattttaacgagaaacggcgggttgacccggctcag
tcccgtaacggccaagtcctgaaacgtctcaatgccgcttccggtttccggtcagctcaatg
ccgtaacggtcggcggcgttttcctgataccgggagacggcattcgtaatcggatcctctagag
tgacctgcaggcatgcaagctttgcctcgcgcgtttcggtgatgacggtgaaaacctctgaca
catcagctccggagacggtcacagcttgtctgtaagcggatgccgggagcagacaagcccgt
cagggcgcgtcagcgggtgttggcgggtgtcggggcgcagccatgacccagtcacgtagcgata

Figure 12B

```
gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaagaaggatatggatctggagctgtaata
taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattaccttattaatgaattttcctgctgtaataatgggtagaaggtaattacta
ttattattgatatttaagttaaacccagtaaatgaagtccatggaataatagaaagagaaaag
catttttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatccaataacctaactctccgt
cgctattgtaaccagttctaaaagctgtatttgagtttatcaccttgtcactaagaaaataaa
tgcagggtaaaatttatatccttcttgttttatgtttcggtataaaacactaatatcaatttct
gtggttatactaaaagtcgttgttggttcaaataatgattaaatatctcttttctcttccaat
tgtctaaatcaatttattaaagttcattgatatgcctcctaaattttatctaaagtgaatt
taggaggcttacttgtctgctttcttcattagaatcaatcctttttaaagtcaatattactgt
aacataaatatatattttaaaaatatcccactttatccaatttttcgttgttgaactaatgggt
gctttagttgaagaataaagaccacattaaaaaatgtggtcttttgtgttttttaaaggattt
gagcgtacgcgaaaaatccttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatcccat
atttatccaatattcgttccttaatttcatgaacaatcttcattctttcttctctagtcattat
tattggtccattcactattctcattccttttcagtaaatttagattgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataattttccgttccaattccacattgcaataatagaaaatccatcttcatcggct
ttttcgtcatcatctgtatgaatcaaatcgccttcttctgtgtcatcaaggtttaatttttat
gtatttcttttaacaaaccaccataggagattaacctttacggtgtaaaccttcctccaaatc
agacaaacgtttcaaattctttttcttcatcatcggtcataaaatccgtatcctttacaggatat
tttgcagtttcgtcaattgccgattgtatatccgatttatatttattttcggtcgaatcattt
gaactttacattggatcatagtctaatttcattgccttttccaaaattgaatccattgttt
```

Figure 12C

```
ttgattcacgtagttttctgttattctaaaataagttggttccacacataccattacatgcatg
tgctgattataagaattatctttattatttattgtcacatccgttgcacgcataaaaccaacaa
gattttattaattttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgatttgtttatactctaatatttcagcacaatctttactctttcagccttt
ttaaattcaagaatatgcagaagttcaaagtaatcaacattagcgatttctttctctccatg
gtctcacttttccacttttgtcttgtccactaaaaccttgattttcatctgaataaatgct
actattaggacacataatattaaaagaaaccccatctatttagttattgtttagtcacttat
aactttaacagatggggttttctgtgcaaccaattttaagggttttcaatactttaaaacaca
tacataccaacacttcaacgcacctttcagcaactaaaataaaaatgacgttatttctatatgt
atcaagataagaagaacaagttcaaaccatcaaaaaagacaccttttcaggtgcttttttt
attttataaactcattccctgatctcgacttcgttcttttttacctctcggttatgagttagt
tcaaattcgttcttttaggttctaaatcgtgttttcttggaattgtgctgttttatcctttta
ccttgtctacaaacccctaaaaacgttttaaaggcttttaagccgtctgtacgttccttaag
```

(SEQ ID NO:57)

Figure 13

```
ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTCTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTCTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
(SEQ ID NO:8)
```

Figure 15A

```
   1 TCGACCGGTG AGAAGAACAG CATCGGGACA AGGGAAGGAA GAACAAAGAC AAAGAAAACA
  61 AAAGAAAGCA ATTCAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTC ACCCCCTGTC GCCCTCCTAT
 421 TGCCTTCCGG ATTATCTTCT TGTCCATAAG GTGATCCATC CTTCCTGAAG ATTCCCGAAA
 481 TGTGTCCACT TTGGCGGGGA ATCATTCCAT CCCACTTCTT CTCTCTCGCT TTCCTCATTC
 541 GCCCCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GCTGTTACGC CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACGGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAAGAAGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAC ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAG TCCCCTTTCT CTAAATCCAT CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTCTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTCTTCTTT TATTTCCTTT TTTTCATCTT CAAGGCTTTT CTTTTCTTCC
2461 TCCTCCTCGT TCATCTTGAG GTCTGACCTC TCTCTTACA ATTTGAGCT GTTGCAGCAT
2521 CTTATTTTTT GTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTCAAAG TAGTTGAGCT ATAGTTAAGT GTAAGGGCCC TACTCCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCGGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCACA CATACTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCCA TAACGAACGA GACCTTAACC TGCTAAATAG CTGATCAGC
3121 CATTTTGGCT GATCATTAGC TTCTTAGAGG GACTATTGCC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTGAAAAAA AATCTTTGA TTTTTTATCC TTGGCCGAA GGTCTGGGTA
3301 ATCTTGTTAA ACTCCGTCGT GCTGGGGATA GAGCATTGCA ATTATGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGCA TATAGCGGTA
3721 GTCTAATATC TAGCAAAAAT CTTTTGGGTG AAAAGGCTTG CAATTTCACG ACACCGAACT
3781 ATTTGTCATT TTTAATAAG GAAGTTTTCC ATAAATTCCT GTAATTCTCG GTTGATCTAA
3841 TTGAAAAAAG TAGTTTTGCA TCACGATGAG GAGGGCTTTT GTAGAAAGAA ATACCAACGA
3901 AACGAAAATC AGCGTTGCCA TCGCTTTGGA CAAAGCTCCG TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATGATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGCGACG CCCTATGCTG TTATCGATTT GGGATTAAAG CGTAGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCCGTTAT GGTAAAATTA ATGATGCACA
4801 AACGTCCGAT TCCATATGGG TACACTACAA TTAAATACTT TTAAGCTCAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCTACTAAA GGTTTAGGGA AGAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTTCATT TTTCTTGTTC TATTACAACT TTTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCCGG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGCCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGCAGCAG
5701 GACTGACACG TCCGACGGCG GCCCACGGGT CCCAGGCCTC GGAGATGCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCGGTAGG
6001 GTCTCTGTCT TGGCCTCCTT TCTAGGTCGG GCTGATTCCT CTTCAAGCTC TCTAGGCGCG
6061 CTCACACCAT AGGCAGATAA CGTTCCCCAC CGGCTCGCCT CGTAAGCGCA CAAGGACTGC
6121 TCCCAAAGAT CCTAGGCGSG ATTTTGCCGA TTTCGGCCTA AGGAACCGGA AACACGTAGA
6181 AAGCCAGTCC GCAGAAACGG TGCTGACCCC GGATCAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GCCTTCGAGG TGTCGCAGGA CGTCTTCGAG ACATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTC AGATCGCTGA
1321 CCGATTTTCA CGGCCTCGTG CGATCTTCCT GCGGTGATTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTACAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 CTCGTTGTAT GAGGCCTCCT TCCTCGCTCT TGAGGCCGAG AATATTCTGG ATGAGGCTCC
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAC CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGCAG TGGGTGTGGC CTTTCAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCC CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCCGCAACGC TTGGAAGTCT TCCAGCGGCC CTCTCCAGTT
1261 GATCTTCCCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```
(SEQ ID NO:13)

Figure 18A1
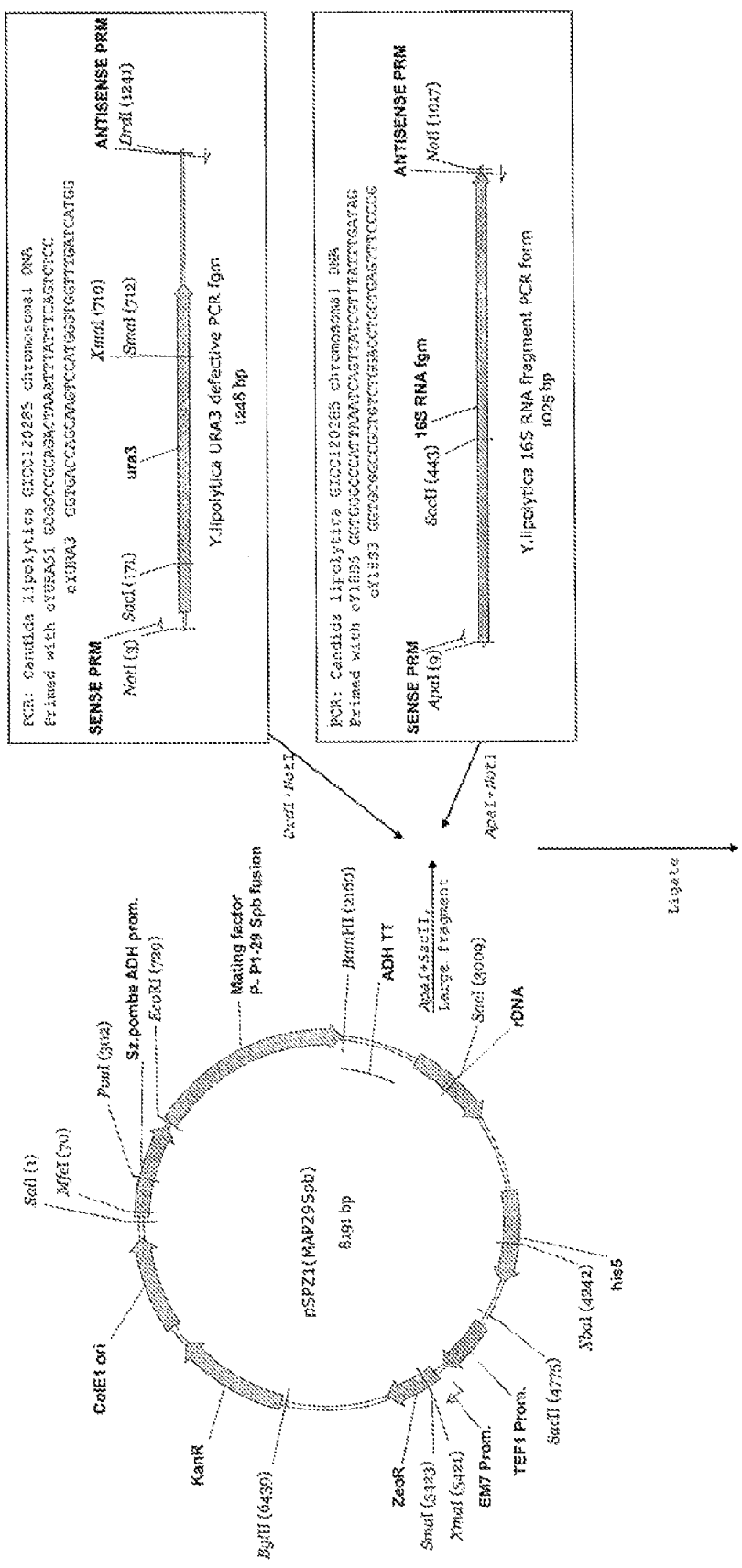

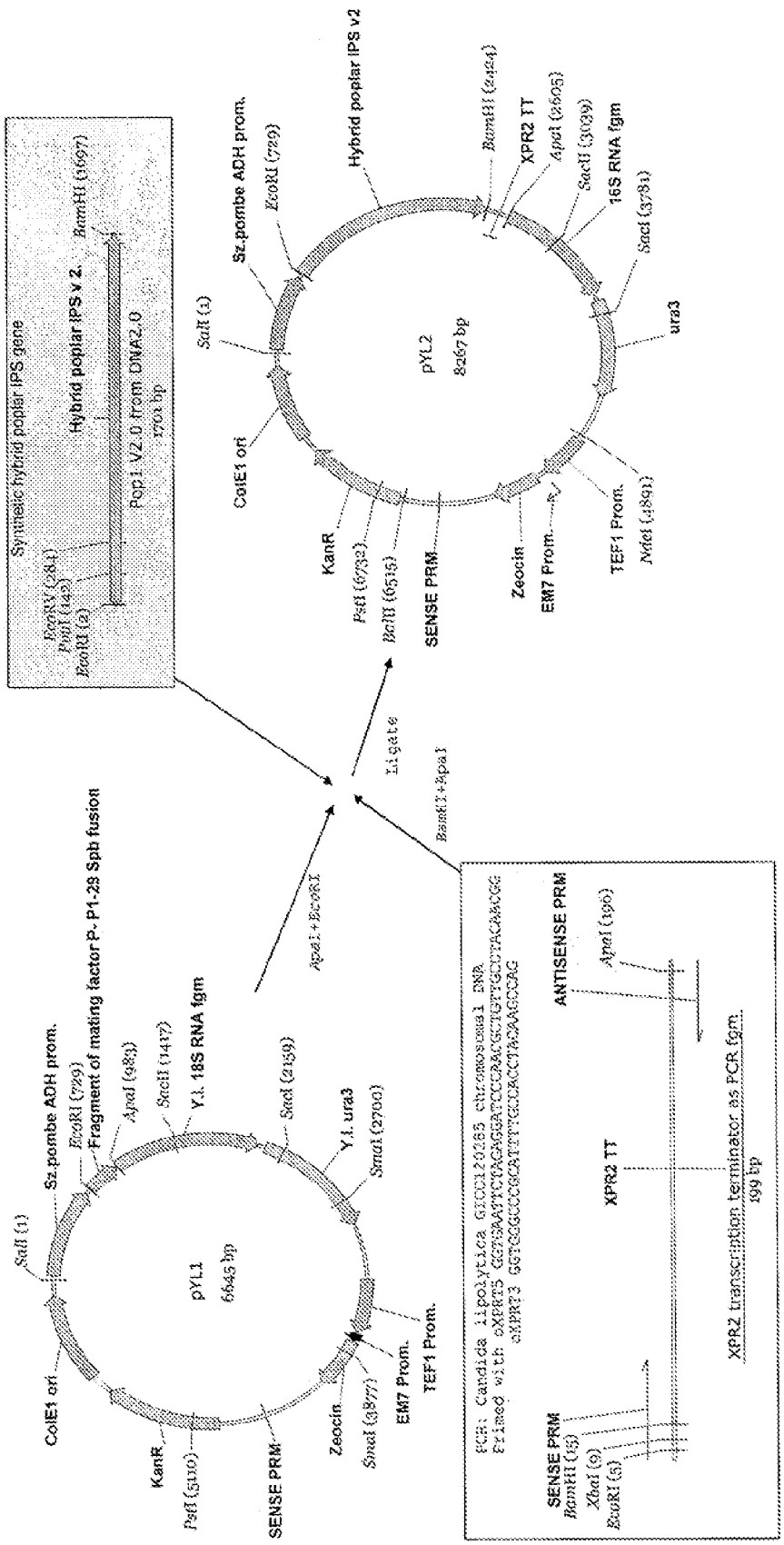
Figure 18A2

Figure 22A

1-
gctggtaccatatgggaattcgaagctttctagaacaaaaactcatctcagaagaggatctgaa
tagcgccgtcgaccatcatcatcatcattgagtttaaacggtctccagcttggctgttttg
gcggatgagagaagattttcagcctgatacagattaaatcagaacgcagaagcggtctgataaa
acagaattgcctggcggcagtagcgcggtggtcccacctgacccatgcgaactcagaagtg
aaacgccgtagcgccgatggtagtgtggggtctcccatgcgagagtaggaactgccaggcat
caaataaaacgaaaggctcagtcgaaagactgggcctttcgttttatctgttgtttgtcggtga
acgctctctgagtaggacaaatccgccgggagcggatttgaacgttgcgaagcaacggcccgg
agggtggcgggcaggacgcccgccataaactgccaggcatcaaattaagcagaaggccatcctg
acggatggccttttgcgtttctacaaactcttttgtttatttttctaaatacattcaaatat
gtatccgcttaaccggaattgccagctggggcgccctctgtaaggttgggaagccctgcaaag
taaactggatggctttctcgccgccaaggatctgatggcgcagggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgcg
tgttccggctgtcagcgcaggggcgcccggttcttttgtcaagaccgacctgtccggtgcct
gaatgaactgcaagacgaggcagcgcggctatcgtggctggccacgacgggcgttccttgcgca
gctgtgctcgatgttgtcactgaagcgggaagggactggctgctattgggcgaagtgccgggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccagggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtatttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggt
gtctcttatcagaccgtttccgcgtggtgaaccaggccagccacgtttctgcgaaaacgcggg
aaaaagtggaagcggcgatggcggagctgaattacattccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacaccatcaacagtattatttctcccatg
aagacggtacgcgactgggcgtggagcatctggtcgcattgggtcaccagcaaatcgcgctgtt
agcgggccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaagaaaaaccaccctggcgcccaatacg
caaaccgcctctcccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgtttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctcttaacaattatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaagacatcattaaagccctggaaaacatcgtactgctggac
gaaaacaaaagaacaaatctgacctgcacgcaaccgctctgtctttccgtctgctgcgtcagc
acggtttcgaggtttctcaggatgttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtacctttccatcacccacctgaagaacaacctgaaag
aaggcattaataccaaggttgcagaacaagtgagccacgcctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatgaagtttatttctggcactgggtatggcgccagaccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacacgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgcgtcttacttttccgta

Figure 22C

```
tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggccggcgaagaactgcgtaaactgatcgacgccgaatggaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaacgcatc
aaactgctgctgattgaccctttcccgattaaccagctgatgtatgtctaactgcatcgcctt
aggaggtaaaaaaaatgactgccgacaacaatagtatgcccatggtgcagtatctagttacg
ccaaattagtgcaaaaccaaacacctgaagacattttggaagagtttcctgaaattattccatt
acaacaaagacctaataccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaagggttt
actacatcgtgcattctccgtctttattttcaatgaacaaggtgaattacttttacaacaaga
gccactgaaaaaataactttccctgatctttggactaacacatgctgctctcatccactatgta
ttgatgacgaattaggtttgaagggtaagctagacgataagattaagggcgctattactgcgg
ggtgagaaaactagatcatgaattaggtattccagaagatgaaactaagacaaggggtaagttt
cacttttaaacagaatccattacatggcaccaagcaatgaaccatggggtgaacatgaaattg
attacatcctatttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctcgggctgggcacg
gtcgaactgacgtggcgctgcactatgtctacaacacccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgcgaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctgggcttatcaccacgctaagaacatgc
gcgacctgaaaggcccgcagttcctgcatatcatgaccaaaaaggtcgtggttatgaaccggc
agaaaagaccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgacctt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaaccatcagggtgcttttgatctctcttacctg
cgctgcataccggaaatggtcattatgacccgagcgatgaaaacgaatgtcgccagatgctct
ataccggctatcactataacgatggcccgtcagcggtgcgctaccgcgtggcaacgcggtcgg
```

Figure 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

Figure 25A

5'-
gtttgacagcttatcatcgactgcacggtgcaccaatgcttctggcgtcaggcagccatcggaa
gctgtggtatggctgtgcaggtcgtaaatcactgcataattcgtgtcgtcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaagaggtatatattaat
gtatcgattaaataaggaggaataaaccatggatccgagctcggatccactagtaacggccgcc
agtgtgctggaattcgcccttaggaggtaaaaaaacatgtcattaccgttcttaacttctgcac
cgggaaaggttattattttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgccccatgccaagaatattaagtttctttaaagt
ctacttacccatcggtgctggttgggctcaagcgcctctatttctgtatcactggcttagc
tatggcctacttggggggttaataggatctaatgacttggaaaagctgtcagaaaacgataag
catatagtgaatcaatggccttcataggtgaaaagtgtattcacggtacccttcaggaatag
ataacgctgtggccacttatggtaatgccctgctatttgaaaagactcacataatggaacaat
aaacacaaacaattttaagttcttagatgatttcccagccattccaatgatcctaacctatact
agaattccaaggtctacaaagatcttgttgctcgcgttcgtgtgttggtcaccgagaaattc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaagaaattgcaagatgatttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtcaaaagtaaacaatttaaag
atggggagtggctgtaccatataagtcctaaaagtggcttcattcctgtttcgataggcggatc
taagaaccctttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaaactacagctttggcc
tccttttttgtatcggacctggaaaataatgtagacaaatatagagaagttattcataatttag
cacaagttgctcattgtcaagctcagggtaaaattggaagcgggtttgatgtagcggcggcagc
atatggatctatcagatatagaagattcccaccgcattaatctctaatttgccagatattgaa
agtgctacttacggcagtaaactggcgcatttggttgatgaagaagactggaatattacgatta
aaagtaaccatttaccttcgggattaaactttatggatgggcgatattaagaatggttcagaaac
agtaaaactggtccagaaggtaaaaaattggtatgattcgcatatgccagaaagcttgaaaata

Figure 25B tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctcccgtacaaactagcttattggatgatt
gccagacgcttaaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactggggtgttaggaagaaaaagatccggaaactt
atcttgataaataattaaggtagctgcatgcagaattcgcccttaaggaggaaaaaaaaatga
ccgtttacacagcatccgttaccgcacccgtcaacatcgcaacccttaagtattgggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aaccacacagcatcgacaatgaagaactcaaaattgtctgcgcgacctacgccaattaagaaa
ggaaatggaatcgaaggacgcctcattgcccacattatctcaatggaaactccacattgtctcc
gaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaaagaattgaacatgtcgtaccaaagagatttgaagtc
atgcgtaaagccattgttgaaaaagatttcgccacctttgcaaaggaaacaatgatggattcca
actctttccatgccacatgtttggactctttcctccaatattctacatgaatgacacttccaa
gcgtatcatcagttggtgccacaccattaatcagttttacggagaaacaatcgttgcatacacg
tttgatgcaggtccaaatgctgtgttgtactactagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgcagagtgattttaactcaagtcggttcaggcccacaagaaacaaacgaatctt
tgattgacgcaaagactggtctaccaaaggaataagatcaattcgctgcatcgcccttaggagg
taaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgttttctggt
catgatgaggagcaaattaagttaatgaatgaaaattgtattgttttggattgggacgataatg
ctattggtgccggtaccaagaaagttttgtcatttaatggaaaatattgaaaagggttactaca
tcgtgcattctccgtctttattttcaatgaacaaggtgaattacttttacaacaaagagccact
gaaaaaataacttttccctgatctttggactaacacatgctgctctcatccactatgtattgatg
acgaattaggttttgaagggtaagctagacgataagattaagggcgctattactgcggcggtgag
aaaactagatcatgaattaggtattccagaagatgaaactaagacaagggtaagtttcacttt
ttaaacagaatccattacatggcaccaagcaatgaaccatgggtgaacatgaaattgattaca
tcctatttataagatcaacgctaagaaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaatcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatcctggagaa
cgacctgaaagtggaaaagctggaggagaaagcgaccaaactggaggaagaagttcgctgcatg

Figure 25C

```
atcaaccgtgtagacacccagccgctgtccctgctggagctgatcgacgatgtgcagcgcctgg
gtctgacctacaaatttgaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgttttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtacctttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgccagactacgcgactgaaaaccgcatcaa
actgctgctgattgaccctttccgattaaccagctgatgtatgtctaactgcagctggtacca
tatggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgacccatgccgaactcagaagtgaaacgccgta
gcgccgatggtagtgtggggtctccccatgcgagagtagggaactgccaggcatcaaataaaac
gaaaggctcagtcgaaagactgggcctttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
tttttgcgtttctacaaactcttttgttttattttttctaaatacattcaaatatgtatccgctt
aaccggaattgccagctggggcgccctctggtaaggttgggaagccctgcaaagtaaactggat
ggctttctcgccgccaaggatctgatggcgcagggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttctttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcagggctcgcgcc
agccgaactgttcgccaggctcaaggcgagcatgcccgacggcgaggatctcgtcgtgacccat
```

Figure 25D ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatccgcgctcccgattcgcag
cgcatcgccttctatcgccttcttgacgagttcttctgacgcatgaccaaaatccct taacgtg
agttttcgttccactgagcgtcagacccgtagaaaagatcaaaggatcttcttgagatccttt
ttttctgcgcgtaatctgctgcttgcaaacaaaaaaaccaccgctaccagcggtggtttgtttg
ccggatcaagagctaccaactcttttccgaaggtaactggcttcagcagagcgcagataccaa
atactgtccttctagtgtagccgtagttaggccaccacttcaagaactctgtagcaccgcctac
ataccTcgctctgctaatcctgttaccagtggctgctgccagtggcgataagtcgtgtcttacc
gggttggactcaagacgatagttaccggataaggcgcagcggtcgggctgaacggggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagctccaggggaaacgcctggtatctttatagtcctgtcgggt
ttcgccacctctgacttgagcgtcgattttgtgatgctcgtcagggggcggagcctatggaa
aaacgccagcaacgcggccttttacggttcctggccttttgctggcctttTgctcacatgttc
tttcctgcgttatcccctgattctgtggataaccgtataccgcctttgagtgagctgataccg
ctcgccgcagccgaacgaccgagcgcagcgagtcagtgagcgaggaagcggaagagcgcctgat
gcggtatttctccttacgcatctgtcggtatttcacaccgcatatggtgcactctcagtaca
atctgctctgatgccgcatagttaagccagtatacactccgctatcgctacgtgactgggtcat
ggctgcgccccgacaccCgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaat
tcagggtggtgaatgtgaaaccagtaacgttatacgatgtcgcagagtatgccggtgtctcta
tcagaccgtttccgcgtggtgaaccaggccagccacgtttctgcgaaaacgcgggaaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtgggctgatca
ttaactatccgctggatgaccaggatgccattgctgtggaagctgcctgcactaatgttccggc
gttatttcttgatgtctctgaccagacacccatcaacagtattatttctccatgaagacggt
acgcactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctgggGcaaaccagcgtggaccgcttgctgcaactctctcagggccaggcggtgaagggca
atcagctgttgcccgtctcactggtgaaaagaaaaaccaccctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg
(SEQ ID NO:33)

Figure 27A

5'-
ccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttatttggcgaaacaattgattcaattaggagaagcggaagttttt
aattgctggcgggattgagaatatgtcccaagcacctaaattacaacgtttaattacgaaaca
gaaagctacgatgcgccttttctagtatgatgtatgatggattaacggatgcctttagtggtc
aggcaatgggcttaactgctgaaaatgtggccgaaaagtatcatgtaactagagaagagcaaga
tcaatttctgtacatcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagttttttaaagaagacggtactgtaacagcagg
gaatgcatcaaccattaatgatgggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtcaaagagaa
ctggctttaccagaggaaaaggtcaacatttatggtggcggtatttcattaggtcatgcgattg
gtgccacaggtgctcgtttattaacgagtttaagttatcaattaaatcaaaagaaaagaaata
tggagtggcttctttatgtatcggcggtggcttaggactcgctatgctactagagagacctcag
caaaaaaaaacagccgatttatcaaatgagtcctgaggaacgcctggcttctcttcttaatg
aaggccagattctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattattggtaccaatggcgacagaagagccctcagttattgcggctt
tgagtaatggtgcaaaaatagcacaaggatttaaaacagtgaatcaacaacgcttaatgcgtgg
acaaatcgttttttacgatgttgcagatcccgagtcattgattgataaactacaagtaagagaa
gcggaagtttttcaacaagcagagttaagttatccatctatcgttaaacggggcggcggcttaa
gagattgcaatatcgtacttttgatgaatcatttgtatctgtcgacttttagtagatgttaa
ggatgcaatggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaattcagttccgcttgctttagcacggttggcggtgccaca
aaagtcttacctaaatctcaagcagctgctgattgttagcagtgacggatgcaaaagaactaa
gtcgagtagtagcggctgttggtttggcacaaaatttagcggcgttacgggccttagtctctga
aggaattcaaaaggacacatggctctacaagcacgttcttagcgatgacggtcggagctact
ggtaaagaagttgaggcagtcgctcaacaattaaaacgtcaaaaacgatgaaccaagaccgag
ccatggctatttaaatgatttaagaaaacaataaaggaggtaaaaaaacatgacaattgggat

Figure 27B

```
tgataaaattagttttttgtgccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaacctttcgctcgctctttcgaaatcaaggaagcttgtt
acggagcaacagcaggcttacagttagctaagaatcacgtagccttacatccagataaaaaagt
cttggtcgtagcggcagatattgcaaaatatggcttaaattctggcggtgagcctacacaagga
gctgggcggttgcaatgttagttgctagtgaaccgcgcattttggctttaaagaggataatg
tgatgctgacgcaagatatctatgacttttggcgtccaacaggccacccgtatcctatggtcga
tggtcctttgtcaaacgaaacctacatccaatcttttgcccaagtctgggatgaacataaaaaa
cgaaccggtcttgatttgcagattatgatgcttagcgttccatattccttacacaaaaatgg
gcaaaaaagccttattagcaaaaatctccgaccaaactgaagcagaacaggaacgaatttagc
ccgttatgaagaaagtatcgtctatagtcgtcgcgtaggaaacttgtatacgggttcactttat
ctgggactcatttcccttttagaaaatgcaacgactttaaccgcaggcaatcaaattggtttat
tcagttatggttctggtgctgtcgctgaattttcactggtgaattagtagctggttatcaaaa
tcatttacaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgaccccatgccgaactcagaagtgaa
acgccgtagcgccgatggtagtgtggggtctcccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggccttttgcgttctacaaactctttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatgcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaagc
cagccttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgtcgctggacctaccaaggcaacgctatgttctcttgcttttgtcagcaagatagccag
atcaatgtcgatcgtggctggctcgaagatacctgcaagaatgtcattgcgtgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
```

Figure 27C

```
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttaggcgactgccctgctgcgtaacatcgttgctgctccat
aacatcaaacatcgacccacggcgtaacgcgcttgctgcttggatgcccgaggcatagactgta
ccccaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgggcgcttgccggtggtgctgacccgg
atgaagtggttcgcatcctcggttttctggaaggcgagcatcgtttgttcgccagcttctgta
tggaacgggcatgcggatcagtgagggtttgcaactgcgggtcaaggatctggatttcgatcac
ggcacgatcatcgtgcgggagggcaagggctccaaggatcgggccttgatgttaccgagagct
tggcacccagcctgcgcgagcaggggaattaattccacgggtttttgctgcccgcaaacgggct
gttctggtgttgctagtttgttatcagaatcgcagatccggcttcagccggtttgccggctgaa
agcgctattctctccagaattgccatgattttttccccacggggaggcgtcactggctccgtgt
tgtcggcagcttgattcgataagcagcatcgcctgtttcaggctgtctatgtgtgactgttga
gctgtaacaagttgtctcaggtgttcaattcatgttctagttgcttgttttactggtttcac
ctgttctattaggtgttacatgctgttcatctgttacattgtcgatctgttcatggtgaacagc
tttgaatgcaccaaaaactcgtaaagctctgatgtatctatcttttacaccgttttcatct
gtgcatatggacagttttcccctttgatatgtaacggtgaacagttgttctactttgttgtta
gtcttgatgcttcactgatagatacaagagccataagaacctcagatccttccgtatttagcca
gtatgttctctagtgtggttcgttgttttgcgtgagccatgagaacgaaccattgagatcata
cttactttgcatgtcactcaaaaattttgcctcaaaactggtgagctgaatttttgcagttaaa
gcatcgtgtagtgttttcttagtccgttatgtaggtaggaatctgatgtaatggttgttggta
ttttgtcaccattcattttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaattttttcgcttgagaacttggcatagtttgtcca
ctggaaatctcaaagcctttaaccaaaggattcctgatttccacagtctcgtcatcagctct
ctggttctttagctaatacaccataagcattttccctactgatgttcatcatctgagcgtatt
ggttataagtgaacgatacgtccgttctttccttgtagggttttcaatcgtggggttgagtag
tgccacacagcataaaattagcttggtttcatgctccgttaagtcatagcgactaatcgctagt
tcatttgctttgaaaacaactaattcagcatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgttttttttgtttatattcaagtggttataatttatagaataaagaaag
aataaaaaagataaaaagaatagatcccagccctgtgtataactcactacttttagtcagttcc
gcagtattacaaaaggatgtcgcaaacgctgtttgctcctctacaaaacagaccttaaaaccct
aaaggcttaagtagcaccctcgcaagctcgggcaaatcgctgaatattccttttgtctccgacc
```

Figure 27D

Atcaggcacctgagtcgctgtctttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Lower Pathway Bacillus Cassette
9371 bp

Figure 29A

5'-
tgtaacctttgctttcaaatgagtagaaataatgcacatccatgtttgtatcgtgcaaataaag
tgtttcatccgtaggaaaaaatgactttagtatctgttccgcttttctgatgaaatgtgctcc
ccgacaaaattgaatgaatcatggacatttgctggctttgatacagcgaaagcagccgttccta
tgttatatatcggatttaacagcaggacaaaaacaccatgacagccatcgtcacccacttatt
cacacgcacataaacctttcctgacttttggaacagatgatagctcatcaaaaatcccgccatt
gccaaataaatcgtatatggcattactgcaccataatctttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatcccatcgggtattccttccaatacgaaaagaaactaaaaa
tcatttgtacgatcggcaaactgacaacagcaaggtcgaacgtataaaacttacccttccgcc
atgatcacgcggcatcagcatatagtgaaagccgtcagcagcacatatccgtataacaaaaaa
tgcagcagcggcagcagttcttttccgtcctctcttaagtaagcgctggtgaagtttgttgatt
gcacctggtgaataagttcaacagacactccgccagcagcacaatccgcaatataacacccgc
caagaacattgtgcgctgccggtttatttgggatgatgcaccaaaagatataagcccgccaga
acaacaattgaccattgaatcagcagggtgctttgtctgttaatataaaataacgttcgaaat
gcaatacataatgactgaataactccaacacgaacaacaactccatttcttctgctatcaaaa
taacagactcgtgattttccaaacgagctttcaaaaagcctctgccccttgcaaatcggatgc
ctgtctataaaattccgatattggttaaacagcggcgcaatggcggccgcatctgatgtcttt
gcttggcgaatgttcatcttatttcttcctccctctcaataattttttcattctatccctttc
tgtaaagtttatttttcagaatacttttatcatcatgctttgaaaaaatatcacgataatatcc
attgttctcacggaagcacacgcaggtcatttgaacgaatttttcgacaggaatttgccggga
ctcaggagcatttaacctaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaatgggtctactaaaatattattccatctattac
aataaattcacagaatagtcttttaagtaagtctactctgaatttttttaaaaggagagggtaa
agagtgtcattaccgttcttaacttctgcaccgggaaaggttattattttggtgaacactctg
ctgtgtacaacaagctgccgtgcctgctagtgtgtctgcgttgagaacctacctgctaataag
cgagtcatctgcaccagatactattgaattggacttccggacattagctttaatcataagtgg
tccatcaatgatttcaatgccatcaccgaggatcaagtaaactccaaaaattggccaaggctc
aacaagccaccgatggcttgtctcaggaactcgttagtcttttggatccgttgttagctcaact
atccgaatccttccactaccatgcagcgttttgttcctgtatatgtttgtttgcctatgcccc
catgccaagaatattaagtttctttaaagtctactttacccatcggtgctgggttgggctcaa
gcgcctctatttctgtatcactggccttagctatggcctacttgggggggttaataggatctaa
tgacttggaaaagctgtcagaaaacgataagcatatagtgaatcaatggccttcataggtgaa
aagtgtattcacggtaccccttcaggaatagataacgctgtggccacttatggtaatgccctgc
tatttgaaaagactcacataatggaacaataaacacaaacaatttaagttcttagatgattt
ccagccattccaatgatcctaacctatactagaattccaaggtctacaaaagatcttgttgct
cgcgttcgtgtgttggtcaccgagaaatttcctgaagttatgaagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctctttgactttgtt
acgaagagacattactcaagagcaaattgacagcttcaaaagaaattgcaagatgatttagt

Figure 29B tacgagacatttgaaacagacttgggtgggactggctgctgtttgttaagcgcaaaaatttga
ataaagatcttaaaatcaaatccctagtattccaattatttgaaaataaaactaccacaaagca
acaaattgacgatctattattgccaggaaacacgaatttaccatggacttcataaaaggagagg
gtgtcagagttgagagccttcagtgcccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaaccctttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
ctttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccaccgcattaatctctaatttgccagatattggaag
tgctacttacggcagtaaactgcgcattggttgatgaagaagactggaatattacgattaaa
agtaaccattaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagctagagatgcagttgccacaattagacgttcctttagaaa
aataactaaagaatctggtgccgatatcgaacctcccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagattttctaaggt
tcaatggctggatgtaactcaggctgactggggtgttaggaaagaaaaagatccggaaacttat
cttgataaataaaaggagagggtgaccgtttacacagcatccgttaccgcacccgtcaacatcg
caaccctaagtattggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaagggtctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaggatgtga
gttccactcagggtatgcaattgaccgtggcaacctccgaactatttaaagaaagaattgaaca
tgtcgtaccaaagagatttgaagtcatgcgtaaagccattgtgaaaaagatttcgccaccttt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctcgttcctggatgggaca
agaaatttactactgagcagcttgaggctttcaaccatcaatttgaatcatctaactttactgc
acgtgaattggatcttgagttgcaaaaggatgttgccagagtgattttaactcaagtcggttca
ggcccacaagaaacaaacgaatcttgattgacgcaaagactggtctaccaaaggaataaaagg
agagggtgactgccgacaacaatagtatgcccatggtgcagtatctagttacgccaaattagt

Figure 29C

```
gcaaaaccaaacacctgaagacattttggaagagtttcctgaaattattccattacaacaaaga
cctaataccgatctagtgagacgtcaaatgacgaaagcggagaaacatgttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttattttcaatgaacaaggtgaattacttttacaacaaagagccactgaaa
aaataactttccctgatcttggactaacacatgctgctctcatccactatgtattgatgacga
attaggtttgaagggtaagctagacgataagattaagggcgctattactgcggcggtgagaaa
ctagatcatgaattaggtattccagaagatgaaactaagacaaggggtaagtttcactttttaa
acagaatccattacatggcaccaagcaatgaaccatggggtgaacatgaaattgattacatcct
atttttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaaccggccttggccccgccg
gttttttattattttcttcctccgcatgttcaatccgctccataatcgacggatggctccctc
tgaaaattttaacgagaaacggcgggttgacccggctcagtccgtaacggccaagtcctgaaa
cgtctcaatcgccgcttccggtttccggtcagctcaatgccgtaacggtcggcggcgttttcc
tgataccgggagacggcattcgtaatttgaatacatacgaacaaattaataaagtgaaaaaat
acttcggaaacatttaaaaaataaccttattggtacttacatgtttggatcaggagttgagagt
ggactaaaaccaaatagtgatcttgactttttagtcgtcgtatctgaaccattgacagatcaaa
gtaaagaaatacttatacaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatataccgg
aaattatgacttagaggaattactacctgatattccatttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgcttttttctgatg
aaatgtgctcccgacaaaattgaatgaatcatggacatttgctggctttgatacagcgaaagc
agccgttcctatgttatatatcggatttaacagcaggacaaaaacaccatgacagccatcgtc
acccacttattcacacgcacataaacctttcctgactttggaacagatgatagctcatcaaaa
atcccgccattgccaaataaatcgtatatggcattactgcaccataatctttgagatttgatt
gggatatggcgcaagcagcaagacaagcagtccgataatcagcgtataaaataagcctagtaag
atcttatccgttctccaatcagcttgaaaaacactacattcaacgcaatgggaagagtgatga
tgaaaaacagaaacacgaatgcaatcggctccatccatccgggtattccttcaatacgaaaa
gaaactaaaaatcattgtacgatcggcaaactgacaacagcaaggtcgaacgtataaaactta
cccttccgccatgatcacgcggcatcagcatatagtgaaaagccgtcagcagcacatatccgt
ataacaaaaaatgcagcagcggcagcagttctttccgtcctctcttaagtaagcgctggtgaa
gttgttgattgcacctggtgaataagtcaacagacactccgccagcagcacaatccgcaat
ataacaccgccaagaacattgtcgcgtgcggtttattttgggatgatgcaccaaagatata
agcccgccagaacaacaattgaccattgaatcagcagggtgctttgtctgcttaatataaata
acgttcgaaatgcaatacataatgactgaataactccaacacgaacaacaaaagtgcgcatttt
```

Figure 29D

Ataaaagctaatgattcagtccacataattgatagacgaattctgctacaggtcacgtggctat
gtgaaggatcgcgcgtccagttaagagcaaaaacattgacaaaaaatttatttatgctaaaat
ttactattaatatatttgtatgtataataagattctcctggccagggggaatcttattttttgtg
gaggatcatttcatgaggaaaaatgagtccagcttaacgtctctaatttcagcttttgcccgtg
catatcacagccgatatgacacacctcttattttttgatgattttatcgcaaaagatctcattaa
cgaaaagagtttatcgacatcagtaaaaatatgattcaagaaatatcgttttttcaacaaagag
atcgccgaacgtcttcaaaatgatcctgaaaaaatattaaaatgggttgcacaaatccagctgt
ctccaacgccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaataagc
tgaaggatgcaaatctgacaattccgggtcatcttcattttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttatttctcatg
tcccgcttggaagctctattgttttttgattatgcggacgaaacacttttttacagcaaaagggac
gtcgaatcgagttgaacatatggtgaagatggctgccgcaagcggggaaccgatgaaatcatgt
ttcacttatcaagagattgaacatctg
(SEQ ID NO:47)

Figure 31A

5'-
tagaaaaactcatcgagcatcaaatgaaactgcaatttattcatatcaggattatcaataccat
attttgaaaaagccgtttctgtaatgaaggagaaaactcaccgaggcagttccataggatggc
aagatcctggtatcggtctgcgattccgactcgtccaacatcaatacaacctattaatttccc
tcgtcaaaaataaggttatcaagtgagaaatcaccatgagtgacgactgaatccggtgagaatg
gcaaaagtttatgcatttctttccagacttgttcaacaggccagccattacgtcgtcatcaaa
atcactcgcatcaaccaaaccgttattcattcgtgattgcgcctgagcgaggcgaaatacgcga
tcgctgttaaaaggacaattacaaacaggaatcgagtgcaaccggcgcaggaacactgccagcg
catcaacaatatttcacctgaatcaggatattcttctaataccgtggaacgctgttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgccgacattatcgcgagcccatttatacccatataaatcagcatccatgttggaa
tttaatcgcggcctcgacgtttccgttgaatatggctcatattcttccttttcaatattatt
gaagcatttatcagggttattgtctcatgagcggatacatatttgaatgtatttagaaaaataa
acaaatagggggtcagtgttacaaccaattaaccaattctgaacattatcgcgagcccatttata
cctgaatatggctcataacacccttgttttgcctggcggcagtagcgcggtggtcccacctgac
cccatgccgaactcagaagtgaaacgccgtagcgccgatggtagtgtggggactcccatgcga
gagtagggaactgccaggcatcaaataaaacgaaaggctcagtcgaaagactgggcctttcgcc
cgggctaattaggggggtgtcgccctttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctccgttggtggcgccgtgtgggcctggc
gaccaaactgcacttcgctaaggaccgcctgattgagtcttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgtgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaatggctgtataa
caaatccactcgacctttgacgattatttcggcaatgcctggaaatccagctctggccgctg
caactgatcttcgcttatttgcggttgtccaaaacatcaaaaggaggaaattgaaacctgc
aaaaataccacgatatcattagccgtccttctcatatctttcgcctgtgcaacgacctggaag
ccgtccgcagagatcgcacgtggcgaaaccgctaactctgtttcctgctacatgcgcaccaag
ggcatttccgaagagctggcaacgagagcgtaatgaatctgatcgacgaaacctgtaagaaaa
tgaacaaagaaaaactgggtggctccctgttcgctaaaccgttcgtagagactgctattaacct

Figure 31B

```
ggcacgtcagagccactgcacctaccacaatggtgacgcacatactagcccggatgaactgact
cgtaaacgtgtactgtctgttatcacgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgcttttttctcatttataaggttaaataattctcatatatcaagcaaagt
gacaggcgcccttaaatattctgacaaatgctctttccctaaactcccccataaaaaaacccg
ccgaagcgggttttacgttatttgcggattaacgattactcgttatcagaaccgcccagggggg
cccgagcttaagactggccgtcgttttacaacacagaaagagtttgtagaaacgcaaaaaggcc
atccgtcagggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtgggctaactacggctacactagaagaacagtatttggtatctgcgctctgctga
agccagttaccttcggaaaaagagttggtagctcttgatccggcaaacaaaccaccgctggtag
cggtggttttttgtttgcaagcagcagattacgcgcagaaaaaaggatctcaagaagatcct
ttgatcttttctacggggtctgacgctcagtggaacgacgcgcgtaactcacgttaagggat
tttggtcatgagcttgcgccgtcccgtcaagtcagcgtaatgctctgcttt
```
(SEQ ID NO:48)

Figure 33A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactcc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggagc
tgaagtgcgccgcgaaattaacaacgagaaagctgaattcctgactctgctggagctgatcgat
aacgtacagcgcctgggtctggttaccgcttcgaatctgatatccgtcgcgcactggatcgtt
tcgtaagcagcggcggtttcgatggcgtgaccaaaacgagcctgcacgctacgcgctgtcctt
ccgtctgctgcgtcagcacggcttcgaagtttctcaggaagcatctccggtttcaaagatcaa
aacggtaacttcctggaaaacctgaaagaagacactaaggcgatcctgagcctgtatgaggcaa
gctttctggcctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtctttactgggcagtcggcgttgcgttcgaacctc
agtattctgactgccgtaacagcgttgcgaaaatgttcagcttcgttactactatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgcttttctgcaagaagcgaaatggctgtataacaaatccact
ccgacctttgacgattatttcggcaatgcctggaaatccagctctggccgctgcaactgatct
tcgcttattttgcggttgtccaaaacatcaaaaaggaggaaattgaaaacctgcaaaaatacca
cgatatcattagccgtccttctcatatcttcgcctgtgcaacgacctggcaagcgcgtccgca
gagatcgcacgtggcgaaaccgctaactctgttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttt
gcgtttctacaaactcttttgtttatttttctaaatacattcaaatatgtatccgctcatgag
acaataaccctgataaatgcttcaataatattgaaaaaggaagagtatgagtattcaacatttc

Figure 33B

```
cgtgtcgccttattccttttttgcggcattttgccttcctgttttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcacttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgttttttgcacaacatggggatc
atgtaactcgccttgatcgttgggaaccggagctgaatgaagccataccaaacgacgagcgtga
caccacgatgcctgtagcaatggcaacaacgttgcgcaaactattaactggcgaactactact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagaccccgtagaaaagatcaaaggatcttcttgagatcctt
ttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtggg
aacaggagagcgcacgagggagcttccaggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctcgccccgacacccgccaacacccgctgacgcgccctgacgggcttgtctgctcccggc
atccgcttacagacaagctgtgaccgtctccggggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaaccttcgcggtatggcatgatagcgcccggaagagagtcaa
ttcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattatttctcccatgaagacgg
tacgcgactggcgtggagcatctggtcgcattgggtcaccagcaaatcgcgctgttagcgggc
ccattaagttctgtctcggcgcgtctgcgtctggctggctggcataaatatctcactcgcaatc
```

Figure 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctcccgcgcgttggccgattcattaatgcagctggcacgacaggttttcccgactggaaag
cgggcagtgagcgcaacgcaattaatgtgagttagcgcgaattgatctg
(SEQ ID NO:49)

Figure 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcaggatggtgaatgtgaaaccagtaacgttatacgatgtcgcagagt
atgccggtgtctcttatcagaccgtttccgcgtggtgaaccaggccagccacgtttctgcgaa
aacgcgggaaaaagtggaagcggcgatggcggagctgaattacattccaaccgcgtggcacaa
caactggcgggcaaacagtcgttgctgattggcgttgccacctccagtctggccctgcacgcgc
cgtcgcaaattgtcgcggcgattaaatctcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatccgccgtcaaccaccat
caaacaggatttttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacattaaagcctggaaaacatgtac
tgctggacgaaaacaaaagaacaaatctgacctgcacgcaaccgctctgtctttccgtctgct
gcgtcagcacggtttcgaggtttctcaggatgttttgagcgtttcaaggataaagaaggtggt
ttcagcggtgaactgaaggtgacgtccaaggcctgctgagcctgtatgaagcgtcttacctgg
gtttcgagggtgagaacctgctggaggaggcggtacctttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggatttaacatggtacagaccctgcaccagaa
agagctgcaagatctgtccgctggtggaccgagatgggcctggctagcaaactggattttgta
ccgcgaccgcctgatggaagtttattctggcactgggtatggcgccagaccgcagtttggtg
aatgtcgcaaagctgttactaaaatgtttggtctggtgacgatcatcgatgacgtgtatgacgt

Figure 35B ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaagctggcg
tgaactgtgcaaagcctttctgcaagaggcgaaatggtccaacaacaaaattatccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgacccttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttatttttcaatgaacaaggtgaattactttac
aacaaagagccactgaaaaataaacttccctgatctttggactaacacatgctgctctcatcc
actatgtattgatgacgaattaggttctgaagggtaagctagacgataagattaagggcgctatt
actgcggcggtgagaaaactagatcatgaattaggtattccagaagatgaaactaagacaaggg
gtaagtttcacttttttaaacagaatccattacatggcaccaagcaatgaaccatgggtgaaca
tgaaattgattacatcctatttttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtgggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtgggtctcccatgcgagagtagggaactg
ccaggcatcaaataaaacgaaaggctcagtcgaaagactgggcctttcgttttatctgttgttt
gtcggtgaacgctctcctgagtaggacaaatccgccggagcggatttgaacgttgcgaagcaa
cggcccggagggtggcgggcaggacgcccgccataaactgccaggcatcaaattaagcagaagg
ccatcctgacggatggcctttttgcgtttctacaaactcttttgttattttctaaatacat
tcaaatatgtatccgcttaacggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttcttttgtcaagaccgacctgtcc
ggtgccctgaatgaactgcaagacgaggcagcgcggctatcgtggctggccacgacggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat

Figure 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagacccgtagaaaagatcaaaggat
cttcttgagatcctttttttctgcgcgtaatctgctgcttgcaaacaaaaaaaccaccgctacc
agcggtggtttgtttgccggatcaagagctaccaactcttttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccaggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacaccgccaacaccgctgacgcgccctgacgggc
(SEQ ID NO:50)

Figure 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttccgcgtggtgaaccaggcagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattattt
ctcccatgaagacggtacgcgactgggcgtggagcatctggtcgcattgggtcaccagcaaatc
gcgctgttagcgggccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctggcgcaatgcgcgccattaccgagtccgggctgcgcgttggtgcggata
tctcggtagtgggatacgacgatacgaagacagctcatgttatatccgccgtcaaccaccat
caaacaggattttcgcctgctggggcaaaccagcgtggaccgcttgctgcaactctctcagggc
caggcggtgaaggcaatcagctgttgcccgtctcactggtgaaaagaaaaccaccctggcgc
ccaatacgcaaacgcctctcccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaagctggaggagaaagcgaccaaactggaggaagaagt
tcgctgcatgatcaaccgtgtagacacccagccgtgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggttttgaggtttctcaggatgttttgagcgttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccactgaagaacaa
cctgaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggatttgta
cgcgaccgcctgatggaagtttatttctgggcactgggtatggcgccagaccgcagtttggtg
aatgtcgcaaagctgttactaaatgtttggtctggtgacgatcatcgatgacgtgtatgacgt
ttatggcactctggacgaactgcaactgttcaccgatgctgtagagcgctgggacgttaacgct

Figure 37B

```
attaacacctgcggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggcttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaagatgaatcg
tgaacgcgttagcgactccaccctgctgcctaaagcgttcatggaaatcgcagttaacatggca
cgtgttcccactgcacctaccagtatggcgatggtctgggtcgccagactacgcgactgaaa
accgcatcaaactgctgctgattgacccttccgattaaccagctgatgtatgtctaactgca
ttcgccttaggaggtaaaaaaacatgagttttgatattgccaaatacccgacctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacacccgtttgaccaattgatttgggatg
tggggcatcaggcttatccgcataaaatttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaagtttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctgggcttatcaccacgctaaagaacatgc
gcgacctgaaaggcccgcagttcctgcatatcatgaccaaaaaaggtcgtggttatgaaccggc
agaaaaagaccgatcactttccacgccgtgcctaaattgatccttccagcggttgtttgccg
aaaagtagcggcggtttgccgagctattcaaaaatctttggcgactggttgtgcgaaacgcag
cgaaagacaacaagctgatggcgattactccggcgatgcgtgaaggttccggcatggtcgagtt
ttcacgtaaattcccggatcgctacttcgacgtggcaattgccgagcaacacgcggtgacctt
gctgcgggtctggcgattggtgggtacaaacccattgtcgcgattactccactttcctgcaac
gcgcctatgatcaggtgctgcatgacgtggcgattcaaaagcttccggtcctgttcgccatcga
ccgcgcgggcattgttggtgctgacggtcaaaaccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctaccgcgtggcaacgcggtcgg
cgtggaactgacgccgctggaaaaactaccaattggcaaaggcattgtgaagcgtgtggcgag
aaactggcgatcctaactttggtacgctgatgccagaagcggcgaaagtcgccgaatcgctga
acgccaccgctggtcgatatgcgtttgtgaaacgcttgatgaagcgttaattctggaaatggc
cgccagcctgaagcgctggtcaccgtagaagaaacgccattatgggcggcgtaggcagcggc
gtgaacgaagtgctgatggcccatcgtaaaccagtaccgtgctgaacattggcctgccggact
tctttattccgcaaggaactcaggaagaaatgcgcgcggaactcggcctgatgcgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg
```

Figure 37C gtggtcccacctgacccatgccgaactcagaagtgaaacgccgtagcgccgatggtagtgtgg
ggtctcccatgcgagagtagggaactgccaggcatcaaataaaacgaaaggctcagtcgaaag
actgggcctttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggccttttgcgtttctacaaa
ctctttttgtttatttttctaaatacattcaaatatgtatccgcttaaccggaattgccagctg
gggcgcctctggtaaggttgggaagccctgcaaagtaaactggatggcttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttcttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatggc
tgaccgcttcctcgtgctttacggtatcgccgctcccgattcgcagcgcatcgccttctatcgc
cttcttgacgagttcttctgacgcatgaccaaaatccttaacgtgagttttcgttccactgag
cgtcagacccgtagaaaagatcaaaggatcttcttgagatcctttttttctgcgcgtaatctg
ctgcttgcaaacaaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccaggggggaaacgcctggtatctttatagtcctgtcgggtttcgccacctctgacttg
agcgtcgatttttgtgatgctcgtcaggggggcggagcctatggaaaaacgccagcaacgcggc
cttttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
(SEQ ID NO:51)

Figure 39A

5' -
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctcaggggaagccg
aagttttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgttttaacttttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgccagcttctgtatggaacgggcatgcggatcagtgacggtttgcaactgcgggt
caaggatctggatttcgatcacggcacgatcatcgtgcgggagggcaagggctccaaggatcgg
gccttgatgttaccgagagcttggcaccagcctgcgcgagcaggggaattaattccacggg
ttttgctgcccgcaaacgggctgttctggtgttgctagtttgttatcagaatcgcagatccggc
ttcagccggtttgccggctgaaagcgctattcttccagaattgcatgatttttcccacgg
gaggcgtcactggctccgtgttgtcggcagctttgattcgataagcagcatcgcctgtttcag
gctgtctatgtgtgactgttgagctgtaacaagttgtctcaggtgttcaattcatgttctagt
tgctttgttttactggttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttcccttttgatatgtaacggtgaaca
gttgttctactttgtttgttagtcttgatgcttcactgatagatacaagagccataagaacct
cagatccttccgtatttagccagtatgttctctagtgtggttcgttgttttttgcgtgagccatg
agaacgaaccattgagatcatacttactttgcatgtcactcaaaaatttgcctcaaaactggt
gagctgaattttgcagttaaagcatcgtgtagtgtttttcttagtccgttatgtaggtaggaa
tctgatgtaatggttgttggtattttgtcaccattcattttatctggttgttctcaagttcgg

Figure 39B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttttaactggaaaagataaggcaatatctcttcactaaaaactaattctaattttcgcttg
agaacttggcatagtttgtccactggaaaatctcaaagcctttaaccaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtgggggttgagtagtgccacacagcataaaattagcttggtttcatgctccgttaa
gtcatagcgactaatcgctagttcattgctttgaaaacaactaattcagacatacatctcaat
tggtctaggtgattttaatcactataccaattgagatgggctagtcaatgataattactagtcc
ttttcctttgagttgtgggtatctgtaaattctgctagaccttgctggaaaacttgtaaattc
tgctagaccctctgtaaattccgctagacctttgtgtgtttttttgttatattcaagtggtt
ataatttatagaataaagaaagaataaaaaagataaaagaatagatccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgtcacggctctggcagtgaatgggggtaaatggcactacaggcgccttttatggattc
atgcaaggaaactacccataatacaagaaagcccgtcacgggcttctcaggcgttttatggc
gggtctgctatgtggtgctatctgacttttgctgttcagcagttcctgccctctgatttcca
gtctgaccacttggattatcccgtgacaggtcattcagactggctaatgcaccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtcctgct
ggagctgatcgacgatgtgcagcgcctgggtctgacctacaaatttgaaaagacatcattaaa
gccctggaaaacatcgtactgctggacgaaaacaaaagaacaaatctgacctgcacgcaaccg
ctctgtctttccgtctgctgcgtcagcacggtttcgaggtttctcaggatgttttgagcgttt
caaggataaagaaggtggtttcagcggtgaactgaaaggtgacgtccaaggcctgctgagcctg
tatgaagcgtcttacctggggtttcgagggtgagaacctgctggaggaggcgcgtaccttttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagttatttctgggcactgggtatggcg
ccagaccgcagtttggtaatgtcgcaaagctgttactaaaatgttggtctggtgacgatca
tcgatgacgtgtatgacgtttatggcactctggacgaactgcaactgtcaaccgatgctgtaga
gcgctgggacgttaacgctattaacaccctgccggactatatgaaactgtgttcctggcactg
tacaacaccgttaacgacacgtcctattctattctgaaagagaaaggtcataacaacctgtcct

Figure 39C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttactttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgcg
aatggaaaagatgaatcgtgaacgcgttagcgactccaccctgctgctaaagcgttcatgga
aatcgcagttaacatggcacgtgtttcccactgcacctaccagtatggcgatggtctgggtcgc
ccagactacgcgactgaaaacgcatcaaactgctgctgattgacccttcccgattaaccagc
tgatgtatgtctaactgcagctggtaccatatggaattcgaagctttctagaacaaaaactca
tctcagaagaggatctgaatagcgccgtcgaccatcatcatcatcatcattgagtttaaacggt
ctccagcttggctgttttggcggatgagagaagatttcagcctgatacagattaaatcagaac
gcagaagcggtctgataaaacagaatttgcctggcggcagtagcgcggtggtccacctgaccc
catgccgaactcagaagtgaaacgccgtagcgccgatggtagtgtggggtctcccatgcgaga
gtagggaactgccaggcatcaaataaaacgaaggctcagtcgaagactgggcctttcgtttt
atctgttgtttgtcggtgaacgctctcctgagtaggacaaatccgccgggagcggatttgaacg
ttgcgaagcaacggcccggagggtggcggcaggacgcccgccataaactgccaggcatcaaat
taagcagaaggccatcctgacggatggcctttttgcgtttctacaaactcttttgtttatttt
tctaaatacattcaaatatgtatccgctcatgagacaataaccctgataaatgcttcaataat
(SEQ ID NO:52)

Figure 41A

5' -
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgccgccacccctccgggccgttgcttcgcaacgttcaaatccgctcccgg
cggatttgtcctactcaggagagcgttcaccgacaaacaacagataaaacgaaaggccagtct
ttcgactgagcctttcgttttatttgatgcctggcagttccctactctcgcatggggagaccc
acactaccatcggcgctacggcgtttcacttctgagttcggcatggggtcaggtgggaccacg
cgctactgcgccaggcaaattctgttttatcagaccgcttctgcgttctgatttaatctgtat
caggctgaaaatcttctctcatccgccaaaacagccaagctggagaccgtttaaactcaatgat
gatgatgatggtcgacggcgctattcagatcctcttctgagatgagttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgagcgtggtcggagat
gtcttcctgctgctggcatacggaaaagtaagacggcgccagcagcgctacaccggaggaggaa
acgctggcgttttccaggtacttggagaaagccgggataattttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcacctcgaaacccaggtaagacgcttcatacaggctcagcaggcttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttcttttgttttcgtccagcagtacgatgttcaggcctttaatgatgtcttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttattaatcgatacattaatatatacctctttaattttaataataaagtta
atcgataattccggtcgagtgcccacacagattgtctgataaattgttaaagagcagtgccgct
tcgcttttctcagcggcgctgtttcctgtgtgaaattgttatccgctcacaattccacacatt
ataagagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 41B tgatgccgcatagttaagccagcccgacaccgccaacacccgctgacgagcttagtaaagcc
ctcgctagattttaatgcggatgttgcgattacttcgccaactattgcgataacaagaaaaagc
cagcctttcatgatatatctcccaatttgtgtaggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactaccttt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactaccctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcaccccggcaact
tgggcagcagcgaagtcgaggcatttctgtcctggctggcgaacgagcgcaaggtttcggtctc
cacgcatcgtcaggcattgcgcggccttgctgttcttctacggcaaggtgctgtgcacggatctg
ccctggcttcaggagatcggaagacctcggccgtcgcggcgcttgccggtggtgctgacccgg
atgaagtggttcgcatcctcggttttctggaaggcgagcatcgttttgttcgcccagcttcttgta
tggaacgggcatgcggatcagtgagggtttgcaactgcgggtcaaggatctggattttcgatcac
ggcacgatcatcgtgcgggagggcaaggctccaggatcgggccttgatgttacccgagagct
tggcacccagcctgcgcgagcaggggaattaattcccacgggttttgctgccgcaaacgggct
gttctggtgttgctagtttgttatcagaatcgcagatccggcttcagccggtttgccggctgaa
agcgctatttcttccagaattgccatgattttttcccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatctttttacaccgttttcatct
gtgcatatggacagttttccctttgatatgtaacggtgaacagttgttctactttgtttgtta
gtcttgatgcttcactgatagatacaagagccataagaacctcagatccttccgtatttagcca
gtatgttctctagtgtggtcgttgtttttgcgtgagccatgagaacgaaccattgagatcata
cttactttgcatgtcactcaaaaattttgcctcaaaactggtgagctgaattttgcagttaaa
gcatcgtgtagtgttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatcttacttattggtttcaaacccattggttaagccttttaaact
catggtagttatttcaagcattaacatgaacttaaattcatcaaggctaatctctatatttgc

Figure 41C cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcatttccctactgatgttcatcatctgagcgtatt
ggttataagtgaacgataccgtccgttcttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgtttttttgtttatattcaagtggttataatttatagaataaagaaag
aataaaaaagataaaagaatagatcccagccctgtgtataactcactactttagtcagttcc
gcagtattacaaaaggatgtcgcaaacgctgtttgctcctctacaaaacagaccttaaaaccct
aaaggcttaagtagcaccctgcaagctcgggcaaatcgctgaatattccttttgtctccgacc
atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

Figure 43A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctcaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaacttgtttttagggcgactgccctgctg
cgtaacatcgttgctgctccataacatcaaacatcgacccacggcgtaacgcgcttgctgcttg
gatgcccgaggcatagactgtaccccaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattgcgggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcaccagctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgattttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgcttgttttactggttcacctgttctattaggtgttacatgctgttcatctgttacattgt
cgatctgttcatggtgaacagctttgaatgcaccaaaaactcgtaaagctctgatgtatctat
cttttttacaccgttttcatctgtgcatatggacagttttcccttttgatatgtaacggtgaaca
gttgttctacttttgtttgttagtcttgatgcttcactgatagatacaagagccataagaacct
cagatccttccgtattagccagtatgttctctagtgtggttcgttgtttttgcgtgagccatg
agaacgaaccattgagatcatacttactttgcatgtcactcaaaaattttgcctcaaaactggt
gagctgaattttttgcagttaaagcatcgtgtagtgtttttcttagtccgttatgtaggtaggaa
tctgatgtaatggttgttggtattttgtcaccattcatttttatctggttgttctcaagttcgg

Figure 43B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttatttcaagcattaacatgaacttaaattcat
caaggctaatctctatatttgccttgtgagtttttcttttgtgttagttcttttaataaccactc
ataaatcctcatagagtatttgttttcaaaagacttaacatgttccagattatattttatgaat
tttttaactggaaaagataaggcaatatctcttcactaaaaactaattctaattttttcgcttg
agaacttggcatagtttgtccactggaaaatctcaaagcctttaaccaaggattcctgatttc
cacagttctcgtcatcagctctctggttgtttagctaatacaccataagcatttccctactg
atgttcatcatctgagcgtattggttataagtgaacgatacgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgatttaatcactataccaattgagatgggctagtcaatgataattactagtcc
ttttccttttgagttgtgggtatctgtaaattctgctagaccttttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaacagaccttaaaacctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgcctttatggattc
atgcaaggaaactaccataatacaagaaagcccgtcacggcttctcagggcgttttatggc
gggtctgctatgtggtgctatctgactttttgctgttcagcagttcctgccctctgatttttcca
gtctgaccacttcggattatcccgtgacaggtcattcagactggctaatgcacccagtaaggca
gcggtatcatcaacaggcttaccccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aattatcagacaatctgtgtggcactcgaccggaattatcgattaactttattattaaaaat
taagagggtatatattaatgtatcgattaaataaggaggaataaaccatgtgtgcgacctcttc
tcaattttactcagattaccgagcataattcccgtcgttccgcaaactatcagccaaacctgtgg
aatttcgaattcctgcaatccctggagaacgacctgaaagtggaaagctggaggagaaagcga
ccaaactggaggaagaagttcgctgcatgatcaacgtgtagacaccagccgctgtccctgct
ggagctgatcgacgatgtgcagcgcctgggtctgacctacaaattttgaaaagacatcattaaa
gccctggaaaacatcgtactgctggacgaaaacaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtaccttttcca
tcacccacctgaagaacaacctgaaagaaggcattaataccaagttgcagaacaagtgagcca
cgccctggaactgccatatcaccagcgtctgcaccgtctggaggcacgttggttcctgcataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacacccgtccggactatatgaaactgtgtttcctggcactg
tacaacaccgttaacgacacgtcctattctattctgaaagagaaaggtcataacaacctgtcct

Figure 43C

```
atctgacgaaaagctggcgtgaactgtgcaaagcctttctgcaagaggcgaaatggtccaacaa
caaaattatcccggctttctccaagtacctggaaaacgccagcgtttcctcctcggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgcg
aatggaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaacgcatcaaactgctgctgattgacccttccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaataccgatctagtgagacgtca
aatgacgaaagcggagaaacatgttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttatttttcaatgaa
caaggtgaattacttttacaacaaagagccactgaaaaaataacttttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaagggggtaagtttcacttttaaacagaatccattacatggcaccaagca
atgaaccatggggtgaacatgaaattgattacatcctatttttataagatcaacgctaaagaaaa
cttgactgtcaacccaaacgtcaatgaagttagagacttcaaatggggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaattgcctggcggcagtagcgcggtggtccca
cctgaccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactcttttg
tttatttttctaaatacattcaaatatgtatccgctcatgagacaataaccctgataaatgctt
caataat
(SEQ ID NO:54)
```

Figure 45A

5'-
ccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggcgttgcttcgcascgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatgggtcaggtgggaccaccg
cgctactgccgccaggcaaattctgttttatcagaccgctctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttttgttctagaaa
gcttcgaattcccatatggtaccagctgcagttatgccagccaggccttgattttggcttccat
accagcggcatcgaggccgagttcggcgcgcatttcttctgagttccttgcggaataaagaag
tccggcaggccaatgttcagcacgggtactggttttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattccgcgactttcgccgcttctggcatcagcgtaccaaagttaaggatcgccagtttct
cgccacgacgcttcacaatgcctttgccaattggtagttttttccagcggcgtcagttccacgcc
gaccgcgttgccacgcgggtagcgcaccgctgacgggccatcgttatagtgatagccggtatag
agcatctggcgacattcgttttcatgctcggggtcataatgaccatttccggtatgcagcgca
ggtaagagagatcaaaagcacctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagaccgcagcaa
aggtcaccgcgtgttgctcggcaattgccacgtcgaagtagcgatccgggaattacgtgaaaa
ctcgaccatgccggaaccttcacgcatcgccggagtaatcgccatcagcttgttgtcttcgct
gccgtttcgcacaaccagtcgccaaagattttgaatagctcggcaaacgccgctactttcg
gcaaacaaccgctggagggatcaaattaggcacggcgtggaaagtgatcgggtcttttctgc
cggttcataaccacgaccttttttggtcatgatatgcaggaactgcgggcctttcaggtcgcgc
atgttctttagcgtggtgataagcccagcacatcgtgaccgtccacgggcgatgtagttaa
agccagctcttcaaacaacgtgccaggcactaccatgcctttaatatgttcttcggtgcgttt
gagcagctcttaattggcggcacgcagagaaaacttttttcccgccttcgcgcagtgaagag
taaagcttaccggaaagcagctgtgcagatggttgttgagcgcgccgacattttcggaaatcg
acatttcattgtcgttgagaatcaccagcatatcaggacggatatcgccgcgtgattcatcgc
ttcaaacgccatgcctgcggtaatcgcgccatcgcaatgacacagacggtgcggcgattttg
ccttcttttcggcagcaaccgcaataccaattccggcactgatggaggttgatgaatgccga
cgcttaatacgtcatattcgctttcgccgcgccacgggaacgggtgcagaccgcctttctgacg
gatggtgcgattttgtcgcggcgtccggtcaaaatttatgcggataagcctgatgcccaca
tcccaaatcaattggtcaaacggggtgttgtagacatagtgcagcgccacggtcagttcgaccg
tgccagcccggaggcgaagtgccgctggaacggctcagctgtcgagtaaatagcggcgcag
ttgtcgcagagtttcggtaaactctcttcggcaacagtcgtaactcctggtggagtcgacc
agtgccagggtcgggtatttggcaatatcaaaactcatgttttttacctcctaagggcgaatg
cagttagacatacatcagctggttaatcgggaaagggtcaatcagcagcagtttgatgcggttt
tcagtcgcgtagtctgggcgacccagaccatcgccataclggtaggtcagtgggaaacacgtg
ccatgttaactgcgatttccatgaacgcttaggcagcagggtggagtcgctaacgcgttcacg

Figure 45B

```
attcatcttttccattcggcgtcgatcagtttacgcagttcttcgcgggcctgttcctcgctg
gtaccatcgtttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataattttgttgttggaccatttcgctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtccagcgctctacagcatcggtgaacagttgcagttcgtccagagtgccataaac
gtcatacacgtcatcgatgatcgtcaccagaccaaacattttagtaacagctttgcgacattca
ccaaactgcgggtctggcgccataccagtgccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcacctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaagacagagcggttgcgtgcaggtcagatttgttcttttttgttttcgtccagcagt
acgatgttttccagggctttaatgatgtcttttcaaatttgtaggtcagaccaggcgctgca
catcgtcgatcagctccagcagggacagcggctgggtgtctacacggttgatcatgcagcgaac
ttcttcctccagttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctcctttatttaatcgatacat
taatatatcctcttttaattttttaataataaagttaatcgataattccggtcgagtgcccacac
agattgtctgataaattgttaaagagcagtgccgcttcgcttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
caccccgccaacacccgctgacgagcttagtaaagccctcgctagattttaatgcggatgttgcg
attacttcgccaactattgcgataacaagaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactggccggcaggcgctccattgcccagtggcagcgac
atccttcggcgcgattttgccggttacgtgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgcgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccagggaagccgaagtttccaaaaggtcgttgatcaaagctcgccgcgttgtttcatcaagc
```

Figure 45C

```
cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtacccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgct
tcatccgtttccacggtgtgcgtcaccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgacccggatgaagtggttcgcatcctcggttttct
ggaaggcgagcatcgtttgttcgcccagcttctgtatggaacgggcatgcggatcagtgaggt
ttgcaactgcgggtcaaggatctggatttcgatcacggcacgatcatcgtgcgggaggcaagg
gctccaaggatcgggccttgatgttacccgagagcttggcacccagcctgcgcgagcagggaa
ttaattccacgggttttgctgccgcaaacgggctgttctggtgttgctagtttgttatcaga
atcgcagatccggcttcagccggtttgccggctgaaagcgctatttcttccagaattgccatga
ttttttcccacgggaggcgtcactggctccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagcttgaatgcaccaaaaactcgtaaaagc
tctgatgtatctatcttttttacaccgttttcatctgtgcatatggacagtttccctttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaattt
gcctcaaaactggtgagctgaattttgcagttaaagcatcgtgtagtgtttttcttagtccgt
tatgtaggtaggaatctgatgtaatggttgttggtattttgtcaccattcattttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtattgttttcaaaagacttaacatgttccagat
tatattttatgaattttttttaactggaaaagataaggcaatatctcttcactaaaaactaattc
taattttcgcttgagaacttggcatagttgtccactggaaaatctcaaagcctttaaccaaa
ggattcctgatttccacagttctcgtcatcagctctctggttgctttagctaatacaccataag
cattttcnctactgatgttcatcatctgagcgtattggttataagtgaacgataccgtccgtc
tttccttgtagggttttcaatcgtgcggttgagtagtgccacacagcataaaattagcttggtt
tcatgctccgttaagtcatagcgactaatcgctagttcatttgctttgaaaacaactaattcag
acatacatctcaattggtctaggtgatttaatcactataccaattgagatgggctagtcaatg
ataattactagtccttttcctttgagttgtgggtatctgtaaattctgctagacctttgctgga
aaacttgtaaattctgctagaccctctgtaaattccgctagacctttgtgtgtttttttgttt
atattcaagtggttataatttatagaataagaagaataaaaaagataaaaagaatagatcc
cagccctgtgtataactcactactttagtcagttccgcagtattacaaaaggatgtcgcaaacg
ctgtttgctcctctacaaacagacctaaaaccctaaaggcttaagtagcaccctcgcaagct
cgggcaaatcgctgaatattccttttgtctccgaccatcaggcacctgagtcgctgtctttc
```

Figure 45D

Gtgacattcagttcgctgcgctcacggctctggcagtgaatgggggtaaatggcactacaggcg
cctttatggattcatgcaaggaaactacccataatacaagaaaagcccgtcacgggcttctca
gggcgttttatggcgggtctgctatgtggtgctatctgacttttgctgttcagcagttcctgc
cctctgattttccagtctgaccacttcggattatcccgtgacaggtcattcagactggctaatg
cacccagtaaggcagcggtatcatcaacaggctta
(SEQ ID NO:55)

5'-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggtttttt
tgtttgcaagcagcagattacgcgcagaaaaaaaggatctcaagaagatcctttgatctttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttcctttttc
aatattattgaagcatttatcaggttattgtctcatgagcggatacatatttgaatgtattta
gaaaaataaacaaataggggttccgcgcacatttccccgaaaagtgccacctgacgtctaagaa
accattattatcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaaagcatttttcaggtataggtgttttgggaaacaatttccccgaaccattatattctctaca
tcagaaaggtataaatcataaaactctttgaagtcattctttacaggagtccaaataccagaga
atgttttagatacaccatcaaaaattgtataaagtggctctaacttatcccaataacctaactc
tccgtcgctattgtaaccagttctaaaagctgtatttgagtttatcacccttgtcactaagaaa
ataaatgcagggtaaaattatatccttcttgtttatgtttc

Figure 51B

```
ggtataaaacactaatatcaatttctgtggttatactaaaagtcgtttgttggttcaaataatg
attaaatatctcttttctcttccaattgtctaaatcaattttattaaagttcatttgatatgcc
tcctaaatttttatctaaagtgaatttaggaggcttacttgtctgctttcttcattagaatcaa
tcctttttaaaagtcaatattactgtaacataaatatatattttaaaaatatcccactttatc
caattttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaaggggggatg
tgctgcaagcgattaagttgggtaacgccagggttttcccagtcacgacgttgtaaaacgacg
gccagtgccaagcttgcatgcctgcactccatttcttctgctatcaaaataacagactcgtga
ttttccaacgagctttcaaaaagcctctgcccttgcaaatcggatgcctgtctataaaatt
cccgatattggttaaacagcggcgcaatggcggccgcatctgatgtctttgcttggcgaatgtt
catcttatttcttcctccctctcaataatttttcattctatcccttttctgtaaagtttattt
ttcagaatactttatcatcatgctttgaaaaatatcacgataatatccattgttctcacgga
agcacacgcaggtcatttgaacgaattttttcgacaggaatttgccgggactcaggagcattta
acctaaaaaagcatgacatttcagcataatgaacatttactcatgtctatttcgttctttct
gtatgaaaatagttatttcgagtctctacggaaatagcgagagatgatataccaaatagagat
aaaatcatctcaaaaaaatgggtctactaaatatattccatctattacaataaattcacaga
atagtctttaagtaagtctactctgaattttttaaaaggagagggtaaagagtgaaaacagt
agttattattgatgcattacgaacaccaattggaaaatataaaggcagcttaagtcaagtaagt
gccgtagacttaggaacacatgttacaacacaactttaaaaagacattccactatttctgaag
aaattgatcaagtaatctttggaaatgttttacaagctggaaatgccaaaatcccgcacgaca
aatagcaataaacagcggtttgtctcatgaaattcccgcaatgacggttaatgaggtctgcga
tcaggaatgaaggccgttatttggcgaaacaattgattcattaggagaagcggaagttttaa
ttgctggcgggattgagaatatgtcccaagcacctaaattacaacgttttaattacgaaacaga
aagctacgatgcgccttttctagtatgatgtatgatggattaacggatgcctttagtggtcag
gcaatgggcttaactgctgaaaatgtggccgaaaagtatcatgtaactagagaagagcaagatc
aatttctgtacattcacaattaaaagcagctcaagcacaagcagaagggatattcgctgacga
aatagccccattagaagtatcaggaacgcttgtggagaaagatgaagggattcgcctaattcg
agcgttgagaagctaggaacgcttaaaacagtttttaaagaagacggtactgtaacagcagga
atgcatcaaccattaatgatggggcttctgcttgattattgcttcacaagaatatgccgaagc
acacggtcttccttattagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaagagaact
ggctttaccagaggaaaaggtcaacattatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaacagccgatttatcaaatgagtcctgaggaacgcctggcttctcttcttaatgaa
ggccagatttctgctgatacaaaaaagaatttgaaaatacggctttatcttcgcagattgcca
atcatatgattgaaaatcaaatcagtgaaacagaagtgccgatgggcgttggcttacatttaac
agtggacgaaactgattatttggtccaatggcgacagaagagccctcagttattgcggctttg
agtaatggtgcaaaaatagcacaaggatttaaaacagtgaatcaacaacgcttaatgcgtggac
aaatcgttttttacgatgttgcagatccgagtcattgattgataaactacaagtaagagaagc
ggaagtttttcaacaagcagagttaagttatccatctatcgttaaacgggcggcggcttaaga
gatttgcaatatcgtacttttgatgaatcatttgtatctgtcgacttttagtagatgttaagg
atgcaatggggggcaaatatcgttaacgctatgttggaaggtgtg
```

Figure 51C

```
gccgagttgttccgtgaatggtttgcggagcaaaagatttattcagtattttaagtaattatg
ccacggagtcggttgttacgatgaaaacggctattccagtttcacgtttaagtaaggggagcaa
tggccgggaaattgctgaaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaggacacatggctctacaagcacgttctttagcg
atgacggtcggagctactggtaaagaagttgaggcagtcgctcaacaattaaaacgtcaaaaaa
cgatgaaccaagaccgagccatggctatttaaatgatttaagaaaacaataaaaggagagggt
gacaattgggattgataaaattagttttttttgtgcccccttattatattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctcttttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcattttggctttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgatttttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcatttcccttttagaaaatgcaacgactttaaccgcaggcaatc
aaattggtttattcagttatggttctggtgctgtcgctgaatttttcactggtgaattagtagc
tggttatcaaaatcatttacaaaaagaaactcatttagcactgctggataatcggacagaactt
tctatcgctgaatatgaagccatgtttgcagaaacttagacacagacattgatcaaacgttag
aagatgaattaaaatatagtatttctgctattaataataccgttcgttcttatcgaaactaaaa
aaaaccggccttggccccgccggttttttattatttttcttcctccgcatgttcaatccgctcc
ataatcgacggatggctccctctgaaaatttaacgagaaacggcgggttgacccggctcagtc
ccgtaacggccaagtcctgaaacgtctcaatcgccgcttcccggtttccggtcagctcaatgcc
gtaacggtcggcggcgttttcctgatacgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
```

(SEQ ID NO:56)

Figure 55A 1-
tggcgaatgggacgcgccctgtagcggcgcattaagcgcggcgggtgtggtggttacgcgcagcgtgaccgctacacttgccagcgcc
tagcgcccgctccttcgctttcttcccttcctttctcgccacgttcgccggctttccccgtcaagctctaaatcgggggctcccttagggttcc
gatttagtgcttacggcacctcgaccccaaaaaacttgattagggtgatggttcacgtagtgggccatcgccctgatagacggttttcgccc
tttgacgttggagtccacgttcttaatagtggactcttgttccaaactggaacaacactcaaccctatctcggtctattcttttgatttataagggat
tttgccgatttcggcctattggttaaaaaatgagctgatttaacaaaaatttaacgcgaatttttaacaaaatatttaacgtttacaatttcaggtggca
cttttcggggaaatgtgcgcggaaccccctattgtttattttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatatttcacctgaatcaggatattcttc
taatacctggaatgctgtttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccattataccctataaatcagcatccatgttggaa
tttaatcgcggcctagagcaagacgtttcccgttgaatatggctcataacaccccctgtattactgtttatgtaagcagacagtttattgttcatga
ccaaaatcccttaacgtgagttttcgttccactgagcgtcagaccccgtagaaaagatcaaaggatcttcttgagatccttttttttctgcgcgtaa
tctgctgcttgcaaacaaaaaaaccaccgctaccagcggtggtttgtttgccggatcaagagctaccaactctttttccgaagggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtatttttctcctacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtagggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttcaaccagcatcgcagtgggaacgatgccctcattcagc
atttgcatggtttgttgaaaaccggacatggcactccagtcgccttcccgttccgctatcggctgaatttgattgcgagtgagatatttatgccag

Figure 55B ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcgcggatagttaatgatcagcccactgacgcgttgcgcgagaagattgtgaccgc
cgctttacaggcttcgacgccgcttcgttctaccatcgacaccaccacgctggcacccagttgatcggcgcgagattaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttccgcgcgttttcgcagaaacgtggctggcctggttcaccacgcgggaaacggtct
gataagagacaccggcatactctgcgacatcgtataacgttactggtttcacattcaccaccctgaattgactctcttccggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
acegcacctgtggcgccggtgatgccggccacgatgcgtccggcgtagaggatcgagatctcgatcccgcgaattaatacgactcacta
tagggggaattgtgagcggataacaattcccctctagaaataattttgtttaactttaagaaggagatatacatatgcgttgtagcgtgtccaccg
aaaatgtgtctttcaccgaaactgaaaccgaagctcgtcgtctgcgaactacgaacctaacagctgggactatgattacctgctgtcctccga
cacggacgagtccatcgaagtatacaaagacaaagcgaaaaagctggaagccgaagttgctcgcgagattaataacgaaaaagcagaat
ttctgaccctgctggaactgattgacaacgtccagcgcctgggcctgggttaccgttcgagtctgatatccgtggtgcgctggatcgcttcgt
ttcctccggcggcttcgatgcggtaaccaagacttccctgcacggtacggcactgtctttccgtctgctgcgtcaacacggttttgaggttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggtttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgttttctttcgtaaccattatcgacgatatctacgatgtat
acggcaccctggacgaactggagctgtttactgatgcagttgagcgttgggacgtaaacgccatcaacgacctgccggattacatgaaact
gtgcttctggctctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgaccttgacgactacttcggcaacgcatg
gaaatcctcttctggcccgctgcaactggtgttcgcttacttcgctgtcgtgcagaacattaaaaaggaagagatcgaaacctgcaaaaata
ccatgacaccatctctgtcctccccatatcttccgtctgtgcaatgacctggctagcgcgtctgcggaaattgcgcgtggtgaaaccgcaaat
agcgttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacgcgcatacctctccggatgagctgaccgcaaacgcgtctgtctgtaatcactgaaccgattctgccgtttgaacgctaaggat
ccgaattcgagctccgtcgacaagcttgcggccgcactcgagcaccaccaccaccaccactgagatccggctgctaacaaagcccgaaa
ggaagctgagttggctgctgccaccgctgagcaataactagcataaccccttggggcctctaaacgggtcttgaggggttttttgctgaaag
gaggaactatatccggat (SEQ ID NO:87)

Figure 58A

1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgtttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctggttaccgtttcgagtctgatatccgtggtgcgctggatcgcttcgttcctccggcggcttcgatgcggtaaccaagacttcc
ctgcacggtacggcactgtctttccgtctgctgcgtcaacacggttttgaggttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaacctgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatcgcgtgaaacgtcccgttggtggcgtcgtgtggggtctg
gcgaccaaactgcactttgctctgtgaccgcctgattgagagcttctactggccgtgggtgtagcattcgaaccgcaatacctccgactgccg
taactccgtcgcaaaaatgtttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgcttcctgcaagaagcca
agtggctgtacaacaaatctactccgaccttgacgactacttcggcaacgcatggaaatcctctctggcccgctgcaactggtgttcgctta
cttcgctgtcgtgcagaacattaaaaaggtagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgtcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcagctggtaccatatgggaattcgaagcttctagaac
aaaaactcatctcagaagaggatctgaatagcgccgtcgaccatcatcatcatcatcattgagtttaaacggtctccagcttggctgttttggcg
gatgagagaagattttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtgggggtctcccatgcgagagtagggaact
gccaggcatcaaataaaacgaaaggctcagtcgaaagactgggcctttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactcttttgtttatttttctaaatacattcaaatatgtatccgctcatgaga
caataaccctgataaatgcttcaataatattgaaaaaggaagagtatgagtattcaacatttccgtgtcgcccttattccctttttgcggcattttg
ccttcctgtttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcactttaaagttctgctatgtggcgcggtattatcccg
tgttgacgccgggcaagagcaactcggtcgccgcatacactattctcagaatgacttggttgagtactcaccagtcacagaaaagcatctac
ggatggcatgacagtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatatata
ctttagattgatttaaaacttcatttttaatttaaaaggatctaggtgaagatcctttttgataatctcatgaccaaaatcccttaacgtgagttttcgtt
ccactgagcgtcagaccccgtagaaaagatcaaaggatcttcttgagatcctttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

Figure 58B tgccagtggcgataagtcgtgtcttaccggggttggactcaagacgatagttaccggataaggcgcagcggtcgggctgaacggggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggggaaacgcctggtat
ctttatagtcctgtcgggtttcgccacctctgacttgagcgtcgattttgtgatgctcgtcagggggggcggagcctatggaaaaacgccagca
acgcggcctttttacggttcctggcctttttgctggcctttttgctcacatgttcttttcctgcgttatcccctgattctgtggataaccgtattaccgcct
ttgagtgagctgataccgctcgccgcagccgaacgaccgagcgcagcgagtcagtgagcgaggaagcggaagagcgcctgatgcggt
attttctccttacgcatctgtgcggtatttcacaccgcatatggtgcactctcagtacaatctgctctgatgccgcatagttaagccagtatacact
ccgctatcgctacgtgactgggtcatggctgcgccccgacaccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
atcgcgcgcgaaggcgaagcggcatgcatttacgttgacaccatcgaatggtgcaaaaccttttcgcggtatggcatgatagcgcccggaa
gagagtcaattcagggtggtgaatgtgaaaccagtaacgttatacgatgtcgcagagtatgccggtgtctcttatcagaccgtttccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttatttcttgatgtctctgaccagacacccatcaacagtattatttttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctggccgcaatgcgcgccattaccgagtccgggctgcgcgttggtgcggat
atctcggtagtgggatacgacgataccgaagacagctcatgttatatcccgccgtcaaccaccatcaaacaggatttcgcctgctgggggca
aaccagcgtggaccgcttgctgcaactctctcagggccaggcggtgaagggcaatcagctgttgcccgtctcactggtgaaaagaaaaac
cacccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:88)

Figure 61A

1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgtttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaaccatgagatgtagcgtgtccaccgaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgttcctccggcggcttcgatgcggtaaccaagacttcc
ctgcacggtacggcactgtctttccgtctgctgcgtcaacacggttttgaggtttctcaggaagccgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgttttctttcgtaaccattatcgacgtatatctacgatgtatacggcaccctggacgaactggagctgttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgcttcctgcaagaagcca
agtggctgtacaacaaatctactccgaccttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgttctgttacatgcgcactaaaggtatctccgaa
gaactggctaccgaaagcgtgatgaatctgatcgatgaaacctggaaaaagatgaacaaggaataaactgggtggtagcctgtcgcgaaa
ccgttcgtggaaaccgcgatcaacctggcacgtcaatctcactgcacttatcataacggcgacgcgcataactctccggatgagctgaccc
gcaaacgcgttctgtctgtaatcactgaaccgattctgccgtttgaacgctaactgcataaaggaggtaaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcaccctatgtgtctgcggtaattgagaaa
atgcgcaaatctatcctattaacggtgttttcttgaccgtcgattccgacatccggtgggctccggtctgggtagcagcgcagccgttactat
cgcgtctattggtgcgctgaacgagctgttcggctttggcctcagcctgcaagaaatcgctaaactggggccacgaaatcgaaattaaagtac
agggtgccgcgtccccaaccgatacgtatgtttctaccttcggcggcgtggttaccatcccggaacgtcgcaaactgaaaactccggactg
cggcattgtgattggcgataccggcgtttctcctccaccaagagttagtagctaacgtacgtcagctgcgcgaaagctaccggatttgat
cgaaccgctgatgacctctattggcaaaatctctcgtatcggcgaacaactggttctgtctggcgactacgcatccatcggccgcctgatgaa
cgtcaaccagggtctcctggacgccctgggcgttaacatcttagaactgagccagctgatctatccgctcgtgcggcaggtgcgtttggcg
ctaaaatcacggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagtaaagttaaacggtctccagcttggct
gttttggcggatgagagaagattttcagcctgatacagattaaatcagaacgcagaagcggtctgataaaacagaattgcctggcggcagt
agcgcggtggtcccacctgaccccatgccgaactcagaagtgaaacgccgtagcgccgatggtagtgtgggggtctccccatgcgagagt
agggaactgccaggcatcaaataaaacgaaaggctcagtcgaaagactgggccttcgttttatctgttgtttgtcggtgaacgctctcctgag
taggacaaatccgccgggagcggatttgaacgttgcgaagcaacggcccggagggtggcgggcaggacgcccgccataaaactgccag
gcatcaaattaagcagaaggccatcctgacggatggcctttttgcgtttctacaaactctttttgtttattttctaaatacattcaaatatgtatccg
ctcatgagacaataaccctgataaatgcttcaataatattgaaaaaggaagagtatgagtattcaacatttccgtgtcgcccttattcccttttttg
cggcattttgccttcctgtttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcactttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

Figure 61B atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcgggtatcattgcagcactggggccagatggtaagccctcccgtatcgtagttatctacacgac
ggggagtcaggcaactatggatgaacgaaatagacagatcgctgagataggtgcctcactgattaagcattggtaactgtcagaccaagttt
actcatatatacttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatccttttttctgcgcgtaatctgctgcttgcaaaca
aaaaaaccaccgctaccagcggtggtttgtttgccggatcaagagctaccaactcttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cgggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccaggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtatttctccttacgcatctgtgcggtatttcacaccgcatatggtgcactctcagtacaatctgctctgatgccgcatagttaag
ccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgtttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagctgcctg
cactaatgttccggcgttatttcttgatgtctctgaccagacacccatcaacagtattattttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaaagaaaaaccaccctggcgcccaatacgcaaaccgcctctccccgcgcgttggccgattcattaatgcagctggcacgacaggtttccc
gactggaaagcgggcagtgagcgcaacgcaattaatgtgagttagcgcgaattgatctg (SEQ ID NO:89)

Figure 63A

1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
attttctaaatacattcaaatatgtatccgctcatgagacaataaaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatccttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgagccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaacccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataaggctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 63B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccagggtggtttttctttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgcccttcattcagcatttgcatggtttgttgaaaaccggacatggcactcca
gtcgccttcccgttccgctatcggctgaattgattgcgagtgagatatttatgccagccagccagacgcagacgcgccgagacagaactta
atgggccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccactt
ttcccgcgttttgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataatttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggcccttcgcgccaccttccactcctcc
cctagtcaggaagttccccccgccccgcagctcgcgtcgtgcaggacgtgacaaatggaagtagcacgtctcactagtctcgtgcagatg
gacagcaccgctgagcaatggaagcgggtaggcctttgggcagcggccaatagcagctttgctccttcgctttctgggctcagaggctg
ggaagggggtgggtccgggggcgggctcagggcgggctcaggggcggggcgggcgccgaaggtcctccggaggcccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaatcactggatataccaccgttgatatatcc
caatggcatcgtaaagaacattttgaggcatttcagtcagttgctcaatgtacctataaccagaccgttcagctggatattacggccttttaaag
accgtaaagaaaataagcacaagttttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagcttatttcatgatctgtgtgttggttttgtgtgcggcgcggaagttcctattctctag
aaagtataggaacttcctcgagcccttatagtgagtcgtattagatcgcggccgcgcccttgacaatgccacatcctgagcaaataattcaacc
actaattgtgagcggataacaaggaggtaaaaaaaacatggtatcctgttctgcgccgggtaagatttacctgttcggtgaacacgccgtagt
ttatggcgaaactgcaatgcgtgtgcggtggaactgcgtacccgtttcgcgcggaactcaatgactctatcactattcagagccagatcgg
ccgcaccggtctggatttcgaaaagcaccctatgtgtctgcggtaattgagaaaatgcgcaaatcattcctattaacggtgttttcttgaccgt
cgattccgacatcccggtgggctccggtctgggtagcagcgcagccgtactatcgcgtctattggtgcgctgaacgagctgttcggctttg
gcctcagcctgcaagaaatcgctaaactgggccacgaaatcgaattaaagtacaggtgccgcgtcccaaccgatacgtatgtttctacc
ttcggcggcgtggttaccatcccggaacgtcgcaaactgaaaactccggactgcggcattgtgattggcgataccggcgtttctcctccac
caaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccaggtcctggacgccctgggcgttaac
atcttagaactgagccagctgatctattccgctcgtgccggcaggtgcgtttggcgctaaaatcacgggcgctggcggcggtggctgtatggt

Figure 63C tgcgctgaccgctccggaaaaatgcaaccaagtggcagaagcggtagcaggcgctggcggtaaagtgactatcactaaaccgaccgag caaggtctgaaagtagattaa (SEQ ID NO:90)

Figure 64A

1-
aagggcgagctcaacgatccggctgctaacaaagcccgaaaggaagctgagttggctgctgccaccgctgagcaataactagcataacc
ccttgggggcctctaaacgggtcttgaggagttttttgctgaaaggaggaactatatccggatatccgcaagaggcccggcagtaccggcat
aaccaagcctatgcctacagcatccagggtgacggtgccgaggatgacgatgagcgcattgttagatttcatacacggtgcctgactgcgtt
agcaattlaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcactttcggggaaatgtgcgcggaacccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgtctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcagggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagttactcatatatactttagattgatttaaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatccttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcatctgctaaccagtaaggcaacccgccagcctagccgggtctcaacgacaggagcacgatcatgcgcaccgtggcc
aggacccaacgctgcccgagatgcgccgcgtgcggctgctggagatggcggacgcgatggatatgttctgccaaggcttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtataggcgcgccctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcgggtcctcgccgaaaatgacccagagcgctgccggcacctgtcctacgagttgcatgataaagaagacagtcataag

Figure 64B tgcggcgacgatagtcatgccccgcgcccaccggaaggagctgactgggttgaaggctctcaagggcatcggtcgagatcccggtgcct
aatgagtgagctaactracattaatgcgttgcgctcactgcccgctttccagtcgggaaacctgtcgtgccagctgcattaatgaatcggcca
acgcgcggggagaggcggtttgcgtattgggcgccagggtggttttcttttcaccagtgagacgggcaacagctgattgcccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgcttacaggcttcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccactt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccataccacgccgaaacaagcgctcatgagcccg
aagtggcgagcccgatcttccccatcggtgatgtcggcgataggcgccagcaaccgcacctgtgcgccggtgatgccggccacgat
gcgtccggcgtagaggatcgagatctgatcccgcgaaattaatacgactcactatagggggaattgtgagcggataacaattcccctctaga
aataattttgtttaactttaagaaggagatatacatatgaattaaccctcactaagggcggccgcgaagttcctattctctagaaagtataggaa
cttcattctaccgggtaggggaggcgcttttcccaaggcagtctggagcatgcgcttagcagcccgctgggcacttggcgctacacaagt
ggcctctggcctcgcacacattccacatccaccggtaggcgccaaccggctccgttctttggtggccccttcgcgccaccttccactcctcc
cctagtcaggaagttccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttcgctttctgggctcagaggctg
ggaaggggtgggtccggggggcgggctcaggggcgggctcagggggcggggcgggcgcccgaaggtcctccggaggccggcattct
gcacgcttcaaaagcgcacgtctgccgcgctgttctcctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctggatattacggcctttttaaag
accgtaaagaaaaataagcacaagtttatccggcctttattcacattcttgcccgcctgatgaatgctcatccggaattccgtatggcaatgaa
agacggtgagctggtgatatgggatagtgttcaccctgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgttttcgtctcagccaatccctgggtgagtttcaccagttttgatttaaacgtggccaatatggacaacttcttcgcccccgttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctgggggtcgaataaagaccgaccaagcgacgtct
gagagctccctggcgaattcggtaccaataaaagagctttatttcatgatctgtgtgttggttttgtgtgcggcgcggaagttcctattctctag
aaagtataggaacttcctcgagccctatagtgagtcgtattagatcgcggccgcgccttgaccatgccacatcctgagcaaataattcaacc
actaattgtgagcggataacaagagaggtaaaaaaacatggtatcctgttctgcgccgggtaagatttacctgttcggtgaacacgccgtagt
ttatggcgaaactgcaattgcgtgtgcggtggaactgcgtacccgtgttcgcgcggaactcaatgactctatcactattcagagccagatcgg
ccgcaccggtctggattcgaaaagcacccttatgtgtctgcggtaattgagaaaatgcgcaaatctattcctattaacggtgttctgaccgt
cgattccgacatcccggtggctccggtctgggtagcagcgcagccgtactatcgcgtctattggtgcgctgaacgagctgttcggcttctg
gcctcagcctgcaagaaatcgctaaactgggccacgaaatcgaaattaaagtacaggggtgccgcgtccccaaccgatacgtatgtttctacc
ttcggcggcgtggttaccatcccggaacgtcgcaaactgaaaactccggactcgcgcattgtgattggcgataccggcgttttctcctccac
caaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccaggtctcctggacgccctgggcgtaaac
atcttagaactgagccagctgatctattccgctcgtgcggcaggtgcgtttggcgctaaaatcacgggcgctggcggcggtggctgtatggt

Figure 64C tgcgctgaccgctccggaaaaatgcaaccaagtggcagaagcggtagcaggcgctggcggtaaagtgactatcactaaaccgaccgag
caaggtctgaaagtagattaa (SEQ ID NO:91)

Figure 65A

1- aagggcgagctcaacgatccggctgctaacaaagcccgaaaggaagctgagttggctgctgccaccgctgagcaataactagcataacc
ccttgggggcctctaaacggggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttatatggttaatgtcatgataataatggttcttagacgtcaggtggcactttcggggaaatgtgcgcggaaccccctatttgttt
atttttctaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactgggcacaactgacaatcggctgctctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaaggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttcttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtatttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaacccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccattcttggagtggtgaatccgttagcgaggtgccgccggcttccattcaggtcgaggtggc
ccggctccatgcaccgcgacgcaacgcggggaggcagacaaggtataggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctaccgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatggcctgcttctcgccg
aaacgtttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 65B tgcggcgacgatagtcatgccccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtattgggcgccaggtggttttttcttttcaccagtgagacgggcaacagctgattgccttcaccgcc
tggccctgagagagttgcagcaagcggtccacgctggtttgccccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgcattgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttcgacgccgttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgccgccagttgttgtgccacgcggttgggaatgtaattcagctccgccatcgccgcttccacttt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaat
ggtgcatgcaaggagatggcgcccaacagtccccgggccacggggcctgccaccatacccacgccgaaacaagcgctcatgagcccg
aagtggcgagcccgatcttccccatcggtgatgtcggcgataggcgccagcaaccgcacctgtggcgccggtgatgccggccacgat
gcgtccggcgtagaggatcgagatctcgatcccgcgaaattaatacgactcactatagggaattgtgagcggataacaattcccttctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagcccgctgggcacttggcgctacacaagt
ggcctctggcctcgcacacattccacatccaccggtaggcgccaaccggctccgttcttggtggccccttcgcgccaccttccactcctcc
cctagtcaggaagttccccccgcccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctccttgctttctgggctcagaggctg
ggaagggtgggtccgggggcgggctcaggggcgggctcagggcggggcggcgcccgaaggtcctccggaggcccggcattct
gcacgcttcaaaagcgcacgtctgccgcgctgttctctcttcctcatctccgggcctttcgacctgcagcagcacgtgttgacaattaatcat
cggcatagtatatcggcatagtataatacgacaaggtgaggaactaaaccatggagaaaaaaatcactggatataccaccgttgatatatcc
caatggcatcgtaaagaacattttgaggcatttcagtcagttgctcaatgtacctataaccagaccgttcagctgatattacggcctttttaaag
accgtaaagaaaaataagcacaagtttatccggcctttattcacattcttgcccgcctgatgaatgctcatccggaattccgtatggcaatgaa
agacggtgagctggtgatatgggatagtgttcacccttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggtttattgagaat
atgtttttcgtctcagccaatccctgggtgagtttcaccagttttgatttaaacgtggccaatatggacaacttcttcgcccccgtttttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcaggcggggcgtaagcgggactctggggttcgaataagaccgaccaagcgacgtct
gagagctccctggcgaattcggtaccaataaaagagctttattttcatgatctgtgtgttggttttttgtgtgcgcgcgcggaagttcctattctctag
aaagtataggaacttcctcgagcctatagtgagtcgtattagatcgcggccgcgccctgacgatgccacatcctgagcaaataattcaacc
actaattgtgagcggataacaaggaggtaaaaaaacatggtatcctgtctctgcgccgggtaagatttacctgttcggtgaacacgccgtagt
ttatggcgaaactgcaattgcgtgtgcggtggaaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgttttcttgaccgt
cgattccgacatcccggtgggctccggtctgggtagcagcgcagccgttactatcgcgtctattggtgcgctgaacgagctgttcggctttg
gcctcagcctgcaagaaatcgctaaactgggccacgaaatcgaattaaagtacaggggtgccgcgtccccaaccgatacgtatgttctacc
ttcggcggcgtggttaccatccccgaacgtcgcaaactgaaaactccggactgcggcattgtgattggcgataccggcgtttctcctccac
caaagagttagtagctaacgtacgtcagctgcgcgaaagctaccggatttgatcgaaccgctgatgacctctattggcaaaatctctcgtat
cggcgaacaactggttctgtctggcgactacgcatccatcggccgcctgatgaacgtcaaccagggtctcctggacgccctgggcgttaac
atctagaactgagccagctgatctattccgctcgtgcggcaggtgcgtttggcgctaaaatcacgggcgctggcggcggtggctgtatggt

Figure 65C tgcgctgaccgctccggaaaaatgcaaccaagtggcagaagcggtagcaggcgctggcggtaaagtgactatcactaaaccgaccgag
caaggtctgaaagtagattaa (SEQ ID NO:92)

Figure 66A

1-
aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaaggcctcgtg
atacgcctatttttataggttaatgtcatgataataatggtttcttagacgtcaggtggcactttcggggaaatgtgcgcggaacccctatttgttt
attttctaaatacattcaaatatgtatccgctcatgagacaataaccctgataaatgcttcaataatattgaaaaaggaagagtatgattgaacaa
gatggattgcacgcaggttctccggccgcttgggtggagaggctattcggctatgactggcacaactgacaatcggctgtctgatgccg
ccgtgttccggctgtcagcgcaggggcgcccggttcttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcacctgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcattttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctgcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaacccc]gccagcctagccgggtcctcaacgacaggagcacgatcatgcgcacccgtggcc
aggacccaacgctgcccgagatgcgccgcgtgcggctgctggagatggcggacgcgatggatatgttctgccaaggcttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtataggcggcgcctacaatccatgccaacccgttccatgtgctc
gccgaggcggcataatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgtcggccgccatgccggcgataatgcctgcttctctgccg
aaacgttggtggcgggaccagtgacgaaggcttgagcgagggcgtgcaagattccgaataccgcaagcgacaggccgatcatcgtcgc
gctccagcgaaagcggtcctcgccgaaaatgacccagagcgctgccggcacctgtcctacgagttgcatgataaagaagacagtcataag

Figure 66B tgcggcgacgatagtcatgcccgcgcccaccggaaggagctgactgggttgaaggctctcaagggcatcggtcgagatcccggtgcct
aatgagtgagctaacttacattaattgcgttgcgctcactgcccgctttccagtcgggaaacctgtcgtgccagctgcattaatgaatcggcca
acgcgcggggagaggcggtttgcgtatgggcgccaggggtggttttcttttcaccagtgagacgggcaacagctgattgcccttcaccgcc
tggccctgagagagttgcagcaagcggtccacgctggtttgcccagcaggcgaaaatcctgtttgatggtggttaacggcgggatataac
atgagctgtcttcggtatcgtcgtatcccactaccgagatatccgcaccaacgcgcagcccggactcggtaatggcgcgcattgcgcccag
cgccatctgatcgttggcaaccagcatcgcagtgggaacgatgccctcattcagcatttgcatggtttgttgaaaaccggacatggcactcca
gtcgccttcccgttccgctatcggctgaatttgattgcgagtgagatatttatgccagccagccagacgcagacgcgccgagacagaactta
atgggcccgctaacagcgcgatttgctggtgacccaatgcgaccagatgctccacgcccagtcgcgtaccgtcttcatgggagaaaataat
actgttgatgggtgtctggtcagagacatcaagaaataacgccggaacattagtgcaggcagcttccacagcaatggcatcctggtcatcca
gcggatagttaatgatcagcccactgacgcgttgcgcgagaagattgtgcaccgccgctttacaggctcgacgccgcttcgttctaccatc
gacaccaccacgctggcacccagttgatcggcgcgagatttaatcgccgcgacaatttgcgacggcgcgtgcagggccagactggaggt
ggcaacgccaatcagcaacgactgtttgcccgccagttgttgtgccacgcggttgggaatgtaattcagctccgccatcgccgcttccactt
ttcccgcgttttcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcgatggtgtcc
gggatctcgacgctctccttatgcgactcctgcattaggaagcagccagtagtaggttgaggccgttgagcaccgccgccgcaaggaat
ggtgcatgcaaggagatggcgcccaacagtcccccggccacggggcctgccaccataccacgccgaaacaagcgctcatgagcccg
aagtggcgagcccgatcttccccatcggtgatgtcgcgatataggcgccagcaaccgcacctgtggcgccggtgatgccggccacgat
gcgtccggcgtagaggatcgagatctcgatcccgcgaaattaatacgactcactataggggaattgtgagcggataacaattcccctctaga
aataattttgtttaactttaagaaggagatatacatatgaattaaccctcactaaagggcggccgcgaagttcctattctctagaaagtataggaa
cttcattctaccgggtaggggaggcgcttttcccaaggcagtctggagcatgcgctttagcagccccgctgggcacttggcgctacacaagt
ggcctctggcctcgcacacattccacatccaccggtaggcgccaaccggctccgttctttggtggcccttcgcgccacccttccactcctcc
cctagtcaggaagttcccccccgccccgcagctcgcgtcgtgcaggacgtgacaaatggaagtagcacgtctcactagtctcgtgcagatg
gacagcaccgctgagcaatggaagcgggtaggcctttggggcagcggccaatagcagctttgctcctcgcttctgggctcagaggctg
ggaaggggtgggtccggggcgggctcaggggcgggctcaggggcgggcgggcgcccgaaggtcctccggaggcccggcattct
gcacgcttcaaaagcgcacgtctgccgcgctgttctcctcttctcatctccgggccttcgacctgcagcagcacgtgttgacaattaatcat
cggcatagtatatcggcatagtataatacgacanggtgaggaactaaaccatggagaaaaaaatcactggatataccaccgttgatatatcc
caatggcatcgtaaagaacatttgaggcatttcagtcagttgctcaatgtacctataaccagaccgttcagctggatattacggcctttttaaag
accgtaaagaaaaataagcacaagtttatccggcctttattcacattcttgcccgcctgatgaatgctcatccggaattccgtatggcaatgaa
agacggtgagctggtgatatgggatagtgttcaccctttgttacaccgttttccatgagcaaactgaaacgttttcatcgctctggagtgaatacc
acgacgatttccggcagtttctacacatatattcgcaagatgtggcgtgttacggtgaaaacctggcctatttccctaaagggttattgagaat
atgtttttcgtctcagccaatccctgggtgagttcaccagttttgatttaaacgtggcaatatggacaacttcttcgcccccgtttcaccatgg
gcaaatattatacgcaaggcgacaaggtgctgatgccgctggcgattcaggttcatcatgccgtttgtgatggcttccatgtcggcagaatgc
ttaatgaattacaacagtactgcgatgagtggcagggcggggcgtaagcgggactctggggttcgaataaagaccgaccaagcgacgtct
gagagctccctggcgaattcggtaccaataaaagagcttatttcatgatctgtgtgttggttttgtgtgccggcgcggaagttcctattctctag
aaagtataggaacttcctcgagcccatagtgagtcgtattagatcgcggccgcgcccttgactatgccacatcctgagcaaataattcaacc
actaattgtgagcggataacaaaggaggtaaaaaacatggtatcctgttctgcgccgggtaagatttacctgttcggtgaacacgccgtagt
ttatgcgaaactgcaatgcgtgtgcggtggaactgcgtacccgtgttcgcgcggaactcaatgactctatcactattcagagccagatcgg
ccgcaccggtctggatttcgaaaagcacccttatgtgtctgcggtaattgagaaaatgcgcaaatctattcctattaacggtgtttcttgaccgt
cgattccgacatcccggtgggctccggctgggtagcagcgcagccgttactatcgcgtctattggtcgctgaacgagctgttcggctttg
gcctcagcctgcaagaaatcgctaaactgggccacgaaatcgaaattaaagtacagggtgccgcgtccccaaccgatacgtatgtttctacc
ttcggcggcgtggttaccatcccggaacgtgcaaactgaaaactccggactgcggcattgtgattggcgataccggcgttttctcctccac
caaagagttagtagctaacgtacgtcagctgcgcgaaagctacccggatttgatcgaaccgctgatgacctctattggcaaaatctctcgtat
cggcgaacaactggtctgtctgcgactacgcatccatcggccgcctgatgaacgtcaaccagggtctcctggacgccctgggcgttaac
atcttagaactgagccagctgatctattccgctcgtgcggcaggtgcgtttggcgctaaaatcacgggcgctggcggcggtggctgtatggt

Figure 66C tgcgctgaccgctccggaaaaatgcaaccaagtggcagaagcggtagcaggcgctggcggtaaagtgactatcactaaaccgaccgag
caaggtctgaaagtagattaa (SEQ ID NO:93)

Figure 73B gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatctattcctattaacggtgtttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaaattaaagtacagggtgccgcgtccccaaccgatacgtatgtttctacct
tcggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagagcggtagcaggcgct
ggcggtaaagtgactatcactaaaccgaccgagcaaggtctgaaagtagattaagccttgacttaatagctgcttatttcgccctta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaattctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgattccgaagtatgattctatcctgaactttgacatctctggcatgtacgatcgcctgtatcgccgtaacgcctctgttt
gcggttacggcccgatcaccgctatgctgacggcaagcaaaaagctgggcggctctcgtgcgactttgctgaaatacgcaaac
agccggtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaaagctcgcctccaaagttgtaggtgtctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacggcgacgtcgcaatggatattgaactgggcactgtatcctgtccggtgatcaaatcgttccttacctg
gccaaagaactgggtatctcccgcctcggcctgggcagcgcagaggatggtgtgctggatatggagggcaaacctgtaccgg
aaatcaccccagaaactttcgaagagttccgccactgcatcggtggttctggttctactgatgtaaccggtggcatgctgggcaaa
gtgctggaactctggaattgagcaaaaattcttccattactagctacatttcaacgctggtaaagcagacaacatctaccgcttct
gaatggtgagtccatcggcactcgcatcagcccggacaagcgtgtttaagctagttaatcctaaatgctctaaaccagttatga
gctctacaaggaggaaaaaaacatgattaacactaccagccgccgcaaaattgaacacctgaaactctgcgcagaatcccgg
ttgaagcgcgtcaggtatctgccggctttgaagacgttactctgatccaccgcgctttaccggagctgaacatggatgaactgga
cctcagcgttgattcctgggtaaacgcatcaaagcgccgttcctgattgcgtctatcacgggtggtcaccagataccatccgg
ttaacgctgcgctggcagctgctgctgaggagctgggtgttggcatggccgttggctctcagcgcgcggccattgatgatccga
gccaggaagacagcttccgtgtagtgcgtgatgaagccccagatgcgtttgtttatggcaacgtcggcgcagcacagatccgtc
agtatggtgttgaaggtgttgaaaaactgatcgaaatgattgacgcagatgccttggcaatccaccttgaactttctgcaagaagcg
gtccaaccggaaggtgaccgcgacgcgaccggttgcctggacatgattaccgaaattgctctcagattaaaactccggtaatcg
tganagnaaccggtgcaggcattagccgtgaagatgcgattctgttccagaaagctggcgtgagcgcaatcgacgttggcggc
gcgggcggcaccctgggctggcgtcgaggtctaccgtgctaaagaaagccgtgactctgttagcgagcgttaggtgagct
gttttgggatttcggcattccgacggtagcttctctgattgaatccgcgtttccttgccgctgatcgcaaccggcggtatccgtaac
ggtctggacattgctaaaagcattgctctcggcgcaagcgctgccagcgccgctctgccgttcgttggtccgtccctggagggc
aaagaatccgttgtacgtgtgctgagctgcatgctggaagaatttaaagcagcaatgtttgtgcggttgcggcaacatcaaaga

Figure 73C cctgcacaactctccagtagtggtaactggttggacccgcgaatacctggagcagcgcggtttaacgttaaggacctctccctg
ccgggcaacgctctgtaagcttcaacgcgtctacaaataaaaaaggcacgtcagatgacgtgccttttcttgtctaga
(SEQ ID NO:113)

MCM376 - MVK from M. mazei archeal Lower in pET200D
6647 bp

Figure 74B aagggcgagctcaacgatccggctgctaacaaagcccgaaaggaagctgagttggctgctgccaccgctgagcaataactag
cataacccettgggggcctctaaacgggtcttgaggagtttttgctgaaaggaggaactatatccggatatcccgcaagaggccc
ggcagtaccggcataaccaagcctatgcctacagcatccagggtgacggtgccgaggatgacgatgagcgcattgttagattc
atacacggtgcctgactgcgttagcaatttaactgtgataaactaccgcattaaagcttatcgatgataagctgtcaaacatgagaa
ttaattcttgaagacgaaagggcctcgtgatacgcctattttataggttaatgtcatgataataatggtttcttagacgtcaggtggca
cttttcggggaaatgtgcgcggaacccctatttgttattttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tcttttgtcaagaccgacctgtccggtgccctgaatgaactgcaggacgaggcagcgcggctatcgtggctggccacgacgg
gcgttcctgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatggaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagacccgtaga
aaagatcaaaggatcttcttgagatccttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggcctttttgctggcctttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacaccccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggatttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataaggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaacccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtataggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

Figure 74C cggccgccatgccggcgataatggcctgcttctcgccgaaacgttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactggggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggttttcttttcaccagtgagacgggcaacagctgattgcccttcaccgcctggccctga
gagagttgcagcaagcggtccacgctggtttgcccagcaggcgaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcgcgatagttaatgatcagcccactgacgcgttgcgcgagaagattgtgc
accgccgctttacaggcttcgacgccgctcgttctaccatcgacaccaccacgcctggcacccagttgatcggcgcgagatttaa
tcgccgcgacaattgcgacggcgcgtgcagggccagactggaggtggcaacgccaatcagcaacgactgtttgcccgccag
ttgttgtgccacgcggttgggaatgtaattcagctccgccatgccgcttccactttttcccgcgtttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgccgggatctcgacgctct
ccctatgcgactcctgcattaggaagcagcccagtagtaggttgaggccgttgagcaccgccgccgcaaggaatggtgcatg
caaggagatggcgcccaacagtccccggccacggggcctgccaccataccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactatagggaaattgtgagcggataac
aattcccctctagaaataattttgttaactttaagaaggagatatacatatgcgggttctcatcatcatcatcatggtatggcta
gcatgactggtggacagcaaatgggtcgggatctgtacgacgatgacgataaggatcatccttcaccatggtatcctgttctgc
gccgggtaagattacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcaccttatgtgtc
tgcggtaattgagaaaatgcgcaaatctattcctattaacggtgttttcttgaccgtcgattccgacatcccggtggcctccggtctg
ggtagcagcgcagccgttactatcgcgtctattggtgcgctgaacgagctgttcggctttggcctcagcctgcaagaaatcgcta
aactgggccacgaaatcgaaattaaagtacaggtgcgcgtcccaaccgatacgtatgtttctaccttcggcggcgtggttac
catcccggaacgtcgcaaactgaaaactccggactgcggcattgtgattggcgataccggcgttttctcctccaccaaagagtta
gtagctaacgtacgtcagctgcgcgaaagctaccggattgatcgaaccgctgatgacctctattggcaaaatctctcgtatcgg
cgaacaactggttcgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:114)

CDS 2: Gentamycin resistance gene; CDS1: E. coli replication protein.

Figure 77A

1- ctcgggccgtctcttgggcttgatcggccttcttgcgcatctcacgcgctcctgcggcggcctgtagggcaggctcatacccctgccgaacc
gcttttgtcagccggtcggccacggcttccggcgtctcaacgcgcttgagattcccagctttcggccaatccctgcggtgcataggcgcgt
ggctcgaccgcttgcgggctgatggtgacgtggccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgctttgttgcga
tgaactccttggccgacagcctgccgtcctgcgtcagcggcaccacgaacgcggtcatgtgcgggctggtttcgtcacggtggatgctggc
cgtcacgatgcgatccgccccgtactttgtccgccagccacttgtgcgccttctctgaagaacgccgcctgctgttcttggctggccgacttcca
ccattccgggctggccgtcatgacgtactcgaccgccaacacagcgtccttgcgccgcttctctggcagcaactcgcgcagtcggccatc
gcttcatcggtgctgctggccgccagtgctcgttctctggcgtcctgctggcgtcagcgttggcgtctcgcgctcgcggtaggcgtgctt
gagactggccgccacgttgcccatttctcgccagcttcttgcatcgcatgatcgcgtatgccgccatgcctgccctccctttggtgtccaacc
ggctcgacggggcagcgcaaggcggtgcctccggcgggccactcaatgcttgagtatactcactagactttgcttcgcaaagtcgtgac
cgcctacggcggctgcggcgccctacgggcttgctctccgggcttcgcctgcgcggtcgctgcgctccttgccagcccgtggatatgtg
gacgatggccgcgagcggccaccggctggctcgcttcgctcggcccgtggacaacctgctggacaagctgatggacaggctgcgcct
gcccacgagcttgaccacagggattgcccaccggctaccagccttcgaccacatacccaccggctccaactgcgcggcctgcggcctt
gccccatcaatttttttaattttctctggggaaagcctccggcctgcggcctgcgcggcttcgcttgcggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgcccccgagcctcacggcggcgagtgccgggggttccaaggggggcagcgccaccttgggcaaggccgaag
gccgcgcagtcgatcaacaagcccggaggggccactttttgccggagggggagccgcgccgaaggcgtgggggaaccccgcaggg
gtgcccttctttgggcaccaaagaactagatataggcgaaatgcgaaagacttaaaaatcaacaacttaaaaaaggggggtacgcaacag
ctcattgcggcaccccccgcaatagctcattgcgtaggttaaagaaaatctgtaattgactgccactttacgcaacgcataattgttgtcgcgc
tgccgaaaagttgcagctgatgcgcatggtgccgcaaccgtgcggcaccctaccgcatggagataagcatggccacgcagtccagaga
aatcggcattcaagccaagaacaagcccggtcactgggtgcaaacggaacgcaaagcgcatgaggcgtgggccggcttattgcgagg
aaacccacggcggcaatgctgctgcatcacctcgtggcgcagatgggccaccagaacgccgtggtggtcagccagaagacactttccaa
gctcatcggacgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgcgt
ggtggttgatcacgacgaccaggacgaatcgctgttggggcatggcgacctgcgccgcatcccgaccctgtaccgggcgagcagcaac
taccgaccggccccggcgaggagccgccagccagcccggcattccgggcatggaaccagacctgccagccttgaccgaaacggag
gaatgggaacggcgcggcgagcagcgcctgccgatgccgatgagccgtgttttctggacgatgcgagccgttggagccgccgacac
gggtcacgctgccgcgcggtagcacttggttgcgcagcaaccgtaagtgcgctgttccagactatcggctgtagccgcctcgccgcc
ctatacccttgtctgcctcccgcgttcgtcgcggtcatggagccgggcccacctcgacctgaatggaagccggcggcacctcgctaacg
gattcaccgtttttatcaggctctgggaggcagaataaaatgatcatatcgtcaattattacctccacggggagagcctgagcaaactggcctca
ggcatttgagaagcacacggtcacactgcttccggtagtcaataaaccggtaaaccagcaatagacataagcggctatttaacgacctgcc
ctgaaccgacgaccgggtcgaatttgctttcgaatttctgccattcatccgcttattatcacttattcaggcgtagcaccaggcgtttaagggca
ccaataactgccttaaaaaaattacgccccgccctgccactcatcgcagtcggcctattggttaaaaatgagctgatttaacaaaaatttaac
gcgaatttaacaaaatattaacgcttacaattccattcgccatcaggctgcgcaactgttgggaagggcgatcggtgcgggcctcttcgct
attacgccagctggcgaaggggatgtgctgcaaggcgattaagttgggtaacgccagggttttcccagtcacgacgttgtaaaacgacg
gccagtgagcgcgcgtaatacgactcactatagggcgaattggagctccaccgcggtggcggccgctctagaactagtggatccccgg
gctgcatgctcgagcggccgccagtgtgatggatatctgcagaattcgcccttcttgatatctagtgtgcgttaaccaccacccacattggtc
cctgcccgaccgcatagcggcctttttcatgcagtagcccctgctcgccaacaatttcgtataccgagatgtggtgagattttgcccggcgg
caatcagatacttgccgctgtgatcaacattgaagccgcgcggctgggtttccgttggctggaagccttctttactcaacacgctgccatcttc
cgaaacgctgaaaacggtaatcaggctggcggtacggtcgcaggcgtataaatggcgaccatccgggtgatatgaatatcagccgcc
aacgggtgtcggagaagttttccggcatcatatccagcgtctggacacattcgatattaccgtgcggatctttcagttcccagacatccactga
gctgtttaactcattgacgcaatacgcatattgttcgtttggatggaataccatatgacgcgggccggccccttcaacggtggtcacttccgca
gggtcctgcgccacgagatgaccatcatcgctgaccgtaaacaggcaaatgcgatcctgctttaatgccggaacccacagcgtacggtgt

Figure 77B ccggtgagatattggcggaatggcaaccgtccagcccctcgaccacatcgacgacgcccactggcaggccatcttccagacgcgttacgc
tcacgttaccggcattgtaagaacctacaaagacaaactgcccctggtgatcggtggaaatatgcgtcggactaccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaaccgtgtcagcgtcagtgcgccttcatgattcagattccagac
gtgaatttgctggctctcaggggctggcgatataaactgtttgcttcatgaatgctcctttgggttacctccgggaaacgcggttgatttgtttagtg
gttgaattatttgctcaggatgtggcatagtcaagggcgtgacggctcgctaatacaactcactataggggctcgaggaagttcctatacttteta
gagaataggaacttccgcgccgcacacaaaaaccaacacacagatcatgaaaataaagctctttattggtaccgaattcgccagggagct
ctcagacgtcgcttggtcggtctttattcgaacccagagtcccgcttacgcccgccctgccactcatcgcagtactgttgtaatticatiaagc
attctgccgacatggaagccatcacaaacggcatgatgaacctgaatcgccagcggcatcagcaccttgtcgccttgcgtataatattigccc
atggtgaaaacgggggcgaagaagttgtccatattggccacgtttaaatcaaaactggtgaaactcacccagggattggctgagacgaaaa
acatattctaataaacccttagggaaataggccaggttttcaccgtaacacgccacatctgcgaatatatgtgtagaaactgccggaaatc
gtcgtggtattcactccagagcgatgaaaacgtttcagtttgctcatggaaaacggtgtaacaagggtgaacactatcccatatcaccagctc
accgtcttcattgccatacggaattccggatgagcattcatcaggcggcaagatgtgaataaaggccggataaaacttgtgcttattttict
ttacggtcttaaaaaggccgtaatatccagctgaacggtctggttataggtacattgagcaactgactgaaatgcctcaaaatgttctttacgat
gccattgggatatatcaacggtggtatatccagtgatttttttctccatggtttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggacctttcgggcgcccgccccgccctgagcccgccctgagccgccccggacccaccctt
cccagcctctgagcccagaaagcgaaggagcaaagctgctattggccgctgccccaaaggcctacccgcttccattgctcagcggtgctg
tccatctgcacgagactagtgagacgtgctacttccatttgtcacgtcctgcacgacgcgagctgcggggcgggggggaacttcctgacta
ggggaggagtggaaggtggcgcgaaggggccaccaaagaacggagccggttggcgcctaccggtggatgtggaatgtgtgcgaggc
cagaggccacttgtgtagcgccaagtgcccagcggggctgctaaagcgcatgctccagactgccttgggaaaagcgcctcccctacccg
gtagaatgaagttcctatactttctagagaataggaacttcgcggccgcccctttagtgagggttaattcaactgactgtaacagctaaaattagt
cgcttttggcggtaagggcgaattccagcacactggcggccgttactagtggatccgagctcggtaccaagcttgatgcaggaattcgatat
caagcttatcgataccgtcgacctcgagggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgccta
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatattigcccatggacgcacaccgtggaaacggatgaa
ggcacgaacccagttgacataagcctgttccggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgtcttgatctttc
ggtcgtgagttcggagacgtagccacctactcccaacatcagccggactccgattacctcggaactgctccgtagtaagacattcatcgc
gcttgctgccttcgaccaagaagcggttgttggcgctctcgcgcggcttacgttctgcccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtcaagcagattacggtgacgatcccgcagtggctctctatacaaagttgggcatacgggaagaagtgatgcactttgat
atcgacccaagtaccgccacctaacaattcgttcaagccgagatcggcttcccggccgcggagttgttcggtaaattgtcacaacgccgcc
aggtggcacttttcggggaaatgtgcgcgcccgcgttcctgctggcgctgggcctgttctggcgctggacttccgctgttccgtcagcag
ctttcgcccacggccttgatgatcgcggcggccttggcctgcatatcccgattcaacggccccagggcgtccagaacgggcttcaggcgc
tcccgaaggt (SEQ ID NO:122).

Figure 78B
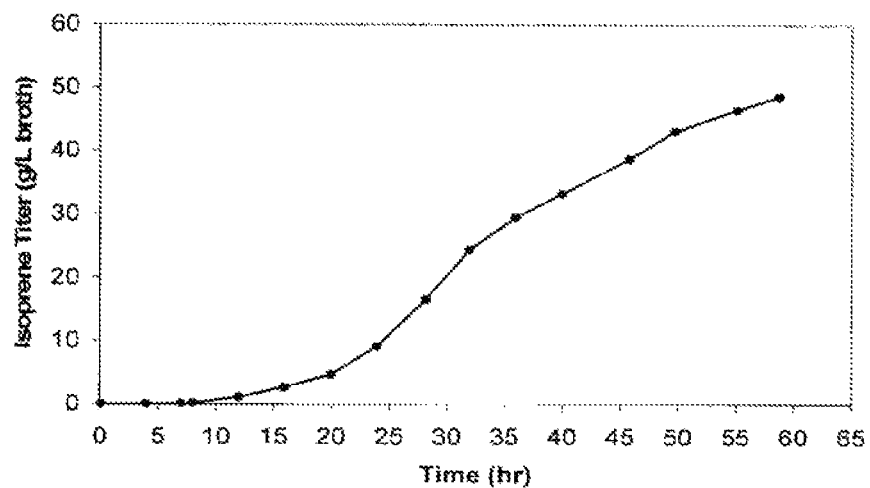
Titer 78C
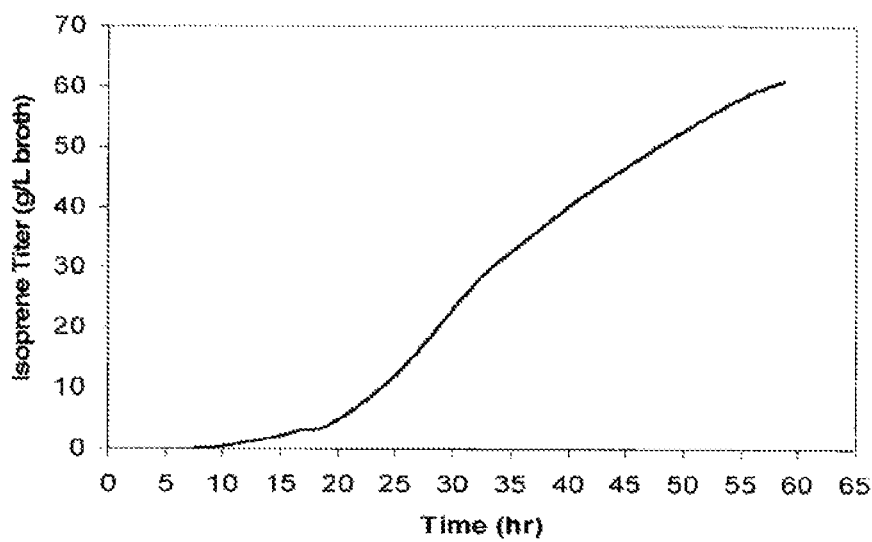

Figure 79B

5'-
tagaaaaactcatcgagcatcaaatgaaactgcaattattcatatcaggattatcaataccatattttgaaaaagccgttctgtaatgaagga
gaaaactcaccgaggcagttccataggatggcaagatcctggtatcggtctgcgattccgactcgtccaacatcaatacaacctattaatttcc
cctcgtcaaaaataaggttatcaagtgagaaatcaccatgagtgacgactgaatccggtgagaatggcaaaagtttatgcatttctttccagac
ttgttcaacaggccagccattacgctcgtcatcaaaatcactcgcatcaaccaaaccgttattcattcgtgattgcgcctgagcgaggcgaaat
acgcgatcgctgttaaaaggacaattacaaacaggaatcgagtgcaaccggcgcaggaacactgccagcgcatcaacaatattttcacctg
aatcaggatattcttctaatacctggaacgctgttttttccggggatcgcagtggtgagtaaccatgcatcatcaggagtacggataaaatgctt
gatggtcggaagtggcataaattccgtcagccagtttagtctgaccatctcatctgtaacatcattggcaacgctacctttgccatgtttcagaa
acaactctggcgcatcggcttcccatacaagcgatagattgtcgcacctgattgcccgacattatcgcgagcccatttatacccatataaatc
agcatccatgttggaatttaatcgcggcctcgacgtttcccgttgaatatggctcatattcttccttttcaatattattgaagcatttatcaggettat
tgtctcatgagcggatacatatttgaatgtatttagaaaaaataaacaaataggggtcagtgttacaaccaattaaccaattctgaacattatcgcg
agcccatttatacctgaatatggctcataacaccccttgtttgcctggcggcagtagcgcggtggtcccacctgacccatgccgaactcaga
agtgaaacgccgtagcgccgatggtagtgtggggactccccatgcgagagtagggaactgccaggcatcaaataaaacgaaaggctcag
tcgaaagactgggccttcgcccggcgctaattaggggggtgtcgcccttcgattgacggttacgggatcctcacacgtacatcagctggttgat
ggggaacgggtcgatgagcagcagcttgatgcggttctcggtggcgtaatccgggcggcccagcccgtccccatattggtaggtgcagtg
gctcacgcgggccatgttcacggcgatctccatgaacgccttcggcagcagggtgctgtccgacacgcgctcgcggttcatttcttccact
cggcgtcgatcagcttgcgcagctcttcgcgggcctgttcctcgctcgtgccgtcgttctcgtgcatgtagctgatgatgctgttggtggtttcg
ccgcgttcgagttccgccgccgaggtcgccagatcgttgcacagccgaaagatcacgcaggacgagcgcaccaggccgtggaagtcgg
tcagggagcggagggcgtggtccgagatatcttcctgctgctggcagaccgagaagtagctcggcgccagcagcgcgacccgctgga
ggacacgctggcgttctccaggtacttgctgaaggcggggatgatcttgttattgctccacttggcttcttgcaggaaggccttgcacagttcg
cgccagcttttggtcagatagctcaggttattgtggcccttctccttcaggatggagtaggacgtgtcgttcacggtgttgtacagaggccagga
agcacagcttcatatagtcgggcagcgtgttgatggcgttcacgtcccagcgttccaccgcgtcggtgaagagctgcagttcgtccagggta
ccgtacacgtcatagacgtcatcgataatggtgaccagaccgaacatcttggtgacggccttgcggcatcgccgaactgcgggtccggcg
ccatgcccagcgcccagaagtacacttccatcaggcggtcccgcacgaaatccagcttgctggcgaggcccatctcggtccaccacgg
ctcaggtcctgcagctctttttggtgcagggtctggaccatgttgaaatcgagtttggccagttccagcagcagctggtgatgcggctccttgg
gttcgtacttgtccagaaaccaccgcgcctccaggcggtgcaggcgttgatgatacggcagctccagcgcgtgggacaccgtgctcggcca
cctcgtgttgatcccctcctgaggttgttcttcagatgggtgatgctgaaggtacgggcctcctccagcagatttcgccttcgaaaccgaga
tagctggcctcgtacaggctcagcaggccctgcacgtcaccttcagttccccggagaagccccttctttgtccttgaagcgctcgaacac
gtcctggctcacctcaaagccatgctgccgcagcaggcggaagctcagggcggtcgcgtgcagatcgcttttgttcttcttattctcgtccag
caggacgatgtctccagcgccttgatgatatctttctcaaacttgtaggtcaggcccaggcgctgcacgtcgtcgatgagctccagcaggct
caggggctgggtgtccacccggttgatcatgcaacgcaccctcctccagcttggtggccttctcttcgagcttctccaccttcaggtcgtttt
ccaggctctgcaggaactcgaagttccacaggttgggctggtagttcgcggaccgacggctattatgctcggtgatcgggtgaactggctg
ctggtggcgcacatatgtatatctccttcttaaagttaaacaagcttaagatgttcagcgacaagggcgacacaaaatttattctaaatgcataat
aaatactgataacatcttatagtttgtattatatttgtattatcgttgacatgtataatttgatatcaaaaactgattttcccttattattttcgagatta
ttttcttaattctctttaacaaactagaaatattgtatatacaaaaaatcataaataalagatgaaagttttaatatlaggtgttcatcaatcgaaaag
caacgtatcttattaaagtgcgttgcttttttctcatttataaggttaaataattctcatatatcaagcaaagtgacaggcgcccttaaatattctga
caaatgctctttccctaaactccccccataaaaaaaccgccgaagcgggttttacgttatttgcggattaacgattactcgttatcagaaccg
cccaggggggccgagcttaagactggccgtcgttttacaacacagaaagagtttgtagaaacgcaaaaaggccatccgtcagggccttct
gcttagtttgatgcctggcagttccctactctcgccttccgcttcctcgctcactgactcgctgcgctcggtcgttcggctgcggcgagcggtat
cagctcactcaaaggcggtaatacggttatccacagaatcaggggataacgcaggaaagaacatgtgagcaaaaggccagcaaaggc
caggaaccgtaaaaaggccgcgttgctggcgtttttccataggctccgccccctgacgagcatcacaaaaatcgacgctcaagtcagag
gtggcgaaacccgacaggactataaagataccaggcgtttccccctggaagctccctcgtgcgctctcctgttccgaccctgccgcttaccg
gatacctgtccgcctttctcccttcgggaagcgtggcgctttctcatagctcacgctgtaggtatctcagttcggtgtaggtcgttcgctccaag
ctgggctgtgtgcacgaaccccccgttcagcccgaccgctgcgccttatccggtaactatcgtcttgagtccaacccggtaagacacgactt

Figure 79C atcgccactggcagcagccactggtaacaggattagcagagcgaggtatgtaggcggtgctacagagttcttgaagtggtgggctaactac
ggctacactagaagaacagtatttggtatctgcgctctgctgaagccagttaccttcggaaaaagagttggtagctcttgatccggcaaacaa
accaccgctggtagcggtggttttttttgtttgcaagcagcagattacgcgcagaaaaaaaggatctcaagaagatcctttgatctttctacgg
ggtctgacgctcagtggaacgacgcgcgcgtaactcacgttaagggattttggtcatgagcttgcgccgtcccgtcaagtcagcgtaatgct
ctgcttt (SEQ ID NO:123)

```
                         SEQUENCE LISTING

<160> NUMBER OF SEQ ID NOS: 123

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca aatttgaaaa agacatcatt aaagccctgg aaaacatcgt actgctggac     300
gaaaacaaaa gaacaaatc tgacctgcac gcaaccgctc tgtctttccg tctgctgcgt     360
cagcacggtt tcgaggtttc tcaggatgtt tttgagcgtt tcaaggataa agaaggtggt     420
ttcagcggtg aactgaaagg tgacgtccaa ggcctgctga gcctgtatga agcgtcttac     480 ctgggttttcg agggtgagaa cctgctggag gaggcgcgta ccttttccat cacccacctg     540
aagaacaacc tgaaagaagg cattaatacc aaggttgcag aacaagtgag ccacgccctg     600
gaactgccat atcaccagcg tctgcaccgt ctggaggcac gttggttcct ggataaatac     660
gaaccgaaag aaccgcatca ccagctgctg tggagctgg cgaagctgga ttttaacatg     720
gtacagaccc tgcaccagaa agagctgcaa gatctgtccc gctggtggac cgagatgggc     780
ctggctagca aactggattt tgtacgcgac cgcctgatgg aagtttattt ctgggcactg     840
ggtatggcgc cagacccgca gtttggtgaa tgtcgcaaag ctgttactaa aatgtttggt     900
ctggtgacga tcatcgatga cgtgtatgac gtttatggca ctctggacga actgcaactg     960
ttcaccgatg ctgtagagcg ctgggacgtt aacgctatta caccctgcc ggactatatg    1020 aaactgtgtt tcctggcact gtacaacacc gttaacgaca cgtcctattc tattctgaaa    1080
gagaaaggtc ataacaacct gtcctatctg acgaaaagct ggcgtgaact gtgcaaagcc    1140
tttctgcaag aggcgaaatg gtccaacaac aaaattatcc cggctttctc caagtacctg    1200
gaaaacgcca cgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
```

| | |
|---|---|
| gagctggaac gtggcgagac taccaattct atcattagct acatgcacga aaacgatggt | 1440 |
| accagcgagg aacaggcccg cgaagaactg cgtaaactga tcgacgccga atggaaaaag | 1500 |
| atgaatcgtg aacgcgttag cgactccacc ctgctgccta aagcgttcat ggaaatcgca | 1560 |
| gttaacatgg cacgtgtttc ccactgcacc taccagtatg cgatggtct gggtcgccca | 1620 |
| gactacgcga ctgaaaaccg catcaaactg ctgctgattg acccttccc gattaaccag | 1680 |
| ctgatgtatg tctaactgca g | 1701 |

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg caaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgtgc | 420 |
| gacctcttct caatttactc agattaccga gcataattcc cgtcgttccg caaactatca | 480 |
| gccaaacctg tggaatttcg aattcctgca atccctggag aacgacctga agtggaaaa | 540 |
| gctggagag aaagcgacca aactggagga agaagttcgc tgcatgatca accgtgtaga | 600 |
| cacccagccg ctgtccctgc tggagctgat cgacgatgtg cagcgcctgg gtctgaccta | 660 |
| caaatttgaa aaagacatca ttaaagcccc tggaaaacatc gtactgctgg acgaaaacaa | 720 |
| aaagaacaaa tctgacctgc acgcaaccgc tctgtctttc cgtctgctgc gtcagcacgg | 780 |
| tttcgaggtt tctcaggatg ttttttgagcg ttttcaagga aaaagaaggtg gtttcagcgg | 840 |
| tgaactgaaa ggtgacgtcc aaggcctgct gagcctgtat gaagcgtctt acctgggttt | 900 |
| cgagggtgag aacctgctgg aggaggcgcg taccttttcc atcacccacc tgaagaacaa | 960 |
| cctgaaagaa ggcattaata ccaaggttgc agaacaagtg agccacgccc tggaactgcc | 1020 |
| atatcaccag cgtctgcacc gtctggaggc acgttggttc ctggataaat acgaaccgaa | 1080 |
| agaaccgcat caccagctgc tgctggagct ggcgaagctg gatttaaca tggtacagac | 1140 |
| cctgcaccag aaagagctgc aagatctgtc ccgctggtgg accgagatgg gcctggctag | 1200 |
| caaactggat tttgtacgcg accgcctgat ggaagtttat ttctgggcac tgggtatggc | 1260 |
| gccagacccg cagtttggtg aatgtcgcaa agctgttact aaaatgtttg gtctggtgac | 1320 |
| gatcatcgat gacgtgtatg acgtttatgg cactctggac gaactgcaac tgttcaccga | 1380 |
| tgctgtagag cgctgggacg ttaacgctat taacaccctg ccggactata tgaaactgtg | 1440 |
| tttcctggca ctgtacaaca ccgttaacga cacgtcctat tctattctga agagaaagg | 1500 |
| tcataacaac ctgtcctatc tgacgaaaag ctggcgtgaa ctgtgcaaag cctttctgca | 1560 |
| agaggcgaaa tggtccaaca caaaattat cccggctttc tccaagtacc tggaaaacgc | 1620 |
| cagcgtttcc tcctccggtg tagcgctgct ggcgccgtct tactttccg tatgccagca | 1680 |
| gcaggaagac atctccgacc acgcgctgcg ttccctgacc gacttccatg gtctggtgcg | 1740 |

```
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgacccttc ccgattaacc agctgatgta    2100
tgtctaactg cagctggtac catatgggaa ttcgaagctt tctagaacaa aaactcatct    2160
cagaagagga tctgaatagc gccgtcgacc atcatcatca tcatcattga gtttaaacgg    2220
tctccagctt ggctgttttg gcggatgaga agattttc agcctgatac agattaaatc    2280
agaacgcaga agcggtctga taaaacagaa tttgcctggc ggcagtagcg cggtggtccc    2340
acctgacccc atgccgaact cagaagtgaa acgccgtagc gccgatggta gtgtggggtc    2400
tccccatgcg agagtaggga actgccaggc atcaaataaa acgaaaggct cagtcgaaag    2460
actgggcctt tcgttttatc tgttgtttgt cggtgaacgc tctcctgagt aggacaaatc    2520
cgccgggagc ggatttgaac gttgcgaagc aacggcccgg agggtggcgg gcaggacgcc    2580
cgccataaac tgccaggcat caaattaagc agaaggccat cctgacggat ggcctttttg    2640
cgtttctaca aactctttt gtttattttt ctaaatacat tcaaatatgt atccgctcat    2700
gagacaataa ccctgataaa tgcttcaata atattgaaaa aggaagagta tgagtattca    2760
acatttccgt gtcgcccta ttcccttttt tgcggcattt tgccttcctg tttttgctca    2820
cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcactttta aagttctgct atgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660 ttttaatt aaaaggatct aggtgaagat cctttttgat aatctcatga ccaaaatccc    3720
ttaacgtgag ttttcgttcc actgagcgtc agaccccgta gaaaagatca aggatcttc    3780 ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
```

| | |
|---|---|
| ggcgcagcgg tcgggctgaa cgggggggttc gtgcacacag cccagcttgg agcgaacgac | 4140 |
| ctacaccgaa ctgagatacc tacagcgtga gctatgagaa agcgccacgc ttcccgaagg | 4200 |
| gagaaaggcg gacaggtatc cggtaagcgg cagggtcgga acaggagagc gcacgaggga | 4260 |
| gcttccaggg ggaaacgcct ggtatcttta tagtcctgtc gggtttcgcc acctctgact | 4320 |
| tgagcgtcga ttttgtgat gctcgtcagg ggggcggagc ctatggaaaa acgccagcaa | 4380 |
| cgcggccttt ttacggttcc tggccttttg ctggcctttt gctcacatgt tctttcctgc | 4440 |
| gttatcccct gattctgtgg ataaccgtat taccgccttt gagtgagctg ataccgctcg | 4500 |
| ccgcagccga acgaccgagc gcagcgagtc agtgagcgag gaagcggaag agcgcctgat | 4560 |
| gcggtatttt ctccttacgc atctgtgcgg tatttcacac cgcatatggt gcactctcag | 4620 |
| tacaatctgc tctgatgccg catagttaag ccagtataca ctccgctatc gctacgtgac | 4680 |
| tgggtcatgg ctgcgcccg acacccgcca acacccgctg acgcgccctg acgggcttgt | 4740 |
| ctgctcccgg catccgctta cagacaagct gtgaccgtct ccgggagctg catgtgtcag | 4800 |
| aggttttcac cgtcatcacc gaaacgcgcg aggcagcaga tcaattcgcg cgcgaaggcg | 4860 |
| aagcggcatg catttacgtt gacaccatcg aatggtgcaa aacctttcgc ggtatggcat | 4920 |
| gatagcgccc ggaagagagt caattcaggg tggtgaatgt gaaaccagta acgttatacg | 4980 |
| atgtcgcaga gtatgccggt gtctcttatc agaccgtttc ccgcgtggtg aaccaggcca | 5040 |
| gccacgtttc tgcgaaaacg cgggaaaaag tggaagcggc gatggcggag ctgaattaca | 5100 |
| ttcccaaccg cgtggcacaa caactggcgg gcaaacagtc gttgctgatt ggcgttgcca | 5160 |
| cctccagtct ggccctgcac gcgccgtcgc aaattgtcgc ggcgattaaa tctcgcgccg | 5220 |
| atcaactggg tgccagcgtg gtggtgtcga tggtagaacg aagcggcgtc gaagcctgta | 5280 |
| aagcggcggt gcacaatctt ctcgcgcaac gcgtcagtgg gctgatcatt aactatccgc | 5340 |
| tggatgacca ggatgccatt gctgtggaag ctgcctgcac taatgttccg gcgttatttc | 5400 |
| ttgatgtctc tgaccagaca cccatcaaca gtattatttt ctcccatgaa gacggtacgc | 5460 |
| gactgggcgt ggagcatctg gtcgcattgg gtcaccagca atcgcgctg ttagcgggcc | 5520 |
| cattaagttc tgtctcggcg cgtctgcgtc tggctggctg gcataaatat ctcactcgca | 5580 |
| atcaaattca gccgatagcg gaacgggaag gcgactggag tgccatgtcc ggttttcaac | 5640 |
| aaaccatgca aatgctgaat gagggcatcg ttcccactgc gatgctggtt gccaacgatc | 5700 |
| agatggcgct gggcgcaatg cgcgccatta ccgagtccgg gctgcgcgtt ggtgcggata | 5760 |
| tctcggtagt gggatacgac gataccgaag acagctcatg ttatatcccg ccgtcaacca | 5820 |
| ccatcaaaca ggattttcgc ctgctggggc aaaccagcgt ggaccgcttg ctgcaactct | 5880 |
| ctcagggcca ggcggtgaag ggcaatcagc tgttgcccgt ctcactggtg aaaagaaaaa | 5940 |
| ccaccctggc gcccaatacg caaaccgcct ctccccgcgc gttggccgat tcattaatgc | 6000 |
| agctggcacg acaggtttcc cgactggaaa gcgggcagtg agcgcaacgc aattaatgtg | 6060 |
| agttagcgcg aattgatctg | 6080 |

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| cgtgagatca tatgtgtgcg acctcttctc aatttac | 37 |

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4

```
cggtcgacgg atccctgcag ttagacatac atcagctg                                 38
```

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5

```
ttctcatgtt tgacagctta tcatcgataa gctttaatgc ggtagtttat cacagttaaa         60
ttgctaacgc agtcaggcac cgtgtatgaa atctaacaat gcgctcatcg tcatcctcgg        120
caccgtcacc ctggatgctg taggcatagg cttggttatg ccggtactgc cgggcctctt       180
gcgggatatc cggatatagt tcctcctttc agcaaaaaac ccctcaagac ccgtttagag       240
gccccaaggg gttatgctag ttattgctca gcggtggcag cagccaactc agcttccttt       300
cgggctttgt tagcagccgg atccctgcag ttagacatac atcagctggt taatcgggaa       360
agggtcaatc agcagcagtt tgatgcggtt ttcagtcgcg tagtctgggc gacccagacc       420
atcgccatac tggtaggtgc agtgggaaac acgtgccatg ttaactgcga tttccatgaa       480
cgctttaggc agcagggtgg agtcgctaac gcgttcacga ttcatctttt tccattcggc       540
gtcgatcagt ttacgcagtt cttcgcgggc ctgttcctcg ctggtaccat cgttttcgtg       600
catgtagcta atgatagaat tggtagtctc gccacgttcc agctccgccg cagaggtggc       660
cagatcgttg cacaggcgga agataacgca gctagaacgc accagaccat ggaagtcggt       720
cagggaacgc agcgcgtggt cggagatgtc ttcctgctgc tggcatacgg aaaagtaaga       780
cggcgccagc agcgctacac cggaggagga aacgctggcg ttttccaggt acttggagaa       840
agccgggata ttttgttgt tggaccattt cgcctcttgc agaaaggctt gcacagttc         900
acgccagctt ttcgtcagat aggacaggtt gttatgacct ttctctttca gaatagaata       960
ggacgtgtcg ttaacggtgt tgtacagtgc caggaaacac agtttcatat agtccggcag      1020
ggtgttaata gcgttaacgt cccagcgctc tacagcatcg gtgaacagtt gcagttcgtc      1080
cagagtgcca taaacgtcat acacgtcatc gatgatcgtc accagaccaa acattttagt      1140
aacagctttg cgacattcac caaactgcgg gtctggcgcc atacccagtg cccagaaata      1200
aacttccatc aggcggtcgc gtacaaaatc cagtttgcta gccaggccca tctcggtcca      1260
ccagcgggac agatcttgca gctctttctg gtgcagggtc tgtaccatgt aaaatccag       1320
cttcgccagc tccagcagca gctggtgatg cggttctttc ggttcgtatt tatccaggaa      1380
ccaacgtgcc tccagacggt gcagacgctg tgatatggc agttccaggg cgtggctcac       1440
ttgttctgca accttggtat taatgccttc tttcaggttg ttcttcaggt gggtgatgga      1500
aaaggtacgc gcctcctcca gcaggttctc accctcgaaa cccaggtaag acgcttcata      1560
caggctcagc aggccttgga cgtcaccttt cagttcaccg ctgaaccac cttctttatc       1620
cttgaaacgc tcaaaaacat cctgagaaac ctcgaaaccg tgctgacgca gcagacggaa      1680
```

```
agacagagcg gttgcgtgca ggtcagattt gttcttttg ttttcgtcca gcagtacgat    1740
gttttccagg gctttaatga tgtcttttc aaatttgtag gtcagaccca ggcgctgcac    1800
atcgtcgatc agctccagca gggacagcgg ctgggtgtct acacggttga tcatgcagcg    1860
aacttcttcc tccagtttgg tcgcttctc ctccagcttt tccactttca ggtcgttctc    1920
cagggattgc aggaattcga aattccacag gtttggctga tagtttgcgg aacgacggga    1980
attatgctcg gtaatctgag taaattgaga agaggtcgca cacatatgac gaccttcgat    2040
atggccgctg ctgtgatgat gatgatgatg atgatgatga tggcccatgg tatatctcct    2100
tcttaaagtt aaacaaaatt atttctagag gggaattgtt atccgctcac aattcccta    2160
tagtgagtcg tattaatttc gcgggatcga gatctcgatc ctctacgccg gacgcatcgt    2220
ggccggcatc accggcgcca caggtgcggt tgctggcgcc tatatcgccg acatcaccga    2280
tggggaagat cgggctcgcc acttcgggct catgagcgct tgtttcggcg tgggtatggt    2340
ggcaggcccc gtggccgggg gactgttggg cgccatctcc ttgcatgcac cattccttgc    2400
ggcggcggtg ctcaacggcc tcaacctact actgggctgc ttcctaatgc aggagtcgca    2460
taagggagag cgtcgagatc ccggacacca tcgaatggcg caaaaccttt cgcggtatgg    2520
catgatagcg cccggaagag agtcaattca gggtggtgaa tgtgaaacca gtaacgttat    2580
acgatgtcgc agagtatgcc ggtgtctctt atcagaccgt ttcccgcgtg gtgaaccagg    2640
ccagccacgt ttctgcgaaa acgcgggaaa agtggaagc ggcgatgcg gagctgaatt     2700
acattcccaa ccgcgtggca caacaactgg cgggcaaaca gtcgttgctg attggcgttg    2760
ccacctccag tctggccctg cacgcgccgt cgcaaattgt cgcggcgatt aaatctcgcg    2820
ccgatcaact gggtgccagc gtggtggtgt cgatggtaga acgaagcggc gtcgaagcct    2880
gtaaagcggc ggtgcacaat cttctcgcgc aacgcgtcag tgggctgatc attaactatc    2940
cgctggatga ccaggatgcc attgctgtgg aagctgcctg cactaatgtt ccggcgttat    3000
ttcttgatgt ctctgaccag acacccatca acagtattat tttctcccat gaagacggta    3060
cgcgactggg cgtggagcat ctggtcgcat tgggtcacca gcaaatcgcg ctgttagcgg    3120
gcccattaag ttctgtctcg gcgcgtctgc gtctggctgg ctggcataaa tatctcactc    3180
gcaatcaaat tcagccgata gcggaacggg aaggcgactg gagtgccatg tccggttttc    3240
aacaaaccat gcaaatgctg aatgagggca tcgttcccac tgcgatgctg gttgccaacg    3300
atcagatggc gctgggcgca atgcgcgcca ttaccgagtc cgggctgcgc gttggtgcgg    3360
atatctcggt agtgggatac gacgataccg aagacagctc atgttatatc cgccgttaa    3420
ccaccatcaa acaggatttt cgcctgctgg ggcaaaccag cgtggaccgc ttgctgcaac    3480
tctctcaggg ccaggcggtg aagggcaatc agctgttgcc cgtctcactg gtgaaaagaa    3540
aaaccaccct ggcgcccaat acgcaaaccg cctctccccg cgcgttggcc gattcattaa    3600
tgcagctggc acgacaggtt tcccgactgg aaagcgggca gtgagcgcaa cgcaattaat    3660
gtaagttagc tcactcatta ggcaccggga tctcgaccga tgcccttgag agccttcaac    3720
ccagtcagct ccttccggtg ggcgcggggc atgactatcg tcgccgcact tatgactgtc    3780
ttctttatca tgcaactcgt aggacaggtg ccggcagcgc tctgggtcat tttcggcgag    3840
gaccgctttc gctggagcgc gacgatgatc ggcctgtcgc ttgcggtatt cggaatcttg    3900
cacgccctcg ctcaagcctt cgtcactggt cccgccacca aacgtttcgg cgagaagcag    3960
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
```

```
gcgttgcagg ccatgctgtc caggcaggta gatgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacggattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt tccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg attttttctct    4800 ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatcccctt tacacggagg catcagtgac caaacaggaa aaaccgccc    4980 ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggt gttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag gcgctcttcc    5400
gcttcctcgc tcactgactc gctgcgctcg tcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
ttttctacgg ggtctgacgc tcagtggaac gaaaactcac gttaagggat tttggtcatg    6240
agattatcaa aaaggatctt cacctagatc cttttaaatt aaaaatgaag ttttaaatca    6300
atctaaagta tatatgagta aacttggtct gacagttacc aatgcttaat cagtgaggca    6360
cctatctcag cgatctgtct atttcgttca tccatagttg cctgactccc cgtcgtgtag    6420
```

```
ataactacga tacgggaggg cttaccatct ggccccagtg ctgcaatgat accgcgagac    6480
ccacgctcac cggctccaga tttatcagca ataaaccagc cagccggaag ggccgagcgc    6540
agaagtggtc ctgcaacttt atccgcctcc atccagtcta ttaattgttg ccgggaagct    6600
agagtaagta gttcgccagt taatagtttg cgcaacgttg ttgccattgc tgcaggcatc    6660
gtggtgtcac gctcgtcgtt tggtatggct tcattcagct ccggttccca acgatcaagg    6720
cgagttacat gatcccccat gttgtgcaaa aaagcggtta gctccttcgg tcctccgatc    6780
gttgtcagaa gtaagttggc cgcagtgtta tcactcatgg ttatggcagc actgcataat    6840
tctcttactg tcatgccatc cgtaagatgc ttttctgtga ctggtgagta ctcaaccaag    6900
tcattctgag aatagtgtat gcggcgaccg agttgctctt gcccggcgtc aacacgggat    6960
aataccgcgc cacatagcag aactttaaaa gtgctcatca ttggaaaacg ttcttcgggg    7020
cgaaaactct caaggatctt accgctgttg agatccagtt cgatgtaacc cactcgtgca    7080
cccaactgat cttcagcatc ttttactttc accagcgttt ctgggtgagc aaaaacagga    7140
aggcaaaatg ccgcaaaaaa gggaataagg gcgacacgga aatgttgaat actcatactc    7200
ttcctttttc aatattattg aagcatttat cagggttatt gtctcatgag cggatacata    7260
tttgaatgta tttagaaaaa taaacaaata ggggttccgc gcacatttcc ccgaaaagtg    7320
ccacctgacg tctaagaaac cattattatc atgacattaa cctataaaaa taggcgtatc    7380
acgaggccct ttcgtcttca agaa                                          7404

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
catatgaaag cttgtatcga ttaaataagg aggaataaac c                        41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt     60
ttcccgactg gaaagcgggc agtgagcgca acgcaattaa tgtgagttag ctcactcatt    120
aggcacccca ggctttacac tttatgcttc cggctcgtat gttgtgtgga attgtgagcg    180
gataacaatt tcacacagga aacagctatg accatgatta cgccaagctt gtatcgatta    240
aataaggagg aataaaccat gtgtgcgacc tcttctcaat ttactcagat taccgagcat    300
aattcccgtc gttccgcaaa ctatcagcca aacctgtgga atttcgaatt cctgcaatcc    360
ctggagaacg acctgaaagt ggaaaagctg gaggagaaag cgaccaaact ggaggaagaa    420
gttcgctgca tgatcaaccg tgtagacacc cagccgctgt ccctgctgga gctgatcgac    480
gatgtgcagc gcctgggtct gacctacaaa tttgaaaaag acatcattaa agccctggaa    540
aacatcgtac tgctggacga aaacaaaaag aacaaatctg acctgcacgc aaccgctctg    600
tctttccgtc tgctgcgtca gcacggtttc gaggtttctc aggatgtttt tgagcgtttc    660
aaggataaag aaggtggttt cagcggtgaa ctgaaaggtg acgtccaagg cctgctgagc    720
```

```
ctgtatgaag cgtcttacct gggtttcgag ggtgagaacc tgctggagga ggcgcgtacc     780
ttttccatca cccacctgaa gaacaacctg aaagaaggca ttaataccaa ggttgcagaa     840
caagtgagcc acgccctgga actgccatat caccagcgtc tgcaccgtct ggaggcacgt     900
tggttcctgg ataaatacga accgaaagaa ccgcatcacc agctgctgct ggagctggcg     960
aagctggatt taacatggt acagaccctg caccagaaag agctgcaaga tctgtcccgc    1020
tggtggaccg agatgggcct ggctagcaaa ctggattttg tacgcgaccg cctgatggaa    1080
gtttatttct gggcactggg tatggcgcca gacccgcagt ttggtgaatg tcgcaaagct    1140
gttactaaaa tgtttggtct ggtgacgatc atcgatgacg tgtatgacgt ttatggcact    1200
ctggacgaac tgcaactgtt caccgatgct gtagagcgct gggacgttaa cgctattaac    1260
accctgccgg actatatgaa actgtgtttc ctggcactgt acaacaccgt taacgacacg    1320
tcctattcta ttctgaaaga gaaaggtcat aacaacctgt cctatctgac gaaaagctgg    1380
cgtgaactgt gcaaagcctt tctgcaagag gcgaaatggt ccaacaacaa aattatcccg    1440
gctttctcca gtacctgga aaacgccagc gtttcctcct ccggtgtagc gctgctggcg    1500
ccgtcttact tttccgtatg ccagcagcag gaagacatct ccgaccacgc gctgcgttcc    1560
ctgaccgact ccatggtct ggtgcgttct agctgcgtta tcttccgcct gtgcaacgat    1620
ctggccacct ctgcggcgga gctggaacgt ggcgagacta ccaattctat cattagctac    1680
atgcacgaaa acgatggtac cagcgaggaa caggcccgcg aagaactgcg taaactgatc    1740
gacgccgaat ggaaaaagat gaatcgtgaa cgcgttagcg actccaccct gctgcctaaa    1800
gcgttcatgg aaatcgcagt taacatggca cgtgtttccc actgcaccta ccagtatggc    1860
gatggtctgg tcgcccaga ctacgcgact gaaaaccgca tcaaactgct gctgattgac    1920
cctttcccga ttaaccagct gatgtatgtc taactgcagg tcgactctag aggatccccg    1980
ggtaccgagc tcgaattcac tggccgtcgt tttacaacgt cgtgactggg aaaaccctgg    2040
cgttacccaa cttaatcgcc ttgcagcaca tcccccttc gccagctggc gtaatagcga    2100
agaggcccgc accgatcgcc cttcccaaca gttgcgcagc ctgaatggcg aatggcgcct    2160
gatgcggtat tttctcctta cgcatctgtg cggtatttca caccgcatat ggtgcactct    2220
cagtacaatc tgctctgatg ccgcatagtt aagccagccc cgacacccgc caacacccgc    2280
tgacgagctt agtaaagccc tcgctagatt ttaatgcgga tgttgcgatt acttcgccaa    2340
ctattgcgat aacaagaaaa agccagcctt tcatgatata tctcccaatt tgtgtagggc    2400
ttattatgca cgcttaaaaa taataaaagc agacttgacc tgatagtttg gctgtgagca    2460
attatgtgct tagtgcatct aacgcttgag ttaagccgcg ccgcgaagcg gcgtcggctt    2520
gaacgaattg ttagacatta tttgccgact accttggtga tctcgccttt cacgtagtgg    2580
acaaattctt ccaactgatc tgcgcgcgag gccaagcgat cttcttcttg tccaagataa    2640
gcctgtctag cttcaagtat gacgggctga tactgggccg gcaggcgctc cattgcccag    2700
tcggcagcga catccttcgg cgcgattttg ccggttactg cgctgtacca atgcgggac    2760
aacgtaagca ctacatttcg ctcatcgcca gcccagtcgg gcggcgagtt ccatagcgtt    2820
aaggtttcat ttagcgcctc aaatagatcc tgttcaggaa ccggatcaaa gagttcctcc    2880
gccgctggac ctaccaaggc aacgctatgt tctcttgctt ttgtcagcaa gatagccaga    2940
tcaatgtcga tcgtggctgg ctcgaagata cctgcaagaa tgtcattgcg ctgccattct    3000
ccaaattgca gttcgcgctt agctggataa cgccacggaa tgatgtcgtc gtgcacaaca    3060
```

```
atggtgactt ctacagcgcg gagaatctcg ctctctccag gggaagccga agtttccaaa    3120
aggtcgttga tcaaagctcg ccgcgttgtt tcatcaagcc ttacggtcac cgtaaccagc    3180
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact ttgttttagg gcgactgccc    3360
tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accaccgctg cgttcggtca aggttctgga ccagttgcgt    3540
gagcgcatac gctacttgca ttacagctta cgaaccgaac aggcttatgt ccactgggtt    3600
cgtgccttca tccgtttcca cggtgtgcgt cacccggcaa ccttgggcag cagcgaagtc    3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg gaagacctcg gccgtcgcgg cgcttgccgg tggtgctgac cccggatgaa    3840
gtggttcgca tcctcggttt tctggaaggc gagcatcgtt tgttcgccca gcttctgtat    3900
ggaacgggca tgcggatcag tgaggggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat tcccacgggt tttgctgccc    4080
gcaaacgggc tgttctggtg ttgctagttt gttatcagaa tcgcagatcc ggcttcagcc    4140
ggtttgccgg ctgaaagcgc tatttcttcc agaattgcca tgattttttc cccacgggag    4200
gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag cttgaatgc accaaaaact cgtaaaagct    4440
ctgatgtatc tatctttttt acaccgtttt catctgtgca tatggacagt tttcccttg    4500 atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740 agtgttttc ttagtccgtt atgtaggtag gaatctgatg taatggttgt ggtattttg    4800 tcaccattca tttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaacccattg gttaagcctt    4980
ttaaactcat ggtagttatt ttcaagcatt aacatgaact taaattcatc aaggctaatc    5040
tctatatttg ccttgtgagt tttcttttgt gttagttctt ttaataacca ctcataaatc    5100
ctcatagagt atttgttttc aaaagactta acatgttcca gattatattt tatgaatttt    5160
tttaactgga aaagataagg caatatctct tcactaaaaa ctaattctaa tttttcgctt    5220
gagaacttgg catagtttgt ccactggaaa atctcaaagc ctttaaccaa aggattcctg    5280
atttccacag ttctcgtcat cagctctctg gttgctttag ctaatacacc ataagcattt    5340
tccctactga tgttcatcat ctgagcgtat tggttataag tgaacgatac cgtccgttct    5400
ttccttgtag ggttttcaat cgtggggttg agtagtgcca cacagcataa aattagcttg    5460
```

```
gtttcatgct ccgttaagtc atagcgacta atcgctagtt catttgcttt gaaaacaact    5520
aattcagaca tacatctcaa ttggtctagg tgattttaat cactatacca attgagatgg    5580
gctagtcaat gataattact agtccttttc ctttgagttg tgggtatctg taaattctgc    5640
tagacctttg ctggaaaact tgtaaattct gctagaccct ctgtaaattc cgctagacct    5700
ttgtgtgttt tttttgttta tattcaagtg gttataattt atagaataaa gaaagaataa    5760
aaaaagataa aagaataga tcccagccct gtgtataact cactacttta gtcagttccg    5820
cagtattaca aaggatgtc gcaaacgctg tttgctcctc tacaaaacag accttaaaac    5880
cctaaaggct taagtagcac cctcgcaagc tcgggcaaat cgctgaatat tccttttgtc    5940
tccgaccatc aggcacctga gtcgctgtct ttttcgtgac attcagttcg ctgcgctcac    6000
ggctctggca gtgaatgggg gtaaatggca ctacaggcgc cttttatgga ttcatgcaag    6060
gaaactaccc ataatacaag aaaagcccgt cacgggcttc tcagggcgtt ttatggcggg    6120
tctgctatgt ggtgctatct gacttttgc tgttcagcag ttcctgccct ctgattttcc    6180
agtctgacca cttcggatta tcccgtgaca ggtcattcag actggctaat gcacccagta    6240
aggcagcggt atcatcaaca ggctta    6266

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8
atgtgtgcaa cctcctccca gtttactcag attaccgagc ataattctcg acgatctgct      60
aactaccagc cgaacctttg gaactttgag tttctccagt ctctcgaaaa tgacctgaag     120
gtggaaaagc tcgaggagaa ggcgaccaaa ctcgaggagg aggtgcgatg tatgatcaac     180
agagttgaca cccaaccccct gtctttgctg gagctgatcg acgatgtgca gcggttgggt     240
ttgacttata aattcgagaa ggacattatc aaggcactgg agaacattgt gctcctcgac     300
gagaacaaga agaacaagtc tgatcttcac gctaccgctc tctctttccg acttcttcga     360
caacacggct tcgaggtgtc gcaggacgtc ttcgagagat ttaaggacaa ggagggagga     420
tttagcggcg agctgaaggg agacgttcag ggtcttctct ccttgtacga ggcgtcctac     480
ctgggattcg agggagagaa cctcctggag gaagctcgta catttccat cactcacctt     540 aagaataacc ttaaggaggg aattaacacc aaggtggccg agcaggtttc tcacgccctg     600
gagctcccct accaccaacg gctccataga ctggaggctc gttggttcct ggacaaatat     660
gagccaaagg agcctcatca tcagttgctg ttggagttgg ccaagctgga cttcaatatg     720
gttcagacgc tgcaccaaaa ggagttgcag gacctgtctc gatggtggac cgagatggga     780
ttggcctcga gctggatttt gtccgtgac cgacttatgg aggtctattt ttgggccctt     840
ggaatggcgc ctgaccccca gttcggagag tgccggaagg cggtgacgaa gatgttcggt     900
cttgtgacta tcatcgacga cgtctacgat gtctacggca cactcgacga gttgcagctg     960
ttcactgacg ccgtcgagcg atgggatgtg aacgccatta atactctccc tgactatatg    1020
aagctgtgct tcctggctct gtacaacact gtcaacgata cctcgtactc tatcctcaag    1080
gagaagggac acaacaatct ctcctacttg accaaatcct ggcgagaact gtgcaaggct    1140
tttctgcagg aggctaaatg gtccaataac aagatcattc ctgctttttc taaataccctg    1200
```

```
gaaaatgcct cggtgtcgag ctctggcgtc gcccttctgg cccctttccta cttctccgtc    1260 tgccagcagc aggaggatat ttccgatcat gctcttagat cgctgaccga ttttcacggc    1320
ctcgtgcgat cttcctgcgt gattttcgg ttgtgtaatg accttgcgac ctctgctgct    1380
gagctggaac gaggcgagac tacaaattcc attatttctt acatgcacga aaacgatgga    1440
acatctgaag aacaggctag agaggaactg cgaaagttga tcgacgccga gtggaagaag    1500
atgaacagag agcgggtgtc cgactctacc ctgcttccca aggccttcat ggagatcgcc    1560
gtgaacatgg ctcgagtttc ccattgtact taccagtacg gtgacggcct gggtcgtccg    1620
gactacgcta cagagaaccg aatcaagctg ctgctcatcg accccttccc tatcaaccaa    1680
ttgatgtacg tgtaa                                                     1695

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcttatggat cctctagact attacacgta catcaattgg                            40

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac                                       30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca      60 aagaaagca attgaaaaca aaacaaaaca attttcattc cttctcttat cattcctttt     120
cttttctttt ctctcattca acgcactcca tcgtatccgt attcctctta ttttttctct     180
ttctctatat ccatttcttt ctctctaggt gtgtcctctc tctctcttca atttctctac     240
tccgcattcc aacgcatcct tcccccaacc tcccatttcc tccttacggc ccgatagcga     300
tcgtctttcc ctcgctatca ctcgctaccg gccccctcctc tgcaccgtaa cctcctacgt     360
atttaccata tcataaagtt ttttccgacg cttatcgctg accccctgtc gccctcctat     420
tggcttccgg attatcttct tgtccataag gtgatccatg cttcctgaag attcccgaaa     480
tgtgtccact ttggcgggga atcattccat ccacttcttt ctctctcgct ttcctcattc     540
ggcgctcccc ttccgcgtct cattggtctt ccgctccgtt tttgctttgc cgatgttact     600
tggggagagg tgcgataatc ctttcgcaaa aactcggttt gacgcctccc atggtataaa     660
tagtgggtgg tggacaggtg ccttcgcttt tctttaagca agagaatccc attgtcttga     720
ctatcacgaa ttcacataca ttatgaagat caccgctgtc attgcccttt tattctcact     780
tgctgctgcc tcacctattc cagttgccga tcctggtgtg gtttcagtta gcaagtcata     840
```

-continued

```
tgctgatttc cttcgtgttt accaaagttg gaacactttt gctaatcctg atagacccaa      900
ccttaagaag agaaatgata cacctgcaag tggatatcaa gttgaaaaag tcgtaatttt      960
gtcacgtcac ggtgttaggg cccctacaaa aatgactcaa accatgcgtg atgtcactcc     1020
taatacatgg ccagaatggc ccgttaaatt aggatatatt acaccaagag gtgaacactt     1080
gatatcactt atgggcggtt tttaccgtca aaaattccag caacaaggaa tcctttctca     1140
gggctcctgt cctactccta actccatata tgtctgggct gacgtcgatc agcgtacttt     1200
aaaaactggt gaagcattcc ttgctggttt ggcaccacaa tgtggcttga caattcatca     1260
ccaacaaaat cttgagaaag ctgatcctct ttttcatccc gttaaagctg aacctgctc      1320 tatggataaa actcaagttc aacaagctgt tgagaaggag gcacaaactc ctatagataa     1380
tttgaatcaa cattacatcc cctttttagc tttaatgaat acaacattaa attttagtac     1440
ttctgcctgg tgccaaaaac actctgctga taaatcctgt gacctaggtt tatccatgcc     1500
ttctaaattg tccataaaag ataatggtaa caaggtcgca ttggatggag ctattggtct     1560
atcctctact ttggccgaga ttttttcttct tgaatatgct caaggcatgc ctcaagctgc     1620
ttggggtaac atccactcag agcaagagtg ggcttccttg ctaaagttgc ataatgttca     1680
attcgatttg atggcccgaa caccttatat tgctcgacat aacggtactc ctttattgca     1740
agctatatca aatgcccttaa atcccaacgc cactgaatca aaacttccag atatttcacc     1800
tgataacaaa atattgttca ttgcaggtca tgacacaaat attgctaata tagccggcat     1860
gttaaatatg cgttggacat taccaggtca accagataat actcctccag gtggtgccct     1920
agtatttgaa cgtcttgctg ataaaagtgg aaaacaatat gtttctgtat ctatggttta     1980
tcaaacacta gaacaacttc gatcacagac tccccttct ctaaatcagc ctgccggatc     2040
tgttcaactt aaaattccag gttgcaatga tcaaacagcc gagggttact gtcctctttc     2100
cacttttaca agagttgttt cccaatctgt tgaacctgga tgccaacttc aataatgagg     2160
atccaagtaa gggaatgaga atgtgatcca cttttaattc ctaatgaata catgcctata     2220
gttctttcct tttgttcttt atgtcgtttt tcgatggtac ggccgttgtc aatctcagtt     2280
tgtgtgcttg gttgcagctt ggtttcaaat ctgttcatct catgaatctt ttaccatttc     2340
accacacgtt tataccattc tctcatagaa tcttcatcaa accatctcgg ggttagagtg     2400
gaaagaaagt cttgttcttt tatttccttt tttccatctt caaggctttt cttttcttcc     2460
tcctcctcgt tcatcttgag gtttgacgtg tctgtttaga attttgagct gttgcagcat     2520 cttattttt gttttgcgaa aacgaagcgc tttactctct tcatcagttg gacgattgta     2580
cctttgaaaa ccaactactt ttgcatgttt tgtatagaaa tcaatgatat tagaatccca     2640
tcctttaatt tcttcaaag tagttgagct atagttaagt gtaagggccc tactgcgaaa     2700
gcatttgcca aggatgtttt cattaatcaa gaacgaaagt taggggatcg aagacgatca     2760
gataccgtcg tagtcttaac cataaactat gccgactagg gatcgggcaa tgtttcattt     2820
atcgacttgc tcggcacctt acgagaaatc aaagtctttg ggttccgggg ggagtatggt     2880
cgcaaggctg aaacttaaag gaattgacgg aagggcacca caatggagtg gagcctgcgg     2940
cttaatttga ctcaacacgg ggaaactcac caggtccaga catagtaagg attgacagat     3000
tgagagctct ttcttgattc tatgggtggt ggtgcatggc cgttcttagt tggtggagtg     3060
atttgtctgc ttaattgcga taacgaacga gaccttaacc tgctaaatag ctggatcagc     3120
cattttggct gatcattagc ttcttagagg gactattggc ataaagccaa tggaagtttg     3180
```

```
aggcaataac aggtctgtga tgcccttaga tgttctgggc cgcacgcgcg ctacactgac    3240
ggagccaacg agttgaaaaa aatcttttga tttttttatcc ttggccggaa ggtctgggta    3300
atcttgttaa actccgtcgt gctggggata gagcattgca attattgcgg ccgctcctca    3360
attcgatgtt gcagatttta caagttttta aaatgtattt cattattact ttttatatgc    3420
ctaataaaaa agccatagtt taatctatag ataacttttt ttccagtgca ctaacggacg    3480
ttacattccc atacaaaact gcgtagttaa agctaaggaa aagttaatat catgttaatt    3540
aaatacgcta tttacaataa gacattgaac tcatttatat cgttgaatat gaataaccaa    3600
tttcagcgaa ttttttaacaa acatcgttca cctcgtttaa ggatatcttg tgtatggggt    3660
gttgacttgc tttatcgaat aattaccgta cctgtaattg gcttgctgga tatagcggta    3720
gtctaatatc tagcaaaaat cttttgggtg aaaaggcttg caatttcacg acaccgaact    3780
atttgtcatt ttttaataag gaagttttcc ataaattcct gtaattctcg gttgatctaa    3840
ttgaaaagag tagttttgca tcacgatgag gagggctttt gtagaaagaa atacgaacga    3900
aacgaaaatc agcgttgcca tcgctttgga caaagctccc ttacctgaag agtcgaattt    3960
tattgatgaa cttataactt ccaagcatgc aaaccaaaag ggagaacaag taatccaagt    4020
agacacggga attggattct tggatcacat gtatcatgca ctggctaaac atgcaggctg    4080
gagcttacga ctttactcaa gaggtgattt aatcatcgat gatcatcaca ctgcagaaga    4140
tactgctatt gcacttggta ttgcattcaa gcaggctatg ggtaactttg ccggcgttaa    4200
aagatttgga catgcttatt gtccacttga cgaagctctt tctagaagcg tagttgactt    4260
gtcgggacgg cccatatgctg ttatcgattt gggattaaag cgtgaaaagg ttggggaatt    4320
gtcctgtgaa atgatccctc acttactata ttccttttcg gtagcagctg gaattacttt    4380
gcatgttacc tgcttatatg gtagtaatga ccatcatcgt gctgaaagcg ctttttaaatc    4440 tctggctgtt gccatgcgcg cggctactag tcttactgga agttctgaag tcccaagcac    4500
gaagggagtg ttgtaaagat gaattggatt atgtcaggaa aagaacgaca attttgcatc    4560
caaattgtct aaattttaga gttgcttgaa aacaatagaa ccttacttgc tttataatta    4620
cgttaattag aagcgttatc tcgtgaagga atatagtacg tagccgtata aattgaattg    4680
aatgttcagc ttatagaata gagacacttt gctgttcaat gcgtcgtcac ttaccatact    4740
cactttatta tacgacttta agtataaact ccgcggttat ggtaaaatta atgatgcaca    4800
aacgtccgat tccatatggg tacactacaa ttaaatactt ttaagctgat cccccacaca    4860
ccatagcttc aaaatgtttc tactcctttt ttactcttcc agattttctc ggactccgcg    4920
catcgccgta ccacttcaaa acacccaagc acagcatact aaattttccc tctttcttcc    4980
tctagggtgt cgttaattac ccgtactaaa ggtttggaaa agaaaaaaga gaccgcctcg    5040 tttcttttc ttcgtcgaaa aaggcaataa aaattttat cacgtttctt tttcttgaaa    5100 ttttttttt tagtttttt ctcttcagt gacctccatt gatatttaag ttaataaacg    5160
gtcttcaatt tctcaagttt cagtttcatt tttcttgttc tattacaact tttttactt    5220 cttgttcatt agaaagaaag catagcaatc taatctaagg gcggtgttga caattaatca    5280
tcggcatagt atatcggcat agtataatac gacaaggtga ggaactaaac catgccaag    5340 ttgaccagtg ccgttccggt gctcaccgcg cgcgacgtcg ccggagcggt cgagttctgg    5400
accgaccggc tcgggttctc ccgggacttc gtggaggacg acttcgccgg tgtggtccgg    5460
gacgacgtga ccctgttcat cagcgcgtc caggaccagg tggtgccgga caacaccctg    5520
gcctgggtgt gggtgcgcgg cctggacgag ctgtacgccg agtggtcgga ggtcgtgtcc    5580
```

```
acgaacttcc gggacgcctc cgggccggcc atgaccgaga tcggcgagca gccgtggggg   5640
cgggagttcg ccctgcgcga cccggccggc aactgcgtgc acttcgtggc cgaggagcag   5700
gactgacacg tccgacggcg gcccacgggt cccaggcctc ggagatccgt ccccctttc    5760 ctttgtcgat atcatgtaat tagttatgtc acgcttacat tcacgcctc cccccacatc   5820 cgctctaacc gaaaggaag gagttagaca acctgaagtc taggtcccta tttattttt    5880 tatagttatg ttagtattaa gaacgttatt tatatttcaa attttctttt ttttctgta   5940 cagacgcgag cttcccagta aatgtgccat ctcgtaggca gaaaacggtt ccccgtagg    6000 gtctctctct tggcctcctt tctaggtcgg gctgattgct cttgaagctc tctagggggg   6060
ctcacaccat aggcagataa cgttccccac cggctcgcct cgtaagcgca caaggactgc   6120
tcccaaagat cctaggcggg attttgccga tttcggccta aaggaaccgg aacacgtaga   6180
aagccagtcc gcagaaacgg tgctgacccc ggatgaatgt cagctactgg gctatctgga   6240
caagggaaaa cgcaagcgca aagagaaagc aggtagcttg cagtgggctt acatggcgat   6300
agctagactg ggcggttta tggacagcaa gcgaaccgga attgccagct ggggcgccct    6360
ctggtaaggt tgggaagccc tgcaaagtaa actggatggc tttcttgccg ccaaggatct   6420
gatggcgcag gggatcaaga tctgatcaag agacaggatg aggatcgttt cgcatgattg   6480
aacaagatgg attgcacgca ggttctccgg ccgcttgggt ggagaggcta ttcggctatg   6540
actgggcaca acagacaatc ggctgctctg atgccgccgt gttccggctg tcagcgcagg   6600
ggcgcccggt tctttttgtc aagaccgacc tgtccggtgc cctgaatgaa ctgcaggacg   6660
aggcagcgcg gctatcgtgg ctggccacga cgggcgttcc ttgcgcagct gtgctcgacg   6720
ttgtcactga agcgggaagg gactggctgc tattgggcga agtgccgggg caggatctcc   6780
tgtcatctcg ccttgctcct gccgagaaag tatccatcat ggctgatgca atgcggcggc   6840
tgcatacgct tgatccggct acctgcccat tcgaccacca agcgaaacat cgcatcgagc   6900
gagcacgtac tcggatggaa gccggtcttg tcgatcagga tgatctggac gaagagcatc   6960
aggggctcgc gccagccgaa ctgttcgcca ggctcaaggc gcgcatgccc gacggcgagg   7020
atctcgtcgt gatccatggc gatgcctgct tgccgaatat catggtggaa aatggccgct   7080
tttctggatt caacgactgt ggccggctgg gtgtggcgga ccgctatcag gacatagcgt   7140 tggataccccg tgatattgct gaagagcttg gcggcgaatg ggctgaccgc ttcctcgtgc   7200
tttacggtat cgccgctccc gattcgcagc gcatcgcctt ctatcgcctt cttgacgagt   7260
tcttctgaat tgaaaaaggt accaagttta ctcatatata ctttagattg atttaaaact   7320
tcatttttaa tttaaaagga tctaggtgaa gatcctttt gataatctca tgaccaaaat   7380
cccttaacgt gagttttcgt tccactgagc gtcagacccc gtagaaaaga tcaaaggatc   7440
ttcttgagat cctttttttc tgcgcgtaat ctgctgcttg caaacaaaaa aaccaccgct   7500
accagcggtg gtttgtttgc cggatcaaga gctaccaact cttttccga aggtaactgg    7560 cttcagcaga gcgcagatac caaatactgt ccttctagtg tagccgtagt taggccacca   7620
cttcaagaac tctgtagcac cgcctacata cctcgctctg ctaatcctgt taccagtggc   7680
tgctgccagt ggcgataagt cgtgtcttac cgggttggac tcaagacgat agttaccgga   7740
taaggcgcag cggtcgggct gaacggggg ttcgtgcaca gcccagct tggagcgaac      7800 gacctacacc gaactgagat acctacagcg tgagcattga gaaagcgcca cgcttcccga   7860
agggagaaag gcggacaggt atccggtaag cggcagggtc ggaacaggag agcgcacgag   7920
```

```
ggagcttcca gggggaaacg cctggtatct ttatagtcct gtcgggtttc gccacctctg   7980
acttgagcgt cgattttgt gatgctcgtc agggggcgg agcctatgga aaaacgccag    8040
caacgcggcc ttttacggt tcctggcctt ttgctggcct tttgctcaca tgttctttcc    8100
tgcgttatcc cctgattctg tggataaccg tattaccgcc tttgagtgag ctgataccgc   8160
tcgccgcagc cgaacgaccg agcgcagcga g                                  8191

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12
gaattcaaaa caaaatgtgt gcaacctcct cccagtttac tcagattacc gagcataatt     60
ctcgacgatc tgctaactac cagccgaacc tttggaactt tgagtttctc cagtctctcg    120
aaaatgacct gaaggtggaa aagctcgagg agaaggcgac caaactcgag gaggaggtgc    180
gatgtatgat caacagagtt gacacccaac ccctgtcttt gctggagctg atcgacgatg    240
tgcagcggtt gggtttgact tataaattcg agaaggacat tatcaaggca ctggagaaca    300
ttgtgctcct cgacgagaac aagaagaaca agtctgatct tcacgctacc gctctctctt    360
tccgacttct tcgacaacac ggcttcgagg tgtcgcagga cgtcttcgag agatttaagg    420
acaaggaggg aggatttagc ggcgagctga agggagacgt tcagggtctt ctctccttgt    480
acgaggcgtc ctacctggga ttcgagggag agaacctcct ggaggaagct cgtacatttt    540
ccatcactca ccttaagaat aaccttaagg agggaattaa caccaaggtg gccgagcagg    600
tttctcacgc cctggagctc ccctaccacc aacggctcca tagactggag gctcgttggt    660
tcctggacaa atatgagcca aaggagcctc atcatcagtt gctgttggag ttggccaagc    720
tggacttcaa tatggttcag acgctgcacc aaaaggagtt gcaggacctg tctcgatggt    780
ggaccgagat gggattggcc tcgaagctgg attttgtccg tgaccgactt atggaggtct    840
attttttggg ccttggaatg gcgcctgacc cccagttcgg agagtgccgg aaggcggtga    900
cgaagatgtt cggtcttgtg actatcatcg acgacgtcta cgatgtctac ggcacactcg    960
acgagttgca gctgttcact gacgccgtcg agcgatggga tgtgaacgcc attaatactc   1020
tccctgacta tatgaagctg tgcttcctgg ctctgtacaa cactgtcaac gatacctcgt   1080
actctatcct caaggagaag ggacacaaca atctctccta cttgaccaaa tcctggcgag   1140
aactgtgcaa ggcttttctg caggaggcta atggtccaa taacaagatc attcctgctt   1200
tttctaaata cctggaaaat gcctcggtgt cgagctctgg cgtcgccctt ctggcccctt   1260
cctacttctc cgtctgccag cagcaggagg atatttccga tcatgctctt agatcgctga   1320
ccgattttca cggcctcgtg cgatcttcct gcgtgatttt tcggttgtgt aatgaccttg   1380
cgacctctgc tgctgagctg aacgaggcg agactacaaa ttccattatt tcttacatgc   1440
acgaaaacga tggaacatct gaagaacagg ctagagagga actgcgaaag ttgatcgacg   1500
ccgagtggaa gaagatgaac agagagcggg tgtccgactc taccctgctt cccaaggcct   1560
tcatggagat cgccgtgaac atggctcgag tttcccattg tacttaccag tacggtgacg   1620
gcctgggtcg tccggactac gctacagaga accgaatcaa gctgctgctc atcgacccct   1680
tccctatcaa ccaattgatg tacgtgtaat agtctagagg atcc                    1724
```

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

```
gaattcaaca aaaatgtgct ctgtttccac tgagaacgtg tcctttactg agactgagac     60
tgaagcacgt agaagcgcca actacgaacc caactcctgg gattatgact ttctgctgtc    120
ttctgacacc gacgagtcga tcgaggttta aaggataag gccaagaaac ttgaggccga    180
ggtcagacga gagattaaca acgagaaggc cgagttcctg acccttcttg agctgatcga    240
caacgttcaa cgacttggtc ttggttaccg tttcgaatcc gatatccgac gtgcattgga    300
tcgatttgtc tcgtccggag gtttcgatgg tgtgactaag acgtcgctgc acgccacagc    360
tctttccttc agactgttgc ggcagcatgg atttgaggtt tcccaggaag ccttttctgg    420
tttcaaggat cagaacggaa acttttttgga gaatctcaag gaggacacca aggccatcct    480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc    600
cgagcaggtc aaccatgcac ttgaacttcc cctgcatcga cgtacccagc gactggaggc    660
cgtgtggagc atcgaggcgt acagaaaaaa ggaggatgct aatcaggttc tgctcgaact    720
cgctatcctc gactataaca tgattcagag cgtgtaccag cgtgacttgc gagagacaag    780
ccggtggtgg cgacgggtgg gactggccac gaagctccac tttgctaaag atcgattgat    840
tgagtcgttc tactgggcag tgggtgtggc ctttgagcct cagtactccg actgccgaaa    900
ctccgttgca aagatgtttt cttttgtcac tatcatcgac gacatctacg atgtttacgg    960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg cctttttgca ggaagccaag tggctctata acaaatctac   1200
tcctacattt gatgactact tcggcaacgc ttggaagtct tccagcggcc ctctccagtt   1260
gatcttcgct tactttgcag tggtccagaa catcaagaaa gaggagattg agaacctcca   1320
gaagtatcac gacatcatct cccgaccttc gcacatcttt cgactgtgca atgaccttgc   1380
ctccgcatcc gctgagattg cccgaggaga aacagccaat tctgtgtcgt gttacatgcg   1440
tacaaagggc atctccgagg agctggctac cgagtctgtg atgaacctga tcgatgaaac   1500
ctgtaagaag atgaacaaag agaaactggg cggttctctg ttcgccaaac catttgttga   1560
aaccgcgatc aatctggctc gtcagtctca ttgtacttac cataacggtg acgcgcacac   1620
ttcgccggac gaattgaccc gtaagcgtgt gctttcggtg attaccgagc cgatcctgcc   1680
gttcgaaaga taataggatc c                                            1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14

```
gatcaagctt aaccggaatt gccagctg                                       28
```

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc                          33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                     38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                  26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg    60

<210> SEQ ID NO 19
<211> LENGTH: 30
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga                              30

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc    60
tgaatagcgc cgtcgaccat catcatcatc atcattgagt ttaaacggtc tccagcttgg   120
ctgttttggc ggatgagaga agattttcag cctgatacag attaaatcag aacgcagaag   180
cggtctgata aaacagaatt tgcctggcgg cagtagcgcg gtggtcccac ctgaccccat   240
gccgaactca gaagtgaaac gccgtagcgc cgatggtagt gtggggtctc cccatgcgag   300

-continued

```
agtagggaac tgccaggcat caaataaaac gaaaggctca gtcgaaagac tgggcctttc    360
gttttatctg ttgtttgtcg gtgaacgctc tcctgagtag gacaaatccg ccgggagcgg    420
atttgaacgt tgcgaagcaa cggcccgag ggtggcgggc aggacgcccg ccataaactg     480
ccaggcatca aattaagcag aaggccatcc tgacggatgg ccttttttgcg tttctacaaa   540
ctctttttgt ttattttct aaatacattc aaatatgtat ccgcttaacc ggaattgcca     600
gctggggcgc cctctggtaa ggttgggaag ccctgcaaag taaactggat ggctttctcg    660
ccgccaagga tctgatggcg caggggatca agctctgatc aagagacagg atgaggatcg    720
tttcgcatga ttgaacaaga tggattgcac gcaggttctc cggccgcttg ggtggagagg    780
ctattcggct atgactgggc acaacagaca atcggctgct ctgatgccgc cgtgttccgg    840
ctgtcagcgc aggggcgccc ggttcttttt gtcaagaccg acctgtccgg tgccctgaat    900
gaactgcaag acgaggcagc gcggctatcg tggctggcca cgacgggcgt tccttgcgca    960
gctgtgctcg acgttgtcac tgaagcggga agggactggc tgctattggg cgaagtgccg   1020
gggcaggatc tcctgtcatc tcaccttgct cctgccgaga agtatccat catggctgat    1080
gcaatgcggc ggctgcatac gcttgatccg gctacctgcc cattcgacca ccaagcgaaa   1140
catcgcatcg agcgagcacg tactcggatg gaagccggtc ttgtcgatca ggatgatctg   1200
gacgaagagc atcaggggct cgcgccagcc gaactgttcg ccaggctcaa ggcgagcatg   1260
cccgacggcg aggatctcgt cgtgacccat ggcgatgcct gcttgccgaa tatcatggtg   1320
gaaaatggcc gcttttctgg attcatcgac tgtggccggc tgggtgtggc ggaccgctat   1380
caggacatag cgttggctac ccgtgatatt gctgaagagc ttggcggcga atgggctgac   1440
cgcttcctcg tgctttacgg tatcgccgct cccgattcgc agcgcatcgc cttctatcgc   1500
cttcttgacg agttcttctg acatgaccaa aatcccttaa cgtgagtttt cgttccactg   1560
agcgtcagac cccgtagaaa agatcaaagg atcttcttga gatcctttt ttctgcgcgt    1620
aatctgctgc ttgcaaacaa aaaaaccacc gctaccagcg gtggtttgtt tgccggatca   1680
agagctacca actcttttc cgaaggtaac tggcttcagc agagcgcaga taccaaatac    1740
tgtccttcta gtgtagccgt agttaggcca ccacttcaag aactctgtag caccgcctac   1800
atacctcgct ctgctaatcc tgttaccagt ggctgctgcc agtggcgata agtcgtgtct   1860
taccgggttg gactcaagac gatagttacc ggataaggcg cagcggtcgg gctgaacggg   1920
gggttcgtgc acacagccca gcttggagcg aacgacctac accgaactga gatacctaca   1980
gcgtgagcta tgagaaagcg ccacgcttcc gaagggaga aaggcggaca ggtatccggt    2040
aagcggcagg gtcggaacag gagagcgcac gagggagctt ccaggggaa acgcctggta    2100
tctttatagt cctgtcgggt ttcgccacct ctgacttgag cgtcgatttt tgtgatgctc   2160
gtcagggggg cggagcctat ggaaaaacgc cagcaacgcg gcctttttac ggttcctggc   2220
cttttgctgg ccttttgctc acatgttctt cctgcgtta tccctgatt ctgtggataa     2280
ccgtattacc gcctttgagt gagctgatac cgctcgccgc agccgaacga ccgagcgcag   2340
cgagtcagtg agcgaggaag cggaagagcg cctgatgcgg tattttctcc ttacgcatct   2400
gtgcggtatt tcacaccgca tatggtgcac tctcagtaca atctgctctg atgccgcata   2460
gttaagccag tatacactcc gctatcgcta cgtgactggg tcatggctgc gccccgacac   2520
ccgccaacac ccgctgacgc gccctgacgg gcttgtctgc tcccggcatc cgcttacaga   2580
caagctgtga ccgtctccgg gagctgcatg tgtcagaggt tttcaccgtc atcaccgaaa   2640
```

-continued

```
cgcgcgaggc agcagatcaa ttcgcgcgcg aaggcgaagc ggcatgcatt tacgttgaca    2700
ccatcgaatg gtgcaaaacc tttcgcggta tggcatgata gcgcccggaa gagagtcaat    2760
tcagggtggt gaatgtgaaa ccagtaacgt tatacgatgt cgcagagtat gccggtgtct    2820
cttatcagac cgtttcccgc gtggtgaacc aggccagcca cgtttctgcg aaaacgcggg    2880
aaaaagtgga agcggcgatg gcggagctga attacattcc caaccgcgtg gcacaacaac    2940
tggcgggcaa acagtcgttg ctgattggcg ttgccacctc cagtctggcc ctgcacgcgc    3000
cgtcgcaaat tgtcgcggcg attaaatctc gcgccgatca actgggtgcc agcgtggtgg    3060
tgtcgatggt agaacgaagc ggcgtcgaag cctgtaaagc ggcggtgcac aatcttctcg    3120
cgcaacgcgt cagtgggctg atcattaact atccgctgga tgaccaggat gccattgctg    3180
tggaagctgc ctgcactaat gttccggcgt tatttcttga tgtctctgac cagacaccca    3240
tcaacagtat tattttctcc catgaagacg gtacgcgact gggcgtggag catctggtcg    3300
cattgggtca ccagcaaatc gcgctgttag cgggcccatt aagttctgtc tcggcgcgtc    3360
tgcgtctggc tggctggcat aaatatctca ctcgcaatca aattcagccg atagcggaac    3420
gggaaggcga ctggagtgcc atgtccggtt ttcaacaaac catgcaaatg ctgaatgagg    3480
gcatcgttcc cactgcgatg ctggttgcca acgatcagat ggcgctgggc gcaatgcgcg    3540
ccattaccga gtccgggctg cgcgttggtg cggatatctc ggtagtggga tacgacgata    3600
ccgaagacag ctcatgttat atcccgccgt caaccaccat caaacaggat ttcgcctgc    3660
tggggcaaac cagcgtggac cgcttgctgc aactctctca gggccaggcg gtgaagggca    3720
atcagctgtt gcccgtctca ctggtgaaaa gaaaaccac cctggcgccc aatacgcaaa    3780
ccgcctctcc ccgcgcgttg gccgattcat taatgcagct ggcacgacag gtttcccgac    3840
tggaaagcgg gcagtgagcg caacgcaatt aatgtgagtt agcgcgaatt gatctggttt    3900
gacagcttat catcgactgc acggtgcacc aatgcttctg cgtcaggca gccatcggaa    3960
gctgtggtat ggctgtgcag gtcgtaaatc actgcataat tcgtgtcgct caaggcgcac    4020
tcccgttctg gataatgttt tttgcgccga catcataacg gttctggcaa atattctgaa    4080
atgagctgtt gacaattaat catccggctc gtataatgtg tggaattgtg agcggataac    4140
aatttcacac aggaaacagc gccgctgaga aaagcgaag cggcactgct ctttaacaat    4200
ttatcagaca atctgtgtgg gcactcgacc ggaattatcg attaacttta ttattaaaaa    4260
ttaaagaggt atatattaat gtatcgatta ataaggagg aataaaccat gtgtgcgacc    4320
tcttctcaat ttactcagat taccgagcat aattcccgtc gttccgcaaa ctatcagcca    4380
aacctgtgga atttcgaatt cctgcaatcc ctggagaacg acctgaaagt ggaaaagctg    4440
gaggagaaag cgaccaaact ggaggaagaa gttcgctgca tgatcaaccg tgtagacacc    4500
cagccgctgt ccctgctgga gctgatcgac gatgtgcagc gcctgggtct gacctacaaa    4560
tttgaaaaag acatcattaa agccctggaa aacatcgtac tgctggacga aaacaaaaag    4620
aacaaatctg acctgcacgc aaccgctctg tctttccgtc tgctgcgtca gcacggtttc    4680
gaggtttctc aggatgtttt tgagcgtttc aaggataaag aaggtggttt cagcggtgaa    4740
ctgaaaggtg acgtccaagg cctgctgagc ctgtatgaag cgtcttacct gggtttcgag    4800
ggtgagaacc tgctggagga ggcgcgtacc ttttccatca cccacctgaa gaacaacctg    4860
aaagaaggca ttaataccaa ggttgcagaa caagtgagcc acgccctgga actgccatat    4920
caccagcgtc tgcaccgtct ggaggcacgt tggttcctgg ataaatacga accgaaagaa    4980
ccgcatcacc agctgctgct ggagctggcg aagctggatt ttaacatggt acagaccctg    5040
```

```
caccagaaag agctgcaaga tctgtcccgc tggtggaccg agatgggcct ggctagcaaa    5100
ctggattttg tacgcgaccg cctgatgaa gtttatttct gggcactggg tatggcgcca     5160
gacccgcagt ttggtgaatg tcgcaaagct gttactaaaa tgtttggtct ggtgacgatc    5220
atcgatgacg tgtatgacgt ttatggcact ctggacgaac tgcaactgtt caccgatgct    5280
gtagagcgct gggacgttaa cgctattaac accctgccgg actatatgaa actgtgtttc    5340
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg gctttctcca agtacctgga aaacgccagc    5520
gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct     5640 agctgcgtta tcttccgcct gtgcaacgat ctggccacct ctgcggcgga gctggaacgt    5700
ggcgagacta ccaattctat cattagctac atgcacgaaa acgatggtac cagcgaggaa    5760
caggcccgcg aagaactgcg taaactgatc gacgccgaat ggaaaagat gaatcgtgaa     5820 cgcgttagcg actccaccct gctgcctaaa gcgttcatgg aaatcgcagt taacatggca    5880
cgtgtttccc actgcaccta ccagtatggc gatggtctgg tcgcccaga ctacgcgact     5940 gaaaaccgca tcaaactgct gctgattgac ccttttcccga ttaaccagct gatgtatgtc    6000
taactgcatc gcccttagga ggtaaaaaaa aatgactgcc gacaacaata gtatgcccca    6060
tggtgcagta tctagttacg ccaaattagt gcaaaaccaa acacctgaag acattttgga    6120
agagtttcct gaaattattc cattacaaca aagacctaat acccgatcta gtgagacgtc    6180
aaatgacgaa agcggagaaa catgtttttc tggtcatgat gaggagcaaa ttaagttaat    6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattacttt acaacaaaga gccactgaaa aaataacttt      6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcacttttt    6600
aaacagaatc cattacatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttcaccaaa tgatttgaaa actatgtttg ctgacccaag    6780
ttacaagttt acgccttggt ttaagattat ttgcgagaat tacttattca actggtggga    6840
gcaattagat gaccttttctg aagtggaaaa tgacaggcaa attcatagaa tgctataaca    6900
acgcgtcctg cattcgccct taggaggtaa aaaaacatga gttttgatat tgccaaatac    6960 ccgacccttgg cactggtcga ctccacccag gagttacgac tgttgccgaa agagagttta    7020
ccgaaactct gcgacgaact gcgccgctat ttactcgaca gcgtgagccg ttccagcggg    7080
cacttcgcct ccgggctggg cacggtcgaa ctgaccgtgg cgctgcacta tgtctacaac    7140
accccgtttg accaattgat ttgggatgtg ggcatcagg cttatccgca taaaattttg      7200
accggacgcc gcgacaaaat cggcaccatc cgtcagaaag gcggtctgca cccgttcccg    7260
tggcgcggcg aaagcgaata tgacgtatta agcgtcgggc attcatcaac ctccatcagt    7320
gccggaattg gtattgcggt tgctgccgaa aaagaaggca aaaatcgccg caccgtctgt    7380
```

```
gtcattggcg atggcgcgat taccgcaggc atggcgtttg aagcgatgaa tcacgcgggc    7440
gatatccgtc ctgatatgct ggtgattctc aacgacaatg aaatgtcgat ttccgaaaat    7500
gtcggcgcgc tcaacaacca tctggcacag ctgctttccg gtaagcttta ctcttcactg    7560
cgcgaaggcg ggaaaaaagt tttctctggc gtgccgccaa ttaaagagct gctcaaacgc    7620
accgaagaac atattaaagg catggtagtg cctggcacgt tgtttgaaga gctgggcttt    7680
aactacatcg gcccggtgga cggtcacgat gtgctgggc ttatcaccac gctaaagaac    7740
atgcgcgacc tgaaaggccc gcagttcctg catatcatga ccaaaaaagg tcgtggttat    7800
gaaccggcag aaaaagaccc gatcactttc cacgccgtgc ctaaatttga tccctccagc    7860
ggttgtttgc cgaaaagtag cggcggtttg ccgagctatt caaaaatctt tggcgactgg    7920
ttgtgcgaaa cggcagcgaa agacaacaag ctgatggcga ttactccggc gatgcgtgaa    7980
ggttccggca tggtcgagtt ttcacgtaaa ttcccggatc gctacttcga cgtggcaatt    8040
gccgagcaac acgcggtgac ctttgctgcg ggtctggcga ttggtgggta caaacccatt    8100
gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220
caaacccatc agggtgcttt tgatctctct tacctgcgct gcataccgga aatggtcatt    8280
atgaccccga gcgatgaaaa cgaatgtcgc cagatgctct ataccggcta tcactataac    8340 gatgcccgt cagcggtgcg ctacccgcgt ggcaacgcgg tcggcgtgga actgacgccg    8400
ctggaaaaac taccaattgg caaaggcatt gtgaagcgtc gtggcgagaa actggcgatc    8460
cttaactttg gtacgctgat gccagaagcg gcgaaagtcg ccgaatcgct gaacgccacg    8520
ctggtcgata tgcgttttgt gaaaccgctt gatgaagcgt taattctgga atggccgcc    8580 agccatgaag cgctggtcac cgtagaagaa acgccatta tgggcggcgc aggcagcggc    8640
gtgaacgaag tgctgatggc ccatcgtaaa ccagtacccg tgctgaacat tggcctgccg    8700
gacttcttta ttccgcaagg aactcaggaa gaaatgcgcg ccgaactcgg cctcgatgcc    8760
gctggtatgg aagccaaaat caaggcctgg ctggcataac tgca                    8804
```

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21

```
aggaggtaaa aaaacatgtc attaccgttc ttaacttctg c                         41
```

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22

```
atggctgcag gcctatcgca aattagctta tgaagtccat ggtaaattcg tg             52
```

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 23
gaattcgccc ttctgcagct acc                                              23

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
cgactggtgc acccttaagg aggaaaaaaa catgtcag                              38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc                                            25

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg                                    32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc                                           26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac                              38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg                                            25

<210> SEQ ID NO 30
```

```
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg                                    36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact         60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg                                 38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc         60
ggaagctgtg gtatggctgt gcaggtcgta aatcactgca taattcgtgt cgctcaaggc        120
gcactcccgt tctggataat gttttttgcg ccgacatcat aacggttctg gcaaatattc        180
tgaaatgagc tgttgacaat taatcatccg gctcgtataa tgtgtggaat tgtgagcgga        240
taacaatttc acacaggaaa cagcgccgct gagaaaaagc gaagcggcac tgctctttaa        300
caatttatca gacaatctgt gtgggcactc gaccggaatt atcgattaac tttattatta        360
aaaattaaag aggtatatat taatgtatcg attaaataag gaggaataaa ccatggatcc        420
gagctcggat ccactagtaa cggccgccag tgtgctggaa ttcgcccta ggaggtaaaa         480 aaacatgtca ttaccgttct taacttctgc accgggaaag gttattattt ttggtgaaca        540
ctctgctgtg tacaacaagc ctgccgtcgc tgctagtgtg tctgcgttga aacctacct         600 gctaataagc gagtcatctg caccagatac tattgaattg gacttcccgg acattagctt        660
taatcataag tggtccatca atgatttcaa tgccatcacc gaggatcaag taaactccca        720
aaaattggcc aaggctcaac aagccaccga tggcttgtct caggaactcg ttagtctttt        780
ggatccgttg ttagctcaac tatccgaatc cttccactac catgcagcgt tttgtttcct        840
gtatatgttt gtttgcctat gccccatgc caagaatatt aagttttctt taaagtctac         900
tttacccatc ggtgctgggt tgggctcaag cgcctctatt tctgtatcac tggccttagc        960
tatggcctac ttggggggt taataggatc taatgacttg gaaaagctgt cagaaaacga       1020
taagcatata gtgaatcaat gggccttcat aggtgaaaag tgtattcacg gtaccccttc       1080
```

```
aggaatagat aacgctgtgg ccacttatgg taatgccctg ctatttgaaa aagactcaca    1140
taatggaaca ataaacacaa acaattttaa gttcttagat gatttcccag ccattccaat    1200
gatcctaacc tatactagaa ttccaaggtc tacaaaagat cttgttgctc gcgttcgtgt    1260
gttggtcacc gagaaatttc ctgaagttat gaagccaatt ctagatgcca tgggtgaatg    1320
tgccctacaa ggcttagaga tcatgactaa gttaagtaaa tgtaaaggca ccgatgacga    1380
ggctgtagaa actaataatg aactgtatga acaactattg gaattgataa gaataaatca    1440
tggactgctt gtctcaatcg gtgtttctca tcctggatta gaacttatta aaaatctgag    1500
cgatgatttg agaattggct ccacaaaact taccggtgct ggtggcggcg gttgctcttt    1560
gactttgtta cgaagagaca ttactcaaga gcaaattgac agcttcaaaa agaaattgca    1620
agatgatttt agttacgaga catttgaaac agacttgggt gggactggct gctgtttgtt    1680
aagcgcaaaa aatttgaata agatcttaa aatcaaatcc ctagtattcc aattatttga    1740
aaataaaact accacaaagc aacaaattga cgatctatta ttgccaggaa acacgaattt    1800
accatggact tcataagcta atttgcgata ggcctgcacc cttaaggagg aaaaaaacat    1860
gtcagagttg agagccttca gtgccccagg gaaagcgtta ctagctggtg atatttagt    1920 tttagataca aaatatgaag catttgtagt cggattatcg gcaagaatgc atgctgtagc    1980
ccatccttac ggttcattgc aagggtctga taagtttgaa gtgcgtgtga aaagtaaaca    2040
atttaaagat ggggagtggc tgtaccatat aagtcctaaa agtggcttca ttcctgtttc    2100
gataggcgga tctaagaacc ctttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag cttttggcctc cttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaaaggg acacgaagtt gaatctgccc accaattcgt    3360
ccatatcagt gactttatcg caagatgacc tcagaacgtt gacctctgcg gctactgcac    3420
```

```
ctgagtttga acgcgacact tgtggttaa atggagaacc acacagcatc gacaatgaaa      3480
gaactcaaaa ttgtctgcgc gacctacgcc aattaagaaa ggaaatggaa tcgaaggacg      3540
cctcattgcc cacattatct caatggaaac tccacattgt ctccgaaaat aactttccta      3600
cagcagctgg tttagcttcc tccgctgctg gctttgctgc attggtctct gcaattgcta      3660
agttatacca attaccacag tcaacttcag aaatatctag aatagcaaga aagggtctg       3720 gttcagcttg tagatcgttg tttggcggat acgtggcctg ggaatggga aaagctgaag       3780 atggtcatga ttccatggca gtacaaatcg cagacagctc tgactggcct cagatgaaag      3840
cttgtgtcct agttgtcagc gatattaaaa aggatgtgag ttccactcag ggtatgcaat      3900
tgaccgtggc aacctccgaa ctatttaaag aaagaattga acatgtcgta ccaaagagat      3960
ttgaagtcat gcgtaaagcc attgttgaaa aagatttcgc cacctttgca aaggaaacaa      4020
tgatggattc caactctttc catgccacat gtttggactc tttccctcca atattctaca      4080
tgaatgacac ttccaagcgt atcatcagtt ggtgccacac cattaatcag ttttacggag      4140
aaacaatcgt tgcatacacg tttgatgcag gtccaaatgc tgtgttgtac tacttagctg      4200
aaaatgagtc gaaactcttt gcatttatct ataaattgtt tggctctgtt cctggatggg      4260
acaagaaatt tactactgag cagcttgagg cttttcaacca tcaatttgaa tcatctaact      4320
ttactgcacg tgaattggat cttgagttgc aaaaggatgt tgccagagtg attttaactc      4380
aagtcggttc aggcccacaa gaaacaaacg aatctttgat tgacgcaaag actggtctac      4440
caaaggaata agatcaattc gctgcatcgc ccttaggagg taaaaaaaaa tgactgccga      4500
caacaatagt atgccccatg gtgcagtatc tagttacgcc aaattagtgc aaaaccaaac      4560
acctgaagac attttggaag agtttcctga aattattcca ttacaacaaa gacctaatac      4620 ccgatcagt gagacgtcaa atgacgaaag cggagaaaca tgttttttctg gtcatgatga      4680 ggagcaaatt aagttaatga atgaaaattg tattgttttg gattgggacg ataatgctat      4740
tggtgccggt accaagaaag tttgtcattt aatggaaaat attgaaaagg tttactaca       4800 tcgtgcattc tccgtcttta ttttcaatga acaaggtgaa ttactttttac aacaaagagc      4860 cactgaaaaa ataactttcc ctgatctttg gactaacaca tgctgctctc atccactatg      4920
tattgatgac gaattaggtt tgaagggtaa gctagacgat aagattaagg gcgctattac      4980
tgcggcggtg agaaaactag atcatgaatt aggtattcca gaagatgaaa ctaagacaag      5040
gggtaagttt cactttttaa acagaatcca ttacatggca ccaagcaatg aaccatgggg      5100
tgaacatgaa attgattaca tcctatttta taagatcaac gctaaagaaa acttgactgt      5160
caacccaaac gtcaatgaag ttagagactt caaatgggtt tcaccaaatg atttgaaaac      5220
tatgtttgct gacccaagtt acaagtttac gccttggttt aagattattt gcgagaatta      5280
cttattcaac tggtgggagc aattagatga cctttctgaa gtggaaatg acaggcaaat      5340 tcatagaatg ctataacaac gcgtcctgca ttcgcccctta ggaggtaaaa aaacatgtgt      5400
gcgacctctt ctcaatttac tcagattacc gagcataatt cccgtcgttc cgcaaactat      5460
cagccaaacc tgtggaattt cgaattcctg caatccctgg agaacgacct gaaagtggaa      5520
aagctggagg agaaagcgac caaactggag gaagaagttc gctgcatgat caaccgtgta      5580
gacacccagc cgctgtccct gctggagctg atcgacgatg tgcagcgcct gggtctgacc      5640
tacaaatttg aaaagacat cattaaagcc ctgaaaaaca tcgtactgct ggacgaaaac      5700
aaaaagaaca atctgacct gcacgcaacc gctctgtctt tccgtctgct gcgtcagcac      5760
ggtttcgagg tttctcagga tgttttgag cgtttcaagg ataaagaagg tggtttcagc      5820
```

```
ggtgaactga aaggtgacgt ccaaggcctg ctgagcctgt atgaagcgtc ttacctgggt    5880
ttcgagggtg agaacctgct ggaggaggcg cgtacctttt ccatcaccca cctgaagaac    5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggattttaa catggtacag    6120
accctgcacc agaaagagct gcaagatctg tcccgctggt ggaccgagat gggcctggct    6180
agcaaactgg attttgtacg cgaccgcctg atggaagttt atttctgggc actgggtatg    6240
gcgccagacc gcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa caacaaaatt atcccggctt ctccaagta cctggaaaac    6600 gccagcgttt cctcctccgg tgtagcgctg ctggcgccgt cttacttttc cgtatgccag    6660
cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgaccctt cccgattaa ccagctgatg    7080 tatgtctaac tgcagctggt accatatggg aattcgaagc tttctagaac aaaaactcat    7140
ctcagaagag gatctgaata gcgccgtcga ccatcatcat catcatcatt gagttaaac    7200 ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggccttt    7620 tgcgtttcta caaactcttt ttgtttattt ttctaaatac attcaaatat gtatccgctt    7680
aaccggaatt gccagctggg gcgccctctg gtaaggttgg aagccctgca aagtaaact    7740 ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccgcctgtca gcgcagggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
```

```
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
tcgccttcta tcgccttctt gacgagttct tctgacgcat gaccaaaatc ccttaacgtg    8640
agttttcgtt ccactgagcg tcagacccccg tagaaaagat caaaggatct tcttgagatc    8700
cttttttttct gcgcgtaatc tgctgcttgc aaacaaaaaa accaccgcta ccagcggtgg    8760
tttgtttgcc ggatcaagag ctaccaactc tttttccgaa ggtaactggc ttcagcagag    8820
cgcagatacc aaatactgtc cttctagtgt agccgtagtt aggccaccac ttcaagaact    8880
ctgtagcacc gcctacatac ctcgctctgc taatcctgtt accagtggct gctgccagtg    8940
gcgataagtc gtgtcttacc gggttggact caagacgata gttaccggat aaggcgcagc    9000
ggtcgggctg aacggggggt tcgtgcacac agcccagctt ggagcgaacg acctacaccg    9060
aactgagata cctacagcgt gagctatgag aaagcgccac gcttcccgaa gggagaaagg    9120
cggacaggta tccggtaagc ggcagggtcg gaacaggaga gcgcacgagg gagcttccag    9180
ggggaaacgc ctggtatctt tatagtcctg tcgggtttcg ccacctctga cttgagcgtc    9240
gatttttgtg atgctcgtca ggggggcgga gcctatggaa aaacgccagc aacgcggcct    9300
ttttacggtt cctggccttt tgctggcctt ttgctcacat gttctttcct gcgttatccc    9360
ctgattctgt ggataaccgt attaccgcct ttgagtgagc tgataccgct cgccgcagcc    9420
gaacgaccga gcgcagcgag tcagtgagcg aggaagcgga agagcgcctg atgcggtatt    9480
ttctccttac gcatctgtgc ggtatttcac accgcatatg gtgcactctc agtacaatct    9540
gctctgatgc cgcatagtta agccagtata cactccgcta tcgctacgtg actgggtcat    9600
ggctgcgccc cgacacccgc caacaccccgc tgacgcgccc tgacgggctt gtctgctccc    9660
ggcatccgct tacagacaag ctgtgaccgt ctccgggagc tgcatgtgtc agaggttttc    9720
accgtcatca ccgaaacgcg cgaggcagca gatcaattcg cgcgcgaagg cgaagcggca    9780
tgcatttacg ttgacaccat cgaatggtgc aaaacctttc gcggtatggc atgatagcgc    9840
ccggaagaga gtcaattcag ggtggtgaat gtgaaaccag taacgttata cgatgtcgca    9900
gagtatgccg gtgtctctta tcagaccgtt tcccgcgtgg tgaaccaggc cagccacgtt    9960
tctgcgaaaa cgcgggaaaa agtggaagcg gcgatggcgg agctgaatta cattcccaac   10020
cgcgtggcac aacaactggc gggcaaacag tcgttgctga ttggcgttgc cacctccagt   10080
ctggccctgc acgcgccgtc gcaaattgtc gcggcgatta atctcgcgc cgatcaactg    10140
ggtgccagcg tggtggtgtc gatggtagaa cgaagcggcg tcgaagcctg taaagcggcg   10200
gtgcacaatc ttctcgcgca acgcgtcagt gggctgatca ttaactatcc gctggatgac   10260
caggatgcca ttgctgtgga agctgcctgc actaatgttc cggcgttatt cttgatgtc    10320
tctgaccaga cacccatcaa cagtattatt ttctcccatg aagacggtac gcgactgggc   10380
gtggagcatc tggtcgcatt gggtcaccag caaatcgcgc tgttagcggg cccattaagt   10440
tctgtctcgg cgcgtctgcg tctggctggc tggcataaat atctcactcg caatcaaatt   10500
cagccgatag cggaacggga aggcgactgg agtgccatgt ccggttttca acaaaccatg   10560
```

-continued

```
caaatgctga atgagggcat cgttcccact gcgatgctgg ttgccaacga tcagatggcg    10620
ctgggcgcaa tgcgcgccat taccgagtcc gggctgcgcg ttggtgcgga tatctcggta    10680
gtgggatacg acgataccga agacagctca tgttatatcc cgccgtcaac caccatcaaa    10740
caggattttc gcctgctggg gcaaaccagc gtggaccgct tgctgcaact ctctcagggc    10800
caggcggtga agggcaatca gctgttgccc gtctcactgg tgaaaagaaa aaccaccctg    10860
gcgcccaata cgcaaaccgc ctctccccgc gcgttggccg attcattaat gcagctggca    10920
cgacaggttt cccgactgga aagcgggcag tgagcgcaac gcaattaatg tgagttagcg    10980
cgaattgatc tg                                                        10992
```

<210> SEQ ID NO 34
<211> LENGTH: 49
<212> TYPE: DNA
<213> ORGANISM: Artificial Sequence
<220> FEATURE:
<223> OTHER INFORMATION: Synthetic Construct

<400> SEQUENCE: 34

```
gagacatgag ctcaggaggt aaaaaaacat gaaaacagta gttattatt              49
```

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35

```
tttatcaatc ccaattgtca tgttttttta cctcctttat tgttttctta aatc         54
```

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36

```
gatttaagaa aacaataaag gaggtaaaaa aacatgacaa ttgggattga taaa         54
```

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37

```
gacatgacat agatctttag tttcgataag aacgaacggt                         40
```

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38

```
atgaaaacag tagttattat tgatgc                                        26
```

<210> SEQ ID NO 39

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc                                    33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
atgacaattg ggattgataa aattag                                            26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt                                              24

<210> SEQ ID NO 42
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc                                               23

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ttgccaatca tatgattgaa aatc                                              24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg                                             25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
```
gaaacctaca tccaatctttt tgccc                                          25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaattaaag      240
aggtatatat taatgtatcg attaaataag gaggaataaa ccatggatcc gagctcagga     300
ggtaaaaaaa catgaaaaca gtagttatta ttgatgcatt acgaacacca attggaaaat     360
ataaaggcag cttaagtcaa gtaagtgccg tagacttagg aacacatgtt acaacacaac     420
ttttaaaaag acattccact atttctgaag aaattgatca agtaatcttt ggaaatgttt     480
tacaagctgg aaatggccaa atcccgcac gacaaatagc aataaacagc ggtttgtctc      540
atgaaattcc cgcaatgacg gttaatgagg tctgcggatc aggaatgaag gccgttattt     600
ggcgaaaaca attgattcaa ttaggagaag cggaagtttt aattgctggc gggattgaga     660
atatgtccca agcacctaaa ttacaacgtt ttaattacga acagaaagc tacgatgcgc      720
cttttttctag tatgatgtat gatggattaa cggatgcctt tagtggtcag gcaatgggct     780
taactgctga aaatgtggcc gaaaagtatc atgtaactag agaagagcaa gatcaatttt     840
ctgtacattc acaattaaaa gcagctcaag cacaagcaga agggatattc gctgacgaaa     900
tagccccatt agaagtatca ggaacgcttg tggagaaaga tgaagggatt cgccctaatt     960
cgagcgttga agctagga acgcttaaaa cagttttaa agaagacggt actgtaacag    1020
cagggaatgc atcaaccatt aatgatgggg cttctgctt gattattgct tcacaagaat    1080
atgccgaagc acacggtctt ccttatttag ctattattcg agacagtgtg gaagtcggta    1140
ttgatccagc ctatatggga atttcgccga ttaaagccat tcaaaaactg ttagcgcgca    1200
atcaacttac tacggaagaa attgatctgt atgaaatcaa cgaagcatt gcagcaactt     1260
caatcgtggt ccaaagagaa ctggctttac cagaggaaaa ggtcaacatt tatggtggcg    1320
gtatttcatt aggtcatgcg attggtgcca caggtgctcg tttattaacg agtttaagtt    1380
atcaattaaa tcaaaagaa aagaaatatg gagtggcttc tttatgtatc ggcggtggct    1440
taggactcgc tatgctacta gagagacctc agcaaaaaaa aaacagccga ttttatcaaa    1500
tgagtcctga ggaacgcctg gcttctcttc ttaatgaagg ccagatttct gctgatacaa    1560
aaaagaatt tgaaaatacg gctttatctt cgcagattgc caatcatatg attgaaaatc    1620
aaatcagtga aacagaagtg ccgatgggcg ttggcttaca tttaacagtg gacgaaactg    1680
attatttggt accaatggcg acagaagagc cctcagttat tgcggctttg agtaatggtg    1740
caaaaatagc acaaggattt aaaacagtga atcaacaacg cttaatgcgt ggacaaatcg    1800
tttttttacga tgttgcagat cccgagtcat tgattgataa actacaagta agagaagcgg    1860
aagttttcca acaagcagag ttaagttatc atctatcgt taaacggggc ggcggcttaa    1920
gagatttgca atatcgtact tttgatgaat catttgtatc tgtcgacttt ttagtagatg    1980
```

-continued

```
ttaaggatgc aatgggggca aatatcgtta acgctatgtt ggaaggtgtg gccgagttgt      2040
tccgtgaatg gtttgcggag caaaagattt tattcagtat tttaagtaat tatgccacgg      2100
agtcggttgt tacgatgaaa acggctattc cagtttcacg tttaagtaag gggagcaatg      2160
gccgggaaat tgctgaaaaa attgttttag cttcacgcta tgcttcatta gatccttatc      2220
gggcagtcac gcataacaaa ggaatcatga atggcattga agctgtagtt ttagctacag      2280
gaaatgatac acgcgctgtt agcgcttctt gtcatgcttt tgcggtgaag gaaggtcgct      2340
accaaggctt gactagttgg acgctggatg gcgaacaact aattggtgaa atttcagttc      2400
cgcttgcttt agccacggtt ggcggtgcca caaagtctt acctaaatct caagcagctg       2460
ctgatttgtt agcagtgacg gatgcaaaag aactaagtcg agtagtagcg gctgttggtt      2520
tggcacaaaa tttagcggcg ttacgggcct tagtctctga aggaattcaa aaaggacaca      2580
tggctctaca agcacgttct ttagcgatga cggtcggagc tactggtaaa gaagttgagg      2640
cagtcgctca acaattaaaa cgtcaaaaaa cgatgaacca agaccgagcc atggctattt      2700
taaatgattt aagaaaacaa taaggaggt aaaaaaacat gacaattggg attgataaaa       2760
ttagtttttt tgtgccccct tattatattg atatgacggc actggctgaa gccagaaatg      2820
tagaccctgg aaaatttcat attggtattg ggcaagacca aatggcggtg aacccaatca      2880
gccaagatat tgtgacattt gcagccaatg ccgcagaagc gatcttgacc aaagaagata      2940
aagaggccat tgatatggtg attgtcggga ctgagtccag tatcgatgag tcaaaagcgg      3000
ccgcagttgt cttacatcgt ttaatgggga ttcaacctt cgctcgctct ttcgaaatca       3060
aggaagcttt ttacggagca acagcaggct tacagttagc taagaatcac gtagccttac      3120
atccagataa aaaagtcttg gtcgtagcgg cagatattgc aaaatatggc ttaaattctg      3180
gcggtgagcc tacacaagga gctggggcgg ttgcaatgtt agttgctagt gaaccgcgca      3240
ttttggcttt aaaagaggat aatgtgatgc tgacgcaaga tatctatgac ttttggcgtc      3300
caacaggcca cccgtatcct atggtcgatg gtcctttgtc aaacgaaacc tacatccaat      3360
cttttgccca agtctgggat gaacataaaa aacgaaccgg tcttgatttt gcagattatg      3420
atgctttagc gttccatatt ccttacacaa aaatgggcaa aaaagcctta ttagcaaaaa      3480
tctccgacca aactgaagca gaacaggaac gaattttagc ccgttatgaa gaaagtatcg      3540
tctatagtcg tcgcgtagga aacttgtata cgggttcact ttatctggga ctcatttccc      3600
ttttagaaaa tgcaacgact ttaaccgcag gcaatcaaat tggtttattc agttatggtt      3660
ctggtgctgt cgctgaattt ttcactggtg aattagtagc tggttatcaa aatcatttac      3720
aaaaagaaac tcatttagca ctgctggata tcggacaga actttctatc gctgaatatg       3780
aagccatgtt tgcagaaact ttagacacag acattgatca aacgttagaa gatgaattaa      3840
aatatagtat ttctgctatt aataataccg ttcgttctta tcgaaactaa gagatctgca      3900
gctggtacca tatgggaatt cgaagcttgg gcccgaacaa aaactcatct cagaagagga      3960
tctgaatagc gccgtcgacc atcatcatca tcatcattga gtttaaacgg tctccagctt      4020
ggctgttttg gcggatgaga gaagattttc agcctgatac agattaaatc agaacgcaga      4080
agcggtctga taaaacagaa tttgcctggc ggcagtagcg cggtggtccc acctgacccc      4140
atgccgaact cagaagtgaa acgccgtagc gccgatggta gtgtggggtc tccccatgcg      4200
agagtaggga actgccaggc atcaaataaa acgaaaggct cagtcgaaag actgggcctt      4260
tcgttttatc tgttgtttgt cggtgaacgc tctcctgagt aggacaaatc cgccgggagc      4320
ggatttgaac gttgcgaagc aacggcccgg agggtggcgg gcaggacgcc cgccataaac      4380
```

-continued

```
tgccaggcat caaattaagc agaaggccat cctgacggat ggccttttg cgtttctaca    4440
aactctttt  gtttattttt ctaaatacat tcaaatatgt atccgctcat gagacaataa   4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagatttta atgcggatgt tgcgattact tcgccaacta ttgcgataac aagaaaaagc   4800
cagcctttca tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat tgcccagtcg gcagcgacat ccttcggcgc   5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
gctatgttct cttgcttttg tcagcaagat agccagatca atgtcgatcg tggctggctc   5400
gaagatacct gcaagaatgt cattgcgctg ccattctcca aattgcagtt cgcgcttagc   5460
tggataacgc cacggaatga tgtcgtcgtg cacaacaatg gtgacttcta cagcgcggag   5520
aatctcgctc tctccagggg aagccgaagt ttccaaaagg tcgttgatca agctcgccg    5580
cgttgtttca tcaagcctta cggtcaccgt aaccagcaaa tcaatatcac tgtgtggctt   5640
caggccgcca tccactgcgg agccgtacaa atgtacggcc agcaacgtcg gttcgagatg   5700
gcgctcgatg acgccaacta cctctgatag ttgagtcgat acttcggcga tcaccgcttc   5760
cctcatgatg tttaactttg ttttagggcg actgccctgc tgcgtaacat cgttgctgct   5820
ccataacatc aaacatcgac ccacggcgta acgcgcttgc tgcttggatg cccgaggcat   5880
agactgtacc ccaaaaaaac agtcataaca agccatgaaa accgccactg cgccgttacc   5940
accgctgcgt tcggtcaagg ttctggacca gttgcgtgag cgcatacgct acttgcatta   6000
cagcttacga accgaacagg cttatgtcca ctgggttcgt gccttcatcc gtttccacgg   6060
tgtgcgtcac ccggcaacct tgggcagcag cgaagtcgag gcatttctgt cctggctggc   6120
gaacgagcgc aaggtttcgg tctccacgca tcgtcaggca ttggcggcct tgctgttctt   6180
ctacggcaag gtgctgtgca cggatctgcc ctggcttcag gagatcggaa gacctcggcc   6240
gtcgcggcgc ttgccggtgg tgctgacccc ggatgaagtg gttcgcatcc tcggttttct   6300
ggaaggcgag catcgtttgt tcgcccagct tctgtatgga acgggcatgc ggatcagtga   6360
gggtttgcaa ctgcgggtca aggatctgga tttcgatcac ggcacgatca tcgtgcggga   6420
gggcaagggc tccaaggatc gggccttgat gttacccgag agcttggcac ccagcctgcg   6480
cgagcagggg aattaattcc cacgggtttt gctgcccgca acgggctgtt ctgtggtgttg  6540
ctagtttgtt atcagaatcg cagatccggc ttcagccggt tgccggctg aaagcgctat    6600
ttcttccaga attgccatga ttttttcccc acggagggcg tcactggctc ccgtgttgtc   6660
ggcagctttg attcgataag cagcatcgcc tgtttcaggc tgtctatgtg tgactgttga   6720
```

```
gctgtaacaa gttgtctcag gtgttcaatt tcatgttcta gttgctttgt tttactggtt    6780
tcacctgttc tattaggtgt tacatgctgt tcatctgtta cattgtcgat ctgttcatgg    6840
tgaacagctt tgaatgcacc aaaaactcgt aaaagctctg atgtatctat ctttttttaca   6900 ccgttttcat ctgtgcatat ggacagtttt cccttttgata tgtaacggtg aacagttgtt   6960 ctactttgt ttgttagtct tgatgcttca ctgatagata caagagccat aagaacctca     7020
gatccttccg tatttagcca gtatgttctc tagtgtggtt cgttgttttt gcgtgagcca    7080
tgagaacgaa ccattgagat catacttact ttgcatgtca ctcaaaaatt ttgcctcaaa    7140
actggtgagc tgaattttg cagttaaagc atcgtgtagt gttttcttta gtccgttatg     7200
taggtaggaa tctgatgtaa tggttgttgg tattttgtca ccattcattt ttatctggtt    7260
gttctcaagt tcggttacga gatccatttg tctatctagt tcaacttgga aaatcaacgt    7320
atcagtcggg cggcctcgct tatcaaccac caatttcata ttgctgtaag tgtttaaatc    7380
tttacttatt ggtttcaaaa cccattggtt aagccttta aactcatggt agttattttc     7440
aagcattaac atgaacttaa attcatcaag gctaatctct atatttgcct tgtgagtttt    7500
cttttgtgtt agttctttta ataccactc ataaatcctc atagagtatt tgttttcaaa     7560
agacttaaca tgttccagat tatatttat gaattttttt aactggaaaa gataaggcaa     7620
tatctcttca ctaaaaacta attctaattt ttcgcttgag aacttggcat agtttgtcca    7680
ctggaaaatc tcaaagcctt taaccaaagg attcctgatt tccacagttc tcgtcatcag    7740
ctctctggtt gctttagcta atacaccata agcatttttcc ctactgatgt tcatcatctg   7800
agcgtattgg ttataagtga acgataccgt ccgttctttc cttgtagggt tttcaatcgt    7860
ggggttgagt agtgccacac agcataaaat tagcttggtt tcatgctccg ttaagtcata    7920
gcgactaatc gctagttcat ttgctttgaa acaactaat tcagacatac atctcaattg     7980
gtctaggtga tttaatcac tataccaatt gagatgggct agtcaatgat aattactagt     8040
ccttttcctt tgagttgtgg gtatctgtaa attctgctag acctttgctg gaaaacttgt    8100
aaattctgct agaccctctg taaattccgc tagaccttg tgtgttttt tgtttatat       8160 tcaagtggtt ataatttata gaataaagaa agaataaaaa aagataaaaa gaatagatcc    8220
cagccctgtg tataactcac tactttagtc agttccgcag tattacaaaa ggatgtcgca    8280
aacgctgttt gctcctctac aaaacagacc ttaaaaccct aaaggcttaa gtagcacccct   8340 cgcaagctcg ggcaaatcgc tgaatattcc ttttgtctcc gaccatcagg cacctgagtc    8400
gctgtctttt tcgtgacatt cagttcgctg cgctcacggc tctggcagtg aatgggggta    8460
aatggcacta caggcgcctt ttatggattc atgcaaggaa actacccata atacaagaaa    8520
agcccgtcac gggcttctca gggcgtttta tggcgggtct gctatgtggt gctatctgac    8580
tttttgctgt tcagcagttc ctgccctctg attttccagt ctgaccactt cggattatcc    8640
cgtgacaggt cattcagact ggctaatgca cccagtaagg cagcggtatc atcaacaggc    8700
tta                                                                  8703
```

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

```
tgtaaccttt gctttcaaat gagtagaaat aatgcacatc catgtttgta tcgtgcaaat       60
```

-continued

```
aaagtgtttc atccgtagga aaaaatgact ttagtatctg ttccgctttt tctgatgaaa    120
tgtgctcccc gacaaaattg aatgaatcat ggacatttgc tggctttgat acagcgaaag    180
cagccgttcc tatgttatat atcggattta acagcaggac aaaaaacacc atgacagcca    240
tcgtcaccca cttattcaca cgcacataaa cctttcctga cttttggaac agatgatagc    300
tcatcaaaaa tcccgccatt gccaataaaa tcgtatatgg cattactgca ccataatctt    360
ttgagatttg attgggatat ggcgcaagca gcaagacaag cagtccgata atcagcgtat    420
aaaataagcc tagtaagatc ttatccgttc tccaatacag cttgaaaaac actacattca    480
acgcaatggg aagagtgatg atgaaaaaca gaaacacgaa tgcaatcggc tccatcccat    540
ccgggtattc cttccaatac gaaagaaac taaaaatcat ttgtacgatc ggcaaactga    600
caacagcaag gtcgaacgta taaaacttac cctttccgcc atgatcacgc ggcatcagca    660
tatagtgaaa agccgtcagc agcacatatc cgtataacaa aaaatgcagc agcggcagca    720
gttcttttcc gtcctctctt aagtaagcgc tggtgaagtt tgttgattgc acctggtgaa    780
taagttcaac agacactccc gccagcagca caatccgcaa tataacaccc gccaagaaca    840
ttgtgcgctg ccggtttatt tgggatgat gcaccaaaag atataagccc gccagaacaa    900
caattgacca ttgaatcagc agggtgcttt gtctgcttaa tataaaataa cgttcgaaat    960
gcaatacata atgactgaat aactccaaca cgaacaacaa ctccattttc ttctgctatc   1020
aaaataacag actcgtgatt ttccaaacga gctttcaaaa aagcctctgc cccttgcaaa   1080
tcggatgcct gtctataaaa ttcccgatat tggttaaaca gcggcgcaat ggcggccgca   1140
tctgatgtct ttgcttggcg aatgttcatc ttatttcttc ctccctctca ataatttttt   1200
cattctatcc cttttctgta aagtttattt ttcagaatac ttttatcatc atgctttgaa   1260
aaaatatcac gataatatcc attgttctca cggaagcaca cgcaggtcat ttgaacgaat   1320
tttttcgaca ggaatttgcc gggactcagg agcatttaac ctaaaaaagc atgacatttc   1380
agcataatga acatttactc atgtctattt tcgttctttt ctgtatgaaa atagttattt   1440
cgagtctcta cggaaatagc gagagatgat atacctaaat agagataaaa tcatctcaaa   1500
aaaatgggtc tactaaaata ttattccatc tattacaata aattcacaga atagtctttt   1560
aagtaagtct actctgaatt tttttaaaag gagagggtaa agagtgtcat taccgttctt   1620
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980
ccccatgcc aagaatatta agttttcttt aaagtctact ttacccatcg gtgctgggtt   2040
gggctcaagc gcctctattt ctgtatcact ggccttagct atggcctact tgggggggtt   2100
aataggatct aatgacttgg aaaagctgtc agaaaacgat aagcatatag tgaatcaatg   2160
ggccttcata ggtgaaaagt gtattcacgg taccccttca ggaatagata acgctgtggc   2220
cacttatggt aatgccctgc tatttgaaaa agactcacat aatggaacaa taaacacaaa   2280
caattttaag ttcttagatg atttcccagc cattccaatg atcctaacct atactagaat   2340
tccaaggtct acaaaagatc ttgttgctcg cgttcgtgtg ttggtcaccg agaaatttcc   2400
```

-continued

```
tgaagttatg aagccaattc tagatgccat gggtgaatgt gccctacaag gcttagagat    2460
catgactaag ttaagtaaat gtaaaggcac cgatgacgag gctgtagaaa ctaataatga    2520
actgtatgaa caactattgg aattgataag aataaatcat ggactgcttg tctcaatcgg    2580
tgtttctcat cctggattag aacttattaa aaatctgagc gatgatttga gaattggctc    2640
cacaaaactt accggtgctg gtggcggcgg ttgctctttg actttgttac gaagagacat    2700
tactcaagag caaattgaca gcttcaaaaa gaaattgcaa gatgatttta gttacgagac    2760
atttgaaaca gacttgggtg ggactggctg ctgtttgtta agcgcaaaaa atttgaataa    2820
agatcttaaa atcaaatccc tagtattcca attatttgaa aataaaacta ccacaaagca    2880
acaaattgac gatctattat tgccaggaaa cacgaattta ccatggactt cataaaagga    2940
gagggtgtca gagttgagag ccttcagtgc cccagggaaa gcgttactag ctggtggata    3000
tttagtttta gatacaaaat atgaagcatt tgtagtcgga ttatcggcaa gaatgcatgc    3060
tgtagcccat ccttacggtt cattgcaagg gtctgataag tttgaagtgc gtgtgaaaag    3120
taaacaattt aaagatgggg agtggctgta ccatataagt cctaaaagtg gcttcattcc    3180
tgtttcgata ggcggatcta agaaccctt cattgaaaaa gttatcgcta acgtatttag    3240
ctactttaaa cctaacatgg acgactactg caatagaaac ttgttcgtta ttgatatttt    3300
ctctgatgat gcctaccatt ctcaggagga tagcgttacc gaacatcgtg caacagaag    3360 attgagtttt cattcgcaca gaattgaaga agttcccaaa acagggctgg gctcctcggc    3420
aggtttagtc acagttttaa ctacagcttt ggcctccttt tttgtatcgg acctggaaaa    3480
taatgtagac aaatatagag aagttattca taatttagca caagttgctc attgtcaagc    3540
tcagggtaaa attggaagcg ggtttgatgt agcggcggca gcatatggat ctatcagata    3600
tagaagattc ccacccgcat taatctctaa tttgccagat attggaagtg ctacttacgg    3660
cagtaaactg gcgcatttgg ttgatgaaga agactggaat attacgatta aaagtaacca    3720
tttaccttcg ggattaactt tatggatggg cgatattaag aatggttcag aaacagtaaa    3780
actggtccag aaggtaaaaa attggtatga ttcgcatatg ccagaaagct tgaaaatata    3840
tacagaactc gatcatgcaa attctagatt tatggatgga ctatctaaac tagatcgctt    3900
acacgagact catgacgatt acagcgatca gatatttgag tctcttgaga ggaatgactg    3960
tacctgtcaa aagtatcctg aaatcacaga agttagagat gcagttgcca caattagacg    4020
ttcctttaga aaaataacta agaatctggg tgccgatatc gaacctcccg tacaaactag    4080
cttattggat gattgccaga ccttaaaagg agttcttact tgcttaatac ctggtgctgg    4140
tggttatgac gccattgcag tgattactaa gcaagatgtt gatcttaggg ctcaaaccgc    4200
taatgacaaa agattttcta aggttcaatg gctggatgta actcaggctg actgggtgt    4260 taggaaagaa aaagatccgg aaacttatct tgataaataa aaggagaggg tgaccgttta    4320
cacagcatcc gttaccgcac ccgtcaacat cgcaaccctt aagtattggg ggaaagggga    4380
cacgaagttg aatctgccca ccaattcgtc catatcagtg actttatcgc aagatgacct    4440
cagaacgttg acctctgcgg ctactgcacc tgagtttgaa cgcgacactt tgtggttaaa    4500
tggagaacca cacagcatcg acaatgaaag aactcaaaat tgtctgcgcg acctacgcca    4560
attaagaaag gaaatggaat cgaaggacgc ctcattgccc acattatctc aatggaaact    4620
ccacattgtc tccgaaaata actttcctac agcagctggt ttagcttcct ccgctgctgg    4680
ctttgctgca ttggtctctg caattgctaa gttataccaa ttccacagt caacttcaga    4740 aatatctaga atagcaagaa aggggtctgg ttcagcttgt agatcgttgt ttggcggata    4800
```

```
cgtggcctgg gaaatgggaa aagctgaaga tggtcatgat tccatggcag tacaaatcgc    4860
agacagctct gactggcctc agatgaaagc ttgtgtccta gttgtcagcg atattaaaaa    4920
ggatgtgagt tccactcagg gtatgcaatt gaccgtggca acctccgaac tatttaaaga    4980
aagaattgaa catgtcgtac caaagagatt tgaagtcatg cgtaaagcca ttgttgaaaa    5040
agatttcgcc acctttgcaa aggaaacaat gatggattcc aactctttcc atgccacatg    5100
tttggactct ttccctccaa tattctacat gaatgacact tccaagcgta tcatcagttg    5160
gtgccacacc attaatcagt tttacggaga acaatcgtt gcatacacgt ttgatgcagg     5220
tccaaatgct gtgttgtact acttagctga aaatgagtcg aaactctttg catttatcta    5280
taaattgttt ggctctgttc ctggatggga caagaaattt actactgagc agcttgaggc    5340
tttcaaccat caatttgaat catctaactt tactgcacgt gaattggatc ttgagttgca    5400
aaaggatgtt gccagagtga ttttaactca agtcggttca ggcccacaag aaacaaacga    5460
atctttgatt gacgcaaaga ctggtctacc aaaggaataa aaggagaggg tgactgccga    5520
caacaatagt atgccccatg gtgcagtatc tagttacgcc aaattagtgc aaaaccaaac    5580
acctgaagac attttggaag agtttcctga aattattcca ttacaacaaa gacctaatac    5640
ccgatctagt gagacgtcaa atgacgaaag cggagaaaca tgttttcctg gtcatgatga    5700
ggagcaaatt aagttaatga atgaaaattg tattgttttg gattgggacg ataatgctat    5760
tggtgccggt accaagaaag tttgtcattt aatggaaaat attgaaaagg gtttactaca    5820
tcgtgcattc tccgtcttta ttttcaatga acaaggtgaa ttacttttac aacaaagagc    5880
cactgaaaaa ataactttcc ctgatctttg gactaacaca tgctgctctc atccactatg    5940
tattgatgac gaattaggtt tgaagggtaa gctagacgat aagattaagg gcgctattac    6000
tgcggcggtg agaaaactag atcatgaatt aggtattcca gaagatgaaa ctaagacaag    6060
gggtaagttt cacttttttaa acagaatcca ttacatggca ccaagcaatg aaccatgggg    6120
tgaacatgaa attgattaca tcctatttta taagatcaac gctaaagaaa acttgactgt    6180
caacccaaac gtcaatgaag ttagagactt caaatgggtt tcaccaaatg atttgaaaac    6240
tatgtttgct gacccaagtt acaagtttac gccttggttt aagattattt gcgagaatta    6300
cttattcaac tggtgggagc aattagatga cctttctgaa gtggaaaatg acaggcaaat    6360
tcatagaatg ctataaaaaa aaccggcctt ggccccgccg gtttttttatt attttttcttc    6420 ctccgcatgt tcaatccgct ccataatcga cggatggctc cctctgaaaa ttttaacgag    6480
aaacggcggg ttgacccggc tcagtcccgt aacggccaag tcctgaaacg tctcaatcgc    6540
cgcttcccgg tttccggtca gctcaatgcc gtaacggtcg cggcgttttt cctgataccg    6600
ggagacggca ttcgtaattt gaatacatac gaacaaatta ataaagtgaa aaaaatactt    6660
cggaaacatt taaaaaataa ccttattggt acttacatgt ttggatcagg agttgagagt    6720
ggactaaaac caaatagtga tcttgacttt ttagtcgtcg tatctgaacc attgacagat    6780
caaagtaaag aaatacttat acaaaaaatt agacctattt caaaaaaaat aggagataaa    6840
agcaacttac gatatattga attaacaatt attattcagc aagaaatggt accgtggaat    6900
catcctccca aacaagaatt tatttatgga gaatggttac aagagcttta tgaacaagga    6960
tacattcctc agaaggaatt aaattcagat ttaaccataa tgctttacca agcaaaacga    7020 aaaaaataaaa gaatatacgg aaaattatgac ttagaggaat tactacctga tattccatttt   7080 tctgatgtga gaagagccat tatggattcg tcagaggaat taatagataa ttatcaggat    7140
```

```
gatgaaacca actctatatt aactttatgc cgtatgattt taactatgga cacgggtaaa    7200
atcataccaa aagatattgc gggaaatgca gtggctgaat cttctccatt agaacatagg    7260
gagagaattt tgttagcagt tcgtagttat cttggagaga atattgaatg gactaatgaa    7320
aatgtaaatt taactataaa ctatttaaat aacagattaa aaaaattata atgtaacctt    7380
tgctttcaaa tgagtagaaa taatgcacat ccatgtttgt atcgtgcaaa taaagtgttt    7440
catccgtagg aaaaaatgac tttagtatct gttccgcttt ttctgatgaa atgtgctccc    7500
cgacaaaatt gaatgaatca tggacatttg ctggctttga tacagcgaaa gcagccgttc    7560
ctatgttata tatcggattt aacagcagga caaaaaacac catgacagcc atcgtcaccc    7620
acttattcac acgcacataa acctttcctg acttttggaa cagatgatag ctcatcaaaa    7680
atcccgccat tgccaaataa atcgtatatg gcattactgc accataatct tttgagattt    7740
gattgggata tggcgcaagc agcaagacaa gcagtccgat aatcagcgta taaaataagc    7800
ctagtaagat cttatccgtt ctccaataca gcttgaaaaa cactcattc aacgcaatgg    7860 gaagagtgat gatgaaaaac agaaacacga atgcaatcgg ctccatccca tccgggtatt    7920
ccttccaata cgaaaagaaa ctaaaaatca tttgtacgat cggcaaactg acaacagcaa    7980
ggtcgaacgt ataaaactta ccctttccgc catgatcacg cggcatcagc atatagtgaa    8040
aagccgtcag cagcacatat ccgtataaca aaaatgcag cagcggcagc agttcttttc    8100
cgtcctctct taagtaagcg ctggtgaagt ttgttgattg cacctggtga ataagttcaa    8160
cagacactcc cgccagcagc acaatccgca atataacacc cgccaagaac attgtgcgct    8220
gccggtttat tttgggatga tgcaccaaaa gatataagcc cgccagaaca caattgacc    8280 attgaatcag cagggtgctt tgtctgctta atataaaata acgttcgaaa tgcaatacat    8340
aatgactgaa taactccaac acgaacaaca aaagtgcgca ttttataaaa gctaatgatt    8400
cagtccacat aattgataga cgaattctgc tacaggtcac gtggctatgt gaaggatcgc    8460
gcgtccagtt aagagcaaaa acattgacaa aaaaatttat ttatgctaaa atttactatt    8520
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgttttttca    8760 acaaagagat cgccgaacgt cttcaaaatg atcctgaaaa aatattaaaa tggggttgcac    8820 aaatccagct gtctccaacg cccctagcac gtgcttctta ttgtgaaaaa gtcttgcaca    8880
acgaattaat cctgggggca aaacagtatg tcattcttgg agcgggactg gatactttct    8940
gctttcggca tccagaatta gaaaacagct tacaggtttt cgaggttgat catccggcca    9000
cacagcaatt gaaaaaaaat aagctgaagg atgcaaatct gacaattccg ggtcatcttc    9060
attttgttcc tatggatttc accaaaacgt tttcgtatga tcctctctta gatgaaggat    9120 taaaaacac aaaaacattc ttcagccttc tcggagtgtc ttattatgta acacgggaag    9180
aaaatgcaag cttgatcagc aatttatttt ctcatgtccc gcctggaagc tctattgttt    9240
ttgattatgc ggacgaaaca cttttttacag caaaagggac gtcgaatcga gttgaacata    9300
tggtgaagat ggctgccgca agcggggaac cgatgaaatc atgtttcact tatcaagaga    9360
ttgaacatct g                                                        9371
```

<210> SEQ ID NO 48
<211> LENGTH: 4339

<212> TYPE: DNA
<213> ORGANISM: Artificial Sequence
<220> FEATURE:
<223> OTHER INFORMATION: Synthetic Construct

<400> SEQUENCE: 48

```
tagaaaaact catcgagcat caaatgaaac tgcaatttat tcatatcagg attatcaata    60
ccatatttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga atcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca cccccttgtt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggccttcg cccgggctaa ttaggggtg tcgccctta gtcgctgaac atgtgctctg   1200
tttctaccga gaacgtttcc ttcactgaga cggaaaccga ggcacgtcgt agcgcgaact   1260
acgagccgaa tagctgggac tacgatttcc tgctgtcttc cgatactgac gaatctattg   1320
aggtgtacaa agacaaagca aagaaactgg aggctgaagt gcgccgcgaa attaacaacg   1380
agaaagctga attcctgact ctgctggagc tgatcgataa cgtacagcgc ctgggtctgg   1440
gttaccgctt cgaatctgat atccgtcgcg cactggatcg tttcgtaagc agcggcggtt   1500
tcgatggcgt gaccaaaacg agcctgcacg ctaccgcgct gtccttccgt ctgctgcgtc   1560
agcacggctt cgaagtttct caggaagcat tctccggttt caaagatcaa aacggtaact   1620
tcctggaaaa cctgaaagaa gacactaagg cgatcctgag cctgtatgag gcaagctttc   1680
tggccctgga gggtgagaac atcctggatg aggcgcgcgt attcgccatc tcccatctga   1740
aagagctgtc tgaagagaaa atcggtaagg aactggcaga gcaggttaat cacgcactgg   1800
aactgccgct gcatcgtcgt acccagcgtc tggaggcggt ttggtccatc gaagcgtacc   1860
gcaaaaagga ggatgctaac caggttctgc tggaactggc catcctggac tacaacatga   1920
tccagtccgt ttaccagcgt gatctgcgtg aaaacctccg ttggtggcgc cgtgtgggcc   1980
tggcgaccaa actgcacttc gctaaggacc gcctgattga gtcttttac tgggcagtcg   2040
gcgttgcgtt cgaaccctcag tattctgact gccgtaacag cgttgcgaaa atgttcagct   2100
tcgttactat tatcgacgac atctacgacg tttacggtac tctggacgag ctggaactgt   2160
```

```
ttaccgacgc tgtcgaacgt tgggatgtta acgccatcaa cgatctgcct gactacatga    2220
aactgtgctt cctggcactg tataacacga tcaacgaaat tgcatacgac aacctgaaag    2280
acaaaggtga aacatcctg ccgtacctga ctaaagcgtg gcggatctg tgtaacgctt    2340 ttctgcaaga agcgaaatgg ctgtataaca atccactcc gacctttgac gattatttcg    2400
gcaatgcctg gaaatccagc tctggcccgc tgcaactgat cttcgcttat tttgcggttg    2460
tccaaaacat caaaaggag gaaattgaaa acctgcaaaa ataccacgat atcattagcc    2520
gtccttctca tatctttcgc ctgtgcaacg acctggcaag cgcgtccgca gagatcgcac    2580
gtggcgaaac cgctaactct gtttcctgct acatgcgcac caagggcatt tccgaagagc    2640
tggcaaccga gagcgtaatg aatctgatcg acgaaacctg taagaaaatg aacaaagaaa    2700
aactgggtgg ctccctgttc gctaaaccgt tcgtagagac tgctattaac ctggcacgtc    2760
agagccactg cacctaccac aatggtgacg cacatactag cccggatgaa ctgactcgta    2820
aacgtgtact gtctgttatc accgaaccga ttctgccgtt cgaacgttaa ctgcagcgtc    2880
aatcgaaagg gcgacacaaa atttattcta aatgcataat aaatactgat aacatcttat    2940
agtttgtatt atattttgta ttatcgttga catgtataat tttgatatca aaaactgatt    3000 ttcccttat tattttcgag attttatttc ttaattctct ttaacaaact agaaatattg    3060
tatatacaaa aaatcataaa taatagatga atagtttaat tataggtgtt catcaatcga    3120
aaaagcaacg tatcttattt aaagtgcgtt gcttttttct catttataag gttaaataat    3180
tctcatatat caagcaaagt gacaggcgcc cttaaatatt ctgacaaatg ctctttccct    3240
aaaactcccc cataaaaaaa cccgccgaag cgggttttta cgttatttgc ggattaacga    3300
ttactcgtta tcagaaccgc ccaggggggcc cgagcttaag actggccgtc gttttacaac    3360
acagaaagag tttgtagaaa cgcaaaaagg ccatccgtca ggggccttct gcttagtttg    3420
atgcctggca gttccctact ctcgccttcc gcttcctcgc tcactgactc gctgcgctcg    3480
gtcgttcggc tgcggcgagc ggtatcagct cactcaaagg cggtaatacg ttatccaca    3540 gaatcagggg ataacgcagg aaagaacatg tgagcaaaag gccagcaaaa ggccaggaac    3600
cgtaaaaagg ccgcgttgct ggcgtttttc cataggctcc gccccctga cgagcatcac    3660 aaaaatcgac gctcaagtca gaggtggcga acccgacag gactataaag ataccaggcg    3720
tttccccctg gaagctccct cgtgcgctct cctgttccga ccctgccgct taccggatac    3780
ctgtccgcct ttctcccttc gggaagcgtg gcgctttctc atagctcacg ctgtaggtat    3840
ctcagttcgg tgtaggtcgt tcgctccaag ctgggctgtg tgcacgaacc ccccgttcag    3900
cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtgggctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tccttttgatc ttttctacgg ggtctgacgc tcagtggaac    4260
gacgcgcgcg taactcacgt taagggatt tggtcatgag cttgcgccgt cccgtcaagt    4320
cagcgtaatg ctctgctttt                                                4339

<210> SEQ ID NO 49
<211> LENGTH: 6065
<212> TYPE: DNA
<213> ORGANISM: Artificial Sequence
```

<220> FEATURE:
<223> OTHER INFORMATION: Synthetic Construct

<400> SEQUENCE: 49

| | | | | | |
|---|---|---|---|---|---:|
| gtttgacagc | ttatcatcga | ctgcacggtg | caccaatgct | tctggcgtca | ggcagccatc | 60 |
| ggaagctgtg | gtatggctgt | gcaggtcgta | aatcactgca | taattcgtgt | cgctcaaggc | 120 |
| gcactcccgt | tctggataat | gttttttgcg | ccgacatcat | aacggttctg | gcaaatattc | 180 |
| tgaaatgagc | tgttgacaat | taatcatccg | gctcgtataa | tgtgtggaat | tgtgagcgga | 240 |
| taacaatttc | acacaggaaa | cagcgccgct | gagaaaaagc | gaagcggcac | tgctctttaa | 300 |
| caatttatca | gacaatctgt | gtgggcactc | gaccggaatt | atcgattaac | tttattatta | 360 |
| aaaattaaag | aggtatatat | taatgtatcg | attaaataag | gaggaataaa | ccatgtgctc | 420 |
| tgtttctacc | gagaacgttt | ccttcactga | gacggaaacc | gaggcacgtc | gtagcgcgaa | 480 |
| ctacgagccg | aatagctggg | actacgattt | cctgctgtct | tccgatactg | acgaatctat | 540 |
| tgaggtgtac | aaagacaaag | caaagaaact | ggaggctgaa | gtgcgccgcg | aaattaacaa | 600 |
| cgagaaagct | gaattcctga | ctctgctgga | gctgatcgat | aacgtacagc | gcctgggtct | 660 |
| gggttaccgc | ttcgaatctg | atatccgtcg | cgcactggat | cgtttcgtaa | gcagcggcgg | 720 |
| tttcgatggc | gtgaccaaaa | cgagcctgca | cgctaccgcg | ctgtccttcc | gtctgctgcg | 780 |
| tcagcacggt | ttcgaagttt | ctcaggaagc | attctccggt | ttcaaagatc | aaaacggtaa | 840 |
| cttcctggaa | aacctgaaag | aagacactaa | ggcgatcctg | agcctgtatg | aggcaagctt | 900 |
| tctggccctg | gagggtgaga | acatcctgga | tgaggcgcgc | gtattcgcca | tctcccatct | 960 |
| gaaagagctg | tctgaagaga | aaatcggtaa | ggaactggca | gagcaggtta | atcacgcact | 1020 |
| ggaactgccg | ctgcatcgtc | gtacccagcg | tctggaggcg | gtttggtcca | tcgaagcgta | 1080 |
| ccgcaaaaag | gaggatgcta | accaggttct | gctggaactg | gccatcctgg | actacaacat | 1140 |
| gatccagtcc | gtttaccagc | gtgatctgcg | tgaaacctcc | cgttggtggc | gccgtgtggg | 1200 |
| cctggcgacc | aaactgcact | cgctaaggac | ccgcctgatt | gagtcttttt | actgggcagt | 1260 |
| cggcgttgcg | ttcgaacctc | agtattctga | ctgccgtaac | agcgttgcga | aaatgttcag | 1320 |
| cttcgttact | attatcgacg | acatctacga | cgtttacggt | actctggacg | agctggaact | 1380 |
| gtttaccgac | gctgtcgaac | gttgggatgt | taacgccatc | aacgatctgc | ctgactacat | 1440 |
| gaaactgtgc | ttcctggcac | tgtataacac | gatcaacgaa | attgcatacg | acaacctgaa | 1500 |
| agacaaaggt | gaaaacatcc | tgccgtacct | gactaaagcg | tgggcggatc | tgtgtaacgc | 1560 |
| tttctctgcaa | gaagcgaaat | ggctgtataa | caaatccact | ccgaccttg | acgattattt | 1620 |
| cggcaatgcc | tggaaatcca | gctctggccc | gctgcaactg | atcttcgctt | attttgcggt | 1680 |
| tgtccaaaac | atcaaaaagg | aggaaattga | aaacctgcaa | aaataccacg | atatcattag | 1740 |
| ccgtccttct | catatctttc | gcctgtgcaa | cgacctggca | agcgcgtccg | cagagatcgc | 1800 |
| acgtggcgaa | accgctaact | ctgtttcctg | ctacatgcgc | accaagggca | tttccgaaga | 1860 |
| gctggcaacc | gagagcgtaa | tgaatctgat | cgacgaaacc | tgtaagaaaa | tgaacaaaga | 1920 |
| aaaactgggt | ggctccctgt | tcgctaaacc | gttcgtagag | actgctatta | acctggcacg | 1980 |
| tcagagccac | tgcacctacc | acaatggtga | cgcacatact | agcccggatg | aactgactcg | 2040 |
| taaacgtgta | ctgtctgtta | tcaccgaacc | gattctgccg | ttcgaacgtt | aactgcagct | 2100 |
| ggtaccatat | gggaattcga | agctttctag | aacaaaaact | catctcagaa | gaggatctga | 2160 |
| atagcgccgt | cgaccatcat | catcatcatc | attgagttta | aacggtctcc | agcttggctg | 2220 |

```
ttttggcgga tgagagaaga ttttcagcct gatacagatt aaatcagaac gcagaagcgg      2280
tctgataaaa cagaatttgc ctggcggcag tagcgcggtg gtcccacctg accccatgcc      2340
gaactcagaa gtgaaacgcc gtagcgccga tggtagtgtg gggtctcccc atgcgagagt      2400
agggaactgc caggcatcaa ataaaacgaa aggctcagtc gaaagactgg gcctttcgtt      2460
ttatctgttg tttgtcggtg aacgctctcc tgagtaggac aaatccgccg ggagcggatt      2520
tgaacgttgc gaagcaacgg cccggagggt ggcgggcagg acgcccgcca taaactgcca      2580
ggcatcaaat taagcagaag gccatcctga cggatggcct ttttgcgttt ctacaaactc      2640
tttttgttta tttttctaaa tacattcaaa tatgtatccg ctcatgagac aataaccctg      2700
ataaatgctt caataatatt gaaaaaggaa gagtatgagt attcaacatt tccgtgtcgc      2760
ccttattccc ttttttgcgg cattttgcct tcctgttttt gctcacccag aaacgctggt      2820
gaaagtaaaa gatgctgaag atcagttggg tgcacgagtg ggttacatcg aactggatct      2880
caacagcggt aagatccttg agagttttcg ccccgaagaa cgttttccaa tgatgagcac      2940
ttttaaagtt ctgctatgtg gcgcggtatt atcccgtgtt gacgccgggc aagagcaact      3000
cggtcgccgc atacactatt ctcagaatga cttggttgag tactcaccag tcacagaaaa      3060
gcatcttacg gatggcatga cagtaagaga attatgcagt gctgccataa ccatgagtga      3120
taacactgcg gccaacttac ttctgacaac gatcggagga ccgaaggagc taaccgcttt      3180
tttgcacaac atgggggatc atgtaactcg ccttgatcgt tgggaaccgg agctgaatga      3240
agccatacca aacgacgagc gtgacaccac gatgcctgta gcaatggcaa caacgttgcg      3300
caaactatta actggcgaac tacttactct agcttcccgg caacaattaa tagactggat      3360
ggaggcggat aaagttgcag gaccacttct gcgctcggcc cttccggctg gctggtttat      3420
tgctgataaa tctggagccg gtgagcgtgg gtctcgcggt atcattgcag cactggggcc      3480
agatggtaag ccctcccgta tcgtagttat ctacacgacg gggagtcagg caactatgga      3540
tgaacgaaat agacagatcg ctgagatagg tgcctcactg attaagcatt ggtaactgtc      3600
agaccaagtt tactcatata ctttagat tgatttaaaa cttcattttt aatttaaaag      3660
gatctaggtg aagatccttt ttgataatct catgaccaaa atcccttaac gtgagttttc      3720
gttccactga gcgtcagacc ccgtagaaaa gatcaaagga tcttcttgag atcctttttt      3780
tctgcgcgta atctgctgct tgcaaacaaa aaaaccaccg ctaccagcgg tggtttgttt      3840
gccggatcaa gagctaccaa ctcttttttcc gaaggtaact ggcttcagca gagcgcagat      3900
accaaatact gtccttctag tgtagccgta gttaggccac cacttcaaga actctgtagc      3960
accgcctaca tacctcgctc tgctaatcct gttaccagtg gctgctgcca gtggcgataa      4020
gtcgtgtctt accgggttgg actcaagacg atagttaccg gataaggcgc agcggtcggg      4080
ctgaacgggg ggttcgtgca cacagcccag cttggagcga acgacctaca ccgaactgag      4140
atacctacag cgtgagctat gagaaagcgc cacgcttccc gaagggagaa aggcggacag      4200
gtatccggta agcggcaggg tcggaacagg agagcgcacg agggagcttc caggggaaa      4260 cgcctggtat ctttatagtc ctgtcgggtt tcgccacctc tgacttgagc gtcgattttt      4320
gtgatgctcg tcaggggggc ggagcctatg gaaaaacgcc agcaacgcgg cctttttacg      4380
gttcctggcc ttttgctggc cttttgctca catgttcttt cctgcgttat cccctgattc      4440
tgtggataac cgtattaccg cctttgagtg agctgatacc gctcgccgca gccgaacgac      4500
cgagcgcagc gagtcagtga gcgaggaagc ggaagagcgc ctgatgcggt attttctcct      4560
tacgcatctg tgcggtattt cacaccgcat atggtgcact ctcagtacaa tctgctctga      4620
```

```
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct tcgcggtat ggcatgatag cgcccggaag    4920
agagtcaatt cagggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaaagtggaa gcggcgatgg cggagctgaa ttacattccc aaccgcgtgg    5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
cggcgcgtct gcgtctggct ggctggcata aatatctcac tcgcaatcaa attcagccga    5580
tagcggaacg ggaaggcgac tggagtgcca tgtccggttt tcaacaaacc atgcaaatgc    5640
tgaatgaggg catcgttccc actgcgatgc tggttgccaa cgatcagatg gcgctgggcg    5700
caatgcgcgc cattaccgag tccgggctgc gcgttggtgc ggatatctcg gtagtgggat    5760
acgacgatac cgaagacagc tcatgttata cccgccgtc aaccaccatc aaacaggatt    5820
ttcgcctgct ggggcaaacc agcgtggacc gcttgctgca actctctcag ggccaggcgg    5880
tgaagggcaa tcagctgttg cccgtctcac tggtgaaaag aaaaaccacc ctggcgccca    5940
atacgcaaac cgcctctccc cgcgcgttgg ccgattcatt aatgcagctg gcacgacagg    6000
tttcccgact ggaaagcggg cagtgagcgc aacgcaatta atgtgagtta gcgcgaattg    6060
atctg                                                               6065
```

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

```
ttgtctgctc ccggcatccg cttacagaca agctgtgacc gtctccggga gctgcatgtg     60
tcagaggttt tcaccgtcat caccgaaacg cgcgaggcag cagatcaatt cgcgcgcgaa    120
ggcgaagcgg catgcattta cgttgacacc atcgaatggt gcaaaacctt cgcggtatg    180 gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
```

```
tgtaaagcgg cggtgcacaa tcttctcgcg caacgcgtca gtgggctgat cattaactat    600
ccgctggatg accaggatgc cattgctgtg aagctgcct  gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggatttt cgcctgctg  gggcaaacca gcgtggaccg cttgctgcaa   1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aagaggtat  atattaatgt atcgattaaa   1740
taaggaggaa taaccatgt  gtgcgacctc ttctcaattt actcagatta ccagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca cggtgaact  gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaaa gaaggcatt  ataccaagg  ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
```

```
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcatcgc ccttaggagg taaaaaaaaa   3480
tgactgccga caacaatagt atgccccatg gtgcagtatc tagttacgcc aaattagtgc   3540
aaaaccaaac acctgaagac attttggaag agtttcctga aattattcca ttacaacaaa   3600
gacctaatac ccgatctagt gagacgtcaa atgacgaaag cggagaaaca tgttttttctg   3660
gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtctttta ttttcaatga acaaggtgaa ttacttttac   3840
aacaaagagc cactgaaaaa ataacttttcc ctgatctttg gactaacaca tgctgctctc   3900
atccactatg tattgatgac gaattaggtt tgaagggtaa gctagacgat aagattaagg   3960
gcgctattac tgcggcggtg agaaaactag atcatgaatt aggtattcca gaagatgaaa   4020
ctaagacaag gggtaagttt cactttttaa acagaatcca ttacatggca ccaagcaatg   4080
aaccatgggg tgaacatgaa attgattaca tcctatttta taagatcaac gctaaagaaa   4140
acttgactgt caacccaaac gtcaatgaag ttagagactt caaatgggtt tcaccaaatg   4200
atttgaaaac tatgtttgct gacccaagtt acaagtttac gccttggttt aagattattt   4260
gcgagaatta cttattcaac tggtgggagc aattagatga cctttctgaa gtggaaaatg   4320
acaggcaaat tcatagaatg ctataacaac gcgtcctgca gctggtacca tatgggaatt   4380
cgaagctttc tagaacaaaa actcatctca gaagaggatc tgaatagcgc cgtcgaccat   4440
catcatcatc atcattgagt ttaaacggtc tccagcttgg ctgttttggc ggatgagaga   4500
agattttcag cctgatacag attaaatcag aacgcagaag cggtctgata aaacagaatt   4560
tgcctggcgg cagtagcgcg gtggtcccac ctgaccccat gccgaactca gaagtgaaac   4620
gccgtagcgc cgatggtagt gtggggtctc cccatgcgag agtagggaac tgccaggcat   4680
caaataaaac gaaaggctca gtcgaaagac tgggcctttc gttttatctg ttgtttgtcg   4740
gtgaacgctc tcctgagtag acaaatccg ccgggagcgg atttgaacgt tgcgaagcaa   4800
cggcccggag ggtggcgggc aggacgcccg ccataaactg ccaggcatca aattaagcag   4860
aaggccatcc tgacgatgg cctttttgcg tttctacaaa ctcttttttgt ttattttttct   4920
aaatacattc aaatatgtat ccgcttaacc ggaattgcca gctggggcgc cctctggtaa   4980
ggttgggaag ccctgcaaag taaactggat ggctttctcg ccgccaagga tctgatggcg   5040
caggggatca agctctgatc aagagacagg atgaggatcg tttcgcatga ttgaacaaga   5100
tggattgcac gcaggttctc cggccgcttg ggtggagagg ctattcggct atgactgggc   5160
acaacagaca atcggctgct ctgatgccgc cgtgttccgg ctgtcagcgc aggggcgccc   5220
ggttcttttt gtcaagaccg acctgtccgg tgccctgaat gaactgcaag acgaggcagc   5280
```

```
gcggctatcg tggctggcca cgacgggcgt tccttgcgca gctgtgctcg acgttgtcac    5340
tgaagcggga agggactggc tgctattggg cgaagtgccg gggcaggatc tcctgtcatc    5400
tcaccttgct cctgccgaga agtatccat catggctgat gcaatgcggc ggctgcatac     5460
gcttgatccg gctacctgcc cattcgacca ccaagcgaaa catcgcatcg agcgagcacg    5520
tactcggatg gaagccggtc ttgtcgatca ggatgatctg gacgaagagc atcagggct     5580 cgcgccagcc gaactgttcg ccaggctcaa ggcgagcatg cccgacggcg aggatctcgt    5640
cgtgacccat ggcgatgcct gcttgccgaa tatcatggtg gaaaatggcc gcttttctgg    5700
attcatcgac tgtggccggc tgggtgtggc ggaccgctat caggacatag cgttggctac    5760
ccgtgatatt gctgaagagc ttggcggcga atgggctgac cgcttcctcg tgctttacgg    5820
tatcgccgct cccgattcgc agcgcatcgc cttctatcgc cttcttgacg agttcttctg    5880
acatgaccaa aatcccttaa cgtgagtttt cgttccactg agcgtcagac cccgtagaaa    5940
agatcaaagg atcttcttga tccttttttt tctgcgcgt aatctgctgc ttgcaaacaa     6000
aaaaaccacc gctaccagcg gtggtttgtt tgccggatca agagctacca actcttttc     6060 cgaaggtaac tggcttcagc agagcgcaga taccaaatac tgtccttcta gtgtagccgt    6120
agttaggcca ccacttcaag aactctgtag caccgcctac atacctcgct ctgctaatcc    6180
tgttaccagt ggctgctgcc agtggcgata agtcgtgtct taccgggttg gactcaagac    6240
gatagttacc ggataaggcg cagcggtcgg gctgaacggg gggttcgtgc acacagccca    6300
gcttggagcg aacgacctac accgaactga gatacctaca gcgtgagcta tgagaaagcg    6360
ccacgcttcc cgaagggaga aaggcggaca ggtatccggt aagcggcagg gtcggaacag    6420
gagagcgcac gagggagctt ccaggggaa acgcctggta tctttatagt cctgtcgggt     6480
ttcgccacct ctgacttgag cgtcgatttt tgtgatgctc gtcaggggg cggagcctat     6540 ggaaaaacgc cagcaacgcg gccttttac ggttcctggc cttttgctgg cttttgctc      6600 acatgttctt cctgcgtta tcccctgatt ctgtggataa ccgtattacc gcctttgagt    6660
gagctgatac cgctcgccgc agccgaacga ccgagcgcag cgagtcagtg agcgaggaag    6720
cggaagagcg cctgatgcgg tatttctcc ttacgcatct gtgcggtatt tcacaccgca    6780
tatggtgcac tctcagtaca atctgctctg atgccgcata gttaagccag tatacactcc    6840
gctatcgcta cgtgactggg tcatggctgc gccccgacac ccgccaacac ccgctgacgc    6900
gccctgacgg gc                                                         6912

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51
ttgtctgctc ccggcatccg cttacagaca agctgtgacc gtctccggga gctgcatgtg      60
tcagaggttt tcaccgtcat caccgaaacg cgcgaggcag cagatcaatt cgcgcgcgaa     120
ggcgaagcgg catgcattta cgttgacacc atcgaatggt gcaaaacctt tcgcggtatg    180
gcatgatagc gcccggaaga gagtcaattc agggtggtga atgtgaaacc agtaacgtta    240
tacgatgtcg cagagtatgc cggtgtctct tatcagaccg tttccgcgt ggtgaaccag      300 gccagccacg tttctgcgaa aacgcgggaa aaagtggaag cggcgatggc ggagctgaat    360
tacattccca accgcgtggc acaacaactg gcgggcaaac agtcgttgct gattggcgtt    420
```

```
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggattt tcgcctgctg gggcaaacca gcgtggaccg cttgctgcaa   1140
ctctctcagg gccaggcggt gaagggcaat cagctgttgc ccgtctcact ggtgaaaaga   1200 aaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aagaggtat atattaatgt atcgattaaa   1740
taaggaggaa taaaccatgt gtgcgacctc ttctcaattt actcagatta ccgagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa   2160 ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaa agaaggcatt aataccaagg ttgcagaaca   2340
agtgagccac gccctggaac tgccatatca ccagcgtctg caccgtctgg aggcacgttg   2400
gttcctggat aaatacgaac gaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
```

-continued

```
cctgccggac tatatgaaac tgtgtttcct ggcactgtac aacaccgtta acgacacgtc    2820
ctattctatt ctgaaagaga aaggtcataa caacctgtcc tatctgacga aaagctggcg    2880
tgaactgtgc aaagcctttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaaagatga atcgtgaacg cgttagcgac tccaccctgc tgcctaaagc    3300
gttcatggaa atcgcagtta acatggcacg tgtttcccac tgcacctacc agtatgcgga    3360
tggtctgggt cgcccagact acgcgactga aaaccgcatc aaactgctgc tgattgaccc    3420
tttcccgatt aaccagctga tgtatgtcta actgcattcg cccttaggag gtaaaaaaac    3480
atgagttttg atattgccaa ataccccgacc ctggcactgg tcgactccac ccaggagtta    3540
cgactgttgc cgaaagagag tttaccgaaa ctctgcgacg aactgcgccg ctatttactc    3600
gacagcgtga gccgttccag cgggcacttc gcctccgggc tgggcacggt cgaactgacc    3660
gtggcgctgc actatgtcta caacaccccg tttgaccaat tgatttggga tgtgggcat    3720 caggcttatc cgcataaaat tttgaccgga cgccgcgaca aaatcggcac catccgtcag    3780
aaaggcggtc tgcacccgtt cccgtggcgc ggcgaaagcg aatatgacgt attaagcgtc    3840
gggcattcat caacctccat cagtgccgga attggtattg cggttgctgc cgaaaaagaa    3900
ggcaaaaatc gccgcaccgt ctgtgtcatt ggcgatggcg cgattaccgc aggcatggcg    3960
tttgaagcga tgaatcacgc gggcgatatc cgtcctgata tgctggtgat tctcaacgac    4020
aatgaaatgt cgatttccga aaatgtcggc gcgctcaaca accatctggc acagctgctt    4080
tccggtaagc tttactcttc actgcgcgaa ggcgggaaaa aagttttctc tggcgtgccg    4140
ccaattaaag agctgctcaa acgcaccgaa gaacatatta aaggcatggt agtgcctggc    4200
acgttgtttg aagagctggg ctttaactac atcggcccgg tggacggtca cgatgtgctg    4260
gggcttatca ccacgctaaa gaacatgcgc gacctgaaag gcccgcagtt cctgcatatc    4320
atgaccaaaa aaggtcgtgg ttatgaaccg gcagaaaaag acccgatcac tttccacgcc    4380
gtgcctaaat ttgatccctc cagcggttgt ttgccgaaaa gtagcggcgg tttgccgagc    4440
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtcgcg atttactcca ctttcctgca acgcgcctat    4680
gatcaggtgc tgcatgacgt ggcgattcaa aagcttccgg tcctgttcgc catcgaccgc    4740
gcgggcattg ttggtgctga cggtcaaacc catcaggtg cttttgatct ctcttacctg    4800
cgctgcatac cggaaatggt cattatgacc ccgagcgatg aaaacgaatg tcgccagatg    4860
ctctataccg gctatcacta taacgatggc ccgtcagcgg tgcgctaccc gcgtggcaac    4920
gcggtcggcg tggaactgac gccgctggaa aaactaccaa ttggcaaagg cattgtgaag    4980
cgtcgtggcg agaaactggc gatccttaac tttggtacgc tgatgccaga agcggcgaaa    5040
gtcgccgaat cgctgaacgc cacgctggtc gatatgcgtt ttgtgaaacc gcttgatgaa    5100
gcgttaattc tggaaatggc cgccagccat gaagcgctgg tcaccgtaga agaaaacgcc    5160
```

-continued

```
attatgggcg gcgcaggcag cggcgtgaac gaagtgctga tggcccatcg taaaccagta    5220
cccgtgctga acattggcct gccggacttc tttattccgc aaggaactca ggaagaaatg    5280
cgcgccgaac tcggcctcga tgccgctggt atggaagcca aaatcaaggc ctggctggca    5340
taactgcagc tggtaccata tgggaattcg aagctttcta gaacaaaaac tcatctcaga    5400
agaggatctg aatagcgccg tcgaccatca tcatcatcat cattgagttt aaacggtctc    5460
cagcttggct gttttggcgg atgagagaag attttcagcc tgatacagat taaatcagaa    5520
cgcagaagcg gtctgataaa acagaatttg cctggcggca gtagcgcggt ggtcccacct    5580
gaccccatgc cgaactcaga agtgaaacgc cgtagcgccg atggtagtgt ggggtctccc    5640
catgcgagag tagggaactg ccaggcatca aataaaacga aaggctcagt cgaaagactg    5700
ggcctttcgt tttatctgtt gtttgtcggt gaacgctctc ctgagtagga caaatccgcc    5760
gggagcggat ttgaacgttg cgaagcaacg gcccggaggg tggcgggcag gacgcccgcc    5820
ataaactgcc aggcatcaaa ttaagcagaa ggccatcctg acggatggcc tttttgcgtt    5880
tctacaaact cttttttgttt attttttctaa atacattcaa atatgtatcc gcttaaccgg    5940
aattgccagc tggggcgccc tctggtaagg ttgggaagcc ctgcaaagta aactggatgg    6000
ctttctcgcc gccaaggatc tgatggcgca ggggatcaag ctctgatcaa gagacaggat    6060
gaggatcgtt tcgcatgatt gaacaagatg gattgcacgc aggttctccg gccgcttggg    6120
tggagaggct attcggctat gactgggcac aacagacaat cggctgctct gatgccgccg    6180
tgttccggct gtcagcgcag gggcgcccgg ttctttttgt caagaccgac ctgtccggtg    6240
ccctgaatga actgcaagac gaggcagcgc ggctatcgtg gctggccacg acgggcgttc    6300
cttgcgcagc tgtgctcgac gttgtcactg aagcgggaag ggactggctg ctattgggcg    6360
aagtgccggg gcaggatctc ctgtcatctc accttgctcc tgccgagaaa gtatccatca    6420
tggctgatgc aatgcggcgg ctgcatacgc ttgatccggc tacctgccca ttcgaccacc    6480
aagcgaaaca tcgcatcgag cgagcacgta ctcggatgga agccggtctt gtcgatcagg    6540
atgatctgga cgaagagcat caggggctcg cgccagccga actgttcgcc aggctcaagg    6600
cgagcatgcc cgacggcgag gatctcgtcg tgacccatgg cgatgcctgc ttgccgaata    6660
tcatggtgga aaatggccgc ttttctggat tcatcgactg tggccggctg ggtgtggcgg    6720
accgctatca ggacatagcg ttggctaccc gtgatattgc tgaagagctt ggcggcgaat    6780
gggctgaccg cttcctcgtg ctttacggta tcgccgctcc cgattcgcag cgcatcgcct    6840
tctatcgcct tcttgacgag ttcttctgac gcatgaccaa atcccttaa cgtgagtttt    6900
cgttccactg agcgtcagac cccgtagaaa agatcaaagg atcttcttga tccttttt    6960
ttctgcgcgt aatctgctgc ttgcaaacaa aaaaaccacc gctaccagcg gtggtttgtt    7020
tgccggatca agagctacca actctttttc cgaaggtaac tggcttcagc agagcgcaga    7080
taccaaatac tgtccttcta gtgtagccgt agttaggcca ccacttcaag aactctgtag    7140
caccgcctac atacctcgct ctgctaatcc tgttaccagt ggctgctgcc agtggcgata    7200
agtcgtgtct taccgggttg gactcaagac gatagttacc ggataaggcg cagcggtcgg    7260
gctgaacggg gggttcgtgc acacagccca gcttggagca acgacctac accgaactga    7320
gatacctaca gcgtgagcta tgagaaagcg ccacgcttcc cgaagggaga aggcggaca    7380
ggtatccggt aagcggcagg gtcggaacag gagagcgcac gagggagctt ccaggggaa    7440
acgcctggta tctttatagt cctgtcgggt ttcgccacct ctgacttgag cgtcgatttt    7500
```

```
tgtgatgctc gtcagggggg cggagcctat ggaaaaacgc cagcaacgcg gccttttttac    7560 ggttcctggc cttttgctgg cctttgtctc acatgttctt tcctgcgtta tccctgatt     7620 ctgtggataa ccgtattacc gcctttgagt gagctgatac cgctcgccgc agccgaacga    7680
ccgagcgcag cgagtcagtg agcgaggaag cggaagagcg cctgatgcgg tatttttctcc   7740 ttacgcatct gtgcggtatt tcacaccgca tatggtgcac tctcagtaca atctgctctg    7800
atgccgcata gttaagccag tatacactcc gctatcgcta cgtgactggg tcatggctgc    7860
gccccgacac ccgccaacac ccgctgacgc gccctgacgg gc                       7902

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52
ctggcgtaat agcgaagagg cccgcaccga tcgcccttcc caacagttgc gcagcctgaa      60
tggcgaatgg cgcctgatgc ggtattttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca gtatgacgg gctgatactg gccggcagg     600 cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata cgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg ataacgcca cggaatgatg    960 tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
```

-continued

```
gatctgccct ggcttcagga gatcggaaga cctcggccgt cgcggcgctt gccggtggtg    1740
ctgaccccgg atgaagtggt tcgcatcctc ggttttctgg aaggcgagca tcgtttgttc    1800
gcccagcttc tgtatggaac gggcatgcgg atcagtgagg gtttgcaact gcgggtcaag    1860
gatctggatt tcgatcacgg cacgatcatc gtgcgggagg gcaagggctc caaggatcgg    1920
gccttgatgt acccgagag cttggcaccc agcctgcgcg agcagggaa ttaattccca     1980
cgggttttgc tgcccgcaaa cgggctgttc tggtgttgct agtttgttat cagaatcgca    2040
gatccggctt cagccggttt gccggctgaa agcgctattt cttccagaat tgccatgatt    2100
tttttcccac gggaggcgtc actggctccc gtgttgtcgg cagctttgat tcgataagca    2160
gcatcgcctg tttcaggctg tctatgtgtg actgttgagc tgtaacaagt tgtctcaggt    2220
gttcaatttc atgttctagt tgctttgttt tactggtttc acctgttcta ttaggtgtta    2280
catgctgttc atctgttaca ttgtcgatct gttcatggtg aacagctttg aatgcaccaa    2340
aaactcgtaa aagctctgat gtatctatct tttttacacc gttttcatct gtgcatatgg    2400
acagttttcc ctttgatatg taacggtgaa cagttgttct acttttgttt gttagtcttg    2460
atgcttcact gatagataca agagccataa gaacctcaga tccttccgta tttagccagt    2520
atgttctcta gtgtggttcg ttgttttgc gtgagccatg agaacgaacc attgagatca     2580
tacttacttt gcatgtcact caaaaatttt gcctcaaaac tggtgagctg aattttgca     2640
gttaaagcat cgtgtagtgt ttttcttagt ccgttatgta ggtaggaatc tgatgtaatg    2700
gttgttggta ttttgtcacc attcattttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gccttttaaa ctcatggtag ttattttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga attttttaa ctggaaaaga taaggcaata tctcttcact aaaaactaat    3120
tctaattttt cgcttgagaa cttggcatag tttgtccact ggaaaatctc aaagccttta    3180
accaaaggat tcctgattc cacagttctc gtcatcagct ctctggttgc tttagctaat    3240
acaccataag cattttccct actgatgttc atcatctgag cgtattggtt ataagtgaac    3300
gataccgtcc gttctttcct tgtagggttt tcaatcgtgg ggttgagtag tgccacacag    3360
cataaaatta gcttggtttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc ttttcctttg agttgtgggt    3540
atctgtaaat tctgctagac ctttgctgga aaacttgtaa attctgctag accctctgta    3600
aattccgcta gaccttgtg tgttttttt gtttatattc aagtggttat aatttataga     3660
ataaagaaag aataaaaaaa gataaaaaga atagatccca gccctgtgta taactcacta    3720
ctttagtcag ttccgcagta ttacaaaagg atgtcgcaaa cgctgttgc tcctctacaa     3780
aacagacctt aaaaccctaa aggcttaagt agcaccctcg caagctcggg caaatcgctg    3840
aatattcctt ttgtctccga ccatcaggca cctgagtcgc tgtcttttc gtgacattca     3900
gttcgctgcg ctcacggctc tggcagtgaa tgggggtaaa tggcactaca ggcgcctttt    3960
atggattcat gcaaggaaac tacccataat acaagaaaag cccgtcacgg gcttctcagg    4020
```

```
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt accegtctta ctgtcgggaa    4200 ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag acacccagcc gctgtccctg ctggagctga    4680
tcgacgatgt gcagcgcctg ggtctgacct acaaatttga aaagacatc attaaagccc    4740 tggaaaacat cgtactgctg gacgaaaaca aaagaacaa atctgacctg cacgcaaccg    4800
ctctgtcttt ccgtctgctg cgtcagcacg gtttcgaggt ttctcaggat gttttgagc    4860 gtttcaagga taaagaaggt ggtttcagcg gtgaactgaa aggtgacgtc caaggcctgc    4920
tgagcctgta tgaagcgtct tacctgggtt tcgagggtga gaacctgctg gaggaggcgc    4980
gtaccttttc catcacccac ctgaagaaca acctgaaaga aggcattaat accaaggttg    5040
cagaacaagt gagccacgcc ctggaactgc catatcacca gcgtctgcac cgtctggagg    5100
cacgttggtt cctggataaa tacgaaccga agaaccgca tcaccagctg ctgctggagc    5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460 ttaacacccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt ttcccactgc acctaccagt    6060
atggcgatgg tctgggtcgc ccagactacg cgactgaaaa ccgcatcaaa ctgctgctga    6120 ttgaccettt cccgattaac cagctgatgt atgtctaact gcagctggta ccatatggga    6180
attcgaagct ttctagaaca aaaactcatc tcagaagagg atctgaatag cgccgtcgac    6240
catcatcatc atcatcattg agtttaaacg gtctccagct tggctgtttt ggcggatgag    6300
agaagatttt cagcctgata cagattaaat cagaacgcag aagcggtctg ataaaacaga    6360
atttgcctgg cggcagtagc gcggtggtcc cacctgaccc catgccgaac tcagaagtga    6420
```

| | | |
|---|---|---|
| aacgccgtag cgccgatggt agtgtggggt ctccccatgc gagagtaggg aactgccagg | 6480 |
| catcaaataa aacgaaaggc tcagtcgaaa gactgggcct ttcgttttat ctgttgtttg | 6540 |
| tcggtgaacg ctctcctgag taggacaaat ccgccgggag cggatttgaa cgttgcgaag | 6600 |
| caacggcccg gagggtggcg ggcaggacgc ccgccataaa ctgccaggca tcaaattaag | 6660 |
| cagaaggcca tcctgacgga tggcctttttt gcgtttctac aaactctttt tgtttatttt | 6720 |
| tctaaataca ttcaaatatg tatccgctca tgagacaata accctgataa atgcttcaat | 6780 |
| aat | 6783 |

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

| | | |
|---|---|---|
| cccgtcttac tgtcgggaat tcgcgttggc cgattcatta atgcagatta ttgaagcatt | 60 |
| tatcagggtt attgtctcat gagcggatac atatttgaat gtatttagaa aaataaacaa | 120 |
| aaagagtttg tagaaacgca aaaaggccat ccgtcaggat ggccttctgc ttaatttgat | 180 |
| gcctggcagt ttatggcggg cgtcctgccc gccaccctcc gggccgttgc ttcgcaacgt | 240 |
| tcaaatccgc tcccggcgga tttgtcctac tcaggagagc gttcaccgac aaacaacaga | 300 |
| taaaacgaaa ggcccagtct ttcgactgag cctttcgttt tatttgatgc ctggcagttc | 360 |
| cctactctcg catggggaga ccccacacta ccatcggcgc tacggcgttt cacttctgag | 420 |
| ttcggcatgg ggtcaggtgg gaccaccgcg ctactgccgc caggcaaatt ctgttttatc | 480 |
| agaccgcttc tgcgttctga tttaatctgt atcaggctga aaatcttctc tcatccgcca | 540 |
| aaacagccaa gctggagacc gtttaaactc aatgatgatg atgatgatgg tcgacggcgc | 600 |
| tattcagatc ctcttctgag atgagttttt gttctagaaa gcttcgaatt cccatatggt | 660 |
| accagctgca gttagacata catcagctgg ttaatcggga aagggtcaat cagcagcagt | 720 |
| ttgatgcggt tttcagtcgc gtagtctggg cgacccagac catcgccata ctggtaggtg | 780 |
| cagtgggaaa cacgtgccat gttaactgcg atttccatga acgctttagg cagcagggtg | 840 |
| gagtcgctaa cgcgttcacg attcatcttt ttccattcgg cgtcgatcag tttacgcagt | 900 |
| tcttcgcggg cctgttcctc gctggtacca tcgttttcgt gcatgtagct aatgatagaa | 960 |
| ttggtagtct cgccacgttc cagctccgcc gcagaggtgg ccagatcgtt gcacaggcgg | 1020 |
| aagataacgc agctagaacg caccagacca tggaagtcgg tcagggaacg cagcgcgtgg | 1080 |
| tcggagatgt cttcctgctg ctggcatacg gaaaagtaag acggcgccag cagcgctaca | 1140 |
| ccggaggagg aaacgctggc gttttccagg tacttggaga agccgggat aattttgttg | 1200 |
| ttggaccatt tcgcctcttg cagaaaggct ttgcacagtt cacgccagct tttcgtcaga | 1260 |
| taggacaggt tgttatgacc tttctctttc agaatagaat aggacgtgtc gttaacggtg | 1320 |
| ttgtacagtg ccaggaaaca cagtttcata tagtccggca gggtgttaat agcgttaacg | 1380 |
| tcccagcgct ctacagcatc ggtgaacagt tgcagttcgt ccagagtgcc ataaacgtca | 1440 |
| tacacgtcat cgatgatcgt caccagacca acatttttag taacagcttt gcgacattca | 1500 |
| ccaaactgcg ggtctggcgc catacccagt gcccagaaat aaacttccat caggcggtcg | 1560 |
| cgtacaaaat ccagtttgct agccaggccc atctcggtcc accagcggga cagatcttgc | 1620 |

```
agctctttct ggtgcagggt ctgtaccatg ttaaaatcca gcttcgccag ctccagcagc   1680
agctggtgat gcggttcttt cggttcgtat ttatccagga accaacgtgc ctccagacgg   1740
tgcagacgct ggtgatatgg cagttccagg gcgtggctca cttgttctgc aaccttggta   1800
ttaatgcctt ctttcaggtt gttcttcagg tgggtgatgg aaaaggtacg cgcctcctcc   1860
agcaggttct caccctcgaa acccaggtaa gacgcttcat acaggctcag caggccttgg   1920
acgtcacctt tcagttcacc gctgaaacca ccttctttat ccttgaaacg ctcaaaaaca   1980
tcctgagaaa cctcgaaacc gtgctgacgc agcagacgga aagacagagc ggttgcgtgc   2040
aggtcagatt tgttcttttt gttttcgtcc agcagtacga tgttttccag ggctttaatg   2100
atgtcttttt caaatttgta ggtcagaccc aggcgctgca catcgtcgat cagctccagc   2160
agggacagcg gctgggtgtc tacacggttg atcatgcagc gaacttcttc ctccagtttg   2220
gtcgctttct cctccagctt ttccactttc aggtcgttct ccaggattg caggaattcg   2280
aaattccaca ggtttggctg atagtttgcg gaacgacggg aattatgctc ggtaatctga   2340
gtaaattgag aagaggtcgc acacatggtt tattcctcct tatttaatcg atacattaat   2400
atatacctct ttaattttta ataataaagt taatcgataa ttccggtcga gtgcccacac   2460
agattgtctg ataaattgtt aaagagcagt gccgcttcgc tttttctcag cggcgctgtt   2520
tcctgtgtga aattgttatc cgctcacaat tccacacatt atacgagccg atgattaat   2580
tgtcaacagc tcatttcaga atctggcgta atagcgaaga ggcccgcacc gatcgccctt   2640
cccaacagtt gcgcagcctg aatggcgaat ggcgcctgat gcggtatttt ctccttacgc   2700
atctgtgcgg tatttcacac cgcatatggt gcactctcag tacaatctgc tctgatgccg   2760
catagttaag ccagccccga cacccgccaa cacccgctga cgagcttagt aaagccctcg   2820
ctagatttta atgcggatgt tgcgattact tcgccaacta ttgcgataac aagaaaaagc   2880
cagcctttca tgatatatct cccaatttgt gtagggctta ttatgcacgc ttaaaaataa   2940
taaaagcaga cttgacctga tagtttggct gtgagcaatt atgtgcttag tgcatctaac   3000
gcttgagtta agccgcgccg cgaagcggcg tcggcttgaa cgaattgtta gacattattt   3060
gccgactacc ttggtgatct cgcctttcac gtagtggaca aattcttcca actgatctgc   3120
gcgcgaggcc aagcgatctt cttcttgtcc aagataagcc tgtctagctt caagtatgac   3180
gggctgatac tgggccggca ggcgctccat tgcccagtcg gcagcgacat ccttcggcgc   3240
gattttgccg gttactgcgc tgtaccaaat gcgggacaac gtaagcacta catttcgctc   3300
atcgccagcc cagtcgggcg cgagttcca tagcgttaag gtttcattta gcgcctcaaa   3360
tagatcctgt tcaggaaccg gatcaaagag ttcctccgcc gctggaccta ccaaggcaac   3420
gctatgttct cttgcttttg tcagcaagat agccagatca atgtcgatcg tggctggctc   3480
gaagatacct gcaagaatgt cattgcgctg ccattctcca aattgcagtt cgcgcttagc   3540
tggataacgc cacggaatga tgtcgtcgtg cacaacaatg gtgacttcta cagcgcggag   3600
aatctcgctc tctccagggg aagccgaagt ttccaaaagg tcgttgatca aagctcgccg   3660
cgttgtttca tcaagcctta cggtcaccgt aaccagcaaa tcaatatcac tgtgtggctt   3720
caggccgcca tccactgcgg agccgtacaa atgtacggcc agcaacgtcg gttcgagatg   3780
gcgctcgatg acgccaacta cctctgatag ttgagtcgat acttcggcga tcaccgcttc   3840
cctcatgatg tttaactttg ttttagggcg actgccctgc tgcgtaacat cgttgctgct   3900
ccataacatc aaacatcgac ccacggcgta acgcgcttgc tgcttggatg cccgaggcat   3960
agactgtacc ccaaaaaaac agtcataaca agccatgaaa accgccactg cgccgttacc   4020
```

```
accgctgcgt tcggtcaagg ttctggacca gttgcgtgag cgcatacgct acttgcatta    4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggttttct    4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttacccgag agcttggcac ccagcctgcg    4560
cgagcagggg aattaattcc cacgggtttt gctgcccgca acgggctgt tctggtgttg     4620
ctagtttgtt atcagaatcg cagatccggc ttcagccggt ttgccggctg aaagcgctat    4680
ttcttccaga attgccatga tttttccccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat cttttttaca    4980
ccgttttcat ctgtgcatat ggacagtttt ccctttgata tgtaacggtg aacagttgtt    5040
ctactttttgt ttgttagtct tgatgcttca ctgatagata caagagccat aagaacctca    5100
gatccttccg tatttagcca gtatgttctc tagtgtggtt cgttgttttt gcgtgagcca    5160
tgagaacgaa ccattgagat catacttact ttgcatgtca ctcaaaaatt ttgcctcaaa    5220
actggtgagc tgaatttttg cagttaaagc atcgtgtagt gtttttctta gtccgttatg    5280
taggtaggaa tctgatgtaa tggttgttgg tattttgtca ccattcattt ttatctggtt    5340
gttctcaagt tcggttacga gatccatttg tctatctagt tcaacttgga aaatcaacgt    5400
atcagtcggg cggcctcgct tatcaaccac caatttcata ttgctgtaag tgtttaaatc    5460
tttacttatt ggtttcaaaa cccattggtt aagcctttta aactcatggt agttattttc    5520
aagcattaac atgaacttaa attcatcaag gctaatctct atatttgcct tgtgagtttt    5580
cttttgtgtt agttctttta ataaccactc ataaatcctc atagagtatt tgttttcaaa    5640
agacttaaca tgttccagat tatattttat gaattttttt aactggaaaa gataaggcaa    5700
tatctcttca ctaaaaacta attctaattt ttcgcttgag aacttggcat agtttgtcca    5760
ctggaaaatc tcaaagcctt taaccaaagg attcctgatt tccacagttc tcgtcatcag    5820
ctctctggtt gctttagcta atacaccata agcatttttcc ctactgatgt tcatcatctg    5880
agcgtattgg ttataagtga acgataccgt ccgttctttc cttgtagggt tttcaatcgt    5940
ggggttgagt agtgccacac agcataaaat tagcttggtt tcatgctccg ttaagtcata    6000
gcgactaatc gctagttcat ttgctttgaa aacaactaat tcagacatac atctcaattg    6060
gtctaggtga ttttaatcac tataccaatt gagatgggct agtcaatgat aattactagt    6120
ccttttcctt tgagttgtgg gtatctgtaa attctgctag acctttgctg gaaaacttgt    6180
aaattctgct agaccctctg taaattccgc tagacctttg tgtgtttttt ttgtttatat    6240
tcaagtggtt ataatttata gaataaagaa agaataaaaa aagataaaaa gaatagatcc    6300
cagccctgtg tataactcac tactttagtc agttccgcag tattacaaaa ggatgtcgca    6360
```

```
aacgctgttt gctcctctac aaaacagacc ttaaaaccct aaaggcttaa gtagcaccct   6420
cgcaagctcg ggcaaatcgc tgaatattcc ttttgtctcc gaccatcagg cacctgagtc   6480
gctgtctttt tcgtgacatt cagttcgctg cgctcacggc tctggcagtg aatgggggta   6540
aatggcacta caggcgcctt ttatggattc atgcaaggaa actacccata atacaagaaa   6600
agcccgtcac gggcttctca gggcgtttta tggcgggtct gctatgtggt gctatctgac   6660
tttttgctgt tcagcagttc ctgccctctg attttccagt ctgaccactt cggattatcc   6720
cgtgacaggt cattcagact ggctaatgca cccagtaagg cagcggtatc atcaacaggc   6780
tta                                                                6783

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54
ctggcgtaat agcgaagagg cccgcaccga tcgcccttcc caacagttgc gcagcctgaa     60
tggcgaatgg cgcctgatgc ggtattttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca gtatgacggg ctgatactgg gccggcagg     600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacgccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtaccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
```

```
tccacgcatc gtcaggcatt ggcggccttg ctgttcttct acggcaaggt gctgtgcacg    1680
gatctgccct ggcttcagga gatcggaaga cctcggccgt cgcggcgctt gccggtggtg    1740
ctgaccccgg atgaagtggt tcgcatcctc ggttttctgg aaggcgagca tcgtttgttc    1800
gcccagcttc tgtatggaac gggcatgcgg atcagtgagg gtttgcaact gcgggtcaag    1860
gatctggatt tcgatcacgg cacgatcatc gtgcgggagg gcaagggctc caaggatcgg    1920
gccttgatgt tacccgagag cttggcaccc agcctgcgcg agcaggggaa ttaattccca    1980
cgggttttgc tgcccgcaaa cgggctgttc tggtgttgct agtttgttat cagaatcgca    2040
gatccggctt cagccggttt gccggctgaa agcgctattt cttccagaat tgccatgatt    2100
ttttccccac gggaggcgtc actggctccc gtgttgtcgg cagctttgat tcgataagca    2160
gcatcgcctg tttcaggctg tctatgtgtg actgttgagc tgtaacaagt tgtctcaggt    2220
gttcaatttc atgttctagt tgctttgttt tactggtttc acctgttcta ttaggtgtta    2280
catgctgttc atctgttaca ttgtcgatct gttcatggtg aacagctttg aatgcaccaa    2340
aaactcgtaa aagctctgat gtatctatct ttttacacc gttttcatct gtgcatatgg    2400
acagttttcc ctttgatatg taacggtgaa cagttgttct acttttgttt gttagtcttg    2460
atgcttcact gatagataca agagccataa gaacctcaga tccttccgta tttagccagt    2520
atgttctcta gtgtggttcg ttgttttttgc gtgagccatg agaacgaacc attgagatca    2580
tacttacttt gcatgtcact caaaaatttt gcctcaaaac tggtgagctg aattttttgca    2640
gttaaagcat cgtgtagtgt ttttcttagt ccgttatgta ggtaggaatc tgatgtaatg    2700
gttgttggta ttttgtcacc attcattttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gccttttaaa ctcatggtag ttattttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga atttttttaa ctggaaaaga taaggcaata tctcttcact aaaaactaat    3120
tctaattttt cgcttgagaa cttggcatag tttgtccact ggaaaatctc aaagccttta    3180
accaaaggat tcctgatttc cacagttctc gtcatcagct ctctggttgc tttagctaat    3240
acaccataag catttccct actgatgttc atcatctgag cgtattggtt ataagtgaac    3300
gataccgtcc gttctttcct tgtagggttt tcaatcgtgg ggttgagtag tgccacacag    3360
cataaaatta gcttggtttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc ttttccttttg agttgtgggt    3540
atctgtaaat tctgctagac ctttgctgga aaacttgtaa attctgctag accctctgta    3600
aattccgcta gacctttgtg tgttttttttt gtttatattc aagtggttat aatttataga    3660
ataaagaaag aataaaaaaa gataaaaaga atagatccca gccctgtgta taactcacta    3720
ctttagtcag ttccgcagta ttacaaaagg atgtcgcaaa cgctgtttgc tcctctacaa    3780
aacagacctt aaaaccctaa aggcttaagt agcaccctcg caagctcggg caaatcgctg    3840
aatattcctt ttgtctccga ccatcaggca cctgagtcgc tgtcttttc gtgacattca    3900
gttcgctgcg ctcacggctc tggcagtgaa tgggggtaaa tggcactaca ggcgcctttt    3960
```

```
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag cacccagcc gctgtccctg ctggagctga    4680
tcgacgatgt gcagcgcctg ggtctgacct acaaatttga aaaagacatc attaaagccc    4740
tggaaaacat cgtactgctg gacgaaaaca aaaagaacaa atctgacctg cacgcaaccg    4800
ctctgtcttt ccgtctgctg cgtcagcacg gtttcgaggt ttctcaggat gttttttgagc   4860 gtttcaagga taagaaggt ggtttcagcg gtgaactgaa aggtgacgtc caaggcctgc    4920
tgagcctgta tgaagcgtct tacctgggtt tcgagggtga gaacctgctg gaggaggcgc    4980 gtacctttc catcacccac ctgaagaaca acctgaaaga aggcattaat accaaggttg    5040
cagaacaagt gagccacgcc ctggaactgc catatcacca gcgtctgcac cgtctggagg    5100
cacgttggtt cctggataaa tacgaaccga agaaccgca tcaccagctg ctgctggagc    5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt ttcccactgc acctaccagt    6060
atggcgatgt tctgggtcgc ccagactacg cgactgaaaa ccgcatcaaa ctgctgctga    6120 ttgaccctt cccgattaac cagctgatgt atgtctaact gcatcgccct taggaggtaa    6180
aaaaaaatga ctgccgacaa caatagtatg ccccatggtg cagtatctag ttacgccaaa    6240
ttagtgcaaa accaaacacc tgaagacatt ttggaagagt ttcctgaaat tattccatta    6300
caacaaagac ctaatacccg atctagtgag acgtcaaatg acgaaagcgg agaaacatgt    6360
```

```
ttttctggtc atgatgagga gcaaattaag ttaatgaatg aaaattgtat tgttttggat    6420
tgggacgata atgctattgg tgccggtacc aagaaagttt gtcatttaat ggaaaatatt    6480
gaaaagggtt tactacatcg tgcattctcc gtctttattt tcaatgaaca aggtgaatta    6540
cttttacaac aaagagccac tgaaaaaata actttccctg atctttggac taacacatgc    6600
tgctctcatc cactatgtat tgatgacgaa ttaggtttga agggtaagct agacgataag    6660
attaagggcg ctattactgc ggcggtgaga aaactagatc atgaattagg tattccagaa    6720
gatgaaacta agacaagggg taagtttcac tttttaaaca gaatccatta catggcacca    6780
agcaatgaac catggggtga acatgaaatt gattacatcc tattttataa gatcaacgct    6840
aaagaaaact tgactgtcaa cccaaacgtc aatgaagtta gagacttcaa atgggtttca    6900
ccaaatgatt tgaaaactat gtttgctgac ccaagttaca agtttacgcc ttggtttaag    6960
attatttgcg agaattactt attcaactgg tgggagcaat tagatgacct ttctgaagtg    7020
gaaaatgaca ggcaaattca tagaatgcta taacgacgcg tcctgcagct ggtaccatat    7080
gggaattcga agctttctag aacgaaaact catctcagaa gaggatctga atagcgccgt    7140
cgaccatcat catcatcatc attgagttta acggtctcc agcttggctg ttttggcgga    7200
tgagagaaga ttttcagcct gatacagatt aaatcagaac gcagaagcgg tctgataaaa    7260
cagaatttgc ctggcggcag tagcgcggtg gtcccacctg accccatgcc gaactcagaa    7320
gtgaaacgcc gtagcgccga tggtagtgtg gggtctcccc atgcgagagt agggaactgc    7380
caggcatcaa ataaaacgaa aggctcagtc gaaagactgg gcctttcgtt ttatctgttg    7440
tttgtcggtg aacgctctcc tgagtaggac aaatccgccg ggagcggatt tgaacgttgc    7500
gaagcaacgg cccggagggt ggcgggcagg acgcccgcca taaactgcca ggcatcaaat    7560
taagcagaag gccatcctga cggatggcct ttttgcgttt ctacaaactc ttttttgttta    7620 tttttctaaa tacattcaaa tatgtatccg ctcatgagac aataaccctg ataaatgctt    7680
caataat                                                              7687
```

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

```
cccgtcttac tgtcgggaat tcgcgttggc cgattcatta atgcagatta ttgaagcatt      60
tatcagggtt attgtctcat gagcggatac atatttgaat gtatttagaa aaataaacaa     120
aaagagtttg tagaaacgca aaaaggccat ccgtcaggat ggccttctgc ttaatttgat     180
gcctggcagt ttatggcggg cgtcctgccc gccaccctcc gggccgttgc ttcgcaacgt     240
tcaaatccgc tcccggcgga tttgtcctac tcaggagagc gttcaccgac aaacaacaga     300
taaaacgaaa ggcccagtct ttcgactgag cctttcgttt tatttgatgc ctggcagttc     360
cctactctcg catggggaga ccccacacta ccatcggcgc tacggcgttt cacttctgag     420
ttcggcatgg ggtcaggtgg gaccaccgcg ctactgccgc caggcaaatt ctgttttatc     480
agaccgcttc tgcgttctga tttaatctgt atcaggctga aaatcttctc tcatccgcca     540
aaacagccaa gctggagacc gtttaaactc aatgatgatg atgatgatgg tcgacggcgc     600
tattcagatc ctcttctgag atgagttttt gttctagaaa gcttcgaatt cccatatggt     660
```

```
accagctgca gttatgccag ccaggccttg attttggctt ccataccagc ggcatcgagg    720
ccgagttcgg cgcgcatttc ttcctgagtt ccttgcggaa taaagaagtc cggcaggcca    780
atgttcagca cgggtactgg tttacgatgg gccatcagca cttcgttcac gccgctgcct    840
gcgccgccca taatggcgtt ttcttctacg gtgaccagcg cttcatggct ggcggccatt    900
tccagaatta acgcttcatc aagcggtttc acaaaacgca tatcgaccag cgtggcgttc    960
agcgattcgg cgactttcgc cgcttctggc atcagcgtac caaagttaag gatcgccagt   1020
ttctcgccac gacgcttcac aatgcctttg ccaattggta gttttttccag cggcgtcagt  1080
tccacgccga ccgcgttgcc acgcgggtag cgcaccgctg acgggccatc gttatagtga   1140
tagccggtat agagcatctg gcgacattcg ttttcatcgc tcggggtcat aatgaccatt   1200
tccggtatgc agcgcaggta agagagatca aaagcaccct gatgggtttg accgtcagca   1260
ccaacaatgc ccgcgcggtc gatggcgaac aggaccggaa gcttttgaat cgccacgtca   1320
tgcagcacct gatcataggc gcgttgcagg aaagtggagt aaatcgcgac aatgggtttg   1380
tacccaccaa tcgccagacc cgcagcaaag gtcaccgcgt gttgctcggc aattgccacg   1440
tcgaagtagc gatccgggaa tttacgtgaa aactcgacca tgccggaacc ttcacgcatc   1500
gccggagtaa tcgccatcag cttgttgtct ttcgctgccg tttcgcacaa ccagtcgcca   1560
aagattttg aatagctcgg caaaccgccg ctactttcg gcaaacaacc gctggaggga    1620
tcaaatttag gcacgcgtg gaaagtgatc gggtcttttt ctgccggttc ataaccacga    1680
cctttttgg tcatgatatg caggaactgc gggcctttca ggtcgcgcat gttctttagc    1740
gtggtgataa gccccagcac atcgtgaccg tccaccgggc cgatgtagtt aaagcccagc   1800
tcttcaaaca acgtgccagg cactaccatg cctttaatat gttcttcggt gcgtttgagc   1860
agctctttaa ttggcggcac gccagagaaa acttttttcc cgccttcgcg cagtgaagag   1920
taaagcttac cggaaagcag ctgtgccaga tggttgttga gcgcgccgac attttcggaa   1980
atcgacattt cattgtcgtt gagaatcacc agcatatcag gacggatatc gcccgcgtga   2040
ttcatcgctt caaacgccat gcctgcggta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaattta   2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400
cggctcacgc tgtcgagtaa atagcggcgc agttcgtcgc agagtttcgg taaactctct   2460
ttcggcaaca gtcgtaactc ctgggtggag tcgaccagtg ccagggtcgg tatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga aacacgtgcc atgttaactg   2700
cgatttccat gaacgcttta ggcagcaggg tggagtcgct aacgcgttca cgattcatct   2760
tttttccattc ggcgtcgatc agtttacgca gttcttcgcg ggcctgttcc tcgctggtac  2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
```

```
ggtacttgga gaaagccggg ataattttgt tgttggacca tttcgcctct tgcagaaagg    3120 cttttgcacag ttcacgccag cttttcgtca gataggacag gttgttatga cctttctctt   3180
tcagaataga ataggacgtg tcgttaacgg tgttgtacag tgccaggaaa cacagtttca    3240
tatagtccgg cagggtgtta atagcgttaa cgtcccagcg ctctacagca tcggtgaaca    3300
gttgcagttc gtccagagtg ccataaacgt catacacgtc atcgatgatc gtcaccagac    3360
caaacatttt agtaacagct tgcgacatt caccaaactg cgggtctggc gccatacccca   3420 gtgcccagaa ataaacttcc atcaggcggt cgcgtacaaa atccagtttg ctagccaggc    3480
ccatctcggt ccaccagcgg gacagatctt gcagctcttt ctggtgcagg gtctgtacca   3540
tgttaaaatc cagcttcgcc agctccagca gcagctggtg atgcggttct ttcggttcgt    3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca    3720
ggtgggtgat ggaaaaggta cgcgcctcct ccagcaggtt ctcaccctcg aaacccaggt   3780
aagacgcttc atacaggctc agcaggcctt ggacgtcacc tttcagttca ccgctgaaac    3840
caccttcttt atccttgaaa cgctcaaaaa catcctgaga aacctcgaaa ccgtgctgac    3900
gcagcagacg gaaagacaga gcggttgcgt gcaggtcaga tttgttcttt ttgttttcgt    3960
ccagcagtac gatgttttcc agggctttaa tgatgtcttt ttcaaatttg taggtcagac    4020
ccaggcgctg cacatcgtcg atcagctcca gcagggacag cggctgggtg tctacacggt    4080
tgatcatgca gcgaacttct tcctccagtt tggtcgcttt ctcctccagc ttttccactt    4140
tcaggtcgtt ctccagggat tgcaggaatt cgaaattcca caggtttggc tgatagtttg   4200
cggaacgacg ggaattatgc tcggtaatct gagtaaattg agaagaggtc gcacacatgg   4260
tttattcctc cttatttaat cgatacatta atatatacct ctttaatttt taataataaa    4320
gttaatcgat aattccggtc gagtgcccac acagattgtc tgataaattg ttaaagagca    4380
gtgccgcttc gcttttttctc agcggcgctg tttcctgtgt gaaattgtta ccgctcaca   4440 attccacaca ttatacgagc cggatgatta attgtcaaca gctcatttca gaatctggcg   4500
taatagcgaa gaggcccgca ccgatcgccc ttcccaacag ttgcgcagcc tgaatggcga   4560
atggcgcctg atgcggtatt ttctccttac gcatctgtgc ggtatttcac accgcatatg    4620
gtgcactctc agtacaatct gctctgatgc cgcatagtta agccagcccc gacacccgcc   4680
aacacccgct gacgagctta gtaaagccct cgctagattt taatgcggat gttgcgatta    4740
cttcgccaac tattgcgata acaagaaaaa gccagccttt catgatatat ctcccaattt    4800
gtgtagggct tattatgcac gcttaaaaat aataaaagca gacttgacct gatagtttgg   4860
ctgtgagcaa ttatgtgctt agtgcatcta acgcttgagt taagccgcgc cgcgaagcgg   4920
cgtcggcttg aacgaattgt tagacattat ttgccgacta ccttggtgat ctcgcctttc   4980
acgtagtgga caaattcttc caactgatct gcgcgcgagg ccaagcgatc ttcttcttgt    5040
ccaagataag cctgtctagc ttcaagtatg acgggctgat actgggccgg caggcgctcc   5100
attgcccagt cggcagcgac atccttcggc gcgattttgc cggttactgc gctgtaccaa   5160
atgcgggaca acgtaagcac tacatttcgc tcatcgccag cccagtcggg cggcgagttc    5220
catagcgtta aggtttcatt tagcgcctca aatagatcct gttcaggaac cggatcaaag   5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc   5400
```

```
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca atcaatatc actgtgtggc ttcaggccgc catccactgc ggagccgtac     5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg gaacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atcttttttta caccgttttc atctgtgcat atggacagtt    6900 ttcccttttga tatgtaacgg tgaacagttg ttctactttt gtttgttagt cttgatgctt    6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgttttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgtttaaa tctttactta ttggtttcaa aacccattgg    7380
ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgtttttca aagacttaa catgttccag attatatttt     7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
```

| | | | | |
|---|---|---|---|---|
| gtccgttctt | tccttgtagg | gttttcaatc | gtggggttga | gtagtgccac acagcataaa | 7860 |
| attagcttgg | tttcatgctc | cgttaagtca | tagcgactaa | tcgctagttc atttgctttg | 7920 |
| aaaacaacta | attcagacat | acatctcaat | tggtctaggt | gattttaatc actataccaa | 7980 |
| ttgagatggg | ctagtcaatg | ataattacta | gtccttttcc | tttgagttgt gggtatctgt | 8040 |
| aaattctgct | agacctttgc | tggaaaactt | gtaaattctg | ctagaccctc tgtaaattcc | 8100 |
| gctagacctt | tgtgtgtttt | ttttgtttat | attcaagtgg | ttataattta tagaataaag | 8160 |
| aaagaataaa | aaagataaa | aagaatagat | cccagccctg | tgtataactc actactttag | 8220 |
| tcagttccgc | agtattacaa | aaggatgtcg | caaacgctgt | tgctcctct acaaaacaga | 8280 |
| ccttaaaacc | ctaaaggctt | aagtagcacc | ctcgcaagct | cgggcaaatc gctgaatatt | 8340 |
| cctttgtct | ccgaccatca | ggcacctgag | tcgctgtctt | tttcgtgaca ttcagttcgc | 8400 |
| tgcgctcacg | gctctggcag | tgaatggggg | taaatggcac | tacaggcgcc ttttatggat | 8460 |
| tcatgcaagg | aaactaccca | taatacaaga | aaagcccgtc | acgggcttct cagggcgttt | 8520 |
| tatgcgggt | ctgctatgtg | gtgctatctg | acttttgct | gttcagcagt tcctgccctc | 8580 |
| tgattttcca | gtctgaccac | ttcggattat | cccgtgacag | gtcattcaga ctggctaatg | 8640 |
| cacccagtaa | ggcagcggta | tcatcaacag | gctta | | 8675 |

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

| | | | | |
|---|---|---|---|---|
| tcgctgcgct | cggtcgttcg | gctgcggcga | gcggtatcag | ctcactcaaa ggcggtaata | 60 |
| cggttatcca | cagaatcagg | ggataacgca | ggaaagaaca | tgtgagcaaa aggccagcaa | 120 |
| aaggccagga | accgtaaaaa | ggccgcgttg | ctggcgtttt | tccataggct ccgcccccct | 180 |
| gacgagcatc | acaaaaatcg | acgctcaagt | cagaggtggc | gaaacccgac aggactataa | 240 |
| agataccagg | cgtttccccc | tggaagctcc | ctcgtgcgct | ctcctgttcc gaccctgccg | 300 |
| cttaccggat | acctgtccgc | ctttctccct | tcgggaagcg | tggcgctttc tcatagctca | 360 |
| cgctgtaggt | atctcagttc | ggtgtaggtc | gttcgctcca | agctgggctg tgtgcacgaa | 420 |
| cccccgttc | agcccgaccg | ctgcgcctta | tccggtaact | atcgtcttga gtccaacccg | 480 |
| gtaagacacg | acttatcgcc | actggcagca | gccactggta | acaggattag cagagcgagg | 540 |
| tatgtaggcg | gtgctacaga | gttcttgaag | tggtggccta | actacggcta cactagaaga | 600 |
| acagtatttg | gtatctgcgc | tctgctgaag | ccagttacct | tcggaaaaag agttggtagc | 660 |
| tcttgatccg | gcaaacaaac | caccgctggt | agcggtggtt | ttttgtttg caagcagcag | 720 |
| attacgcgca | gaaaaaaagg | atctcaagaa | gatcctttga | tcttttctac ggggtctgac | 780 |
| gctcagtgga | acgaaaactc | acgttaaggg | attttggtca | tgagattatc aaaaaggatc | 840 |
| ttcacctaga | tccttttaaa | ttaaaaatga | agttttaaat | caatctaaag tatatatgag | 900 |
| taaacttggt | ctgacagtta | ccaatgctta | atcagtgagg | cacctatctc agcgatctgt | 960 |
| ctatttcgtt | catccatagt | tgcctgactc | cccgtcgtgt | agataactac gatacgggag | 1020 |
| ggcttaccat | ctggccccag | tgctgcaatg | ataccgcgag | acccacgctc accggctcca | 1080 |
| gatttatcag | caataaacca | gccagccgga | agggccgagc | gcagaagtgg tcctgcaact | 1140 |

```
ttatccgcct ccatccagtc tattaattgt tgccgggaag ctagagtaag tagttcgcca    1200
gttaatagtt tgcgcaacgt tgttgccatt gctacaggca tcgtggtgtc acgctcgtcg    1260
tttggtatgg cttcattcag ctccggttcc caacgatcaa ggcgagttac atgatccccc    1320
atgttgtgca aaaagcggt tagctccttc ggtcctccga tcgttgtcag aagtaagttg    1380
gccgcagtgt tatcactcat ggttatggca gcactgcata attctcttac tgtcatgcca    1440
tccgtaagat gcttttctgt gactggtgag tactcaacca agtcattctg agaatagtgt    1500
atgcggcgac cgagttgctc ttgcccggcg tcaatacggg ataataccgc gccacatagc    1560
agaactttaa aagtgctcat cattggaaaa cgttcttcgg ggcgaaaact ctcaaggatc    1620
ttaccgctgt tgagatccag ttcgatgtaa cccactcgtg cacccaactg atcttcagca    1680
tcttttactt tcaccagcgt ttctgggtga gcaaaaacag gaaggcaaaa tgccgcaaaa    1740
aagggaataa gggcgacacg gaaatgttga atactcatac tcttcctttt tcaatattat    1800
tgaagcattt atcagggtta ttgtctcatg agcggataca tatttgaatg tatttagaaa    1860
aataaacaaa taggggttcc gcgcacattt ccccgaaaag tgccacctga cgtctaagaa    1920
accattatta tcatgacatt aacctataaa aataggcgta tcacgaggcc ctttcgtctc    1980
gcgcgtttcg gtgatgacgg tgaaaacctc tgacacatgc agctcccgga cgggtcaca    2040 gcttgtctgt aagcggatgc cgggagcaga caagcccgtc agggcgcgtc agcgggtgtt    2100
ggcgggtgtc ggggctggct taactatgcg gcatcagagc agattgtact gagagtgcac    2160
catagatctg gagctgtaat ataaaaacct tcttcaacta acggggcagg ttagtgacat    2220
tagaaaaccg actgtaaaaa gtacagtcgg cattatctca tattataaaa gccagtcatt    2280
aggcctatct gacaattcct gaatagagtt cataaacaat cctgcatgat aaccatcaca    2340
aacagaatga tgtacctgta aagatagcgg taaatatatt gaattccctt tattaatgaa    2400
ttttcctgct gtaataatgg gtagaaggta attactatta ttattgatat ttaagttaaa    2460
cccagtaaat gaagtccatg gaataataga aagagaaaaa gcattttcag gtataggtgt    2520
tttgggaaac aatttccccg aaccattata tttctctaca tcagaaaggt ataaatcata    2580
aaactctttg aagtcattct ttacaggagt ccaaatacca gagaatgttt tagatacacc    2640
atcaaaaatt gtataaagtg gctctaactt atcccaataa cctaactctc cgtcgctatt    2700
gtaaccagtt ctaaaagctg tatttgagtt tatcaccctt gtcactaaga aaataaatgc    2760
agggtaaaat ttatatcctt cttgttttat gtttcggtat aaaacactaa tatcaatttc    2820
tgtggttata ctaaaagtcg tttgttggtt caaataatga ttaaatatct cttttctctt    2880
ccaattgtct aaatcaattt tattaaagtt catttgatat gcctcctaaa ttttatcta    2940 aagtgaattt aggaggctta cttgtctgct ttcttcatta gaatcaatcc ttttttaaaa    3000
gtcaatatta ctgtaacata aatatatatt ttaaaaatat cccactttat ccaattttcg    3060
tttgttgaac taatgggtgc tttagttgaa gaataaaaga cctatgcggt gtgaaatacc    3120
gcacagatgc gtaaggagaa ataccgcat caggcgccat cgccattca ggctgcgcaa    3180 ctgttgggaa gggcgatcgg tgcgggcctc ttcgctatta cgccagctgg cgaaaggggg    3240
atgtgctgca aggcgattaa gttgggtaac gccagggttt tcccagtcac gacgttgtaa    3300
aacgacggcc agtgccaagc ttgcatgcct gcactccatt tcttctgct atcaaaataa    3360 cagactcgtg attttccaaa cgagctttca aaaagcctc tgcccttgc aaatcggatg    3420 cctgtctata aaattcccga tattggtaa acagcggcgc aatggcggcc gcatctgatg    3480
tctttgcttg gcgaatgttc atcttatttc ttcctccctc tcaataattt tttcattcta    3540
```

```
tcccttttct gtaaagttta tttttcagaa tactttatc atcatgcttt gaaaaaatat    3600
cacgataata tccattgttc tcacggaagc acacgcaggt catttgaacg aattttttcg    3660
acaggaattt gccgggactc aggagcattt aacctaaaaa agcatgacat ttcagcataa    3720
tgaacattta ctcatgtcta ttttcgttct tttctgtatg aaaatagtta tttcgagtct    3780
ctacggaaat agcgagagat gatataccta aatagagata aaatcatctc aaaaaaatgg    3840
gtctactaaa atattattcc atctattaca ataaattcac agaatagtct tttaagtaag    3900
tctactctga atttttttaa aaggagaggg taaagagtga aaacagtagt tattattgat    3960
gcattacgaa caccaattgg aaaatataaa ggcagcttaa gtcaagtaag tgccgtagac    4020
ttaggaacac atgttacaac acaacttta aaaagacatt ccactatttc tgaagaaatt    4080
gatcaagtaa tctttggaaa tgttttacaa gctggaaatg ccaaaatcc cgcacgacaa    4140 atagcaataa acagcggttt gtctcatgaa attcccgcaa tgacggttaa tgaggtctgc    4200
ggatcaggaa tgaaggccgt tattttggcg aaacaattga ttcaattagg agaagcggaa    4260
gttttaattg ctggcgggat tgagaatatg tcccaagcac ctaaattaca acgttttaat    4320
tacgaaacag aaagctacga tgcgcctttt tctagtatga tgtatgatgg attaacggat    4380
gcctttagtg gtcaggcaat gggcttaact gctgaaaatg tggccgaaaa gtatcatgta    4440
actagagaag agcaagatca attttctgta cattcacaat taaaagcagc tcaagcacaa    4500
gcagaaggga tattcgctga cgaaatagcc ccattagaag tatcaggaac gcttgtggag    4560
aaagatgaag ggattcgccc taattcgagc gttgagaagc taggaacgct taaaacagtt    4620 tttaagaag acggtactgt aacagcaggg aatgcatcaa ccattaatga tggggcttct    4680
gctttgatta ttgcttcaca agaatatgcc gaagcacacg gtcttcctta tttagctatt    4740
attcgagaca gtgtggaagt cggtattgat ccagcctata tgggaatttc gccgattaaa    4800
gccattcaaa aactgttagc gcgcaatcaa cttactacgg aagaaattga tctgtatgaa    4860
atcaacgaag catttgcagc aacttcaatc gtggtccaaa gagaactggc tttaccagag    4920
gaaaaggtca acatttatgg tggcggtatt tcattaggtc atgcgattgg tgccacaggt    4980
gctcgtttat taacgagttt aagttatcaa ttaaatcaaa agaaaagaa atatggagtg    5040 gcttcttat gtatcggcgg tggcttagga ctcgctatgc tactagagag acctcagcaa    5100 aaaaaaaca gccgattta tcaaatgagt cctgaggaac gcctggcttc tcttcttaat    5160
gaaggccaga tttctgctga tacaaaaaaa gaatttgaaa atacggcttt atcttcgcag    5220
attgccaatc atatgattga aaatcaaatc agtgaaacag aagtgccgat gggcgttggc    5280
ttacatttaa cagtggacga aactgattat ttggtaccaa tggcgacaga agagccctca    5340
gttattgcgg ctttgagtaa tggtgcaaaa atagcacaag gatttaaaac agtgaatcaa    5400
caacgcttaa tgcgtggaca aatcgttttt tacgatgttg cagatcccga gtcattgatt    5460
gataaactac aagtaagaga agcggaagtt tttcaacaag cagagttaag ttatccatct    5520
atcgttaaac ggggcggcgg cttaagagat ttgcaatatc gtacttttga tgaatcattt    5580
gtatctgtcg acttttagt agatgttaag gatgcaatgg gggcaaatat cgttaacgct    5640
atgttggaag gtgtggccga gttgttccgt gaatggtttg cggagcaaaa gatttattc    5700 agtattttaa gtaattatgc cacggagtcg gttgttacga tgaaaacggc tattccagtt    5760
tcacgtttaa gtaaggggag caatggccgg gaaattgctg aaaaaattgt tttagcttca    5820
cgctatgctt cattagatcc ttatcgggca gtcacgcata acaaaggaat catgaatggc    5880
```

| | |
|---|---|
| attgaagctg tagttttagc tacaggaaat gatacacgcg ctgttagcgc ttcttgtcat | 5940 |
| gcttttgcgg tgaaggaagg tcgctaccaa ggcttgacta gttggacgct ggatggcgaa | 6000 |
| caactaattg gtgaaatttc agttccgctt gctttagcca cggttggcgg tgccacaaaa | 6060 |
| gtcttaccta atctcaagc agctgctgat ttgttagcag tgacggatgc aaaagaacta | 6120 |
| agtcgagtag tagcggctgt tggtttggca caaaatttag cggcgttacg ggccttagtc | 6180 |
| tctgaaggaa ttcaaaaagg acacatggct ctacaagcac gttctttagc gatgacggtc | 6240 |
| ggagctactg gtaaagaagt tgaggcagtc gctcaacaat taaaacgtca aaaaacgatg | 6300 |
| aaccaagacc gagccatggc tattttaaat gatttaagaa acaataaaa ggagagggtg | 6360 |
| acaattggga ttgataaaat tagtttttttt gtgccccctt attatattga tatgacggca | 6420 |
| ctggctgaag ccagaaatgt agaccctgga aaatttcata ttggtattgg gcaagaccaa | 6480 |
| atggcggtga acccaatcag ccaagatatt gtgcatttg cagccaatgc cgcagaagcg | 6540 |
| atcttgacca agaagataa agaggccatt gatatggtga ttgtcgggac tgagtccagt | 6600 |
| atcgatgagt caaaagcggc cgcagttgtc ttacatcgtt taatgggat tcaaccttc | 6660 |
| gctcgctctt tcgaaatcaa ggaagcttgt tacggagcaa cagcaggctt acagttagct | 6720 |
| aagaatcacg tagccttaca tccagataaa aaagtcttgg tcgtagcggc agatattgca | 6780 |
| aaatatggct taaattctgg cggtgagcct acacaaggag ctggggcggt tgcaatgtta | 6840 |
| gttgctagtg aaccgcgcat tttggcttta aagaggata atgtgatgct gacgcaagat | 6900 |
| atctatgact tttggcgtcc aacaggccac ccgtatccta tggtcgatgg tcctttgtca | 6960 |
| aacgaaacct acatccaatc ttttgcccaa gtctgggatg aacataaaa acgaaccggt | 7020 |
| cttgattttg cagattatga tgctttagcg ttccatattc cttacacaaa aatgggcaaa | 7080 |
| aaagccttat tagcaaaaat ctccgaccaa actgaagcag aacaggaacg aattttagcc | 7140 |
| cgttatgaag aaagtatcgt ctatagtcgt cgcgtaggaa acttgtatac gggttcactt | 7200 |
| tatctgggac tcatttccct tttagaaaat gcaacgactt taaccgcagg caatcaaatt | 7260 |
| ggtttattca gttatggttc tggtgctgtc gctgaatttt tcactggtga attagtagct | 7320 |
| ggttatcaaa atcatttaca aaagaaact catttagcac tgctggataa tcggacagaa | 7380 |
| ctttctatcg ctgaatatga agccatgttt gcagaaactt tagacacaga cattgatcaa | 7440 |
| acgttagaag atgaattaaa atatagtatt tctgctatta ataataccgt tcgttccttat | 7500 |
| cgaaactaaa aaaaccggc cttggccccg ccggtttttt attattttc ttcctccgca | 7560 |
| tgttcaatcc gctccataat cgacggatgg ctccctctga aaatttaac gagaaacggc | 7620 |
| gggttgaccc ggctcagtcc cgtaacggcc aagtcctgaa acgtctcaat cgccgcttcc | 7680 |
| cggtttccgg tcagctcaat gccgtaacgg tcggcggcgt tttcctgata ccggagacg | 7740 |
| gcattcgtaa tcgggatccc cgggtaccga gctcgaattc gtaatcatgt catagctgtt | 7800 |
| tcctgtgtga aattgttatc cgctcacaat tccacacaac atacgagccg gaagcataaa | 7860 |
| gtgtaaagcc tggggtgcct aatgagtgag ctaactcaca ttaattgcgt tgcgctcact | 7920 |
| gcccgctttc cagtcgggaa acctgtcgtg ccagctgcat taatgaatcg gccaacgcgc | 7980 |
| ggggagaggc ggtttgcgta ttgggcgctc ttccgcttcc tcgctcactg ac | 8032 |

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57

```
gaattgctcc attttcttct gctatcaaaa taacagactc gtgatttttcc aaacgagctt      60
tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa ttttttcatt ctatccctttt tctgtaaagt ttatttttca     240
gaatactttt atcatcatgc tttgaaaaaa tatcacgata atatccattg ttctcacgga     300
agcacacgca ggtcatttga acgaattttt tcgacaggaa tttgccggga ctcaggagca     360
tttaacctaa aaaagcatga catttcagca taatgaacat ttactcatgt ctattttcgt     420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
acaataaatt cacagaatag tcttttaagt aagtctactc tgaattttt taaaaggaga     600
gggtaaagag tgtgtgcgac ctcttctcaa tttactcaga ttaccgagca taattcccgt     660
cgttccgcaa actatcagcc aaacctgtgg aatttcgaat tcctgcaatc cctggagaac     720
gacctgaaag tggaaaagct ggaggagaaa gcgaccaaac tggaggaaga agttcgctgc     780
atgatcaacc gtgtagacac ccagccgctg tccctgctgg agctgatcga cgatgtgcag     840
cgcctgggtc tgacctacaa atttgaaaaa gacatcatta aagccctgga aaacatcgta     900
ctgctggacg aaaacaaaaa gaacaaatct gacctgcacg caaccgctct gtcttttccgt     960
ctgctgcgtc agcacggttt cgaggtttct caggatgttt ttgagcgttt caaggataaa    1020
gaaggtggtt tcagcggtga actgaaaggt gacgtccaag gcctgctgag cctgtatgaa    1080
gcgtcttacc tgggtttcga gggtgagaac ctgctggagg aggcgcgtac cttttccatc    1140
acccacctga agaacaacct gaaagaaggc attaatacca aggttgcaga acaagtgagc    1200
cacgccctgg aactgccata tcaccagcgt ctgcaccgtc tggaggcacg ttggttcctg    1260
gataaatacg aaccgaaaga accgcatcac cagctgctgc tggagctggc gaagctggat    1320
tttaacatgg tacagaccct gcaccagaaa gagctgcaag atctgtcccg ctggtggacc    1380
gagatgggcc tggctagcaa actggatttt gtacgcgacc gcctgatgga agtttatttc    1440
tgggcactgg gtatggcgcc agacccgcag tttggtgaat gtcgcaaagc tgttactaaa    1500
atgtttggtc tggtgacgat catcgatgac gtgtatgacg tttatggcac tctggacgaa    1560
ctgcaactgt tcaccgatgc tgtagagcgc tgggacgtta acgctattaa caccctgccg    1620
gactatatga aactgtgttt cctggcactg tacaacaccg ttaacgacac gtccatttct    1680
attctgaaag agaaaggtca taacaacctg tcctatctga cgaaaagctg gcgtgaactg    1740
tgcaaagcct ttctgcaaga ggcgaaatgg tccaacaaca aaattatccc ggctttctcc    1800
aagtacctgg aaaacgccag cgtttcctcc tccggtgtag cgctgctggc gccgtcttac    1860
ttttccgtat gccagcagca ggaagacatc tccgaccacg cgctgcgttc cctgaccgac    1920
ttccatggtc tggtgcgttc tagctgcgtt atcttccgcc tgtgcaacga tctggccacc    1980
tctgcggcgg agctggaacg tggcgagact accaattcta tcattagcta catgcacgaa    2040
aacgatggta ccagcgagga acaggcccgc gaagaactgc gtaaactgat cgacgccgaa    2100
tggaaaaaga tgaatcgtga acgcgttagc gactccaccc tgctgcctaa agcgttcatg    2160
gaaatcgcag ttaacatggc acgtgtttcc cactgcacct accagtatgg cgatggtctg    2220
ggtcgcccag actacgcgac tgaaaaccgc atcaaactgc tgctgattga cccttttccg    2280
```

```
attaaccagc tgatgtatgt ctaaaaaaaa ccggccttgg ccccgccggt ttttattat    2340 ttttcttcct ccgcatgttc aatccgctcc ataatcgacg gatggctccc tctgaaaatt    2400
ttaacgagaa acggcgggtt gacccggctc agtcccgtaa cggccaagtc ctgaaacgtc    2460
tcaatcgccg cttcccggtt tccggtcagc tcaatgccgt aacggtcggc ggcgttttcc    2520
tgataccggg agacggcatt cgtaatcgga tcctctagag tcgacctgca ggcatgcaag    2580
ctttgcctcg cgcgtttcgg tgatgacggt gaaaacctct gacacatgca gctcccggag    2640
acggtcacag cttgtctgta agcggatgcc gggagcagac aagcccgtca gggcgcgtca    2700
gcgggtgttg gcgggtgtcg ggcgcagcc atgacccagt cacgtagcga tagcggagtg    2760
tatactggct taactatgcg gcatcagagc agattgtact gagagtgcac catatgcggt    2820
gtgaaatacc gcacagatgc gtaaggagaa ataccgcat caggcgctct ccgcttcct    2880 cgctcactga ctcgctgcgc tcggtcgttc ggctgcggcg agcggtatca gctcactcaa    2940
aggcggtaat acggttatcc acagaatcag gggataacgc aggaaagaac atgtgagcaa    3000
aaggccagca aaaggccagg aaccgtaaaa aggccgcgtt gctggcgttt ttccataggc    3060
tccgcccccc tgacgagcat cacaaaaatc gacgctcaag tcagaggtgg cgaaacccga    3120
caggactata aagataccag gcgtttcccc ctggaagctc cctcgtgcgc tctcctgttc    3180
cgaccctgcc gcttaccgga tacctgtccg cctttctccc ttcgggaagc gtggcgcttt    3240
ctcaatgctc acgctgtagg tatctcagtt cggtgtaggt cgttcgctcc aagctgggct    3300
gtgtgcacga accccccgtt cagcccgacc gctgcgcctt atccggtaac tatcgtcttg    3360
agtccaaccc ggtaagacac gacttatcgc cactggcagc agccactggt aacaggatta    3420
gcagagcgag gtatgtaggc ggtgctacag agttcttgaa gtggtggcct aactacggct    3480
acactagaag gacagtattt ggtatctgcg ctctgctgaa gccagttacc ttcggaaaaa    3540
gagttggtag ctcttgatcc ggcaaacaaa ccaccgctgg tagcggtggt ttttttgttt    3600
gcaagcagca gattacgcgc agaaaaaaag gatctcaaga agatcctttg atcttttcta    3660
cggggtctga cgctcagtgg aacgaaaact cacgttaagg gattttggtc atgagattat    3720
caaaaaggat cgaagtcggt tcagaaaaag aaggatatgg atctggagct gtaatataaa    3780
aaccttcttc aactaacggg gcaggttagt gacattagaa aaccgactgt aaaaagtaca    3840
gtcggcatta tctcatatta taaaagccag tcattaggcc tatctgacaa ttcctgaata    3900
gagttcataa acaatcctgc atgataacca tcacaaacag aatgatgtac ctgtaaagat    3960
agcggtaaat atattgaatt accttttatta atgaattttc ctgctgtaat aatgggtaga    4020
aggtaattac tattattatt gatatttaag ttaaacccag taaatgaagt ccatggaata    4080
atagaaagag aaaaagcatt ttcaggtata ggtgttttgg gaaacaattt aaaagaacca    4140
ttatatttct ctacatcaga aaggtataaa tcataaaact ctttgaagtc attctttaca    4200
ggagtccaaa taccagagaa tgttttagat acaccatcaa aaattgtata agtggctct    4260 aacttatccc aataacctaa ctctccgtcg ctattgtaac cagttctaaa gctgtatttt    4320
gagtttatca cccttgtcac taagaaaata aatgcagggt aaaatttata tccttcttgt    4380
tttatgtttc ggtataaaac actaatatca atttctgtgg ttatactaaa agtcgtttgt    4440
tggttcaaat aatgattaaa tatctctttt ctcttccaat tgtctaaatc aattttatta    4500
aagttcattt gatatgcctc ctaaattttt atctaaagtg aatttaggag gcttacttgt    4560
ctgctttctt cattagaatc aatcctttt taaagtcaat attactgtaa cataaatata    4620
tattttaaaa atatcccact ttatccaatt ttcgtttgtt gaactaatgg gtgctttagt    4680
```

```
tgaagaataa agaccacatt aaaaaatgtg gtcttttgtg ttttttttaaa ggatttgagc    4740 gtacgcgaaa aatccttttc tttcttttctt atcttgataa taagggtaac tattgccggt    4800
tgtccattca tggctgaact ctgcttcctc tgttgacatg acacacatca tctcaatatc    4860
cgaatagggc ccatcagtct gacgaccaag agagccataa acaccaatag ccttaacatc    4920
atccccatat ttatccaata ttcgttcctt aatttcatga acaatcttca ttctttcttc    4980
tctagtcatt attattggtc cattcactat tctcattccc ttttcagata attttagatt    5040
tgcttttcta aataagaata tttggagagc accgttctta ttcagctatt aataactcgt    5100
cttcctaagc atccttcaat cctttttaata acaattatag catctaatct tcaacaaact    5160
ggcccgtttg ttgaactact ctttaataaa ataatttttc cgttcccaat tccacattgc    5220
aataatagaa aatccatctt catcggcttt tcgtcatca tctgtatgaa tcaaatcgcc    5280
ttcttctgtg tcatcaaggt ttaatttttt atgtatttct tttaacaaac caccatagga    5340
gattaacctt ttacggtgta aaccttcctc caaatcagac aaacgtttca aattcttttc    5400
ttcatcatcg gtcataaaat ccgtatcctt tacaggatat tttgcagttt cgtcaattgc    5460
cgattgtata tccgatttat atttattttt cggtcgaatc atttgaactt ttacatttgg    5520
atcatagtct aatttcattg cctttttcca aaattgaatc cattgttttt gattcacgta    5580
gttttctgtt attctaaaat aagttggttc cacacatacc attacatgca tgtgctgatt    5640
ataagaatta tctttattat ttattgtcac atccgttgca cgcataaaac caacaagatt    5700
tttattaatt ttttttatatt gcatcattcg gcgaaatcct tgagccatat ctgtcaaact    5760
cttatttaat tcttcgccat cataaacatt tttaactgtt aatgtgagaa acaaccaacg    5820
aactgttggc ttttgtttaa taacttcagc aacaaccttt tgtgactgaa tgccatgttt    5880
cattgctctc ctccagttgc acattggaca aagcctggat ttgcaaaacc acactcgata    5940
ccactttctt tcgcctgttt cacgattttg tttatactct aatatttcag cacaatcttt    6000
tactctttca gccttttttaa attcaagaat atgcagaagt tcaaagtaat caacattagc    6060
gattttcttt tctctccatg gtctcacttt tccactttttt gtcttgtcca ctaaaaccct    6120 tgattttttca tctgaataaa tgctactatt aggacacata atattaaaag aaaccccat     6180 ctatttagtt atttgtttag tcacttataa ctttaacaga tggggttttt ctgtgcaacc    6240
aattttaagg gttttcaata cttttaaaaca catacatacc aacacttcaa cgcacctttc    6300
agcaactaaa ataaaaatga cgttatttct atatgtatca agataagaaa gaacaagttc    6360
aaaaccatca aaaaaagaca cctttttcagg tgctttttttt attttataaa ctcattccct    6420
gatctcgact tcgttctttt tttacctctc ggttatgagt tagttcaaat tcgttctttt    6480
taggttctaa atcgtgtttt tcttggaatt gtgctgtttt atcctttacc ttgtctacaa    6540 acccccttaaa aacgttttta aaggcttttta agccgtctgt acgttcctta ag          6592
```

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58

```
gacatcaatt gctccatttt cttctgctat c                                     31
```

<210> SEQ ID NO 59

<211> LENGTH: 39
<212> TYPE: DNA
<213> ORGANISM: Artificial Sequence
<220> FEATURE:
<223> OTHER INFORMATION: Synthetic Construct

<400> SEQUENCE: 59
attgagaaga ggtcgcacac actctttacc ctctcctttt    39

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t    41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
ccaaggccgg ttttttttag acatacatca gctggttaat c    41

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g    41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc    32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c    31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65

```
gacatgaatt cctccatttt cttctgc                                                27
```

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66

```
aggagagggt aaagagtgag                                                         20
```

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67

```
cttttccatc acccacctga ag                                                      22
```

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68

```
ggcgaaatgg tccaacaaca aaattatc                                                28
```

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69

```
ggtgaattca gtctactggg gattcccaaa tctatatata ctgcaggtga c                      51
```

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70

```
gcaggtggga aactatgcac tcc                                                     23
```

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71

```
cctgaattct gttggattgg aggattggat agtggg                                       36
```

<210> SEQ ID NO 72
<211> LENGTH: 30
<212> TYPE: DNA

```
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                        30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                                     32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                             40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                                 36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                                37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg                                  35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                                  35
```

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c                                  31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                              7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                              7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                                       27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa                      42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg                      42

<210> SEQ ID NO 85
<211> LENGTH: 45
<212> TYPE: DNA
<213> ORGANISM: Artificial Sequence
<220> FEATURE:

<223> OTHER INFORMATION: Synthetic Construct

<400> SEQUENCE: 85
cggggccaag gccggttttt tttagtttcg ataagaacga acggt                45

<210> SEQ ID NO 86
<211> LENGTH: 45
<212> TYPE: DNA
<213> ORGANISM: Artificial Sequence
<220> FEATURE:
<223> OTHER INFORMATION: Synthetic Construct

<400> SEQUENCE: 86
accgttcgtt cttatcgaaa ctaaaaaaaa ccggccttgg ccccg                45

<210> SEQ ID NO 87
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 87

| | | |
|---|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| cttttctcgcc acgttcgccg gctttccccg tcaagctcta atcggggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct tgacgttgg agtccacgtt | 300 |
| ctttaatagt ggactcttgt tccaaactgg aacaacactc accctatct cggtctattc | 360 |
| ttttgattta tagggattt tgccgatttc ggcctattgg ttaaaaaatg agctgattta | 420 |
| acaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaaccacc gctaccagcg | 1560 |

```
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

```
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccacttttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttcacc gaaactgaaa ccgaagctcg tcgttctgcg aactacgaac ctaacagctg   5160
ggactatgat tacctgctgt cctccgacac ggacgagtcc atcgaagtat acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt ggtgcgctgg atcgcttcgt ttcctccggc ggcttcgatg cggtaaccaa   5400
gacttccctg cacggtacgg cactgtcttt ccgtctgctg cgtcaacacg ttttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gaaccatgca ctggaactgc cactgcatcg   5700
ccgtactcag cgtctggaag cagtatggtc tatcgaggcc taccgtaaaa aggaggacgc   5760
gaatcaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
cttttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgaccctt tgacgactac ttcggcaacg catggaaatc   6300
```

```
ctcttctggc cgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480
tagcgtttct tgttacatgc gcactaaagg tatctccgaa gaactggcta ccgaaagcgt    6540
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taacccttg     6900 gggcctctaa acgggtcttg aggggttttt tgctgaaagg aggaactata tccggat        6957
```

<210> SEQ ID NO 88
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 88

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg cctccgaca cggacgagtc      540 catcgaagta tacaaagaca aagcgaaaaa gctggaagcc gaagttcgtc gcgagattaa     600
taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcgtaaccaa agacttccct gcacggtacg gcactgtctt ccgtctgct      780 gcgtcaacac ggttttgagg tttctcagga agcgttcagc ggcttcaaag accaaaacgg     840
caacttcctg gagaacctga aggaagatat caaagctatc ctgagcctgt acgaggccag     900
cttcctggct ctggaaggcg aaaacatcct ggacgaggcg aaggttttcg caatctctca     960
tctgaaagaa ctgtctgaag aaaagatcgg taaagagctg gcagaacagg tgaaccatgc    1020
actggaactg ccactgcatc gccgtactca gcgtctggaa gcagtatggt ctatcgaggc    1080
ctaccgtaaa aaggaggacg cgaatcaggt tctgctggag ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc     1260 cgtgggtgta gcattcgaac cgcaatactc cgactgccgt aactccgtcg caaaaatgtt    1320
ttctttcgta accattatcg acgatatcta cgatgtatac ggcaccctgg acgaactgga    1380
```

```
gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgctttcctg caagaagcca gtggctgta  caacaaatct actccgacct ttgacgacta    1620
cttcggcaac gcatggaaat cctcttctgg cccgctgcaa ctggtgttcg cttacttcgc    1680
tgtcgtgcag aacattaaaa aggaagagat cgaaaacctg caaaaatacc atgcaccat     1740 ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaaccgcga tcaacctggc    1980
acgtcaatct cactgcactt atcataacgg cgacgcgcat acctctccgg atgagctgac    2040
ccgcaaacgc gttctgtctg taatcactga accgattctg ccgtttgaac gctaactgca    2100
gctggtacca tatgggaatt cgaagctttc tagaacaaaa actcatctca gaagaggatc    2160
tgaatagcgc cgtcgaccat catcatcatc atcattgagt ttaaacggtc tccagcttgg    2220
ctgttttggc ggatgagaga agattttcag cctgatacag attaaatcag aacgcagaag    2280
cggtctgata aaacagaatt tgcctggcgg cagtagcgcg gtggtccac  ctgaccccat     2340 gccgaactca gaagtgaaac gccgtagcgc cgatggtagt gtggggtctc ccatgcgag     2400 agtagggaac tgccaggcat caaataaaac gaaaggctca gtcgaaagac tgggcctttc    2460 gtttatctg ttgtttgtcg gtgaacgctc tcctgagtag acaaatccg  ccgggagcgg     2520 atttgaacgt tgcgaagcaa cggcccggag ggtggcgggc aggacgcccg ccataaactg    2580
ccaggcatca aattaagcag aaggccatcc tgacggatgg cctttttgcg tttctacaaa    2640 ctcttttgt  ttatttttct aaatacattc aaatatgtat ccgctcatga caataacc      2700 ctgataaatg cttcaataat attgaaaaag gaagagtatg agtattcaac atttccgtgt    2760
cgcccttatt cccttttttg cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag    2940
cacttttaaa gttctgctat gtggcgcggt attatcccgt gttgacgccg ggcaagagca    3000
actcggtcgc cgcatacact attctcagaa tgacttggtt gagtactcac cagtcacaga    3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat taatagactg    3360
gatggaggcg gataaagttg caggaccact tctgcgctcg gcccttccgg ctggctggtt    3420
tattgctgat aaatctggag ccggtgagcg tgggtctcgc ggtatcattg cagcactggg    3480
gccagatggt aagcccctcc cgtatcgtagt tatctcacg acgggagtc  aggcaactat     3540 ggatgaacga aatagacaga tcgctgagat aggtgcctca ctgattaagc attggtaact    3600
gtcagaccaa gtttactcat atatacttta gattgattta aaacttcatt tttaatttaa    3660
aaggatctag gtgaagatcc tttttgataa tctcatgacc aaaatccctt aacgtgagtt    3720
ttcgttccac tgagcgtcag accccgtaga aaagatcaaa ggatcttctt gagatccttt    3780
```

```
ttttctgcgc gtaatctgct gcttgcaaac aaaaaaacca ccgctaccag cggtggtttg    3840
tttgccggat caagagctac caactctttt tccgaaggta actggcttca gcagagcgca    3900
gataccaaat actgtccttc tagtgtagcc gtagttaggc caccacttca agaactctgt    3960
agcaccgcct acatacctcg ctctgctaat cctgttacca gtggctgctg ccagtggcga    4020
taagtcgtgt cttaccgggt tggactcaag acgatagtta ccggataagg cgcagcggtc    4080
gggctgaacg gggggttcgt gcacacagcc cagcttggag cgaacgacct acaccgaact    4140
gagataccta cagcgtgagc tatgagaaag cgccacgctt cccgaaggga gaaaggcgga    4200
caggtatccg gtaagcggca gggtcggaac aggagagcgc acgagggagc ttccaggggg    4260
aaacgcctgg tatctttata gtcctgtcgg gtttcgccac ctctgacttg agcgtcgatt    4320
tttgtgatgc tcgtcagggg ggcggagcct atggaaaaac gccagcaacg cggcctttttt    4380
acggttcctg gccttttgct ggccttttgc tcacatgttc tttcctgcgt tatcccctga    4440
ttctgtggat aaccgtatta ccgcctttga gtgagctgat accgctcgcc gcagccgaac    4500
gaccgagcgc agcgagtcag tgagcgagga agcggaagag cgcctgatgc ggtattttct    4560
ccttacgcat ctgtgcggta tttcacaccg catatggtgc actctcagta caatctgctc    4620
tgatgccgca tagttaagcc agtatacact ccgctatcgc tacgtgactg ggtcatggct    4680
gcgccccgac acccgccaac acccgctgac gcgccctgac gggcttgtct gctcccggca    4740
tccgcttaca gacaagctgt gaccgtctcc gggagctgca tgtgtcagag gttttcaccg    4800
tcatcaccga aacgcgcgag gcagcagatc aattcgcgcg cgaaggcgaa gcggcatgca    4860
tttacgttga caccatcgaa tggtgcaaaa cctttcgcgg tatggcatga tagcgcccgg    4920
aagagagtca attcagggtg gtgaatgtga aaccagtaac gttatacgat gtcgcagagt    4980
atgccggtgt ctcttatcag accgtttccc gcgtggtgaa ccaggccagc cacgtttctg    5040
cgaaaacgcg ggaaaaagtg gaagcggcga tggcggagct gaattacatt cccaaccgcg    5100
tggcacaaca actggcgggc aaacagtcgt tgctgattgg cgttgccacc tccagtctgg    5160
ccctgcacgc gccgtcgcaa attgtcgcgg cgattaaatc tcgcgccgat caactgggtg    5220
ccagcgtggt ggtgtcgatg gtagaacgaa gcggcgtcga agcctgtaaa gcggcggtgc    5280
acaatcttct cgcgcaacgc gtcagtgggc tgatcattaa ctatccgctg gatgaccagg    5340
atgccattgc tgtggaagct gcctgcacta atgttccggc gttatttctt gatgtctctg    5400
accagacacc catcaacagt attatttttc tcccatgaaga cggtacgcga ctgggcgtgg    5460
agcatctggt cgcattgggt caccagcaaa tcgcgctgtt agcgggccca ttaagttctg    5520
tctcggcgcg tctgcgtctg gctggctggc ataaatatct cactcgcaat caaattcagc    5580
cgatagcgga acgggaaggc gactggagtg ccatgtccgg ttttcaacaa accatgcaaa    5640
tgctgaatga gggcatcgtt cccactgcga tgctggttgc caacgatcag atggcgctgg    5700
gcgcaatgcg cgccattacc gagtccggc tgcgcgttgg tgcggatatc tcggtagtgg    5760
gatacgacga taccgaagac agctcatgtt atatcccgcc gtcaaccacc atcaaacagg    5820
attttcgcct gctggggcaa accagcgtgg accgcttgct gcaactctct cagggccagg    5880
cggtgaaggg caatcagctg ttgcccgtct cactggtgaa agaaaaaacc accctggcgc    5940
ccaatacgca aaccgcctct ccccgcgcgt tggccgattc attaatgcag ctggcacgac    6000
aggtttcccg actggaaagc gggcagtgag cgcaacgcaa ttaatgtgag ttagcgcgaa    6060
ttgatctg                                                            6068
```

<210> SEQ ID NO 89
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 89

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg tcctccgaca cggacgagtc     540
catcgaagta tacaaagaca agcgaaaaa gctggaagcc gaagttcgtc gcgagattaa     600
taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcggtaacca agacttccct gcacggtacg gcactgtctt tccgtctgct     780
gcgtcaaca ggttttgagg tttctcagga agcgttcagc ggcttcaaag accaaaacgg     840
caacttcctg gagaacctga aggaagatat caaagctatc ctgagcctgt acgaggccag     900
cttcctggct ctggaaggcg aaaacatcct ggacgaggcg aaggttttcg caatctctca     960
tctgaaagaa ctgtctgaag aaagatcgg taaagagctg gcagaacagg tgaaccatgc    1020
actggaactg ccactgcatc gccgtactca gcgtctggaa gcagtatggt ctatcgaggc    1080
ctaccgtaaa aaggaggacg cgaatcaggt tctgctggag ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc    1260
cgtgggtgta gcattcgaac cgcaatactc cgactgccgt aactccgtcg caaaatgtt    1320
ttctttcgta accattatcg acgatatcta cgatgtatac ggcaccctgg acgaactgga    1380
gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgctttcctg caagaagcca gtggctgta caacaaatct actccgacct tgacgacta    1620
cttcggcaac gcatggaaat cctcttctgg cccgctgcaa ctggtgttcg cttacttcgc    1680
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaaccgcga tcaacctggc    1980
acgtcaatct cactgcactt atcataacga cgacgcgcat acctctccgg atgagctgac    2040
ccgcaaacgc gttctgtctg taatcactga accgattctg ccgtttgaac gctaactgca    2100
```

```
taaaggaggt aaaaaaacat ggtatcctgt tctgcgccgg gtaagattta cctgttcggt    2160
gaacacgccg tagtttatgg cgaaactgca attgcgtgtg cggtggaact gcgtacccgt    2220
gttcgcgcgg aactcaatga ctctatcact attcagagcc agatcggccg caccggtctg    2280
gatttcgaaa agcacccctta tgtgtctgcg gtaattgaga aaatgcgcaa atctattcct    2340
attaacggtg ttttcttgac cgtcgattcc gacatcccgg tgggctccgg tctgggtagc    2400
agcgcagccg ttactatcgc gtctattggt gcgctgaacg agctgttcgg cttttggcctc   2460
agcctgcaag aaatcgctaa actgggccac gaaatcgaaa ttaaagtaca gggtgccgcg    2520
tccccaaccg atacgtatgt ttctaccttc ggcggcgtgg ttaccatccc ggaacgtcgc    2580
aaactgaaaa ctccggactg cggcattgtg attggcgata ccggcgtttt ctcctccacc    2640
aaagagttag tagctaacgt acgtcagctg cgcgaaagct acccggattt gatcgaaccg    2700
ctgatgacct ctattggcaa aatctctcgt atcggcgaac aactggttct gtctggcgac    2760
tacgcatcca tcggccgcct gatgaacgtc aaccagggtc tcctggacgc cctgggcgtt    2820
aacatcttag aactgagcca gctgatctat tccgctcgtg cggcaggtgc gttttggcgct   2880
aaaatcacgg gcgctggcgg cggtggctgt atggttgcgc tgaccgctcc ggaaaaatgc    2940
aaccaagtgg cagaagcggt agcaggcgct ggcggtaaag tgactatcac taaaccgacc    3000
gagcaaggtc tgaaagtaga ttaaagtcta gttaaagttt aaacggtctc cagcttggct    3060
gttttggcgg atgagagaag attttcagcc tgatacagat taaatcagaa cgcagaagcg    3120
gtctgataaa acagaatttg cctggcggca gtagcgcggt ggtcccacct gacccccatgc   3180
cgaactcaga agtgaaacgc cgtagcgccg atggtagtgt ggggtctccc catgcgagag    3240
tagggaactg ccaggcatca ataaaaacga aaggctcagt cgaaagactg gcctttcgt     3300
tttatctgtt gtttgtcggt gaacgctctc ctgagtagga caaatccgcc gggagcggat    3360
ttgaacgttg cgaagcaacg gcccggaggg tggcgggcag gacgcccgcc ataaactgcc    3420
aggcatcaaa ttaagcagaa ggccatcctg acggatggcc ttttttgcgtt tctacaaact   3480
ctttttgttt attttctaa atacattcaa atatgtatcc gctcatgaga caataaccct    3540
gataaatgct tcaataatat tgaaaaagga agagtatgag tattcaacat ttccgtgtcg    3600
cccttattcc cttttttgcg gcattttgcc ttcctgtttt tgctcaccca gaaacgctgg    3660
tgaaagtaaa agatgctgaa gatcagttgg gtgcacgagt gggttacatc gaactggatc    3720
tcaacagcgg taagatcctt gagagttttc gccccgaaga acgttttcca atgatgagca    3780
cttttaaagt tctgctatgt ggcgcggtat tatcccgtgt tgacgccggg caagagcaac    3840
tcggtcgccg catacactat tctcagaatg acttggttga gtactcacca gtcacagaaa    3900
agcatcttac ggatggcatg acagtaagag aattatgcag tgctgccata accatgagtg    3960
ataacactgc ggccaactta cttctgacaa cgatcggagg accgaaggag ctaaccgctt    4020
ttttgcacaa catgggggat catgtaactc gccttgatcg ttgggaaccg gagctgaatg    4080
aagccatacc aaacgacgag cgtgacacca cgatgcctgt agcaatggca acaacgttgc    4140
gcaaactatt aactggcgaa ctacttactc tagcttcccg gcaacaatta atagactgga    4200
tggaggcgga taaagttgca ggaccacttc tgcgctcgg ccttccggct ggctggttta    4260
ttgctgataa atctggagcc ggtgagcgtg ggtctcgcgg tatcattgca gcactggggc    4320
cagatggtaa gccctcccgt atcgtagtta tctacacgac ggggagtcag gcaactatgg    4380
atgaacgaaa tagacagatc gctgagatag gtgcctcact gattaagcat tggtaactgt    4440
```

```
cagaccaagt ttactcatat atactttaga ttgatttaaa acttcatttt taatttaaaa    4500
ggatctaggt gaagatcctt tttgataatc tcatgaccaa aatcccttaa cgtgagtttt    4560
cgttccactg agcgtcagac cccgtagaaa agatcaaagg atcttcttga gatccttttt    4620
ttctgcgcgt aatctgctgc ttgcaaacaa aaaaaccacc gctaccagcg gtggtttgtt    4680
tgccggatca agagctacca actcttttc cgaaggtaac tggcttcagc agagcgcaga    4740
taccaaatac tgtccttcta gtgtagccgt agttaggcca ccacttcaag aactctgtag    4800
caccgcctac atacctcgct ctgctaatcc tgttaccagt ggctgctgcc agtggcgata    4860
agtcgtgtct taccgggttg gactcaagac gatagttacc ggataaggcg cagcggtcgg    4920
gctgaacggg gggttcgtgc acacagccca gcttggagcg aacgacctac accgaactga    4980
gatacctaca gcgtgagcta tgagaaagcg ccacgcttcc cgaagggaga aaggcggaca    5040
ggtatccggt aagcggcagg gtcggaacag gagagcgcac gagggagctt ccaggggggaa    5100
acgcctggta tctttatagt cctgtcgggt ttcgccacct ctgacttgag cgtcgatttt    5160
tgtgatgctc gtcaggggggg cggagcctat ggaaaaacgc cagcaacgcg ccttttttac    5220
ggttcctggc cttttgctgg ccttttgctc acatgttctt tcctgcgtta tccctgatt    5280
ctgtggataa ccgtattacc gcctttgagt gagctgatac cgctcgccgc agccgaacga    5340
ccgagcgcag cgagtcagtg agcgaggaag cggaagagcg cctgatgcgg tattttctcc    5400
ttacgcatct gtgcggtatt tcacaccgca tatggtgcac tctcagtaca atctgctctg    5460
atgccgcata gttaagccag tatacactcc gctatcgcta cgtgactggg tcatggctgc    5520
gccccgacac ccgccaacac ccgctgacgc gccctgacgg gcttgtctgc tcccggcatc    5580
cgcttacaga caagctgtga ccgtctccgg gagctgcatg tgtcagaggt tttcaccgtc    5640
atcaccgaaa cgcgcgaggc agcagatcaa ttcgcgcgcg aaggcgaagc ggcatgcatt    5700
tacgttgaca ccatcgaatg gtgcaaaacc tttcgcggta tggcatgata gcgcccggaa    5760
gagagtcaat tcagggtggt gaatgtgaaa ccagtaacgt tatacgatgt cgcagagtat    5820
gccggtgtct cttatcagac cgtttcccgc gtggtgaacc aggccagcca cgtttctgcg    5880
aaaacgcggg aaaagtggaa gcggcgatg cggagctga attacattcc caaccgcgtg    5940
gcacaacaac tggcgggcaa acagtcgttg ctgattggcg ttgccacctc cagtctggcc    6000
ctgcacgcgc cgtcgcaaat tgtcgcggcg attaaatctc gcgccgatca actgggtgcc    6060
agcgtggtgg tgtcgatggt agaacgaagc ggcgtcgaag cctgtaaagc ggcggtgcac    6120
aatcttctcg cgcaacgcgt cagtgggctg atcattaact atccgctgga tgaccaggat    6180
gccattgctg tggaagctgc ctgcactaat gttccggcgt tatttcttga tgtctctgac    6240
cagacaccca tcaacagtat tattttctcc catgaagacg gtacgcgact gggcgtggag    6300
catctggtcg cattgggtca ccagcaaatc gcgctgttag cgggcccatt aagttctgtc    6360
tcggcgcgtc tgcgtctggc tggctggcat aaatatctca ctcgcaatca aattcagccg    6420
atagcggaac gggaaggcga ctggagtgcc atgtccggtt ttcaacaaac catgcaaatg    6480
ctgaatgagg gcatcgttcc cactgcgatg ctggttgcca acgatcagat ggcgctgggc    6540
gcaatgcgcg ccattaccga gtccgggctg cgcgttggtg cggatatctc ggtagtggga    6600
tacgacgata ccgaagacag ctcatgttat atcccgccgt caaccaccat caaacaggat    6660
tttcgcctgc tggggcaaac cagcgtggac cgcttgctgc aactctctca gggccaggcg    6720
gtgaagggca atcagctgtt gcccgtctca ctggtgaaaa gaaaaaccac cctggcgccc    6780
aatacgcaaa ccgcctctcc ccgcgcgttg gccgattcat taatgcagct ggcacgacag    6840
```

```
gtttcccgac tggaaagcgg gcagtgagcg caacgcaatt aatgtgagtt agcgcgaatt    6900
gatctg                                                              6906

<210> SEQ ID NO 90
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 90
aagggcgagc tcaacgatcc ggctgctaac aaagcccgaa aggaagctga gttggctgct      60
gccaccgctg agcaataact agcataaccc cttggggcct ctaaacgggt cttgaggagt     120
tttttgctga aggaggaac  tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aacccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctggggt tcgaaatgac cgaccaagcg    1380
acgcctaact gtcagaccaa gtttactcat atatacttta gattgattta aaacttcatt    1440
tttaatttaa aaggatctag gtgaagatcc ttttgataa tctcatgacc aaaatccctt    1500
aacgtgagtt tcgttccac  tgagcgtcag accccgtaga aaagatcaaa ggatcttctt    1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
```

```
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggcctttt acggttcctg gccttttgct ggccttttgc tcacatgttc tttcctgcgt    2220
tatccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag ttctccaga    2700
agcgttaatg tctggcttct gataaagcgg ccatgttaa gggcggtttt ttcctgtttg    2760
gtcactgatg cctccgtgta aggggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag ggcgctgact ccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgt gaatccgtt agcgaggtgc cgccggcttc cattcaggtc gaggtggccc    3420
ggctccatgc accgcgacgc aacgcgggga ggcagacaag gtatagggcg cgcctacaa    3480
tccatgccaa cccgttccat gtgctcgccg aggcggcata atcgccgtg acgatcagcg    3540
gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
```

```
gagctgtcttc cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc cgctaacag cgcgatttgc     4620 tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct cgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctcccta tgcgactcct gcattaggaa     5280
gcagcccagt agtaggttga ggccgttgag caccgccgcc gcaaggaatg gtgcatgcaa    5340
ggagatggcg cccaacagtc ccccggccac ggggcctgcc accatacccca cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaattaata cgactcacta ggggaatt gtgagcggat       5580 aacaattccc ctctagaaat aattttgttt aactttaaga aggagatata catatgaatt    5640
aaccctcact aaagggcggc cgcgaagttc ctattctcta aaagtatag aacttcatt     5700 ctaccgggta ggggaggcgc ttttcccaag gcagtctgga gcatgcgctt agcagcccc    5760 gctgggcact tggcgctaca caagtggcct ctggcctcgc acacattcca catccaccgg    5820
taggcgccaa ccggctccgt tctttggtgg cccttcgcg ccaccttcca ctcctcccct    5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccggggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
gggatagtgt tcacccttgt tacaccgttt tccatgagca aactgaaacg ttttcatcgc    6600
tctggagtga ataccacgac gatttccggc agtttctaca catatattcg caagatgtgg    6660
```

| | |
|---|---|
| cgtgttacgg tgaaaacctg gcctatttcc ctaaagggtt tattgagaat atgttttcg | 6720 |
| tctcagccaa tccctgggtg agtttcacca gttttgattt aaacgtggcc aatatggaca | 6780 |
| acttcttcgc cccgttttc accatgggca aatattatac gcaaggcgac aaggtgctga | 6840 |
| tgccgctggc gattcaggtt catcatgccg tttgtgatgg cttccatgtc ggcagaatgc | 6900 |
| ttaatgaatt acaacagtac tgcgatgagt ggcagggcgg ggcgtaagcg ggactctggg | 6960 |
| gttcgaataa agaccgacca agcgacgtct gagagctccc tggcgaattc ggtaccaata | 7020 |
| aaagagcttt attttcatga tctgtgtgtt ggttttgtg tgcggcgcgg aagttcctat | 7080 |
| tctctagaaa gtataggaac ttcctcgagc cctatagtga gtcgtattag atcgcggccg | 7140 |
| cgcccttgac aatgccacat cctgagcaaa taattcaacc actaattgtg agcggataac | 7200 |
| aaaggaggta aaaaaacatg gtatcctgtt ctgcgccggg taagatttac ctgttcggtg | 7260 |
| aacacgccgt agtttatggc gaaactgcaa ttgcgtgtgc ggtggaactg cgtacccgtg | 7320 |
| ttcgcgcgga actcaatgac tctatcacta ttcagagcca gatcggccgc accggtctgg | 7380 |
| atttcgaaaa gcacccttat gtgtctgcgg taattgagaa aatgcgcaaa tctattccta | 7440 |
| ttaacggtgt tttcttgacc gtcgattccg acatcccggt gggctccggt ctgggtagca | 7500 |
| gcgcagccgt tactatcgcg tctattggtg cgctgaacga gctgttcggc tttggcctca | 7560 |
| gcctgcaaga aatcgctaaa ctgggccacg aaatcgaaat taagtacag ggtgccgcgt | 7620 |
| ccccaaccga tacgtatgtt tctaccttcg gcggcgtggt taccatcccg gaacgtcgca | 7680 |
| aactgaaaac tccggactgc ggcattgtga ttggcgatac cggcgttttc cctccacca | 7740 |
| aagagttagt agctaacgta cgtcagctgc gcgaaagcta cccggatttg atcgaaccgc | 7800 |
| tgatgaccct tattggcaaa atctctcgta tcggcgaaca actggttctg tctggcgact | 7860 |
| acgcatccat cggccgcctg atgaacgtca accaggtgtct cctggacgcc ctgggcgtta | 7920 |
| acatcttaga actgagccag ctgatctatt ccgctcgtgc ggcaggtgcg tttggcgcta | 7980 |
| aaatcacggg cgctggcggc ggtggctgta tggttgcgct gaccgctccg gaaaaatgca | 8040 |
| accaagtggc agaagcggta gcaggcgctg gcggtaaagt gactatcact aaaccgaccg | 8100 |
| agcaaggtct gaaagtagat taa | 8123 |

<210> SEQ ID NO 91
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 91

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aacccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |

-continued

```
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg ccacgacgg gcgttccttg     780
cgcagctgtg ctcgacgttg tcactgaagc gggaaggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acagggagc    2040
ttccaggggg aaacgcctgg tatctttata gtcctgtcgg gtttcgccac ctctgacttg   2100
agcgtcgatt tttgtgatgc tcgtcagggg gcggagcct atggaaaaac gccagcaacg    2160
cggcctttt acgttcctg ccttttgct ggccttttgc tcacatgttc tttcctgcgt      2220
tatcccctga ttctgtggat aaccgtatta ccgcctttga gtgagctgat accgctcgcc   2280
gcagccgaac gaccgagcgc agcgagtcag tgagcgagga gcggaagag cgcctgatgc    2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg gcttgtctg    2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg ggtaatgat accgatgaaa    2820
cgagagagga tgctcacgat acgggttact gatgatgaac atgcccggtt actggaacgt   2880
tgtgagggta aacaactggc ggtatggatg cggcgggacc agagaaaaat cactcagggt   2940
```

```
caatgccagc gcttcgttaa tacagatgta ggtgttccac agggtagcca gcagcatcct    3000
gcgatgcaga tccggaacat aatggtgcag ggcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg gcgcctacaa    3480
tccatgccaa cccgttccat gtgctcgccg aggcggcata atcgccgtg acgatcagcg     3540 gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg     3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa tgacccaga    3900 gcgctgccgg cacctgtcct acgagttgca tgataaagaa gacagtcata agtgcggcga    3960
cgatagtcat gccccgcgcc accggaagg agctgactgg gttgaaggct ctcaagggca     4020
tcggtcgaga tccggtgcc taatgagtga gctaacttac attaattgcg ttgcgctcac     4080
tgcccgcttt ccagtcggga aacctgtcgt gccagctgca ttaatgaatc ggccaacgcg    4140
cggggagagg cggtttgcgt attgggcgcc agggtggttt tcttttcac cagtgagacg     4200 ggcaacagct gattgcccct caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg atagttaat gatcagccca     4800 ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac     4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
```

```
ggagatggcg cccaacagtc ccccggccac ggggcctgcc accatacccca cgccgaaaca   5400
agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta ggggaatt gtgagcggat     5580
aacaattccc ctctagaaat aattttgttt aactttaaga aggagatata catatgaatt   5640
aaccctcact aaagggcggc cgcgaagttc ctattctcta gaaagtatag gaacttcatt   5700
ctaccgggta ggggaggcgc ttttcccaag gcagtctgga gcatgcgctt tagcagcccc   5760
gctgggcact tggcgctaca caagtggcct ctggcctcgc acacattcca catccaccgg   5820
taggcgccaa ccggctccgt tctttggtgg cccttcgcg ccaccttcca ctcctcccct    5880
agtcaggaag ttccccccg ccccgcagct cgcgtcgtgc aggacgtgac aaatggaagt    5940
agcacgtctc actagtctcg tgcagatgga cagcaccgct gagcaatgga agcgggtagg   6000
cctttggggc agcggccaat agcagctttg ctccttcgct ttctgggctc agaggctggg   6060
aaggggtggg tccgggggcg ggctcagggg cgggctcagg ggcggggcgg gcgcccgaag   6120
gtcctccgga ggcccggcat tctgcacgct tcaaaagcgc acgtctgccg cgctgttctc   6180
ctcttcctca tctccgggcc tttcgacctg cagcagcacg tgttgacaat taatcatcgg   6240
catagtatat cggcatagta taatacgaca aggtgaggaa ctaaaccatg agaaaaaaa    6300
tcactggata taccaccgtt gatatatccc aatggcatcg taaagaacat tttgaggcat   6360
ttcagtcagt tgctcaatgt acctataacc agaccgttca gctggatatt acggcctttt   6420
taaagaccgt aaagaaaaat aagcacaagt tttatccggc ctttattcac attcttgccc   6480
gcctgatgaa tgctcatccg gaattccgta tggcaatgaa agacggtgag ctggtgatat   6540
gggatagtgt tcacccttgt tacaccgttt tccatgagca aactgaaacg ttttcatcgc   6600
tctggagtga ataccacgac gatttccggc agtttctaca catatattcg caagatgtgg   6660
cgtgttacgg tgaaaacctg gcctatttcc ctaaagggtt tattgagaat atgttttcg    6720
tctcagccaa tccctgggtg agtttcacca gttttgattt aaacgtggcc aatatggaca   6780
acttcttcgc ccccgttttc accatgggca aatattatac gcaaggcgac aaggtgctga   6840
tgccgctggc gattcaggtt catcatgccg tttgtgatgg cttccatgtc ggcagaatgc   6900
ttaatgaatt acaacagtac tgcgatgagt ggcagggcgg ggcgtaagcg ggactctggg   6960
gttcgaataa agaccgacca agcgacgtct gagagctccc tggcgaattc ggtaccaata   7020
aaagagcttt attttcatga tctgtgtgtt ggttttgtg tgcggcgcgg aagttcctat    7080
tctctagaaa gtataggaac ttcctcgagc cctatagtga gtcgtattag atcgcggccg   7140
cgcccttgac catgccacat cctgagcaaa taattcaacc actaattgtg agcggataac   7200
aaaggaggta aaaaacatg gtatcctgtt ctgcgccggg taagatttac ctgttcggtg   7260
aacacgccgt agtttatggc gaaactgcaa ttgcgtgtgc ggtggaactg cgtacccgtg   7320
ttcgcgcgga actcaatgac tctatcacta ttcagagcca gatcggccgc accggtctgg   7380
atttcgaaaa gcacccttat gtgtctgcgg taattgagaa aatgcgcaaa tctattccta   7440
ttaacggtgt tttcttgacc gtcgattccg acatcccggt gggctccggt ctgggtagca   7500
gcgcagccgt tactatcgcg tctattggtg cgctgaacga gctgttcggc tttggcctca   7560
gcctgcaaga aatcgctaaa ctgggccacg aaatcgaaat taagtacag ggtgccgcgt    7620
ccccaaccga tacgtatgtt tctaccttcg gcggcgtggt taccatcccg gaacgtcgca   7680
```

-continued

| | | |
|---|---|---|
| aactgaaaac tccggactgc ggcattgtga ttggcgatac cggcgttttc tcctccacca | 7740 | |
| aagagttagt agctaacgta cgtcagctgc gcgaaagcta cccggatttg atcgaaccgc | 7800 | |
| tgatgacctc tattggcaaa atctctcgta tcggcgaaca actggttctg tctggcgact | 7860 | |
| acgcatccat cggccgcctg atgaacgtca accagggtct cctggacgcc ctgggcgtta | 7920 | |
| acatcttaga actgagccag ctgatctatt ccgctcgtgc ggcaggtgcg tttggcgcta | 7980 | |
| aaatcacggg cgctggcggc ggtggctgta tggttgcgct gaccgctccg gaaaaatgca | 8040 | |
| accaagtggc agaagcggta gcaggcgctg gcggtaaagt gactatcact aaaccgaccg | 8100 | |
| agcaaggtct gaaagtagat taa | 8123 | |

<210> SEQ ID NO 92
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 92

| | |
|---|---|
| aagggcgagc tcaacgatcc ggctgctaac aaagcccgaa aggaagctga gttggctgct | 60 |
| gccaccgctg agcaataact agcataaccc cttgggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aaccccctat tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact gacaatcggc tgctctgatg ccgccgtgtt | 660 |
| ccggctgtca gcgcaggggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat tgggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctgggt tcgaaatgac cgaccaagcg | 1380 |
| acgcctaact gtcagaccaa gtttactcat atatacttta gattgattta aacttcatt | 1440 |
| tttaatttaa aaggatctag gtgaagatcc ttttttgataa tctcatgacc aaaatccctt | 1500 |
| aacgtgagtt ttcgttccac tgagcgtcag acccgtaga aagatcaaa ggatcttctt | 1560 |
| gagatccttt ttttctgcgc gtaatctgct gcttgcaaac aaaaaaacca ccgctaccag | 1620 |

```
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggcctttt  acgttcctg  gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg gcttgtctg     2520
ctccggcat  ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctcccaga   2700
agcgttaatg tctggcttct gataaagcgg gccatgttaa gggcggtttt tcctgtttg     2760
gtcactgatg cctccgtgta agggggatt  ctgttcatgg gggtaatgat accgatgaaa    2820
cgagagagga tgctcacgat acgggttact gatgatgaac atgcccggtt actggaacgt    2880
tgtgagggta acaactggc  ggtatggatg cggcggacc  agagaaaaat cactcagggt    2940
caatgccagc gcttcgttaa tacagatgta ggtgttccac agggtagcca gcagcatcct    3000
gcgatgcaga tccggaacat aatggtgcag ggcgctgact ccgcgtttc  cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtataggcg  cgcctacaa     3480
tccatgccaa cccgttccat gtgctcgccg aggcggcata atcgccgtg  acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
```

```
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac     4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccca gccgaaaca   5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat     5580 aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg ccccttcgcg ccaccttcca ctcctcccct    5880
agtcaggaag ttccccccg ccccgcagct cgcgtcgtgc aggacgtgac aaatggaagt     5940
agcacgtctc actagtctcg tgcagatgga cagcaccgct gagcaatgga agcgggtagg    6000 cctttgggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaaagcgc acgtctgccg cgctgttctc    6180
ctcttcctca tctccgggcc tttcgacctg cagcagcacg tgttgacaat taatcatcgg    6240
catagtatat cggcatagta taatacgaca aggtgaggaa ctaaaccatg gagaaaaaaa    6300
tcactggata taccaccgtt gatatatccc aatggcatcg taaagaacat tttgaggcat    6360
```

```
ttcagtcagt tgctcaatgt acctataacc agaccgttca gctggatatt acggccttt      6420
taaagaccgt aaagaaaaat aagcacaagt tttatccggc ctttattcac attcttgccc      6480
gcctgatgaa tgctcatccg gaattccgta tggcaatgaa agacggtgag ctggtgatat      6540
gggatagtgt tcacccttgt tacaccgttt tccatgagca aactgaaacg ttttcatcgc      6600
tctggagtga ataccacgac gatttccggc agtttctaca catatattcg caagatgtgg      6660
cgtgttacgg tgaaaacctg gcctatttcc ctaaagggtt tattgagaat atgttttcg       6720
tctcagccaa tccctgggtg agtttcacca gttttgattt aaacgtggcc aatatggaca      6780
acttcttcgc ccccgttttc accatgggca aatattatac gcaaggcgac aaggtgctga      6840
tgccgctggc gattcaggtt catcatgccg tttgtgatgg cttccatgtc ggcagaatgc      6900
ttaatgaatt acaacagtac tgcgatgagt ggcagggcgg ggcgtaagcg ggactctggg      6960
gttcgaataa agaccgacca agcgacgtct gagagctccc tggcgaattc ggtaccaata      7020
aaagagcttt attttcatga tctgtgtgtt ggttttttgtg tgcggcgcgg aagttcctat      7080
tctctagaaa gtataggaac ttcctcgagc cctatagtga gtcgtattag atcgcggccg      7140
cgcccttgac gatgccacat cctgagcaaa taattcaacc actaattgtg agcggataac      7200
aaaggaggta aaaaacatg gtatcctgtt ctgcgccggg taagatttac ctgttcggtg       7260
aacacgccgt agtttatggc gaaactgcaa ttgcgtgtgc ggtggaactg cgtaccgtg       7320
ttcgcgcgga actcaatgac tctatcacta ttcagagcca gatcggccgc accggtctgg      7380
atttcgaaaa gcacccttat gtgtctgcgg taattgagaa aatgcgcaaa tctattccta      7440
ttaacggtgt tttcttgacc gtcgattccg acatcccggt gggctccggt ctgggtagca      7500
gcgcagccgt tactatcgcg tctattggtg cgctgaacga gctgttcggc tttggcctca      7560
gcctgcaaga aatcgctaaa ctgggccacg aaatcgaaat taagtacag ggtgccgcgt        7620
ccccaaccga tacgtatgtt tctaccttcg gcggcgtggt taccatcccg gaacgtcgca      7680
aactgaaaac tccggactgc ggcattgtga ttggcgatac cggcgttttc tcctccacca      7740
aagagttagt agctaacgta cgtcagctgc gcgaaagcta cccggatttg atcgaaccgc      7800
tgatgacctc tattggcaaa atctctcgta tcggcgaaca actggttctg tctgcgact       7860
acgcatccat cggccgcctg atgaacgtca accagggtct cctggacgcc ctgggcgtta      7920
acatcttaga actgagccag ctgatctatt ccgctcgtgc ggcaggtgcg tttggcgcta      7980
aaatcacggg cgctggcggc ggtggctgta tggttgcgct gaccgctccg gaaaaatgca      8040
accaagtggc agaagcggta gcaggcgctg gcggtaaagt gactatcact aaaccgaccg      8100
agcaaggtct gaaagtagat taa                                              8123
```

<210> SEQ ID NO 93
<211> LENGTH: 8123
<212> TYPE: DNA
<213> ORGANISM: Artificial Sequence
<220> FEATURE:
<223> OTHER INFORMATION: Synthetic Construct

<400> SEQUENCE: 93

```
aagggcgagc tcaacgatcc ggctgctaac aaagcccgaa aggaagctga gttggctgct        60
gccaccgctg agcaataact agcataaccc cttggggcct ctaaacgggt cttgaggagt       120
tttttgctga aggaggaac tatatccgga tatcccgcaa gaggcccggc agtaccggca       180
taaccaagcc tatgcctaca gcatccaggg tgacggtgcc gaggatgacg atgagcgcat      240
```

-continued

```
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcagggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttgataa tctcatgacc aaaatccctt   1500
aacgtgagtt ttcgttccac tgagcgtcag accccgtaga aagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atgaaaaac gccagcaacg   2160
cggcctttt acgttcctg gcctttгct ggcctttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg gcttgtctg    2520
ctcccggcat ccgcttacag acaagctgtg accgtcccg ggagctgcat gtgtcagagg   2580
ttttcaccgt catcaccgaa acgcgcgagg cagctgcggt aaagctcatc agcgtggtcg   2640
```

```
tgaagcgatt cacagatgtc tgcctgttca tccgcgtcca gctcgttgag tttctccaga  2700
agcgttaatg tctggcttct gataaagcgg gccatgttaa gggcggtttt ttcctgtttg  2760
gtcactgatg cctccgtgta agggggattt ctgttcatgg gggtaatgat accgatgaaa  2820
cgagagagga tgctcacgat acgggttact gatgatgaac atgcccggtt actggaacgt  2880
tgtgagggta acaactggc ggtatggatg cggcgggacc agagaaaaat cactcagggt  2940
caatgccagc gcttcgttaa tacagatgta ggtgttccac agggtagcca gcagcatcct  3000
gcgatgcaga tccggaacat aatggtgcag ggcgctgact tccgcgtttc cagactttac  3060
gaaacacgga aaccgaagac cattcatgtt gttgctcagg tcgcagacgt tttgcagcag  3120
cagtcgcttc acgttcgctc gcgtatcggt gattcattct gctaaccagt aaggcaaccc  3180
cgccagccta gccgggtcct caacgacagg agcacgatca tgcgcacccg tggccaggac  3240
ccaacgctgc ccgagatgcg ccgcgtgcgg ctgctggaga tggcggacgc gatggatatg  3300
ttctgccaag ggttggtttg cgcattcaca gttctccgca agaattgatt ggctccaatt  3360
cttggagtgg tgaatccgtt agcgaggtgc cgccggcttc cattcaggtc gaggtggccc  3420
ggctccatgc accgcgacgc aacgcgggga ggcagacaag gtatagggcg cgcctacaa  3480 tccatgccaa cccgttccat gtgctcgccg aggcggcata atcgccgtg acgatcagcg  3540 gtccaatgat cgaagttagg ctggtaagag ccgcgagcga tccttgaagc tgtccctgat  3600
ggtcgtcatc tacctgcctg acagcatgg cctgcaacgc gggcatcccg atgccgccgg  3660
aagcgagaag aatcataatg gggaaggcca tccagcctcg cgtcgcgaac gccagcaaga  3720
cgtagcccag cgcgtcggcc gccatgccgg cgataatggc ctgcttctcg ccgaaacgtt  3780
tggtggcggg accagtgacg aaggcttgag cgagggcgtg caagattccg aataccgcaa  3840
gcgacaggcc gatcatcgtc gcgctccagc gaaagcggtc ctcgccgaaa atgacccaga  3900
gcgctgccgg cacctgtcct acgagttgca tgataaagaa gacagtcata agtgcggcga  3960
cgatagtcat gccccgcgcc caccggaagg agctgactgg gttgaaggct ctcaagggca  4020
tcggtcgaga tcccggtgcc taatgagtga gctaacttac attaattgcg ttgcgctcac  4080
tgcccgcttt ccagtcggga aacctgtcgt gccagctgca ttaatgaatc ggccaacgcg  4140
cggggagagg cggtttgcgt attgggcgcc agggtggttt ttcttttcac cagtgagacg  4200
ggcaacagct gattgccctt caccgcctgg ccctgagaga gttgcagcaa gcggtccacg  4260
ctggtttgcc ccagcaggcg aaaatcctgt ttgatggtgg ttaacggcgg gatataacat  4320
gagctgtctt cggtatcgtc gtatcccact accgagatat ccgcaccaac gcgcagcccg  4380
gactcggtaa tggcgcgcat tgcgcccagc gccatctgat cgttggcaac cagcatcgca  4440
gtgggaacga tgccctcatt cagcatttgc atggtttgtt gaaaaccgga catggcactc  4500
cagtcgcctt cccgttccgc tatcggctga atttgattgc gagtgagata tttatgccag  4560
ccagccagac gcagacgcgc cgagacagaa cttaatgggc ccgctaacag cgcgatttgc  4620
tggtgaccca atgcgaccag atgctccacg cccagtcgcg taccgtcttc atgggagaaa  4680
ataatactgt tgatgggtgt ctggtcagag acatcaagaa ataacgccgg aacattagtg  4740
caggcagctt ccacagcaat ggcatcctgg tcatccagcg gatagttaat gatcagccca  4800
ctgacgcgtt gcgcgagaag attgtgcacc gccgctttac aggcttcgac gccgcttcgt  4860
tctaccatcg acaccaccac gctggcaccc agttgatcgg cgcgagattt aatcgccgcg  4920
acaatttgcg acggcgcgtg cagggccaga ctggaggtgg caacgccaat cagcaacgac  4980
```

```
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatcccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgaatt    5640
aaccctcact aaagggcggc cgcgaagttc ctattctcta gaaagtatag gaacttcatt    5700
ctaccgggta ggggaggcgc ttttcccaag gcagtctgga gcatgcgctt tagcagcccc    5760
gctgggcact tggcgctaca caagtggcct ctggcctcgc acacattcca catccaccgg    5820
taggcgccaa ccggctccgt tctttggtgg ccccttcgcg ccaccttcca ctcctcccct    5880
agtcaggaag ttcccccccg ccccgcagct cgcgtcgtgc aggacgtgac aaatggaagt    5940
agcacgtctc actagtctcg tgcagatgga cagcaccgct gagcaatgga agcgggtagg    6000
cctttggggc agcggccaat agcagctttg ctccttcgct ttctgggctc agaggctggg    6060
aaggggtggg tccgggggcg ggctcagggg cgggctcagg ggcggggcgg gcgcccgaag    6120
gtcctccgga ggcccggcat tctgcacgct tcaaagcgc acgtctgccg cgctgttctc    6180
ctcttcctca tctccgggcc tttcgacctg cagcagcacg tgttgacaat taatcatcgg    6240
catagtatat cggcatagta ataacgaca aggtgaggaa ctaaaccatg gagaaaaaaa    6300
tcactggata taccaccgtt gatatatccc aatggcatcg taaagaacat tttgaggcat    6360
ttcagtcagt tgctcaatgt acctataacc agaccgttca gctggatatt acggcctttt    6420
taaagaccgt aaagaaaaat aagcacaagt tttatccggc ctttattcac attcttgccc    6480
gcctgatgaa tgctcatccg gaattccgta tggcaatgaa agacggtgag ctggtgatat    6540
gggatagtgt tcacccttgt tacaccgttt tccatgagca aactgaaacg ttttcatcgc    6600
tctggagtga ataccacgac gatttccggc agtttctaca catatattcg caagatgtgg    6660
cgtgttacgg tgaaaacctg gcctatttcc ctaaagggtt tattgagaat atgttttttcg    6720 tctcagccaa tccctgggtg agtttcacca gttttgattt aaacgtggcc aatatggaca    6780
acttcttcgc ccccgttttc accatgggca aatattatac gcaaggcgac aaggtgctga    6840
tgccgctggc gattcaggtt catcatgccg tttgtgatgg cttccatgtc ggcagaatgc    6900
ttaatgaatt acaacagtac tgcgatgagt ggcagggcgg ggcgtaagcg ggactctggg    6960
gttcgaataa agaccgacca gcgacgtct gagagctccc tggcgaattc ggtaccaata    7020
aaagagcttt attttcatga tctgtgtgtt ggttttttgtg tgcggcgcgg aagttcctat    7080
tctctagaaa gtataggaac ttcctcgagc cctatagtga gtcgtattag atcgcggccg    7140
cgcccttgac tatgccacat cctgagcaaa taattcaacc actaattgtg agcggataac    7200
aaaggaggta aaaaaacatg gtatcctgtt ctgcgccggg taagatttac ctgttcggtg    7260
aacacgccgt agtttatggc gaaactgcaa ttgcgtgtgc ggtggaactg cgtacccgtg    7320
ttcgcgcgga actcaatgac tctatcacta ttcagagcca gatcggccgc accggtctgg    7380
```

-continued

```
atttcgaaaa gcacccttat gtgtctgcgg taattgagaa aatgcgcaaa tctattccta    7440
ttaacggtgt tttcttgacc gtcgattccg acatcccggt gggctccggt ctgggtagca    7500
gcgcagccgt tactatcgcg tctattggtg cgctgaacga gctgttcggc tttggcctca    7560
gcctgcaaga aatcgctaaa ctgggccacg aaatcgaaat taaagtacag ggtgccgcgt    7620
ccccaaccga tacgtatgtt tctaccttcg gcggcgtggt taccatcccg gaacgtcgca    7680
aactgaaaac tccggactgc ggcattgtga ttggcgatac cggcgttttc tcctccacca    7740
aagagttagt agctaacgta cgtcagctgc gcgaaagcta cccggatttg atcgaaccgc    7800
tgatgacctc tattggcaaa atctctcgta tcggcgaaca actggttctg tctggcgact    7860
acgcatccat cggccgcctg atgaacgtca accagggtct cctggacgcc ctgggcgtta    7920
acatcttaga actgagccag ctgatctatt ccgtcgtgc ggcaggtgcg tttgcgcta    7980 aaatcacggg cgctggcggc ggtggctgta tggttgcgct gaccgctccg gaaaaatgca    8040
accaagtggc agaagcggta gcaggcgctg gcggtaaagt gactatcact aaaccgaccg    8100
agcaaggtct gaaagtagat taa                                           8123

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94
accaattgca cccggcaga                                                  19

<210> SEQ ID NO 95
<211> LENGTH: 21
<212> TYPE: DNA
<213> ORGANISM: Artificial Sequence
<220> FEATURE:
<223> OTHER INFORMATION: Synthetic Construct

<400> SEQUENCE: 95
gctaaagcgc atgctccaga c                                               21

<210> SEQ ID NO 96
<211> LENGTH: 20
<212> TYPE: DNA
<213> ORGANISM: Artificial Sequence
<220> FEATURE:
<223> OTHER INFORMATION: Synthetic Construct

<400> SEQUENCE: 96
gactggcctc agatgaaagc                                                 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct

<400> SEQUENCE: 97
caaacatgtg gcatggaaag                                                 20

<210> SEQ ID NO 98
<211> LENGTH: 52
<212> TYPE: DNA
```

<213> ORGANISM: Artificial Sequence
<220> FEATURE:
<223> OTHER INFORMATION: Synthetic Construct

<400> SEQUENCE: 98
gggcccgttt aaactttaac tagactctgc agttagcgtt caaacggcag aa    52

<210> SEQ ID NO 99
<211> LENGTH: 38
<212> TYPE: DNA
<213> ORGANISM: Artificial Sequence
<220> FEATURE:
<223> OTHER INFORMATION: Synthetic Construct

<400> SEQUENCE: 99
cgcatgcatg tcatgagatg tagcgtgtcc accgaaaa    38

<210> SEQ ID NO 100
<211> LENGTH: 22
<212> TYPE: DNA
<213> ORGANISM: Artificial Sequence
<220> FEATURE:
<223> OTHER INFORMATION: Synthetic Construct

<400> SEQUENCE: 100
acaatttcac acaggaaaca gc    22

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
ccaggcaaat tctgttttat cag    23

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
gcactgtctt tccgtctgct gc    22

<210> SEQ ID NO 103
<211> LENGTH: 66
<212> TYPE: DNA
<213> ORGANISM: Artificial Sequence
<220> FEATURE:
<223> OTHER INFORMATION: Synthetic Construct

<400> SEQUENCE: 103
gcgaacgatg cataaaggag gtaaaaaaac atggtatcct gttctgcgcc gggtaagatt    60
tacctg    66

<210> SEQ ID NO 104
<211> LENGTH: 48
<212> TYPE: DNA
<213> ORGANISM: Artificial Sequence
<220> FEATURE:
<223> OTHER INFORMATION: Synthetic Construct

<400> SEQUENCE: 104

```
gggcccgttt aaactttaac tagactttaa tctactttca gaccttgc        48
```

<210> SEQ ID NO 105
<211> LENGTH: 24
<212> TYPE: DNA
<213> ORGANISM: Artificial Sequence
<220> FEATURE:
<223> OTHER INFORMATION: Synthetic Construct

<400> SEQUENCE: 105

```
gatagtaacg gctgcgctgc tacc                                  24
```

<210> SEQ ID NO 106
<211> LENGTH: 23
<212> TYPE: DNA
<213> ORGANISM: Artificial Sequence
<220> FEATURE:
<223> OTHER INFORMATION: Synthetic Construct

<400> SEQUENCE: 106

```
gacagcttat catcgactgc acg                                   23
```

<210> SEQ ID NO 107
<211> LENGTH: 22
<212> TYPE: DNA
<213> ORGANISM: Artificial Sequence
<220> FEATURE:
<223> OTHER INFORMATION: Synthetic Construct

<400> SEQUENCE: 107

```
caccatggta tcctgttctg cg                                    22
```

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108

```
ttaatctact ttcagacctt gc                                    22
```

<210> SEQ ID NO 109
<211> LENGTH: 81
<212> TYPE: DNA
<213> ORGANISM: Artificial Sequence
<220> FEATURE:
<223> OTHER INFORMATION: Synthetic Construct

<400> SEQUENCE: 109

```
aaagtagccg aagatgacgg tttgtcacat ggagttggca ggatgtttga ttaaaagcaa   60
ttaaccctca ctaaagggcg g                                            81
```

<210> SEQ ID NO 110
<211> LENGTH: 31
<212> TYPE: DNA
<213> ORGANISM: Artificial Sequence
<220> FEATURE:
<223> OTHER INFORMATION: Synthetic Construct

<400> SEQUENCE: 110

```
gatatacata tgaattaacc ctcactaaag g                          31
```

<210> SEQ ID NO 111

```
<211> LENGTH: 125
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 80
<223> OTHER INFORMATION: n = A,T,C or G

<400> SEQUENCE: 111
gcatgcatga catgttttttt tacctccttt gttatccgct cacaattagt ggttgaatta    60
tttgctcagg atgtggcatn gtcaagggcg cggccgcgat ctaatacgac tcactatagg   120
gctcg                                                                125

<210> SEQ ID NO 112
<211> LENGTH: 87
<212> TYPE: DNA
<213> ORGANISM: Artificial Sequence
<220> FEATURE:
<223> OTHER INFORMATION: Synthetic Construct

<400> SEQUENCE: 112
aggctctcaa ctctgacatg ttttttttcct ccttaagggt gcaggcctat cgcaaattag    60
cttaatctac tttcagacct tgctcgg                                         87

<210> SEQ ID NO 113
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 113
gcggccgcgc ccttgacgat gccacatcct gagcaaataa ttcaaccact aattgtgagc    60
ggataacaca aggaggaaac agccatggta tcctgttctg cgccgggtaa gatttacctg   120
ttcggtgaac acgccgtagt ttatggcgaa actgcaattg cgtgtgcggt ggaactgcgt   180
acccgtgttc gcgcggaact caatgactct atcactattc agagccagat cggccgcacc   240
ggtctggatt tcgaaaagca cccttatgtg tctgcggtaa ttgagaaaat gcgcaaatct   300
attcctatta acgtgttttt cttgaccgtc gattccgaca tcccggtggg ctccggtctg   360
ggtagcagcg cagccgttac tatcgcgtct attggtgcgc tgaacgagct gttcggctt   420 ggcctcagcc tgcaagaaat cgctaaactg ggccacgaaa tcgaaattaa agtacagggt   480
gccgcgtccc caaccgatac gtatgtttct accttcggcg gcgtggttac catcccggaa   540
cgtcgcaaac tgaaaactcc ggactgcggc attgtgattg cgataccgg cgttttctcc   600 tccaccaaag agttagtagc taacgtacgt cagctgcgcg aaagctaccc ggatttgatc   660
gaaccgctga tgacctctat tggcaaaatc tctcgtatcg cgaacaact ggttctgtct   720 ggcgactacg catccatcgg ccgcctgatg aacgtcaacc agggtctcct ggacgccctg   780
ggcgttaaca tcttagaact gagccagctg atctattccg ctcgtgcggc aggtgcgttt   840
ggcgctaaaa tcacgggcgc tggcggcggt ggctgtatgg ttgcgctgac cgctccggaa   900
aaatgcaacc aagtggcaga gcggtagca ggcgctggcg gtaaagtgac tatcactaaa   960
ccgaccgagc aaggtctgaa agtagattaa gccttgactt aatagctgct tatttcgccc  1020
ttatggtacc tagtaggagg aaaaaaacat ggaaatgcgt caaccggctg tcgcaggtca  1080
attctaccca ctgcgttgcg agaacctgga aaacgaactg aaacgctgct cgaaggcct  1140
```

```
ggagatccgc gaacaagaag tgctgggcgc agtctgtccg cacgccggtt atatgtactc    1200
tggcaaagtt gcggcgcacg tctatgccac tctgccggaa gctgatacct acgtaatctt    1260
cggcccgaac cacaccggct acggtagccc tgtctctgtg agccgtgaaa cttggaagac    1320
cccgttgggc aatatcgatg ttgacctgga actggcggac ggcttcctgg gttccatcgt    1380
agatgcggat gaactcggtc acaaatacga acactctatc gaagttcagc tgccgtttct    1440
gcaataccgt tttgaacgcg atttcaaaat tctgccaatc tgcatgggta tgcaagacga    1500
agaaaccgcg gtcgaagtag gtaacctgct ggcggatctg atcagcgagt ccggtaaacg    1560
tgctgtgatc atcgcaagct ctgatttcac ccactatgag acggctgaac gtgccaaaga    1620
aatcgattcc gaagttattg attctatcct gaactttgac atctctggca tgtacgatcg    1680
cctgtatcgc cgtaacgcct ctgtttgcgg ttacggcccg atcaccgcta tgctgacggc    1740
aagcaaaaag ctgggcggct ctcgtgcgac tttgctgaaa tacgcaaaca gcggtgacgt    1800
gtccggtgat aaagacgctg tggtgggcta cgccgccatc atcgttgagt aagctgatta    1860
aaggttgaac agataggatt tcgtcatgga tcctacaagg aggaaaaaaa catgaatgct    1920
tctaatgaac cggtgattct gaaactgggt ggctctgcta ttaccgacaa aggtgcctac    1980
gaaggcgtag ttaaggaagc tgatttgctg cgcatcgcac aggaagttag cggtttccgt    2040
ggcaagatga tcgtggttca tggtgctggt agcttcggcc atacgtacgc gaagaaatac    2100
ggcctggacc gtaccttcga cccagagggc gcaattgtta ctcatgaatc tgttaaaaag    2160
ctcgcctcca aagttgtagg tgctctgaat agcttcggcg tgcgtgctat cgcggtgcat    2220
cctatggact gcgcagtatg ccgtaacggt cgtatcgaaa cgatgtatct ggactccatc    2280
aagttaatgc tggaaaaagg tctggtgccg gttctgcacg gcgacgtcgc aatggatatt    2340
gaactgggca cttgtatcct gtccggtgat caaatcgttc cttacctggc caaagaactg    2400
ggtatctccc gcctcggcct gggcagcgca gaggatggtg tgctggatat ggagggcaaa    2460
cctgtaccgg aaatcacccc agaaactttc gaagagttcc gccactgcat cggtggttct    2520
ggttctactg atgtaaccgg tggcatgctg ggcaaagtgc tggaacttct ggaattgagc    2580
aaaaattctt ccattactag ctacattttc aacgctggta aagcagacaa catctaccgc    2640
tttctgaatg gtgagtccat cggcactcgc atcagcccgg acaagcgtgt ttaagctagt    2700
tattaaccta aatgctctaa accagttatg agctctacaa ggaggaaaaa aacatgatta    2760
acactaccag ccgccgcaaa attgaacacc tgaaactctg cgcagaatcc ccggttgaag    2820
cgcgtcaggt atctgccggc tttgaagacg ttactctgat ccaccgcgct ttaccggagc    2880
tgaacatgga tgaactggac ctcagcgttg atttcctggg taaacgcatc aaagcgccgt    2940
tcctgattgc gtctatcacg ggtggtcacc cagataccat cccggttaac gctgcgctgg    3000
cagctgctgc tgaggagctg ggtgttggca tcggcgttgg ctctcagcgc gcggccattg    3060
atgatccgag ccaggaagac agcttccgtg tagtgcgtga tgaagcccca gatgcgtttg    3120
tttatggcaa cgtcggcgca gcacagatcc gtcagtatgg tgttgaaggt gttgaaaaac    3180
tgatcgaaat gattgacgca gatgccttgg caatccacct gaactttctg caagaagcgg    3240
tccaaccgga aggtgaccgc gacgcgaccg gttgcctgga catgattacc gaaatttgct    3300
ctcagattaa aactccggta atcgtgaaag aaaccggtgc aggcattagc cgtgaagatg    3360
cgattctgtt ccagaaagct ggcgtgagcg caatcgacgt tggcgcgcg ggcggcacct    3420 cctgggctgg cgtcgaggtc taccgtgcta agaaagccg tgactctgtt agcgagcgtt    3480
```

-continued

| | |
|---|---|
| taggtgagct gttttgggat tcggcattc cgacggtagc ttctctgatt gaatcccgcg | 3540 |
| tttccttgcc gctgatcgca accggcgta tccgtaacgg tctggacatt gctaaaagca | 3600 |
| ttgctctcgg cgcaagcgct gccagcgccg ctctgccgtt cgttggtccg tccctggagg | 3660 |
| gcaaagaatc cgttgtacgt gtgctgagct gcatgctgga agaatttaaa gcagcaatgt | 3720 |
| ttttgtgcgg ttgcggcaac atcaaagacc tgcacaactc tccagtagtg gtaactggtt | 3780 |
| ggacccgcga atacctggag cagcgcggtt ttaacgttaa ggacctctcc ctgccgggca | 3840 |
| acgctctgta agcttcaacg cgtctacaaa taaaaaaggc acgtcagatg acgtgccttt | 3900 |
| tttcttgtct aga | 3913 |

<210> SEQ ID NO 114
<211> LENGTH: 6648
<212> TYPE: DNA
<213> ORGANISM: Artificial Sequence
<220> FEATURE:
<223> OTHER INFORMATION: Synthetic Construct

<400> SEQUENCE: 114

| | |
|---|---|
| aagggcgagc tcaacgatcc ggctgctaac aaagcccgaa aggaagctga gttggctgct | 60 |
| gccaccgctg agcaataact agcataaccc cttgggccct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aacccctatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact dacaatcggc tgctctgatg ccgccgtgtt | 660 |
| ccggctgtca gcgcaggggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat tgggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |
| ggtggaaaat ggccgctttt ctggattcat cgactgtggc cggctgggtg tggcggaccg | 1200 |
| ctatcaggac atagcgttgg ctacccgtga tattgctgaa gagcttggcg gcgaatgggc | 1260 |
| tgaccgcttc ctcgtgcttt acggtatcgc cgctcccgat tcgcagcgca tcgccttcta | 1320 |
| tcgccttctt gacgagttct tctgagcggg actctgggt tcgaaatgac cgaccaagcg | 1380 |
| acgcctaact gtcagaccaa gtttactcat atatacttta gattgattta aacttcatt | 1440 |
| tttaatttaa aaggatctag gtgaagatc ttttgataa tctcatgacc aaaatccctt | 1500 |
| aacgtgagtt ttcgttccac tgagcgtcag accccgtaga aagatcaaa ggatcttctt | 1560 |
| gagatccttt tttctgcgc gtaatctgct gcttgcaaac aaaaaaacca ccgctaccag | 1620 |

```
cggtggtttg tttgccggat caagagctac caactcttt  tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttacccgggt tggactcaag acgatagtta ccggataagg    1860
cgcagcggtc gggctgaacg ggggttcgt gcacacagcc cagcttggag cgaacgacct    1920
acaccgaact gagatacccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggccttttt acgttcctg gccttttgct ggcctttgc tcacatgttc tttcctgcgt      2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg ccatgttaa gggcggtttt ttcctgtttg     2760
gtcactgatg cctccgtgta agggggattt ctgttcatgg ggtaatgat accgatgaaa    2820 cgagagagga tgctcacgat acgggttact gatgatgaac atgcccggtt actggaacgt    2880
tgtgagggta acaactggc ggtatggatg cggcgggacc agagaaaaat cactcagggt     2940
caatgccagc gcttcgttaa tacagatgta ggtgttccac agggtagcca gcagcatcct    3000
gcgatgcaga tccggaacat aatggtgcag ggcgctgact ccgcgtttc cagactttac     3060 gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata atcgccgtg acgatcagcg    3540 gtccaatgat cgaagttagg ctggtaagag ccgcgagcga tccttgaagc tgtccctgat    3600
ggtcgtcatc tacctgcctg acagcatgg cctgcaacgc gggcatcccg atgccgccgg     3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
```

```
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accatacccda cgccgaaaca    5400 agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaatttcc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtccccaa ccgatacgta tgtttctacc ttcggcggcg    6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
```

```
aacaactggt tctgttctgg cgactacgca tccatcggcc gcctgatgaa cgtcaaccag    6420
ggtctcctgg acgccctggg cgttaacatc ttagaactga gccagctgat ctattccgct    6480
cgtgcggcag gtgcgtttgg cgctaaaatc acgggcgctg gcggcggtgg ctgtatggtt    6540
gcgctgaccg ctccggaaaa atgcaaccaa gtggcagaag cggtagcagg cgctggcggt    6600
aaagtgacta tcactaaacc gaccgagcaa ggtctgaaag tagattaa                 6648
```

<210> SEQ ID NO 115
<211> LENGTH: 67
<212> TYPE: DNA
<213> ORGANISM: Artificial Sequence
<220> FEATURE:
<223> OTHER INFORMATION: Synthetic Construct

<400> SEQUENCE: 115

```
accgccaaaa gcgactaatt ttagctgtta cagtcagttg aattaaccct cactaaaggg    60
cggccgc                                                              67
```

<210> SEQ ID NO 116
<211> LENGTH: 152
<212> TYPE: DNA
<213> ORGANISM: Artificial Sequence
<220> FEATURE:
<223> OTHER INFORMATION: Synthetic Construct

<400> SEQUENCE: 116

```
gctggcgata taaactgttt gcttcatgaa tgctcctttg ggttacctcc gggaaacgcg    60
gttgatttgt ttagtggttg aattatttgc tcaggatgtg gcatagtcaa gggcgtgacg   120
gctcgctaat acgactcact atagggctcg ag                                 152
```

<210> SEQ ID NO 117
<211> LENGTH: 30
<212> TYPE: DNA
<213> ORGANISM: Artificial Sequence
<220> FEATURE:
<223> OTHER INFORMATION: Synthetic Construct

<400> SEQUENCE: 117

```
cttgatatct tagtgtgcgt taaccaccac                                     30
```

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct

<400> SEQUENCE: 118

```
cgtgaatttg ctggctctca g                                              21
```

<210> SEQ ID NO 119
<211> LENGTH: 21
<212> TYPE: DNA
<213> ORGANISM: Artificial Sequence
<220> FEATURE:
<223> OTHER INFORMATION: Synthetic Construct

<400> SEQUENCE: 119

```
ggtttagttc ctcaccttgt c                                              21
```

<210> SEQ ID NO 120

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 120
actgaaacgt tttcatcgct c                                              21

<210> SEQ ID NO 121
<211> LENGTH: 26
<212> TYPE: DNA
<213> ORGANISM: Artificial Sequence
<220> FEATURE:
<223> OTHER INFORMATION: Synthetic Construct

<400> SEQUENCE: 121
accgccaaaa gcgactaatt ttagct                                         26

<210> SEQ ID NO 122
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 122
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg cccgtggaca aaccctgctg acaagctga    1080 tggacaggct gcgcctgccc acgagcttga ccacagggat gcccaccgg ctacccagcc    1140 ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt ggggcagtc gaaggcgaag cccgcccgcc    1380 tgcccccga gcctcacggc ggcgagtgcg ggggttccaa gggggcagcg ccaccttggg    1440
```

```
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaaatcaa caacttaaaa aagggggta    1620 cgcaacagct cattgcggca cccccgcaa tagctcattg cgtaggttaa agaaaatctg    1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacgcgcg ggcagcagcg cctgccgatg cccgatgagc cgtgtttttct  2400 ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg ccacctcga   2580 cctgaatgga agccggcggc acctcgctaa cggattcacc gttttatca ggctctggga    2640 ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag gttttccca gtcacgacgt tgtaaaacga cggccagtga   3180
gcgcgcgtaa tacgactcac tatagggcga attggagctc caccgcggtg gcggccgctc   3240
tagaactagt ggatccccg gctgcatgc tcgagcggcc gccagtgtga tggatatctg    3300
cagaattcgc ccttcttgat atcttagtgt gcgttaacca ccacccacat tggtccctgc   3360
ccgaccgcat agcggccttt ttcatgcagt agcccctgct cgccaacaat ttcgtatacc   3420
gagatgtggt gagatttttg cccggcggca atcagatact tgccgctgtg atcaacattg   3480
aagccgcgcg gctgggtttc cgttggctgg aagccttctt tactcaacac gctgccatct   3540
tccgaaacgc tgaaaacggt aatcaggctg gcggtacggt cgcaggcgta taaatggcga   3600
ccatccgggg tgatatgaat atcagccgcc caacgggtgt cggagaagtt ttccggcatc   3660
atatccagcg tctggacaca ttcgatatta ccgtgcggat ctttcagttc ccagacatcc   3720
actgagctgt ttaactcatt gacgcaatac gcatattgtt cgtttggatg gaataccata   3780
```

```
tgacgcgggc cggcccttc  aacggtggtc acttccgcag ggtcctgcgc cacgagatga   3840
ccatcatcgc tgaccgtaaa caggcaaatg cgatcctgct ttaatgccgg aacccacagc   3900
gtacggttgt ccggtgagat attggcggaa tggcaaccgt ccagcccctc gaccacatcg   3960
acgacgccca ctggcaggcc atcttccaga cgcgttacgc tcacgttacc cgcattgtaa   4020
gaacctacaa agacaaactg cccctggtga tcggtggaaa tatgcgtcgg actacccggc   4080
agcgcagact ctgcggcaaa ggtcagtgcg ccatcgtccg gggcgatacg atacgccagg   4140
acgcgaaact cagggcgaac accaacatag agataacgtt tgtccgggct gaccaccatc   4200
ggctgcacct gccccggcac atcgacaacc tgtgtcagcg tcagtgcgcc ttcatgattc   4260
agattccaga cgtgaatttg ctggctctca gggctggcga tataaactgt ttgcttcatg   4320
aatgctcctt tgggttacct ccgggaaacg cggttgattt gtttagtggt tgaattattt   4380
gctcaggatg tggcatagtc aagggcgtga cggctcgcta atacaactca ctatagggct   4440
cgaggaagtt cctatacttt ctagagaata ggaacttccg cgccgcacac aaaaaccaac   4500
acacagatca tgaaaataaa gctcttttat tggtaccgaa ttcgccaggg agctctcaga   4560
cgtcgcttgg tcgtctttta ttcgaacccc agagtcccgc ttacgccccg ccctgccact   4620
catcgcagta ctgttgtaat tcattaagca ttctgccgac atggaagcca tcacaaacgg   4680
catgatgaac ctgaatcgcc agcggcatca gcaccttgtc gccttgcgta taatatttgc   4740
ccatggtgaa aacgggggcg aagaagttgt ccatattggc cacgtttaaa tcaaaactgg   4800
tgaaactcac ccagggattg gctgagacga aaaacatatt ctcaataaac cctttaggga   4860
aataggccag gttttcaccg taacacgcca catcttgcga atatatgtgt agaaactgcc   4920
ggaaatcgtc gtggtattca ctccagagcg atgaaaacgt ttcagtttgc tcatggaaaa   4980
cggtgtaaca agggtgaaca ctatcccata tcaccagctc accgtctttc attgccatac   5040
ggaattccgg atgagcattc atcaggcggg caagaatgtg aataaaggcc ggataaaact   5100
tgtgcttatt tttctttacg gtctttaaaa aggccgtaat atccagctga acggtctggt   5160
tataggtaca ttgagcaact gactgaaatg cctcaaaatg ttctttacga tgccattggg   5220
atatatcaac ggtggtatat ccagtgattt ttttctccat ggtttagttc ctcaccttgt   5280
cgtattatac tatgccgata tactatgccg atgattaatt gtcaacacgt gctgctgcag   5340
gtcgaaaggc ccgagatga  ggaagaggag aacagcgcgg cagacgtgcg cttttgaagc   5400
gtgcagaatg ccgggcctcc ggaggacctt cgggcgcccg ccccgcccct gagcccgccc   5460
ctgagcccgc ccccggaccc acccttccc  agcctctgag cccagaaagc gaaggagcaa   5520
agctgctatt ggccgctgcc ccaaaggcct acccgcttcc attgctcagc ggtgctgtcc   5580
atctgcacga gactagtgag acgtgctact tccatttgtc acgtcctgca cgacgcgagc   5640
tgcggggcgg gggggaactt cctgactagg ggaggagtgg aaggtggcgc gaaggggcca   5700
ccaaagaacg gagccggttg gcgcctaccg gtggatgtgg aatgtgtgcg aggccagagg   5760
ccacttgtgt agcgccaagt gcccagcggg gctgctaaag cgcatgctcc agactgcctt   5820
gggaaaagcg cctcccctac ccggtagaat gaagttccta ctttctag  agaataggaa   5880
cttcgcggcc gccctttagt gagggttaat tcaactgact gtaacagcta aaattagtcg   5940
cttttggcgg taagggcgaa ttccagcaca ctggcggccg ttactagtgg atccgagctc   6000
ggtaccaagc ttgatgcagg aattcgatat caagcttatc gataccgtcg acctcgaggg   6060
gggcccggt  acccagcttt tgttcccttt agtgagggtt aattgcgcgc ttggcgtaat   6120
catggtcata gctgtttcct gtgtgaaatt gttatccgct cacaattcca cacaacatac   6180
```

| | |
|---|---|
| gagccggaag cataaagtgt aaagcctggg gtgcctaatg agtgagctaa ctcacattaa | 6240 |
| ttgcgttgcg ctcactgccc gctttccagt cgggaaacct gtcgtgccag ctgcattaat | 6300 |
| gaatcggcca acgcgcgggg agaggcggtt tgcgtattgg gcgcatgcat aaaaactgtt | 6360 |
| gtaattcatt aagcattctg ccgacatgga agccatcaca aacggcatga tgaacctgaa | 6420 |
| tcgccagcgg catcagcacc ttgtcgcctt gcgtataata tttgcccatg acgcacacc | 6480 |
| gtggaaacgg atgaaggcac gaacccagtt gacataagcc tgttcggttc gtaaactgta | 6540 |
| atgcaagtag cgtatgcgct cacgcaactg gtccagaacc ttgaccgaac gcagcggtgg | 6600 |
| taacggcgca gtggcggttt tcatggcttg ttatgactgt ttttttgtac agtctatgcc | 6660 |
| tcgggcatcc aagcagcaag cgcgttacgc cgtgggtcga tgtttgatgt tatggagcag | 6720 |
| caacgatgtt acgcagcagc aacgatgtta cgcagcaggg cagtcgccct aaaacaaagt | 6780 |
| taggtggctc aagtatgggc atcattcgca catgtaggct cggccctgac caagtcaaat | 6840 |
| ccatgcgggc tgctcttgat cttttcggtc gtgagttcgg agacgtagcc acctactccc | 6900 |
| aacatcagcc ggactccgat tacctcggga acttgctccg tagtaagaca ttcatcgcgc | 6960 |
| ttgctgccctt cgaccaagaa gcggttgttg gcgctctcgc ggcttacgtt ctgcccaggt | 7020 |
| tgagcagcc gcgtagtgag atctatatct atgatctcgc agtctccggc gagcaccgga | 7080 |
| ggcagggcat tgccaccgcg ctcatcaatc tcctcaagca tgaggccaac gcgcttggtg | 7140 |
| cttatgtgat ctacgtgcaa gcagattacg gtgacgatcc cgcagtggct ctctatacaa | 7200 |
| agttgggcat acgggaagaa gtgatgcact ttgatatcga cccaagtacc gccacctaac | 7260 |
| aattcgttca agccgagatc ggcttcccgg ccgcggagtt gttcggtaaa ttgtcacaac | 7320 |
| gccgccaggt ggcacttttc ggggaaatgt gcgcgcccgc gttcctgctg gcgctgggcc | 7380 |
| tgtttctggc gctggacttc ccgctgttcc gtcagcagct tttcgcccac ggccttgatg | 7440 |
| atcgcggcgg ccttgccctg catatcccga ttcaacggcc ccagggcgtc cagaacgggc | 7500 |
| ttcaggcgct cccgaaggt | 7519 |

<210> SEQ ID NO 123
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 123

| | |
|---|---|
| tagaaaaact catcgagcat caaatgaaac tgcaatttat tcatatcagg attatcaata | 60 |
| ccatattttt gaaaaagccg tttctgtaat gaaggagaaa actcaccgag gcagttccat | 120 |
| aggatggcaa gatcctggta tcggtctgcg attccgactc gtccaacatc aatacaacct | 180 |
| attaatttcc cctcgtcaaa aataaggtta tcaagtgaga aatcaccatg agtgacgact | 240 |
| gaatccggtg agaatggcaa aagtttatgc atttctttcc agacttgttc aacaggccag | 300 |
| ccattacgct cgtcatcaaa atcactcgca tcaaccaaac cgttattcat tcgtgattgc | 360 |
| gcctgagcga ggcgaaatac gcgatcgctg ttaaaaggac aattacaaac aggaatcgag | 420 |
| tgcaaccggc gcaggaacac tgccagcgca tcaacaatat tttcacctga atcaggatat | 480 |
| tcttctaata cctggaacgc tgtttttccg gggatcgcag tggtgagtaa ccatgcatca | 540 |
| tcaggagtac ggataaaatg cttgatggtc ggaagtggca taaattccgt cagccagttt | 600 |
| agtctgacca tctcatctgt aacatcattg gcaacgctac ctttgccatg tttcagaaac | 660 |

```
aactctggcg catcgggctt cccatacaag cgatagattg tcgcacctga ttgcccgaca      720
ttatcgcgag cccatttata cccatataaa tcagcatcca tgttggaatt taatcgcggc      780
ctcgacgttt cccgttgaat atggctcata ttcttccttt ttcaatatta ttgaagcatt      840
tatcagggtt attgtctcat gagcggatac atatttgaat gtatttagaa aaataaacaa      900
ataggggtca gtgttacaac caattaacca attctgaaca ttatcgcgag cccatttata      960
cctgaatatg gctcataaca ccccttgttt gcctggcggc agtagcgcgg tggtcccacc     1020
tgaccccatg ccgaactcag aagtgaaacg ccgtagcgcc gatggtagtg tggggactcc     1080
ccatgcgaga gtagggaact gccaggcatc aaataaaacg aaaggctcag tcgaaagact     1140
gggcctttcg cccgggctaa ttaggggggtg tcgcccttcg attgacggtt acgggatcct     1200
cacacgtaca tcagctggtt gatgggaaac gggtcgatga gcagcagctt gatgcggttc     1260
tcggtggcgt aatccgggcg gcccagcccg tccccatatt ggtaggtgca gtggctcacg     1320
cgggccatgt tcacggcgat ctccatgaac gccttcggca gcagggtgct gtccgacacg     1380
cgctcgcggt tcattttctt ccactcggcg tcgatcagct tgcgcagctc ttcgcgggcc     1440
tgttcctcgc tcgtgccgtc gttctcgtgc atgtagctga tgatgctgtt ggtggtttcg     1500
ccgcgttcga gttccgccgc cgaggtcgcc agatcgttgc acagccgaaa gatcacgcag     1560
gacgagcgca ccaggccgtg gaagtcggtc agggagcgga gggcgtggtc cgagatatct     1620
tcctgctgct ggcagaccga gaagtagctc ggcgccagca gcgcgacccc gctggaggac     1680
acgctggcgt tctccaggta cttgctgaag gcggggatga tcttgttatt gctccacttg     1740
gcttcttgca ggaaggcctt gcacagttcg cgccagcttt tggtcagata gctcaggtta     1800
ttgtggccct tctccttcag gatggagtag gacgtgtcgt tcacggtgtt gtacagggcc     1860
aggaagcaca gcttcatata gtcgggcagc gtgttgatgg cgttcacgtc ccagcgttcc     1920
accgcgtcgg tgaagagctg cagttcgtcc agggtaccgt acacgtcata gacgtcatcg     1980
ataatggtga ccagaccgaa catcttggtg acggccttgc ggcattcgcc gaactgcggg     2040
tccggcgcca tgcccagcgc ccagaagtac acttccatca ggcggtcccg cacgaaatcc     2100
agcttgctgg cgaggcccat ctcggtccac caccggctca ggtcctgcag ctcttttttgg     2160 tgcagggtct ggaccatgtt gaaatcgagt ttggccagtt ccagcagcag ctggtgatgc     2220
ggctccttgg gttcgtactt gtccagaaac caccgcgcct ccaggcggtg caggcgttga     2280
tgatacggca gctccagcgc gtgggacacc tgctcggcca ccttcgtgtt gatcccctcc     2340
ttgaggttgt tcttcagatg ggtgatgctg aaggtacggg cctcctccag cagattttcg     2400
ccttcgaaac cgagatagct ggcctcgtac aggctcagca ggccctgcac gtcacccttc     2460
agttccccgg agaagccccc ttctttgtcc ttgaagcgct cgaacacgtc ctggctcacc     2520
tcaaagccat gctgccgcag caggcggaag ctcagggcgg tcgcgtgcag atcgcttttg     2580
ttcttcttat tctcgtccag caggacgatg ttctccagcg ccttgatgat atctttctca     2640
aacttgtagg tcaggcccag cgcgctgcacg tcgtcgatga gctccagcag gctcaggggc     2700
tgggtgtcca cccggttgat catgcaacgc acctcctcct ccagcttggt ggccttctct     2760
tcgagcttct ccaccttcag gtcgttttcc aggctctgca ggaactcgaa gttccacagg     2820
ttgggctggt agttcgcgga ccgacggcta ttatgctcgg tgatctgggt gaactggctg     2880
ctggtggcgc acatatgtat atctccttct taaagttaaa caagcttaag atgttcagcg     2940
acaagggcga cacaaaattt attctaaatg cataataaat actgataaca tcttatagtt     3000
tgtattatat tttgtattat cgttgacatg tataattttg atatcaaaaa ctgattttcc     3060
```

```
ctttattatt ttcgagattt attttcttaa ttctctttaa caaactagaa atattgtata    3120
tacaaaaaat cataaataat agatgaatag tttaattata ggtgttcatc aatcgaaaaa    3180
gcaacgtatc ttatttaaag tgcgttgctt ttttctcatt tataaggtta aataattctc    3240
atatatcaag caaagtgaca ggcgcccttá aatattctga caaatgctct ttccctaaac    3300 tcccccata aaaaaacccg ccgaagcggg tttttacgtt atttgcggat taacgattac    3360
tcgttatcag aaccgcccag ggggcccgag cttaagactg gccgtcgttt tacaacacag    3420
aaagagtttg tagaaacgca aaaaggccat ccgtcagggg ccttctgctt agtttgatgc    3480
ctggcagttc cctactctcg ccttccgctt cctcgctcac tgactcgctg cgctcggtcg    3540
ttcggctgcg gcgagcggta tcagctcact caaaggcggt aatacggtta tccacagaat    3600
caggggataa cgcaggaaag aacatgtgag caaaaggcca gcaaaaggcc aggaaccgta    3660
aaaaggccgc gttgctggcg ttttccata ggctccgccc ccctgacgag catcacaaaa    3720
atcgacgctc aagtcagagg tggcgaaacc cgacaggact ataaagatac caggcgtttc    3780
cccctggaag ctccctcgtg cgctctcctg ttccgaccct gccgcttacc ggatacctgt    3840
ccgcctttct cccttcggga agcgtggcgc tttctcatag ctcacgctgt aggtatctca    3900
gttcggtgta ggtcgttcgc tccaagctgg gctgtgtgca cgaaccccc gttcagcccg    3960 accgctgcgc cttatccggt aactatcgtc ttgagtccaa cccggtaaga cacgacttat    4020
cgccactggc agcagccact ggtaacagga ttagcagagc gaggtatgta ggcggtgcta    4080
cagagttctt gaagtggtgg gctaactacg gctacactag aagaacagta tttggtatct    4140
gcgctctgct gaagccagtt accttcggaa aaagagttgg tagctcttga tccggcaaac    4200
aaaccaccgc tggtagcggt ggtttttttg tttgcaagca gcagattacg cgcagaaaaa    4260
aaggatctca agaagatcct ttgatctttt ctacggggtc tgacgctcag tggaacgacg    4320
cgcgcgtaac tcacgttaag ggattttggt catgagcttg cgccgtcccg tcaagtcagc    4380
gtaatgctct gcttt                                                    4395
```

COMPOSITIONS AND METHODS FOR PRODUCING ISOPRENE

CROSS-REFERENCE TO RELATED APPLICATIONS

This application is a divisional application of U.S. patent application Ser. No. 12/335,071, filed Dec. 15, 2008, which is now U.S. Pat. No. 8,288,148, which claims priority benefit of U.S. Provisional Application No. 61/013,574, filed Dec. 13, 2007. The disclosures of which are herein incorporated by reference in their entirety.

FIELD OF THE INVENTION

The present invention relates generally to methods for producing isoprene from cultured cells and compositions that include these cultured cells.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIGS. 19A and 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that have an average volumetric productivity of isoprene greater than about 0.1 mg/$L_{broth}$/hr. In some embodiments, the invention provides cells in culture that have a peak volumetric productivity of isoprene greater than about 0.5 mg/$L_{broth}$/hr. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In one aspect, the invention features methods of producing isoprene, such as methods of using any of the cells described herein to produce isoprene. In some embodiments, the method involves culturing cells under conditions resulting in an average volumetric productivity of isoprene greater than about 0.1 mg/$L_{broth}$/hr. In some embodiments, the method involves culturing cells under conditions resulting in a peak volumetric productivity of isoprene greater than about 0.5 mg/$L_{broth}$/hr. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments, the method includes culturing cells under conditions sufficient to convert more than about 0.002% of the carbon in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, component from a yeast extract, or any combination of two or more of the foregoing.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole/$g_{wcm}$/hr isoprene. In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, 90.0 molar %, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisi, Methanosarcina mazei,* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia, Methanosarcina mazei,* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a naturally-occurring polypeptide from a plant such as *Pueraria* (e.g., *Pueraria montana*) or *Populus* (e.g., *Populus tremuloides, Populus alba* (*P. alba*), *Populus nigra, Populus trichocarpa,* or the hybrid, *Populus alba×Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor, Streptomyces coelicolor, Streptomyces albus,* or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments, the *E. coli* cells are *E. coli* FadR atoC mutant cells. In some embodiments, the *E. coli* cells express (such as constitutively express) ybhE (also known as pgl). In some embodiments of any of the aspects of the invention, the cells are fungal, cells such as filamentous funal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention provides a tire comprising polyisoprene. In some embodiments, the polyisoprene is produced by (i) polymerizing isoprene from any of the compositions or methods described herein or (ii) polymerizing isoprene recovered from any of the compositions or methods described herein. In some embodiments, the polyisoprene comprises cis-1,4-polyisoprene.

In one aspect, the invention features a product (such as a tire) produced by any of the compositions or methods of the invention.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIG. 3 is the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIG. 5 is the nucleotide sequence of pETNHisKudzu (SEQ ID NO:5).

FIG. 7 is the nucleotide sequence of pCL-lac-Kudzu (SEQ ID NO:7).

FIG. 9A is a graph showing OD over time of fermentation of *E. coli* BL21/pTrcKudzu in a 14 liter fed batch fermentation.

FIG. 9B is a graph showing isoprene production over time of fermentation of *E. coli* BL21/pTrcKudzu in a 14 liter fed batch fermentation.

FIG. 12 is the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIG. 15 is the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba×Populus tremula*) isoprene synthase gene (SEQ ID NO:13). The ATG start codon is in bold and the stop codon is underlined.

FIG. 18A shows a schematic outlining construction of vectors pYLA 1, pYL1 and pYL2.

FIG. 22 is the nucleotide sequence of pTrcKudzu yIDI DXS Kan (SEQ ID NO:20).

FIG. 25 is a nucleotide sequence of pTrcKKDyIkIS kan (SEQ ID NO:33).

FIG. 27 is a nucleotide sequence of pCL PtrcUpperPathway (SEQ ID NO:46).

FIG. 29 is a nucleotide sequence of cassette containing the lower MVA pathway and yeast idi for integration into the *B. subtilis* chromosome at the nprE locus (SEQ ID NO:47).

FIG. 31 is a nucleotide sequence of p9796-poplar (SEQ ID NO:48).

FIG. 33 is a nucleotide sequence of pTrcPoplar (SEQ ID NO:49).

FIG. 35 is a nucleotide sequence of pTrcKudzu yIDI Kan (SEQ ID NO:50).

FIG. 37 is a nucleotide sequence of pTrcKudzuDXS Kan (SEQ ID NO:51).

FIG. 39 is a nucleotide sequence of pCL PtrcKudzu (SEQ ID NO:52).

FIG. 41 is a nucleotide sequence of pCL PtrcKudzu A3 (SEQ ID NO:53).

FIG. 43 is a nucleotide sequence of pCL PtrcKudzu yIDI (SEQ ID NO:54).

FIG. 45 is a nucleotide sequence of pCL PtrcKudzu DXS (SEQ ID NO:55).

FIG. 51 is the nucleotide sequence of pJMupperpathway2 (SEQ ID NO:56).

FIGS. 55A and 55B are the nucleotide sequence of plasmid pET24 *P. alba* HGS (SEQ ID NO:87).

FIGS. 58A and 58B are the nucleotide sequence of plasmid EWL230 (SEQ ID NO:88).

FIGS. 61A and 61B are the nucleotide sequence of plasmid EWL244 (SEQ ID NO:89).

FIGS. 63A-63C are the nucleotide sequence of plasmid MCM484 (SEQ ID NO:90).

FIGS. 64A-64C are the nucleotide sequence of plasmid MCM485 (SEQ ID NO:91).

FIGS. 65A-65C are the nucleotide sequence of plasmid MCM486 (SEQ ID NO:92).

FIGS. 66A-66C are the nucleotide sequence of plasmid MCM487 (SEQ ID NO:93).

FIG. 67A shows the time course of optical density within the 15-L bioreactor fed with glucose. FIG. 67B shows the time course of isoprene titer within the 15-L bioreactor fed with glucose. The titer is defined as the amount of isoprene produced per liter of fermentation broth. FIG. 67C shows the time course of total isoprene produced from the 15-L bioreactor fed with glucose. FIG. 67D shows the total carbon dioxide evolution rate (TCER), or metabolic activity profile, within the 15-L bioreactor fed with glucose.

FIG. 68A shows the time course of optical density within the 15-L bioreactor fed with glucose. FIG. 68B shows the time course of isoprene titer within the 15-L bioreactor fed with glucose. The titer is defined as the amount of isoprene produced per liter of fermentation broth. FIG. 68C shows the time course of total isoprene produced from the 15-L bioreactor fed with glucose. FIG. 68D shows the volumetric productivity within the 15-L bioreactor fed with glucose. An average value of 1.1 g/L/hr was maintained for a 40-hour period (23-63 hours) with yeast extract feeding. FIG. 68E shows the carbon dioxide evolution rate (CER), or metabolic activity profile, within the 15-L bioreactor fed with glucose.

FIG. 69A shows growth of *E. coli* EWL256, which contains both the MVA pathway and isoprene synthase, on either glucose, biomass hydrolysate, glycerol, or acetate as the only carbon source. The different carbon sources were added to a concentration of 1% in the media. A negative control with no added carbon source was included. Growth was measured as optical density at 600 nM. FIG. 69B shows specific productivity of isoprene from *E. coli* EWL256 containing both the MVA pathway and isoprene synthase when grown on either glucose, biomass hydrolysate, glycerol, or acetate as only carbon source. The different carbon sources were added to a concentration of 1% in the media. A negative control with no added carbon source was included. Samples were taken 190 minutes, 255 minutes and 317 minutes after inoculation and isoprene produced by the bacteria was measured using GC-MS. FIG. 69C shows growth of *E. coli* EWL256 on either glucose or xylose as the only carbon source. The different carbon sources were added to a concentration of 1% in the media. A negative control with no added carbon source was included. Growth was measured as optical density at 600 nM. FIG. 69D shows specific productivity of isoprene from *E. coli* EWL256 when grown on either glucose or xylose as only carbon source. The carbon sources were added to a concentration of 1% in the media. A negative control with no added carbon source was included. Samples were taken 260 minutes, 322 minutes and 383 minutes after inoculation and isoprene produced by the bacteria was measured using GC-MS.

FIGS. 73B and 73C are the nucleotide sequence of the *M. mazei* archaeal lower Pathway operon (SEQ ID NO:113).

FIGS. 74B and 74C are the nucleotide sequence of MCM376-MVK from *M. mazei* archaeal Lowerin pET200D (SEQ ID NO:114).

These values for the OD550 must be multiplied by 6.66 to obtain the actual OD of the culture.

Figure 76:
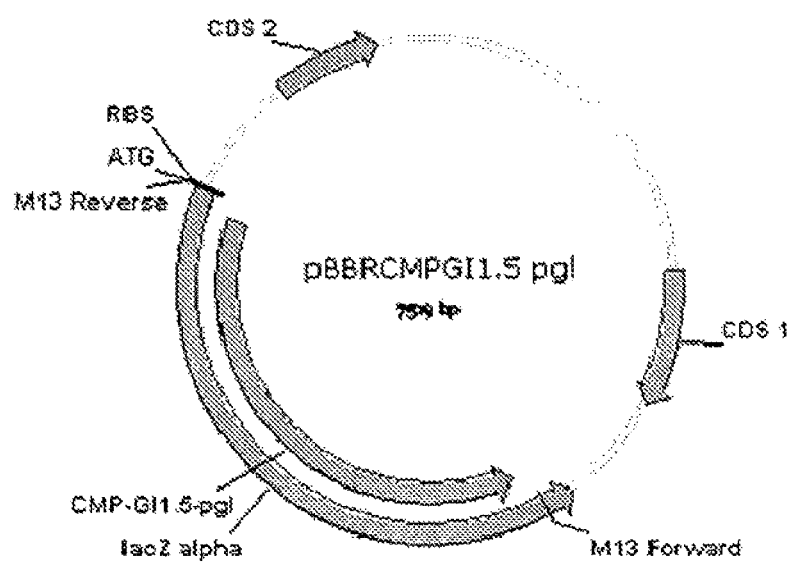

FIG. 76 is a map of plasmid pBBRCMPGI1.5-pgl.

FIGS. 77A and 77B are the nucleotide sequence of plasmid pBBRCMPGI1.5-pgl (SEQ ID NO:122).

Figure 78A:
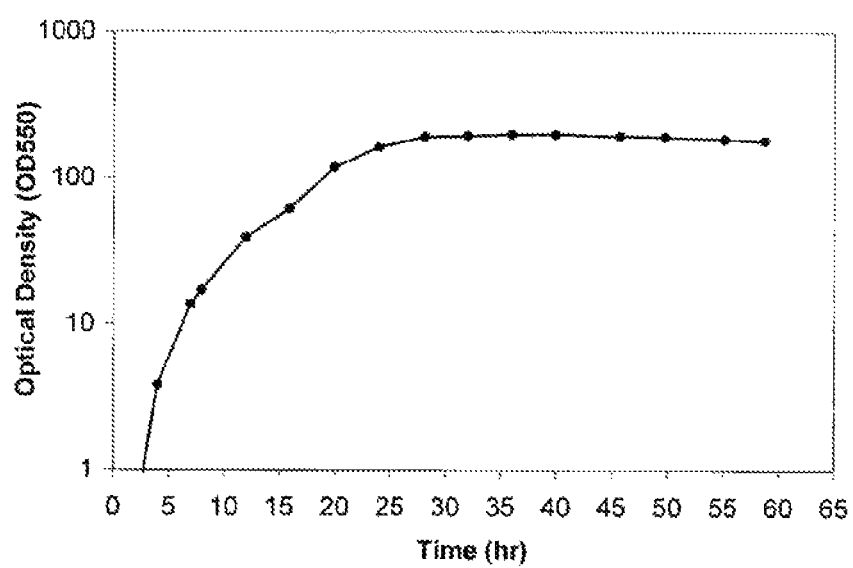
Figure 78D:
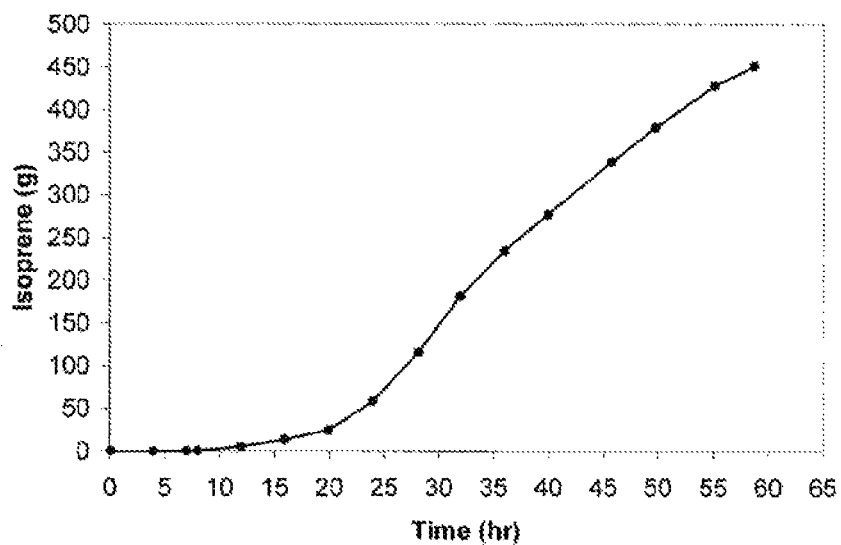
Figure 78E:
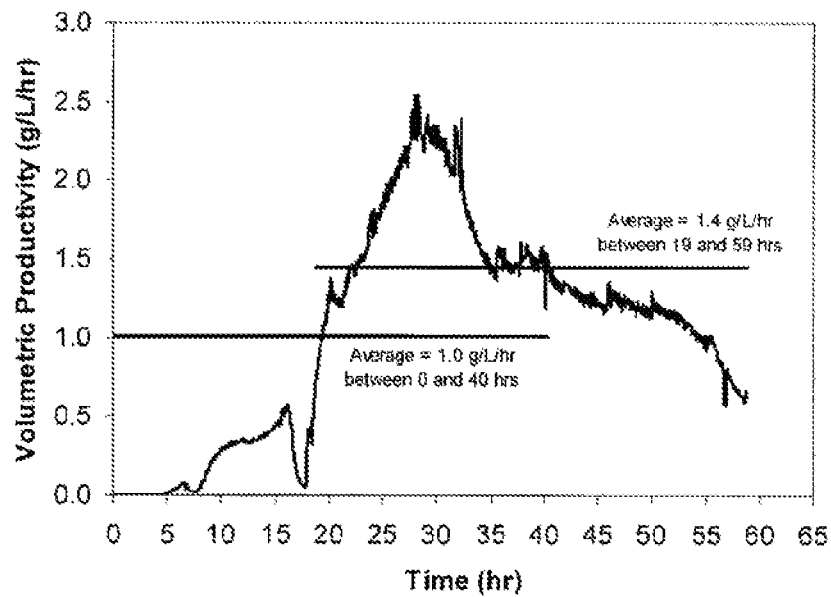
Figure 78F:
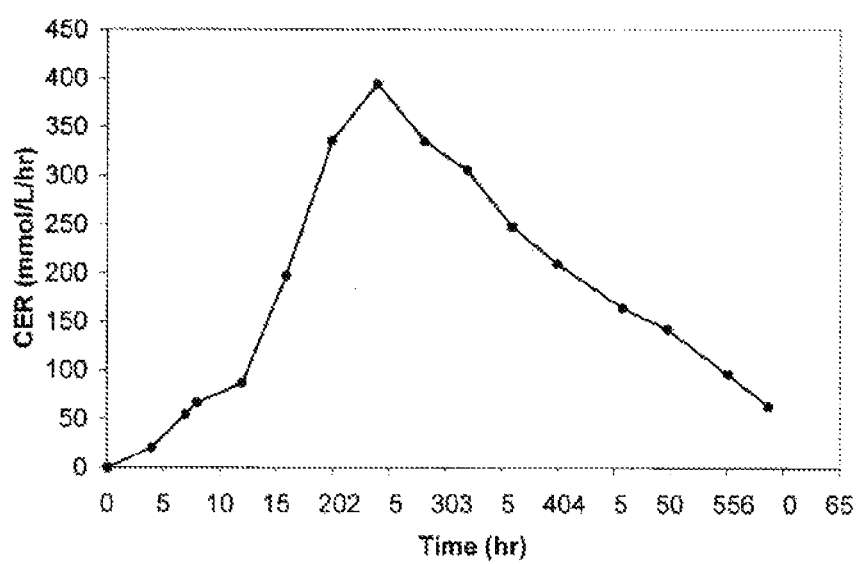

FIGS. 78A-78F are graphs of isoprene production by *E. coli* strain expressing *M. mazei* mevalonate kinase, *P. alba* isoprene synthase, and pgl (RHM111608-2), and grown in fed-batch culture at the 15-L scale. FIG. 78A shows the time course of optical density within the 15-L bioreactor fed with glucose. FIG. 78B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 78C also shows the time course of isoprene titer within the 15-L bioreactor fed with glucose. Method for calculating isoprene: ∫(Instantaneous isoprene production rate, g/L/hr)dt from t=0 to 59 hours [=] g/L broth. FIG. 78D shows the time course of total isoprene produced from the 15-L bioreactor fed with glucose. FIG. 78E shows volumetric productivity within the 15-L bioreactor fed with glucose. FIG. 78F shows carbon dioxide evolution rate (CER), or metabolic activity profile, within the 15-L bioreactor fed with glucose.

Figure 79A:
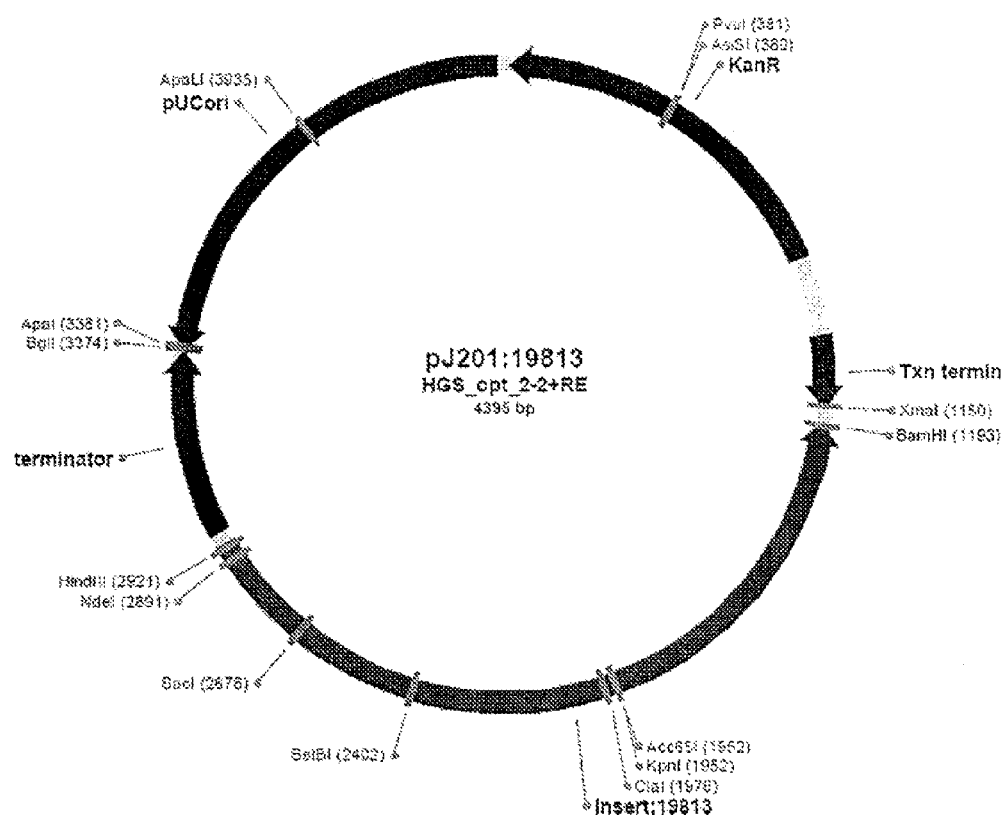

FIG. 79A is a map of plasmid pJ201:19813.

FIGS. 79B and 79C are the nucleotide sequence of pJ201: 19813 (SEQ ID NO:123).

DETAILED DESCRIPTION OF THE INVENTION

The invention features compositions and methods for the production of increased amounts of isoprene. In particular, these compositions and methods increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of ~23.6 molar % yield (10.7 weight % yield) of the carbon that the cells consume from a cell culture medium into isoprene (% carbon yield). As shown in the Examples and Table 2, approximately 60.5 g of isoprene per liter of broth was generated. Isoprene was produced at a peak specific rate of $1.88 \times 10^5$ nmol/OD/hr ($1.88 \times 10^5$ nmole/$g_{wcm}$/hr). If desired, even greater amounts of isoprene can be obtained using other conditions, such as those described herein. In some embodiments, a renewable carbon source is used for the production of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) or *Populus alba* (Poplar) isoprene synthase polypeptide was expressed in a variety of host cells, such as *Escherichia coli, Panteoa citrea, Bacillus subtilis, Yarrowia lipolytica,* and *Trichoderma reesei*. As also shown in the Examples, a heterologous *Methanosarcina mazei* (*M. mazei*) mevalonate kinase (MVK) was expressed in host cells such as *Escherichia coli* to increase isoprene production. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 60.5 g of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| Strain | Isoprene Production in a Headspace vial* | |
|---|---|---|
| | Headspace concentration µg/$L_{gas}$ | Specific Rate µg/$L_{broth}$/hr/OD (nmol/$g_{wcm}$/hr) |
| *E. coli* BL21/pTrcKudzu IS | 1.40 | 53.2 |
| | | (781.2) |
| *E. coli* BL21/Pcl DXS yidi Kudzu IS | 7.61 | 289.1 |
| | | ($4.25 \times 10^3$) |
| *E. coli* BL21/MCM127 with kudzu IS and entire MVA pathway | 23.0 | 874.1 |
| | | ($1.28 \times 10^4$) |
| *E. coli* BL21/Pet N-HisKudzu IS | 1.49 | 56.6 |
| | | (831.1) |
| *Pantoea citrea*/pTrcKudzu IS | 0.66 | 25.1 |
| | | (368.6) |
| *E. coli* w/Poplar IS [Miller (2001)] | — | 5.6 |
| | | (82.2) |
| *Bacillis licheniformis* Fall U.S. Pat. No. 5,849,970 | — | 4.2 |
| | | (61.4) |
| *Yarrowia lipolytica* with kudzu isoprene synthase | ~0.05 µg/L | ~2 |
| | | (~30) |
| *Trichoderma reesei* with kudzu isoprene synthase | ~0.05 µg/L | ~2 |
| | | (~30) |
| *E. coli* BL21/ pTrcKKD$_y$I$_k$IS with kudzu IS and lower MVA pathway | 85.9 | $3.2 \times 10^3$ |
| | | ($4.8 \times 10^4$) |

*Normalized to 1 mL of 1 OD$_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** ($ug/L_{gas}$) | Titer ($mg/L_{broth}$) | Peak Specific rate $\mu g/L_{broth}/hr/OD$ ($nmol/g_{wcm}/hr$) |
| E. coli BL21/ pTrcKudzu with Kudzu IS | 52 | 41.2 | 37 (543.3) |
| E. coli FM5/pTrcKudzu IS | 3 | 3.5 | 21.4 (308.1) |
| E. coli BL21/triple strain (DXS, yidi, IS) | 285 | 300 | 240 ($3.52 \times 10^3$) |
| E. coli FM5/triple strain (DXS, yidi, IS) | 50.8 | 29 | 180.8 ($2.65 \times 10^3$) |
| E. coli/MCM127 with Kudzu IS and entire MVA pathway | 1094 | 250 | 875 ($1.28 \times 10^4$) |
| Bacillus subtilis wild-type | 1.5 | 2.5 | 0.8 (11.7) |
| Bacillus pBS Kudzu IS | 16.6 | ~30 (over 100 hours) | 5 (73.4) |
| Bacillus Marburg 6051 [Wagner and Fall (1999)] | 2.04 | 0.61 | 24.5 (359.8) |
| Bacillus Marburg 6051 Fall U.S. Pat. No. 5,849,970 | 0.7 | 0.15 | 6.8 (100) |
| E. coli BL21/pCLPtrcUpper Pathway and gi1.2KKDyI and pTrcAlba-mMVK | $2.03 \times 10^4$ | $3.22 \times 10^4$ | $5.9 \times 10^3$ ($8.66 \times 10^4$) |
| E. coli BL21/pCLPtrcUpper Pathway and gi1.2KKDyI and pTrcAlba-mMVK plus pBBRCMPGI1.5pgl | $3.22 \times 10^4$ | $6.05 \times 10^4$ | $1.28 \times 10^4$ ($1.88 \times 10^5$) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
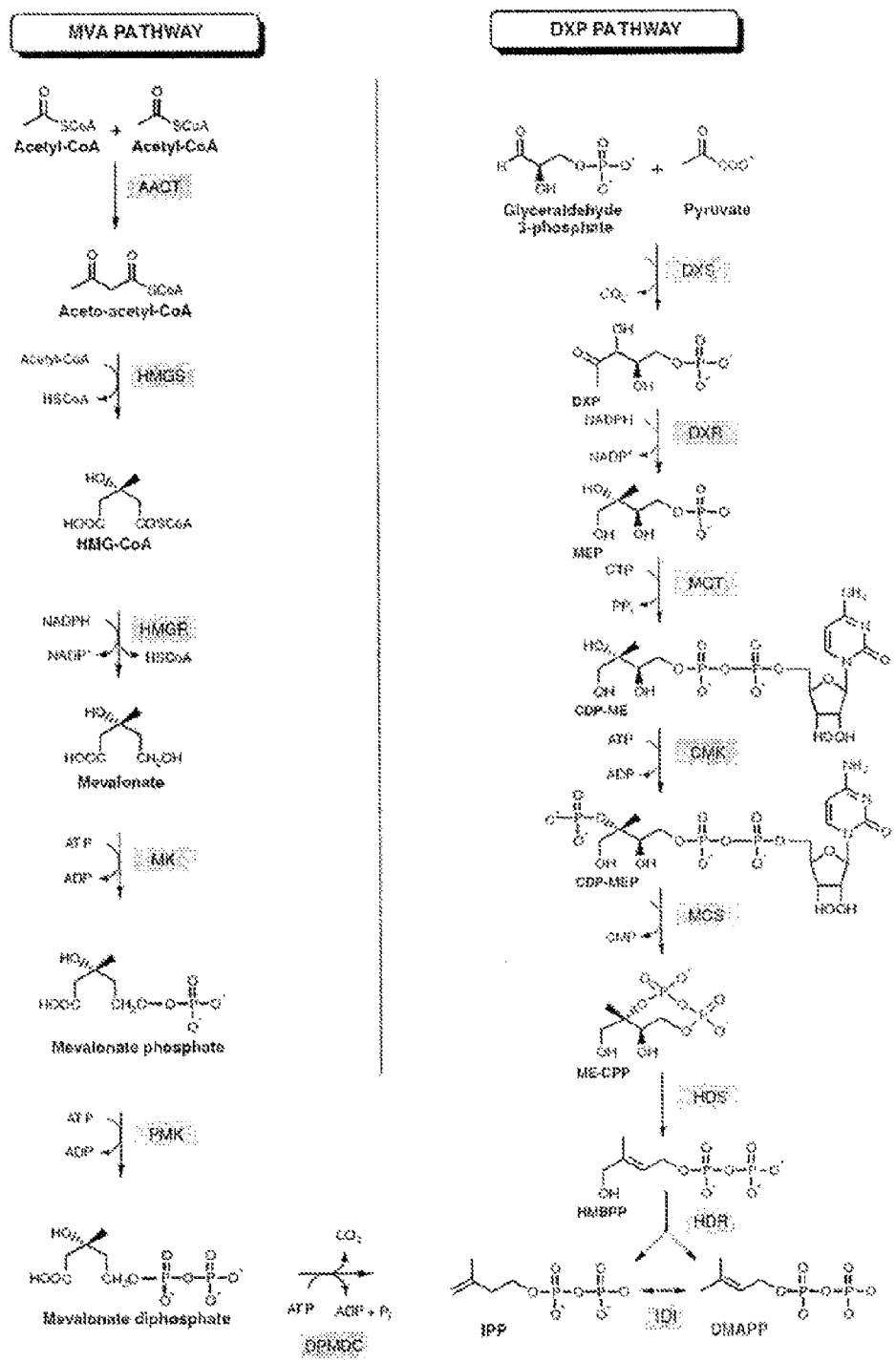
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: *J. Bacteriol.*, 184: 2116-2122, 2002; HMGS; Hydroxymethylglutaryl-CoA synthase, MvaS, EC 2.3.3.10. Assay: *J. Bacteriol.*, 184: 4065-4070, 2002; HMGR; 3-Hydroxy-3-methylglutaryl-CoA reductase, MvaE, EC 1.1.1.34. Assay: *J. Bacteriol.*, 184: 2116-2122, 2002; MVK; Mevalonate kinase, ERG12, EC 2.7.1.36. Assay: *Curr Genet.* 19:9-14, 1991. PMK; Phosphomevalonate kinase, ERG8, EC 2.7.4.2, Assay: *Mol Cell Biol.*, 11:620-631, 1991; DPMDC; Diphosphomevalonate decarboxylase, MVD1, EC 4.1.1.33. Assay: *Biochemistry,* 33:13355-13362, 1994; IDI; Isopentenyl-diphosphate delta-isomerase, IDI1, EC 5.3.3.2. Assay: *J. Biol. Chem.* 264:19169-19175, 1989. DXP Pathway: DXS; 1-Deoxyxylulose-5-phosphate synthase, dxs, EC 2.2.1.7. Assay: *PNAS,* 94:12857-62, 1997; DXR; 1-Deoxy-D-xylulose 5-phosphate reductoisomerase, dxr, EC 2.2.1.7. Assay: *Eur. J. Biochem.* 269:4446-4457, 2002; MCT; 4-Diphosphocytidyl-2C-methyl-D-erythritol synthase, IspD, EC 2.7.7.60. Assay: *PNAS,* 97: 6451-6456, 2000; CMK; 4-Diphosphocytidyl-2-C-methyl-D-erythritol kinase, IspE, EC 2.7.1.148. Assay: *PNAS,* 97:1062-1067, 2000; MCS; 2C-Methyl-D-erythritol 2,4-cyclodiphosphate synthase, IspF, EC 4.6.1.12. Assay: *PNAS,* 96:11758-11763, 1999; HDS; 1-Hydroxy-2-methyl-2-(E)-butenyl 4-diphosphate synthase, ispG, EC 1.17.4.3. Assay: *J. Org. Chem.*, 70:9168-9174, 2005; HDR; 1-Hydroxy-2-methyl-2-(E)-butenyl 4-diphosphate reductase, IspH, EC 1.17.1.2. Assay: *JACS,* 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

For example, fermentation of E. coli cells with a kudzu isoprene synthase, S. cerevisia IDI, and E. coli DXS nucleic acids was used to produce isoprene. The levels of isoprene varied from 50 to 300 μg/L over a time period of 15 hours (Example 7, part VII). As another example, fermentation of E. coli with M. mazei mevalonate kinase (MVK), P. alba isoprene synthase, the upper MVA pathway, and the integrated lower MVA pathway was used to produce isoprene. The levels of isoprene varied from 32 to 35.6 g/L over a time period of 67 hours (Example 10, part III).

In yet another example, fermentation of E. coli with M. mazei mevalonate kinase (MVK), P. alba isoprene synthase, pgl over-expression (RHM111608-2), the upper MVA pathway, and the integrated lower MVA pathway were used to produce isoprene. The levels of isoprene vary from 33.2 g/L to 40.0 g/L over a time period of 40 hours or 48.6 g/L to 60.5 g/L over a time period of 59 hours (Example 13, part (ii)).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by E. coli cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
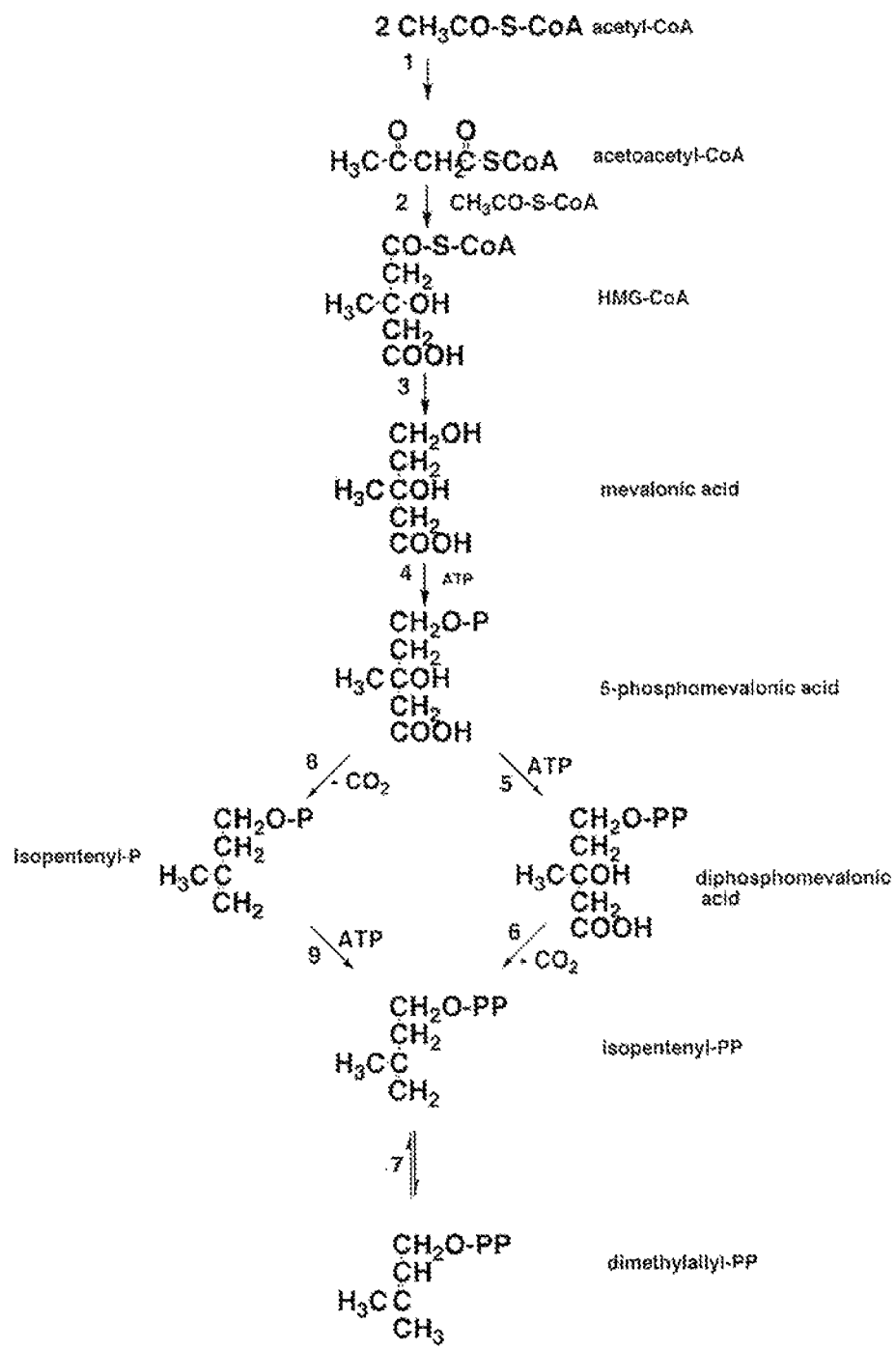
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews,* 71:97-120, 2007, which is incorporated by reference in its entirety, particularly with respect to nucleic acids and polypeptides of the modified MVA pathway. The modified MVA pathway is present, for example, in some archaeal organisms, such as *Methanosarcina mazei*.

In some embodiments, the production of isoprene by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, $E.$ $coli$ cells containing a nucleic acid encoding a kudzu isoprene synthase polypeptide and nucleic acids encoding $Saccharomyces$ $cerevisia$ MVK, PMK, MVD, and IDI polypeptides generated isoprene at a rate of $6.67 \times 10^4$ nmol/$L_{broth}$/OD$_{600}$/hr (see Example 8). Additionally, a 14 liter fermentation of $E.$ $coli$ cells with nucleic acids encoding $Enterococcus$ $faecalis$ AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in $E.$ $coli$. $E.$ $coli$ cells that contain nucleic acids for both the upper MVA pathway and the lower MVA pathway as well as a kudzu isoprene synthase (strain MCM 127) produced significantly more isoprene (874 ☒g/$L_{broth}$/hr/OD) compared to $E.$ $coli$ cells with nucleic acids for only the lower MVA pathway and the kudzu isoprene synthase (strain MCM 131) (see Table 3 and Example 8, part VIII).

As another example, $E.$ $coli$ cells containing a nucleic acid encoding a $P.$ $alba$ isoprene synthase polypeptide and a nucleic acid encoding $M.$ $mazei$ MVK polypeptide generated 320.6 g (at a peak specific rate of $9.54 \times 10^4$ nmol/$L_{broth}$/OD$_{600}$/hr (i.e. $9.5 \times 10^{-5}$ mol/$L_{broth}$/OD$_{600}$/hr)) of isoprene during a 67 hour fermentation in the absence of yeast extract feeding or 395.5 g (at a peak specific rate of $8.66 \times 10^4$ nmol/$L_{broth}$/OD$_{600}$/hr) during a 68 hour fermentation in the presence of yeast extract feeding (see Example 10).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
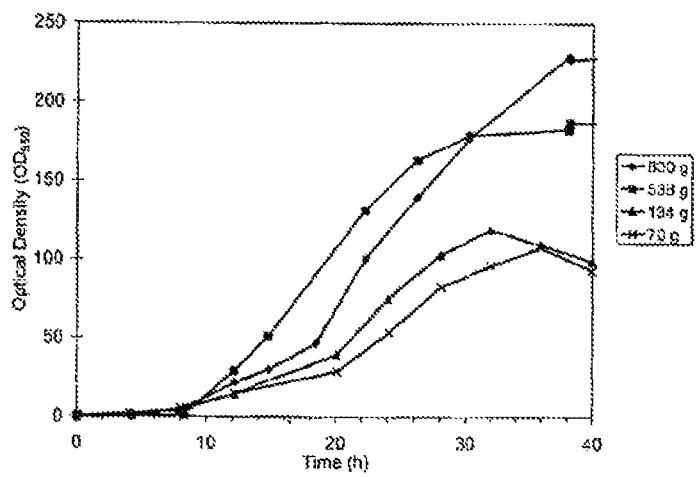
FIG. 48 shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 48B:
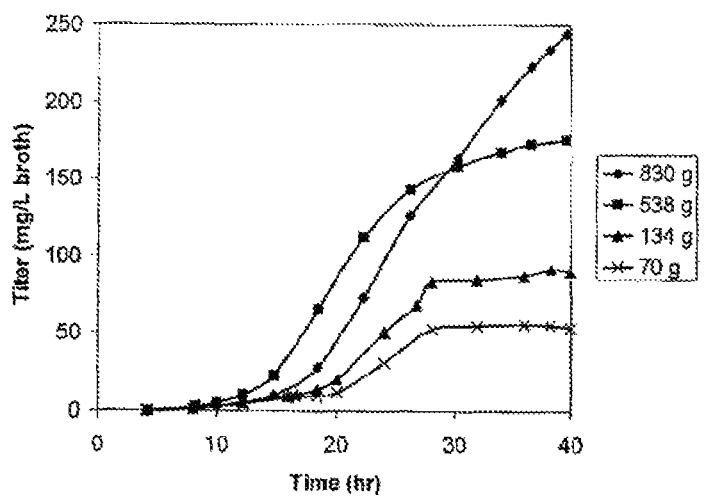
Figure 48C:
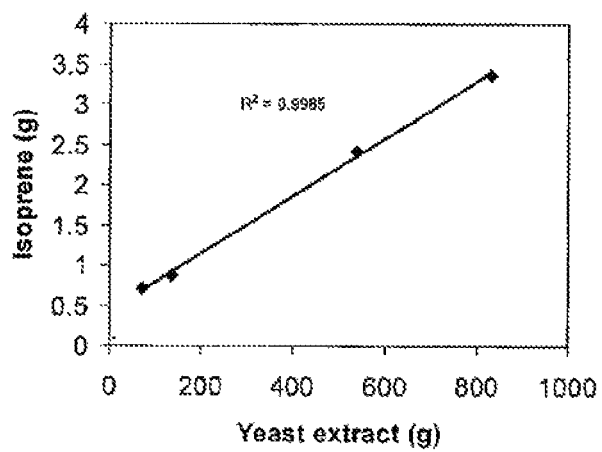

As indicated in Example 7, part VI, the amount of isoprene produced can be further increased by adding yeast extract to the cell culture medium using $E.$ $coli$ cells with kudzu isoprene synthase, $S.$ $cerevisia$ IDI, and $E.$ $coli$ DXS nucleic acids to produce isoprene. In particular, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 69A:
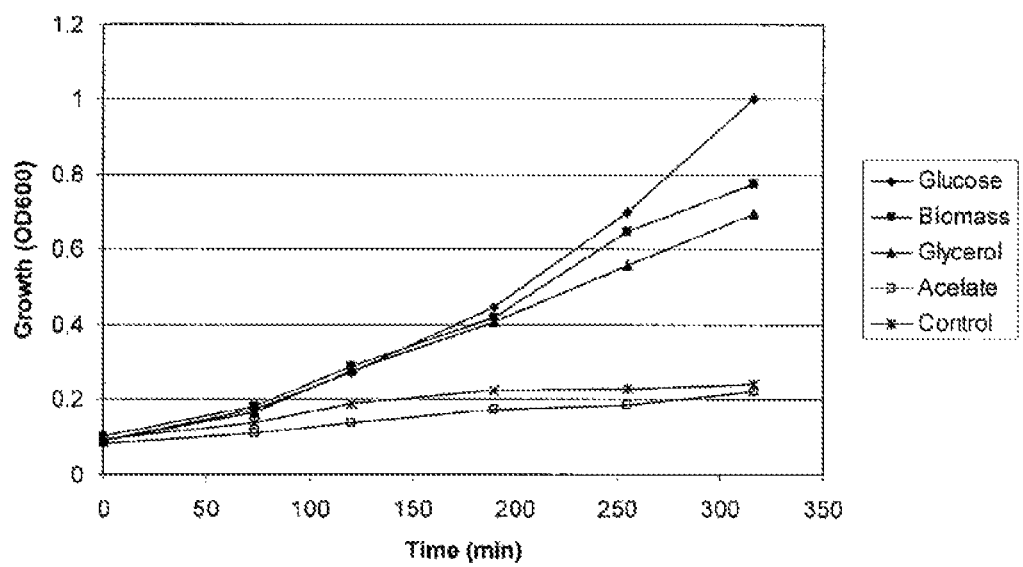
FIGS. 69A-69D shows production of isoprene from different carbon sources via the MVA (pathway).
Figure 69B:
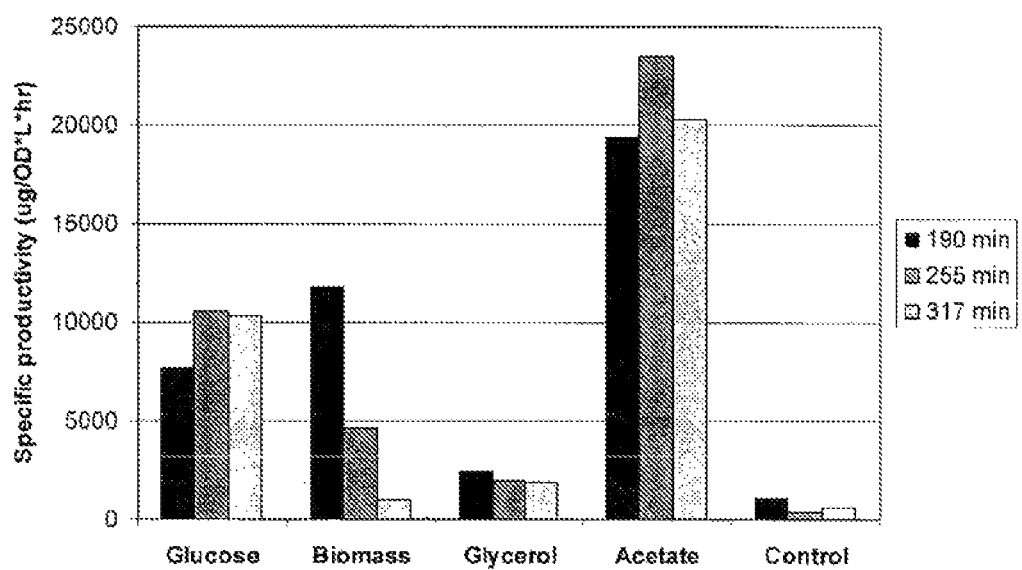
Figure 69C:
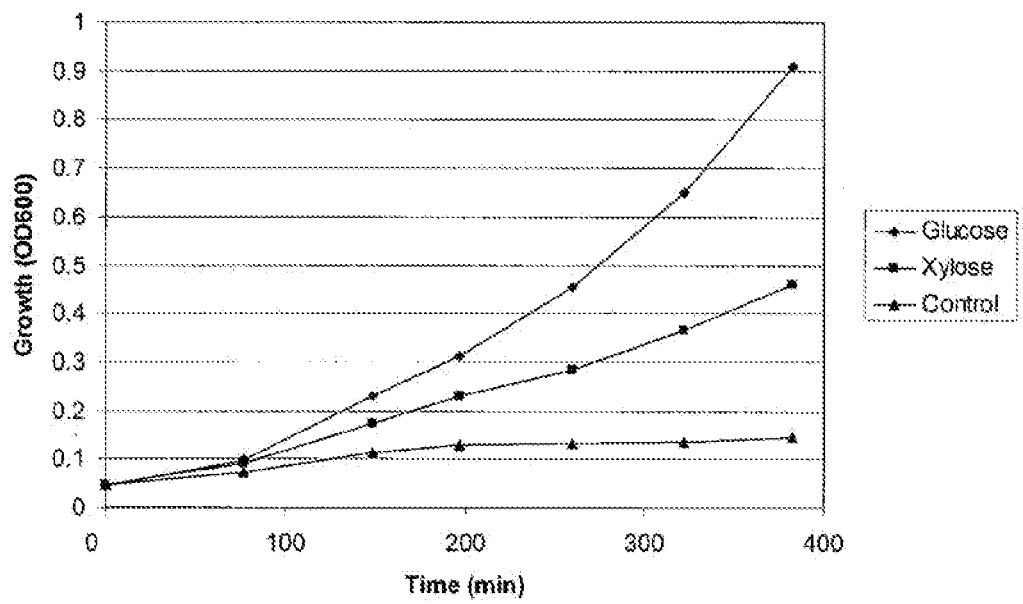

Isoprene production was also demonstrated using three types of hydrolyzed biomass (bagasse, corn stover, and soft wood pulp) as the carbon source (FIGS. 46A-C and FIGS. 69A and 69B). $E.$ $coli$ cells with kudzu isoprene synthase, $S.$ $cerevisia$ IDI, and $E.$ $coli$ DXS nucleic acids produced as much isoprene from these hydrolyzed biomass carbon sources as from the equivalent amount of glucose (e.g., 1% glucose, w/v). $E.$ $coli$ cells expressing $P.$ $alba$ isoprene synthase and the MVA pathway produced isoprene at a higher initial growth rate from ammonia fiber expansion (AFEX) pretreated corn stover than from the equivalent amount of glucose. (FIGS. 69A and 69B). If desired, any other biomass carbon source can be used in the compositions and methods of the invention. Biomass carbon sources are desirable because they are cheaper than many conventional cell mediums, thereby facilitating the economical production of isoprene.

Figure 47A:
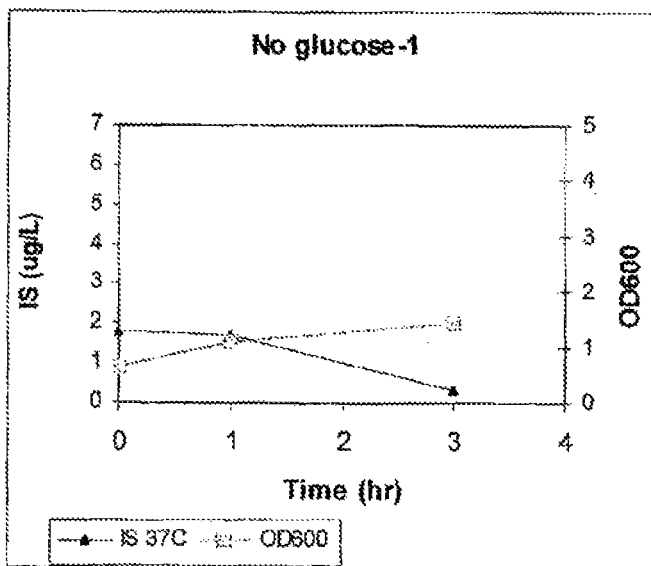
FIG. 47A shows a graph representing isoprene production by BL21 (XDE3) pTrcKudzu yIDI DXS (kan) in a culture with no glucose added. Squares represent $OD_{600}$, and triangles represent isoprene produced (μg/ml).
Figure 47B:
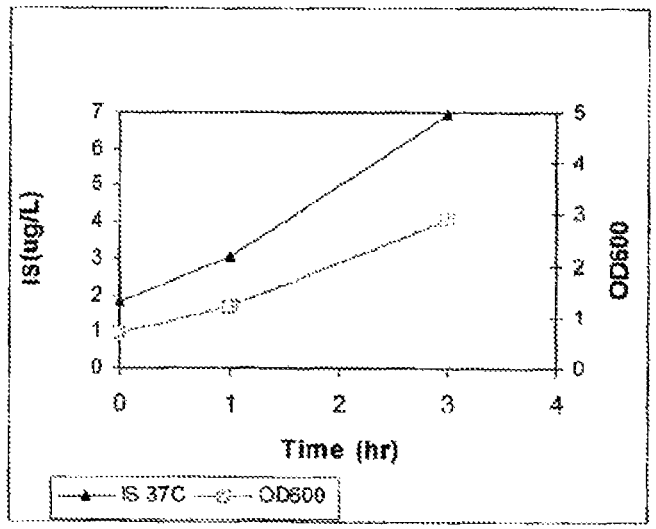
FIG. 47B shows a graph representing isoprene production from 1% glucose feedstock invert sugar by BL21 (XDE3) pTrcKudzu yIDI DXS (kan). Squares represent $OD_{600}$, and triangles represent isoprene produced (μg/ml).
Figure 47C:
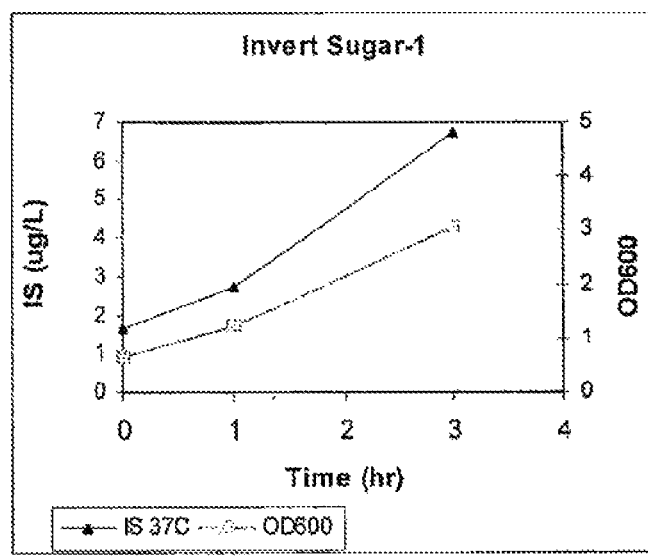
FIG. 47C shows a graph representing isoprene production from 1% invert sugar feedstock by BL21 (XDE3) pTrcKudzu yIDI DXS (kan). Squares represent $OD_{600}$, and triangles represent isoprene produced (μg/ml).
Figure 47D:
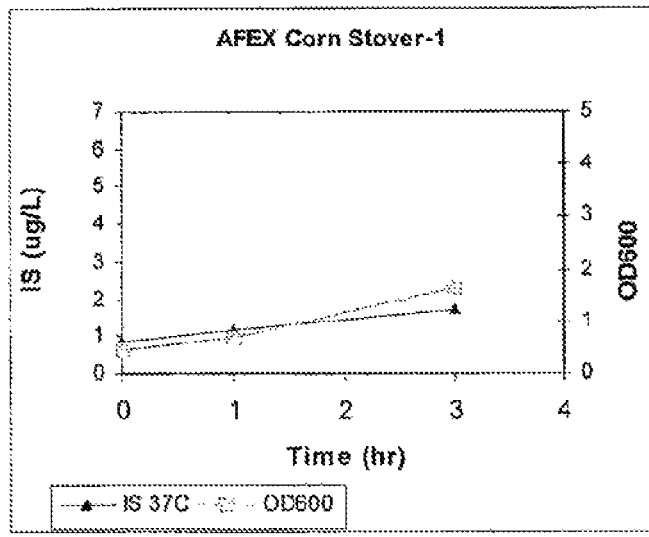
FIG. 47D shows a graph representing isoprene production from 1% AFEX corn stover feedstock by BL21 (XDE3) pTrcKudzu yIDI DXS (kan). Squares represent $OD_{600}$, and triangles represent isoprene produced (μg/ml).

Additionally, invert sugar was shown to function as a carbon source for the generation of isoprene (FIG. 47D).

Additionally, xylose, acetate, and glycerol were also shown to function as a carbon source for the generation of isoprene (FIGS. 69A-69D). For example, $E.$ $coli$ cells with $P.$ $alba$ isoprene synthase and the MVA pathway grown on acetate as the only carbon source had a specific productivity of isoprene about twice as high as during growth on glucose (Example 10, Part IV; FIGS. 69A and 69B).

In some embodiments, an oil is included in the cell medium. For example, $B.$ $subtilis$ cells containing a kudzu isoprene synthase nucleic acid produced isoprene when cultured in a cell medium containing an oil and a source of glucose (Example 4, part III). As another example, $E.$ $coli$ fadR atoC mutant cells containing the upper and lower MVA pathway plus kudzu isoprene synthase produced isoprene when cultured in a cell medium containing palm oil and a source of glucose (Example 12, part II). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides that include part or all of a first polypeptide (e.g., an isoprene synthase, DXS, IDI, or MVA pathway polypeptide) and part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Dec. 11, 2008, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mLs of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., *J. Biol. Chem.* 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 ☒ g/ml) DMAPP, 65 ☒ l of Plant Extract Buffer (PEB) (50 mM Tris-HCl, pH 8.0, 20 mM $MgCl_2$, 5% glycerol, and 2 mM DTT) is added to 25 ☒ l of cell extract in a 20 ml Headspace vial with a metal screw cap and teflon coated silicon septum (Agilent Technologies) and cultured at 37° C. for 15 minutes with shaking. The reaction is quenched by adding 200 ☒ l of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa, Populus albaxtremula* (CAC35696), or *Populus alba*) (Sasaki et al., *FEBS Letters* 579(11): 2514-2518, 2005; Miller et al., *Planta* 213: 483-487, 2001), aspen (such as *Populus tremuloides*) (Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptide phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, 2$^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ☒$P_L$, ☒$P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIG. 19). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A. sojae, A. japonicus, A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae, A. aculeatus, A. niger, A. japonicus, T. reesei, T. viride, F. oxysporum*, or *F. solani. Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. albus, S. lividans*, or *S. rubiginosus*, or strains of *Escherichia* such as *E. coli*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the source organism is a gram-positive bacterium. Non-limiting examples include strains of *Streptomyces* (e.g., *S. albus, S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus albaxtremula* CAC35696 or *Populus alba*) (Sasaki et al., *FEBS Letters* 579(11): 2514-2518, 2005), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: Chroococcales, Pleurocapsales, Oscillatoriales, Nostocales, or Stigonematales.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma* and its Application to the Expression of Both Homologous and Heterologous Genes,*"* in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 µL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), acetate, animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose. In some embodiment, the carbohydrate is xylose or glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include acetate, glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5, 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylene-tetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprene/gram of cells for the wet weight of the cells/hour (nmole/$g_{wcm}$/hr). In some embodiments, the amount of isoprene is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$/hr. In some embodiments, the amount of isoprene is between about 20 to about 200,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, or about 20,000 to about 200,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the average volumetric productivity of isoprene is between about 0.1 to about 3,500 mg/$L_{broth}$/hr, such as between about 0.1 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, or about 3,000 to about 3,500 mg/$L_{broth}$/hr. In some embodiments, the average volumetric productivity of isoprene is between about 10 to about 3,500 mg/$L_{broth}$/hr, about 100 to about 3,500 mg/$L_{broth}$/hr, about 200 to about 1,000 mg/$L_{broth}$/hr, about 200 to about 1,500 mg/$L_{broth}$/hr, about 1,000 to about 3,000 mg/$L_{broth}$/hr, or about 1,500 to about 3,000 mg/$L_{broth}$/hr.

In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments, the peak volumetric productivity of isoprene is between about 0.5 to about 15,000 mg/$L_{broth}$/hr, such as between about 0.5 to about 10 mg/$L_{broth}$/hr, about 1.0 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, about 3,000 to about 3,500 mg/$L_{broth}$/hr, about 3,500 to about 5,000 mg/$L_{broth}$/hr, about 5,000 to about 7,500 mg/$L_{broth}$/hr, about 7,500 to about 10,000 mg/$L_{broth}$/hr, about 10,000 to about 12,500 mg/$L_{broth}$/h, or about 12,500 to about 15,000 mg/$L_{broth}$/hr. In some embodiments, the peak volumetric productivity of isoprene is between about 10 to about 15,000 mg/$L_{broth}$/hr, about 100 to about 2,500 mg/$L_{broth}$/hr, about 1,000 to about 5,000 mg/$L_{broth}$/hr, about 2,500 to about 7,500 mg/$L_{broth}$/hr, about 5,000 to about 10,000 mg/$L_{broth}$/hr, about 7,500 to about 12,500 mg/$L_{broth}$/hr, or about 10,000 to about 15,000 mg/$L_{broth}$/hr.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 2.0, 2.2, 2.4, 2.6, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 23.2, 23.4, 23.6, 23.8, 24.0, 25.0, 30.0, 31.0, 32.0, 33.0, 35.0, 37.5, 40.0, 45.0, 47.5, 50.0, 55.0, 60.0, 65.0, 70.0, 75.0, 80.0, 85.0, or 90.0 molar % of the carbon in the cell culture medium into isoprene. In some embodiments, the percent conversion of carbon into isoprene is between about 0.002 to about 90.0 molar %, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, about 1.0 to about 1.6%, about 1.6 to about 3.0%, about 3.0 to about 5.0%, about 5.0 to about 8.0%, about 8.0 to about 10.0%, about 10.0 to about 15.0%, about 15.0 to about 20.0%, about 20.0 to about 25.0%, about 25.0 to about 30.0%, about 30.0% to 35.0%, about 35.0% to 40.0%, about 45.0% to 50.0%, about 50.0% to 55.0%, about 55.0% to 60.0%, about 60.0% to 65.0%, about 65.0% to 70.0%, about 75.0% to 80.0%, about 80.0% to 85.0%, or about 85.0% to 90.0%. In some embodiments, the percent conversion of carbon into isoprene is between about 0.002 to about 0.4 molar %, 0.002 to about 0.16 molar %, 0.04 to about 0.16 molar %, about 0.005 to about 0.3 molar %, about 0.01 to about 0.3 molar %, about 0.05 to about 0.3 molar %, about 0.1 to 0.3 molar %, about 0.3 to about 1.0 molar %, about 1.0 to about 5.0 molar %, about 2 to about 5.0 molar %, about 5.0 to about 10.0 molar %, about 7 to about 10.0 molar %, about 10.0 to about 20.0 molar %, about 12 to about 20.0 molar %, about 16 to about 20.0 molar %, about 18 to about 20.0 molar %, about 18 to 23.2 molar %, about 18 to 23.6 molar %, about 18 to about 23.8 molar %, about 18 to about 24.0 molar %, about 18 to about 25.0 molar %, about 20 to about 30.0 molar %, about 30 to about 40.0 molar %, about 30 to about 50.0 molar %, about 30 to about 60.0 molar %, about 30 to about 70.0 molar %, about 30 to about 80.0 molar %, or about 30 to about 90.0 molar %

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100     Equation 1

For this calculation, yeast extract can be assumed to contain 50% w/w carbon. As an example, for the 500 liter described in Example 7, part VIII, the percent conversion of carbon into isoprene can be calculated as shown in Equation 2.

Carbon Yield=(39.1 g isoprene*1/68.1 mol/g* 5 C/mol)/[(181221 g glucose*1/180 mol/g* 6 C/mol)+(17780 g yeast extract*0.5*1/12 mol/g)]* 100=0.042%     Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate)     Equation 3

1 nmol isoprene/$g_{wcm}$/hr=1 nmol isoprene/$L_{broth}$/hr/$OD_{600}$     Equation 4

(This conversion assumes that one liter of broth with an $OD_{600}$ value of 1 has a wet cell weight of 1 gram.)

1 nmol isoprene/$g_{wcm}$/hr=68.1 ng isoprene/$g_{wcm}$/hr     Equation 5

(given the molecular weight of isoprene)

1 nmol isoprene/$L_{gas}$ $O_2$/hr=90 nmol isoprene/$L_{broth}$/hr     Equation 6

(at an O$_2$ flow rate of 90 L/hr per L of culture broth)

$$1 \text{ ug isoprene/L}_{gas} \text{ isoprene in off-gas} = 60 \text{ ug isoprene/} \\ \text{L}_{broth}/\text{hr at a flow rate of 60 L}_{gas} \text{ per L}_{broth} \text{ (1 vvm)} \quad \text{Equation 7}$$

Units for Titer (Total and Specific)

$$1 \text{ nmol isoprene/mg cell protein} = 150 \text{ nmol isoprene/} \\ \text{L}_{broth}/\text{OD}_{600} \quad \text{Equation 8}$$

(This conversion assumes that one liter of broth with an OD$_{600}$ value of 1 has a total cell protein of approximately 150 mg) (specific productivity)

$$1 \text{ g isoprene/L}_{broth} = 14.7 \text{ mmol isoprene/L}_{broth} \text{ (total titer)} \quad \text{Equation 9}$$

If desired, Equation 10 can be used to convert any of the units that include the wet weight of the cells into the corresponding units that include the dry weight of the cells.

$$\text{Dry weight of cells} = \text{(wet weight of cells)}/3.3 \quad \text{Equation 10}$$

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, any of the methods described herein further include polymerizing the isoprene. For example, standard methods can be used to polymerize the purified isoprene to form cis-polyisoprene or other down stream products using standard methods.

Additional methods and compositions are described in U.S. Provisional patent application No. 61/097,186, filed on Sep. 15, 2008, U.S. Provisional patent application No. 61/097,189, filed on Sep. 15, 2008, and U.S. Provisional patent application No. 61/097,163, filed on Sep. 15, 2008, all of which are incorporated by reference in their entireties, particular with respect to compositions and methods for producing isoprene.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *E. coli* Expressing Recombinant Kudzu Isoprene Synthase I. Construction of Vectors for Expression of the Kudzu Isoprene Synthase in *E. coli*

The protein sequence for the kudzu (*Pueraria montana*) isoprene synthase gene (IspS) was obtained from GenBank (AAQ84170). A kudzu isoprene synthase gene, optimized for

Figure 2:
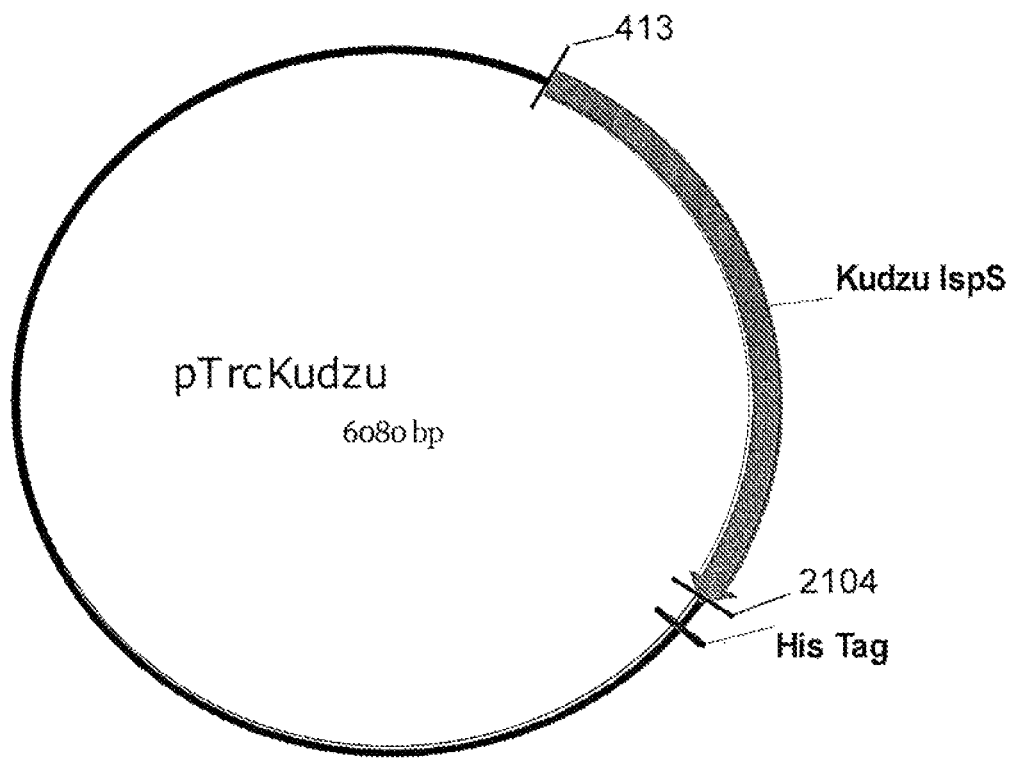
FIG. 2 is a map of pTrcKudzu.

*E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
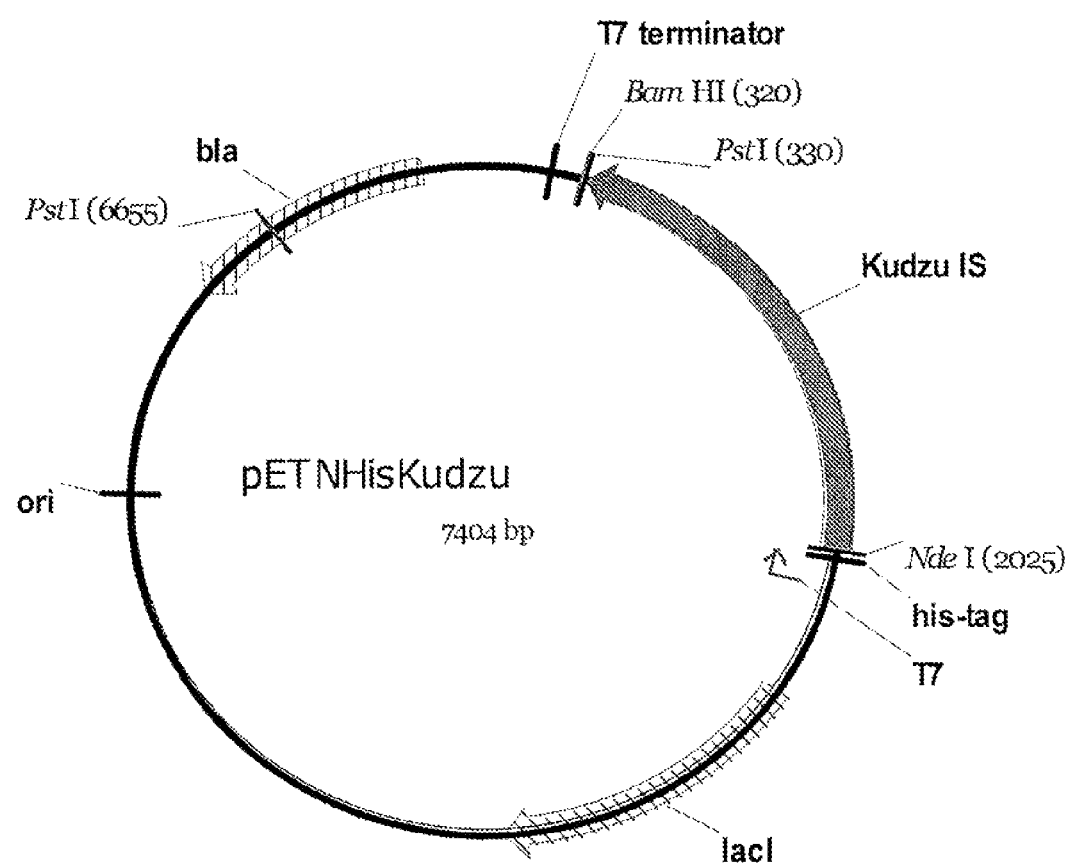
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGAT-CATATGTGTGCGACCTCTTCTCAATTTAC (SEQ ID NO:3) and pET-His-Kudzu-R: 5'-CGGTCGACGGATC-CCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 μl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

Figure 6:
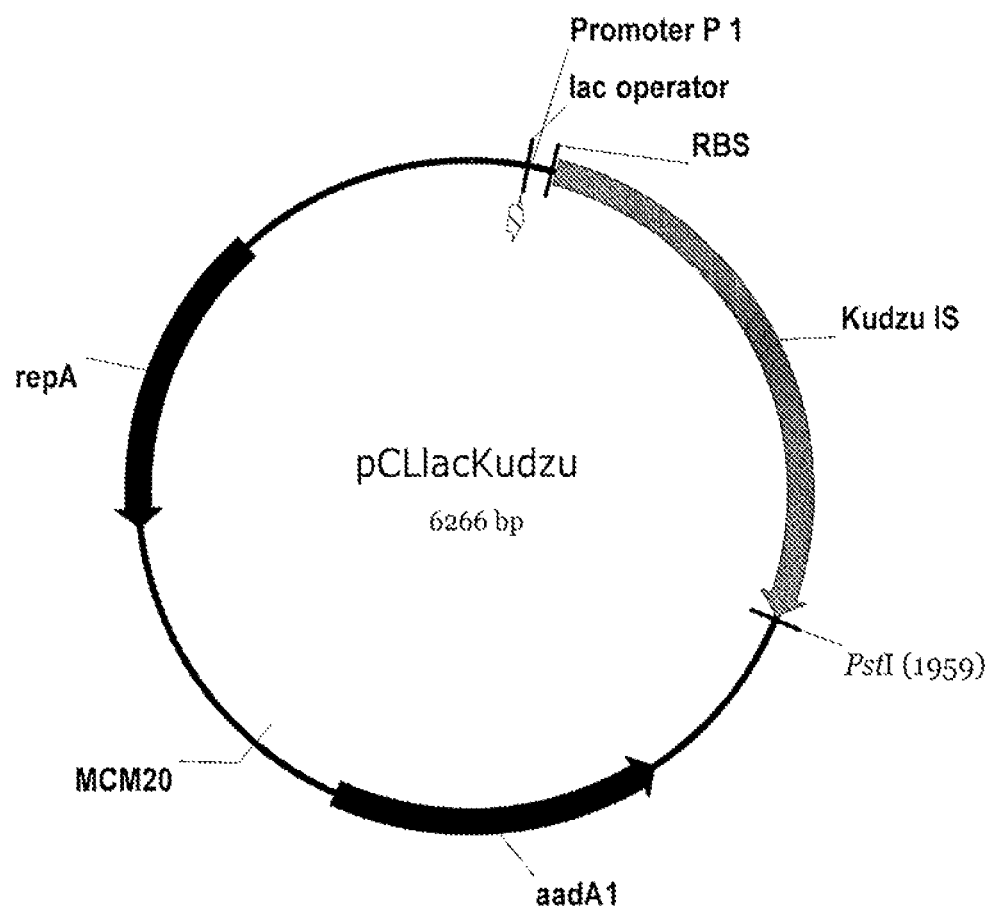
FIG. 6 is a map of pCL-lac-Kudzu.
Figure 8A:
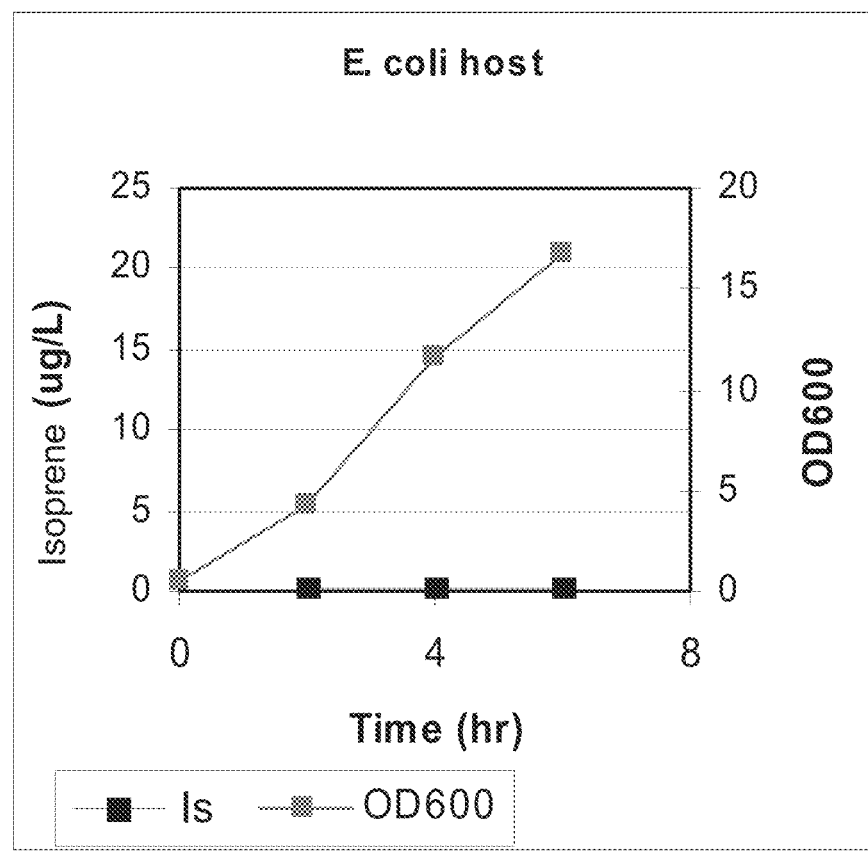
FIG. 8A is a graph showing the production of isoprene in *E. coli* BL21 cells with no vector.
Figure 8B:
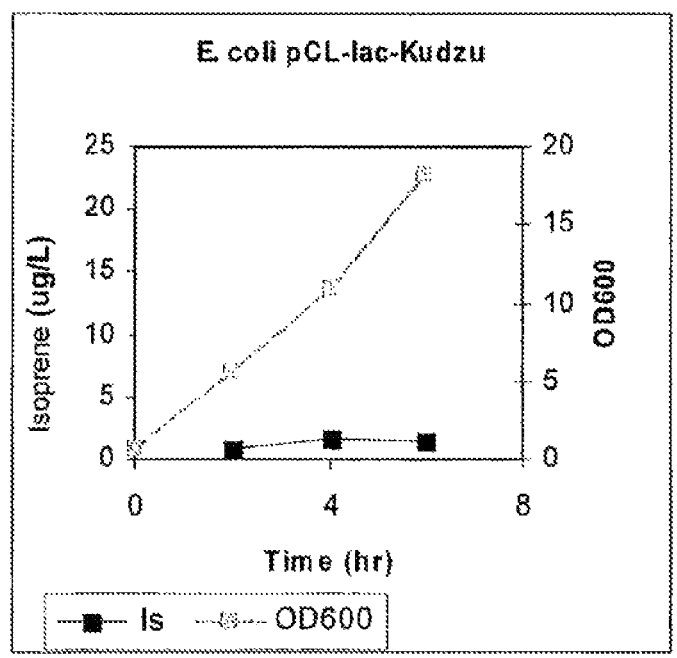
FIG. 8B is a graph showing the production of isoprene in *E. coli* BL21 cells with pCL-lac-Kudzu
Figure 8C:
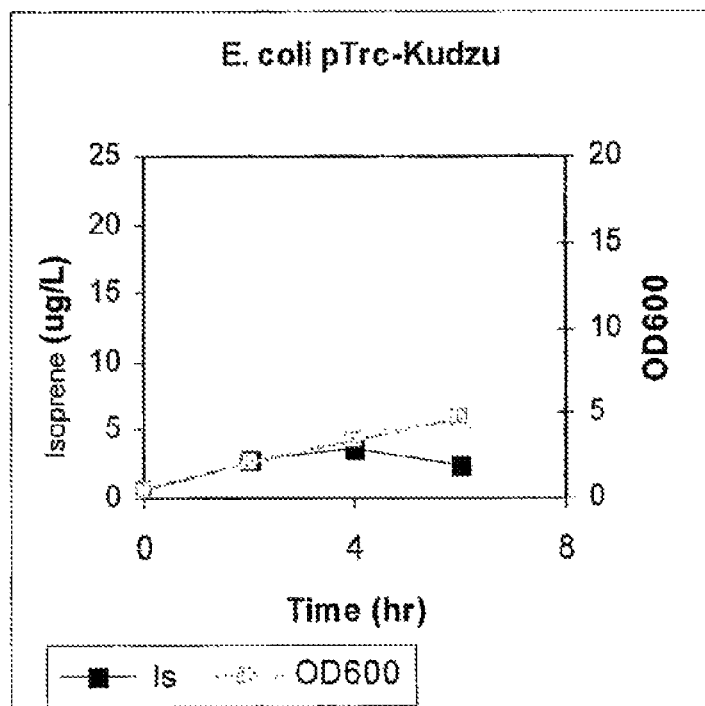
FIG. 8C is a graph showing the production of isoprene in *E. coli* BL21 cells with pTrcKudzu.
Figure 8D:
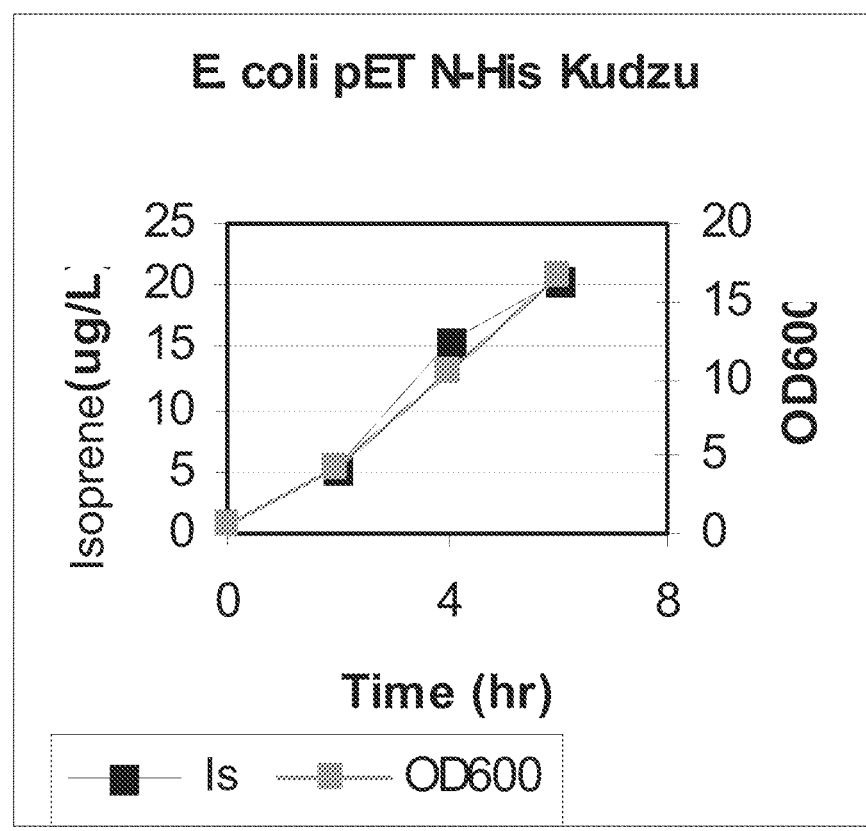
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATC-GATTAAATAAGGAGGAATAAACC (SEQ ID NO:6) and BamH1-Kudzu R:

5'-CGGTCGACGGATCCCTGCAGTTAGA-CATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat #5188 2753; cap cat #5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/minutes. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar) and carbenicillin (50 μg/ml) and incubated overnight at 37° C. Single colonies were inoculated into 250 ml baffled shake flasks containing 20 ml Luria Bertani broth (LB) and carbenicillin (100 μg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen) and carbenicillin (100 μg/ml) to an $OD_{600}$~0.05. The culture was incubated at 30° C. with shaking at 200 rpm. When the $OD_{600}$~0.5-0.8, 400 μM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22μ filter (only, do not autoclave). The recipe for 1000× Modified Trace Metal Solution was as follows: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaOH, then q.s. to volume and filter sterilized with a 0.22μ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 30:
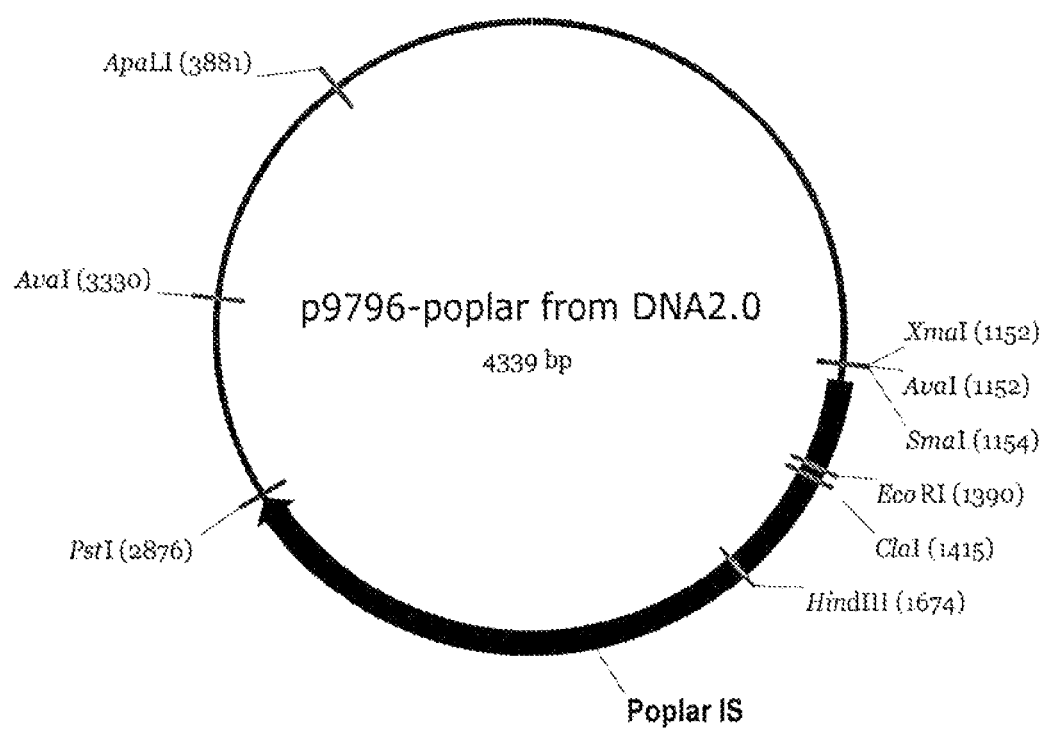
FIG. 30 is a map of p9796-poplar.
Figure 32:
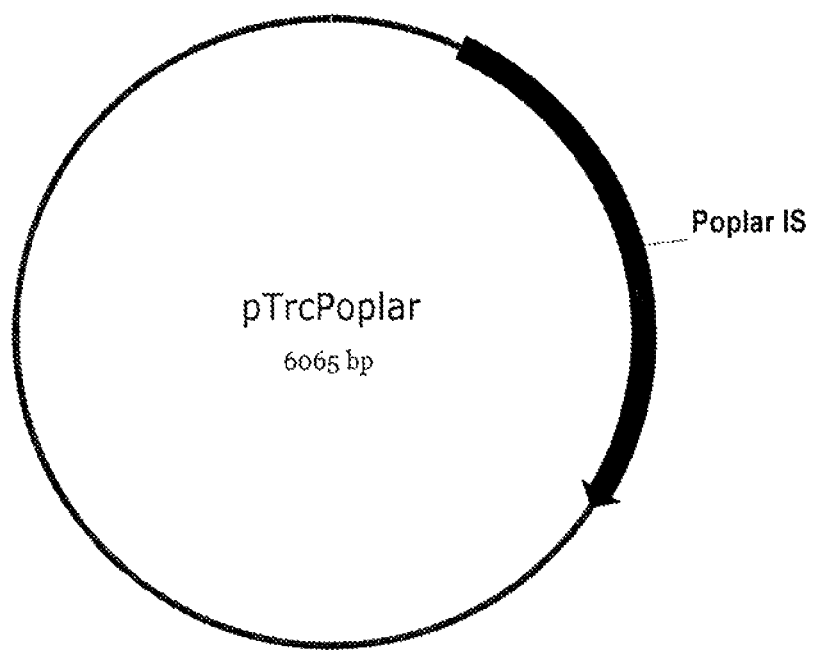
FIG. 32 is a map of pTrcPoplar.

Production of Isoprene in *E. coli* Expressing Recombinant Poplar Isoprene Synthase The protein sequence for the poplar (*Populus alba*×*Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Example 3

Figure 10A:
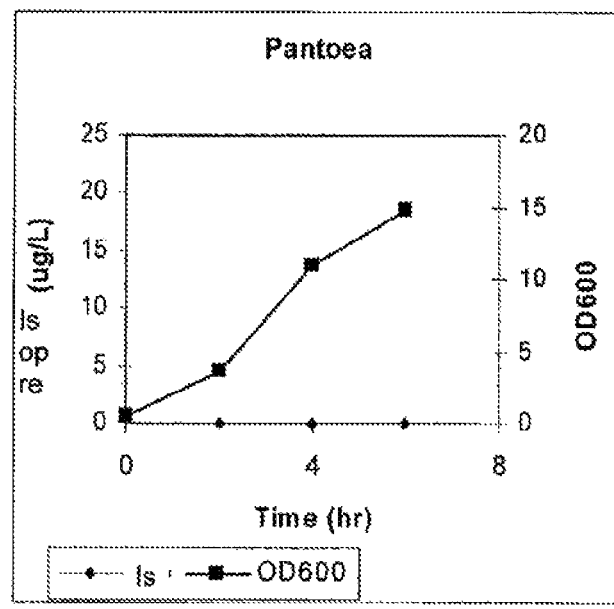
FIG. 10A is a graph showing the production of isoprene in *Panteoa citrea*. Control cells without recombinant kudzu isoprene synthase. Grey diamonds represent isoprene synthesis, black squares represent $OD_{600}$.
Figure 10B:
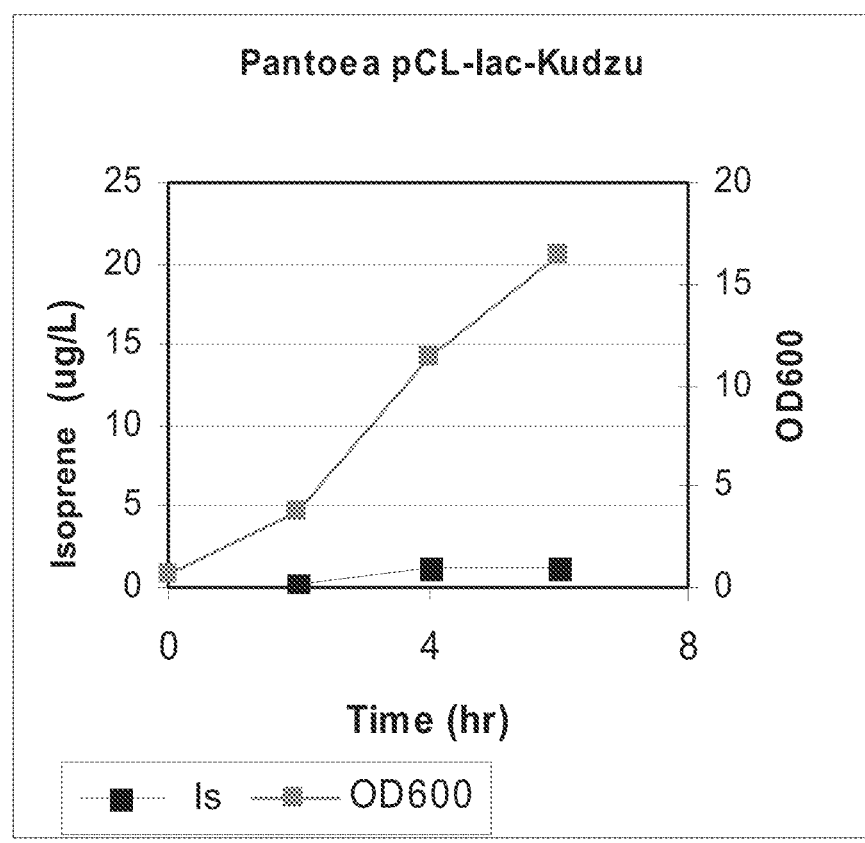
FIG. 10B is a graph showing the production of isoprene in *Panteoa citrea* expressing pCL-lac Kudzu. Grey diamonds represent isoprene synthesis, black squares represent $OD_{600}$.
Figure 10C:
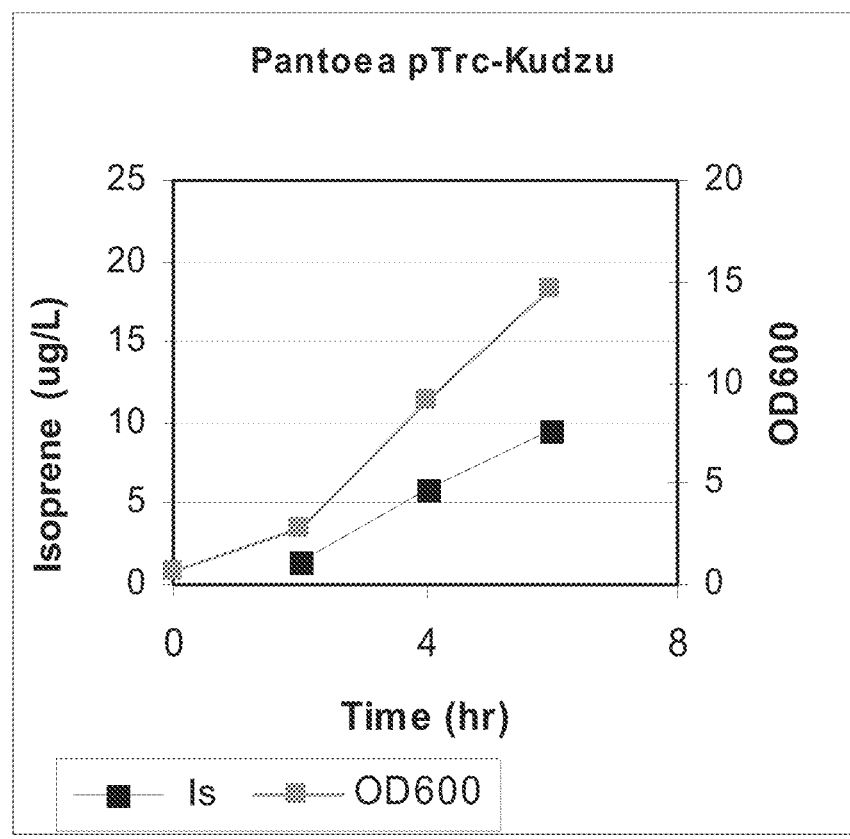
FIG. 10C is a graph showing the production of isoprene in *Panteoa citrea* expressing pTrcKudzu. Grey diamonds represent isoprene synthesis, black squares represent $OD_{600}$.

Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 µg/ml) or spectinomycin (50 µg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.

a) Amplification of the aprE Promoter

The aprE promoter was amplified from chromosomal DNA from *Bacillus subtilis* using the following primers:

```
CF 797 (+) Start aprE promoter MfeI
                                   (SEQ ID NO: 58)
5'-GACATCAATTGCTCCATTTTCTTCTGCTATC CF 07-43 (-) Fuse aprE promoter to Kudzu ispS
                                   (SEQ ID NO: 59)
5'-ATTGAGAAGAGGTCGCACACACTCTTTACCCTCTCCTTTTA
``` b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                   (SEQ ID NO: 60)
5'-TAAAAGGAGAGGGTAAAGAGTGTGTGCGACCTCTTCTCAAT CF 07-45 (-) Fuse the 3' end of kudzu isoprene
synthase gene to the terminator
                                   (SEQ ID NO: 61)
5'-CCAAGGCCGGTTTTTTTTAGACATACATCAGCTGGTTAATC
``` c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                   (SEQ ID NO: 62)
5'-GATTAACCAGCTGATGTATGTCTAAAAAAAACCGGCCTTGG CF 07-46 (-) End of B. amyliquefaciens
terminator (BamHI)
                                   (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                   (SEQ ID NO: 61)
5'-TAAAAGGAGAGGGTAAAGAGTGTGTGCGACCTCTTCTCAAT CF 07-46 (-) End of B. amyliquefaciens
terminator (BamHI)
                                   (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                   (SEQ ID NO: 64)
5'-GACATCAATTGCTCCATTTTCTTCTGCTATC CF 07-46 (-) End of B. amyliquefaciens
terminator (BamHI)
                                   (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA and 50 carbenicillin plates. A total of six colonies were chosen and grown overnight in LB and 50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                      (SEQ ID NO: 65)
5'-GACATGAATTCCTCCATTTTCTTCTGC CF 847 (+) Sequence in pXX 049 (end of aprE
promoter)
                                      (SEQ ID NO: 66)
5'-AGGAGAGGGTAAAGAGTGAG CF 07-45 (-) Fuse the 3' end of kudzu isoprene
synthase to the terminator
                                      (SEQ ID NO: 61)
5'-CCAAGGCCGGTTTTTTTAGACATACATCAGCTGGTTAATC CF 07-48 (+) Sequencing primer for kudzu isoprene
synthase
                                      (SEQ ID NO: 67)
5'-CTTTTCCATCACCCACCTGAAG CF 07-49 (+) Sequencing in kudzu isoprene synthase
                                      (SEQ ID NO: 68)
5'-GGCGAAATGGTCCAACAACAAAATTATC
```

Figure 52:
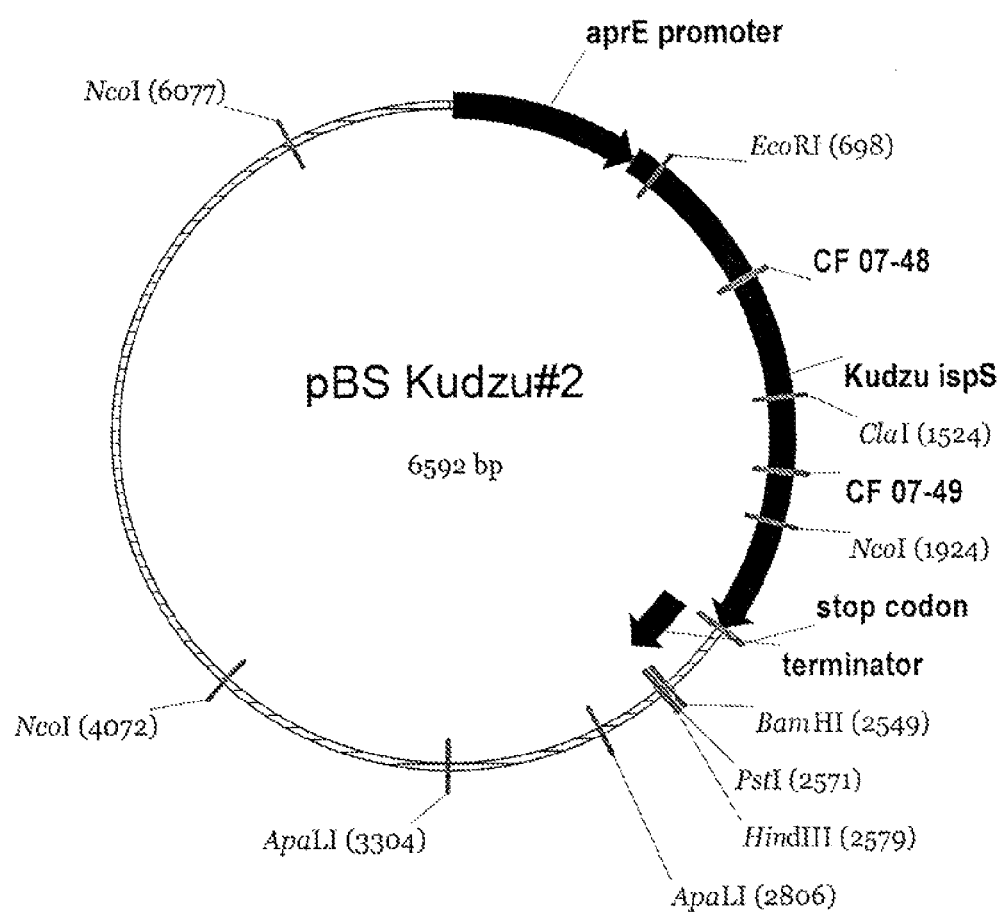
FIG. 52 is a map of pBS Kudzu #2.

The plasmid designated pBS Kudzu #2 (FIGS. 52 and 12) was correct by sequencing and was transformed into BG 3594 comK, a *Bacillus subtilis* host strain. Selection was done on LA and 5 chloramphenicol plates. A transformant was chosen and struck to single colonies on LA and 5 chloramphenicol, then grown in LB and 5 chloramphenicol until it reached an $OD_{600}$ of 1.5. It was stored frozen in a vial at $-80°$ C. in the presence of glycerol. The resulting strain was designated CF 443.

Figure 11:
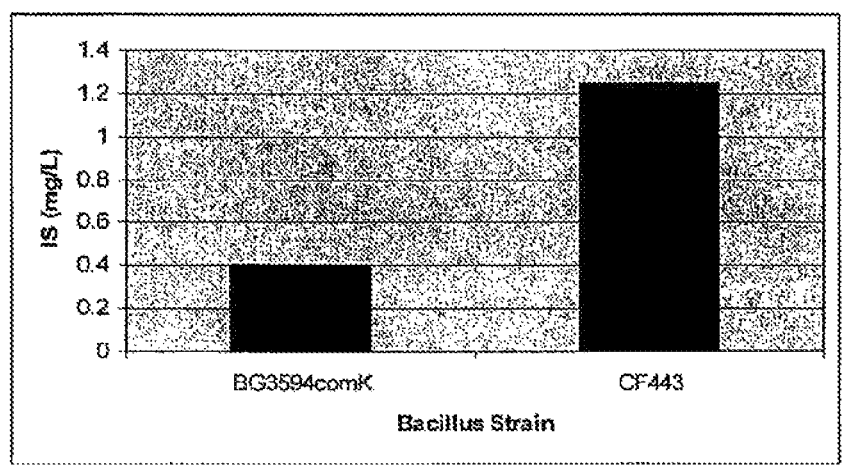
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA and Chloramphenicol (Cm, 25 µg/ml). Cultures were grown in LB and Cm at 37° C. with shaking at 200 rpm. These overnight cultures (1 ml) were used to inoculate 250 ml baffled shake flasks containing 25 ml Grants II media and chloramphenicol at a final concentration of 25 µg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4*2H_2O$, q.s. to 1 L with $H_2O$, Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
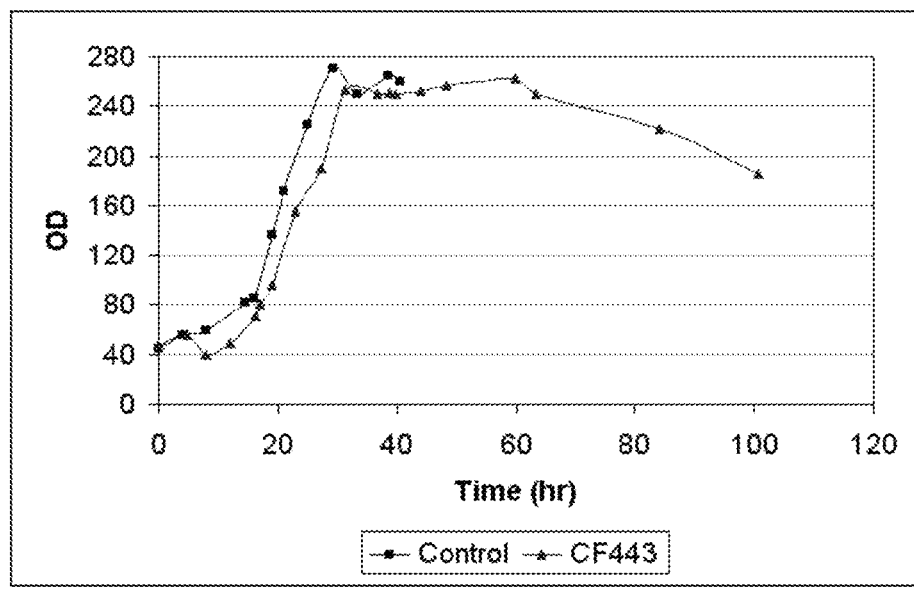
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
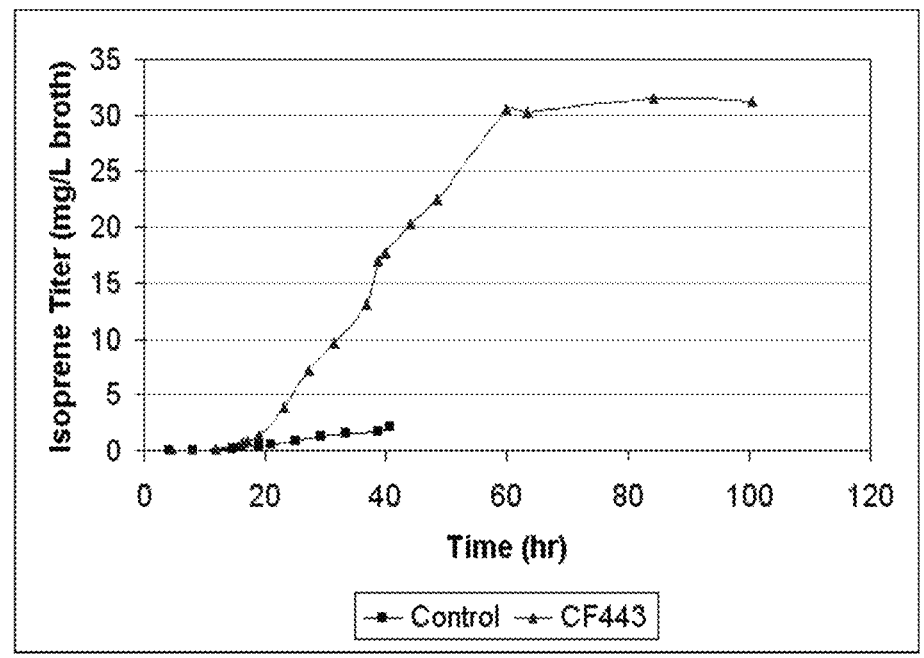
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 pJ plasmid template (20 ng/ul), 1 µl Primer EL-945 (10 uM) 5'-GCTTATGGATCCTCTAGACTATTA-CACGTACATCAATTGG (SEQ ID NO:9), 1 µl Primer EL-965 (10 uM) 5'-CACCATGTGTGCAACCTCCTC-CCAGTTTAC (SEQ ID NO:10), 1 µl dNTP (10 mM), 5 µl 10× PfuUltra II Fusion HS DNA Polymerase Buffer, 1 µl PfuUltra II Fusion HS DNA Polymerase, 40 µl water in a total reaction volume of 50 µl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 µl. The reaction was incubated at room temperature for 5 minutes. One microliter of TOPO reaction was transformed into TOP10 chemically competent *E. coli* cells. The transformants were selected on LA and 50 µg/ml kanamycin plates. Several colonies were picked and each was inoculated into a 5 ml tube containing LB and 50 µg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 µl. The reaction was incubated at room temperature for 1 hour and then 1 µl proteinase K solution was added and the incubation continued at 37° C. for 10 minutes. Then 1 µl of reaction was transformed into TOP10 chemically competent *E. coli* cells. The transformants were selected on LA and 50 µg/ml carbenicillin plates. Several colonies were picked and each was inoculated into a 5 ml tube containing LB and 50 µg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
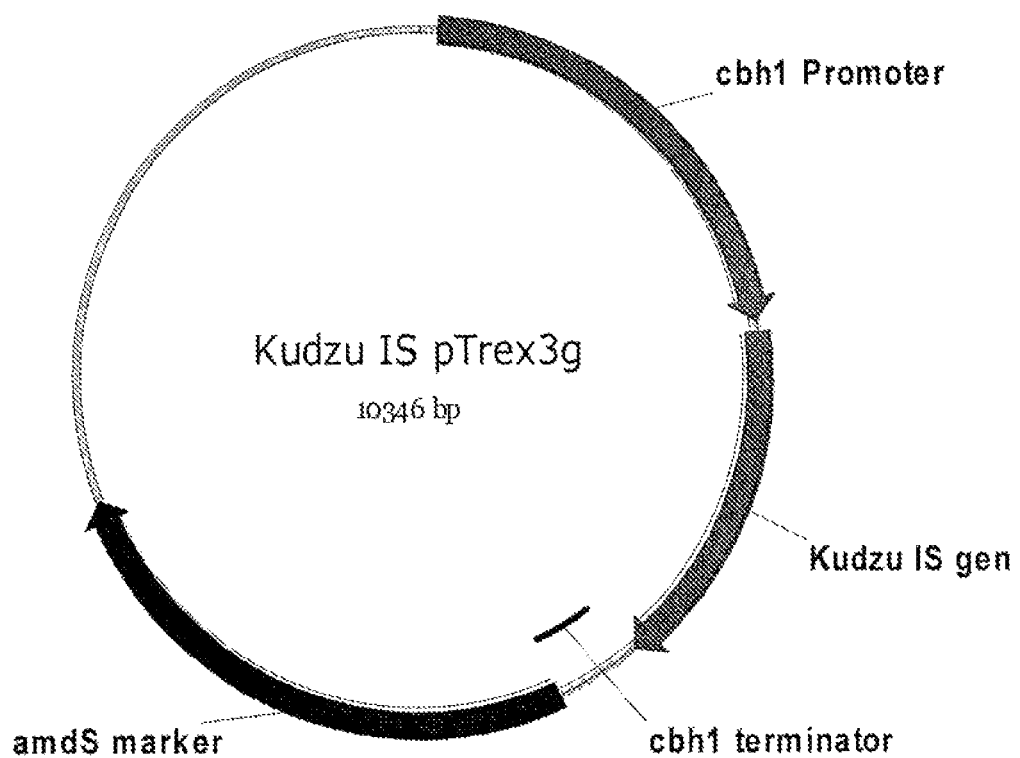
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 µg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia lipolytica*.

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

ICL1 3
(SEQ ID NO: 69)
5'-GGTGAATTCAGTCTACTGGGGATTCCCAAATCTATATATACTGC
AGGTGAC

ICL1 5
(SEQ ID NO: 70)
5'-GCAGGTGGGAAACTATGCACTCC

XPR 3
(SEQ ID NO: 71)
5'-CCTGAATTCTGTTGGATTGGAGGATTGGATAGTGGG

XPR 5
(SEQ ID NO: 72)
5'-GGTGTCGACGTACGGTCGAGCTTATTGACC

XPRT3
(SEQ ID NO: 73)
5'-GGTGGGCCCGCATTTTGCCACCTACAAGCCAG

XPRT 5
(SEQ ID NO: 74)
5'-GGTGAATTCTAGAGGATCCCAACGCTGTTGCCTACAACGG

Y18S3
(SEQ ID NO: 75)
5'-GGTGCGGCCGCTGTCTGGACCTGGTGAGTTTCCCCG

Y18S 5
(SEQ ID NO: 76)
5'-GGTGGGCCCATTAAATCAGTTATCGTTTATTTGATAG

YURA3
(SEQ ID NO: 77)
5'-GGTGACCAGCAAGTCCATGGGTGGTTTGATCATGG

YURA 50
(SEQ ID NO: 78)
5'-GGTGCGGCCGCCTTTGGAGTACGACTCCAACTATG

YURA 51
(SEQ ID NO: 79)
5'-GCGGCCGCAGACTAAATTTATTTCAGTCTCC

For PCR amplification the PfuUltraII polymerase (Stratagene), supplier-provided buffer and dNTPs, 2.5 µM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
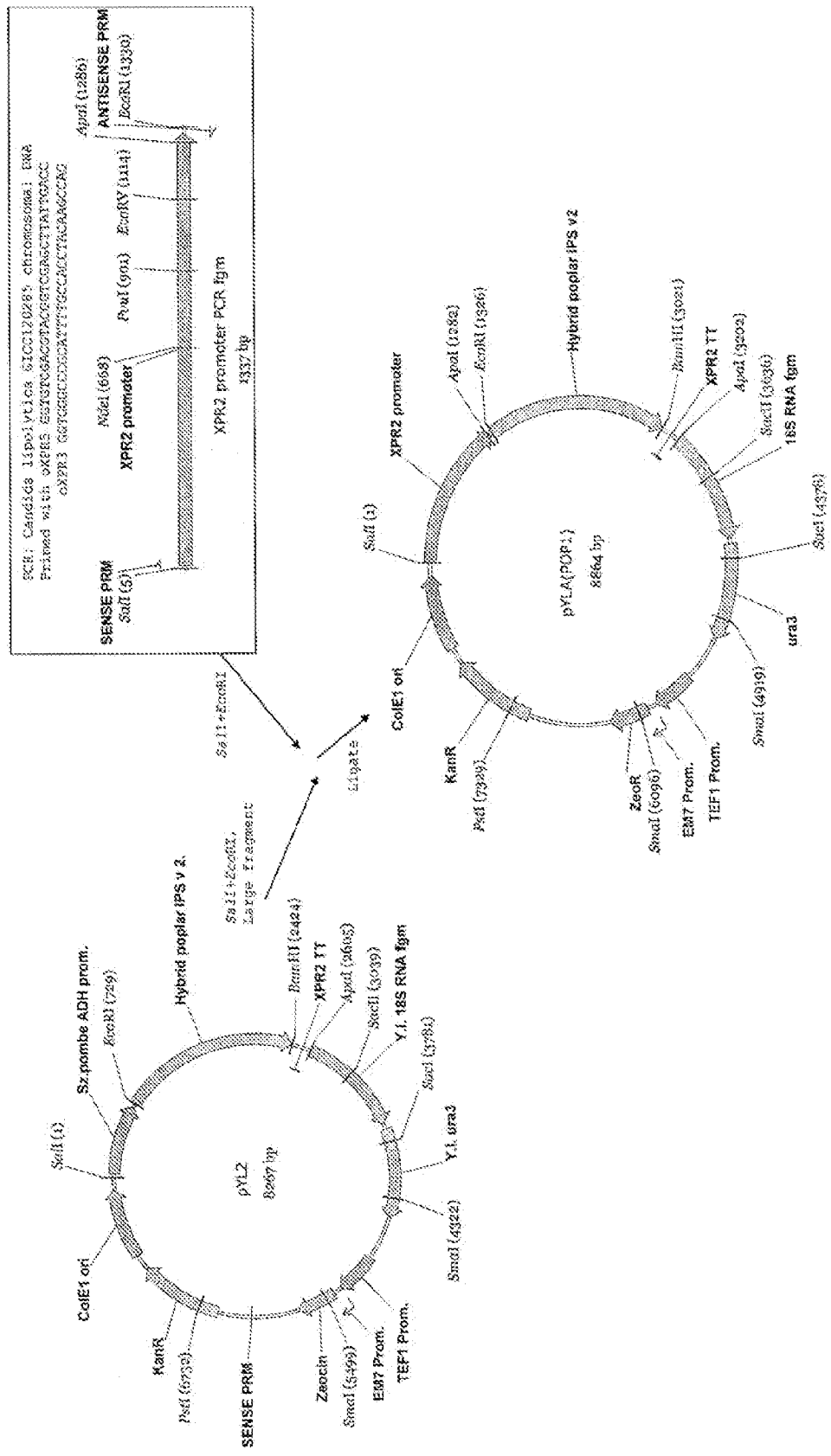
FIG. 18B shows a schematic outlining construction of the vector pYLA(POP1).
Figure 18C:
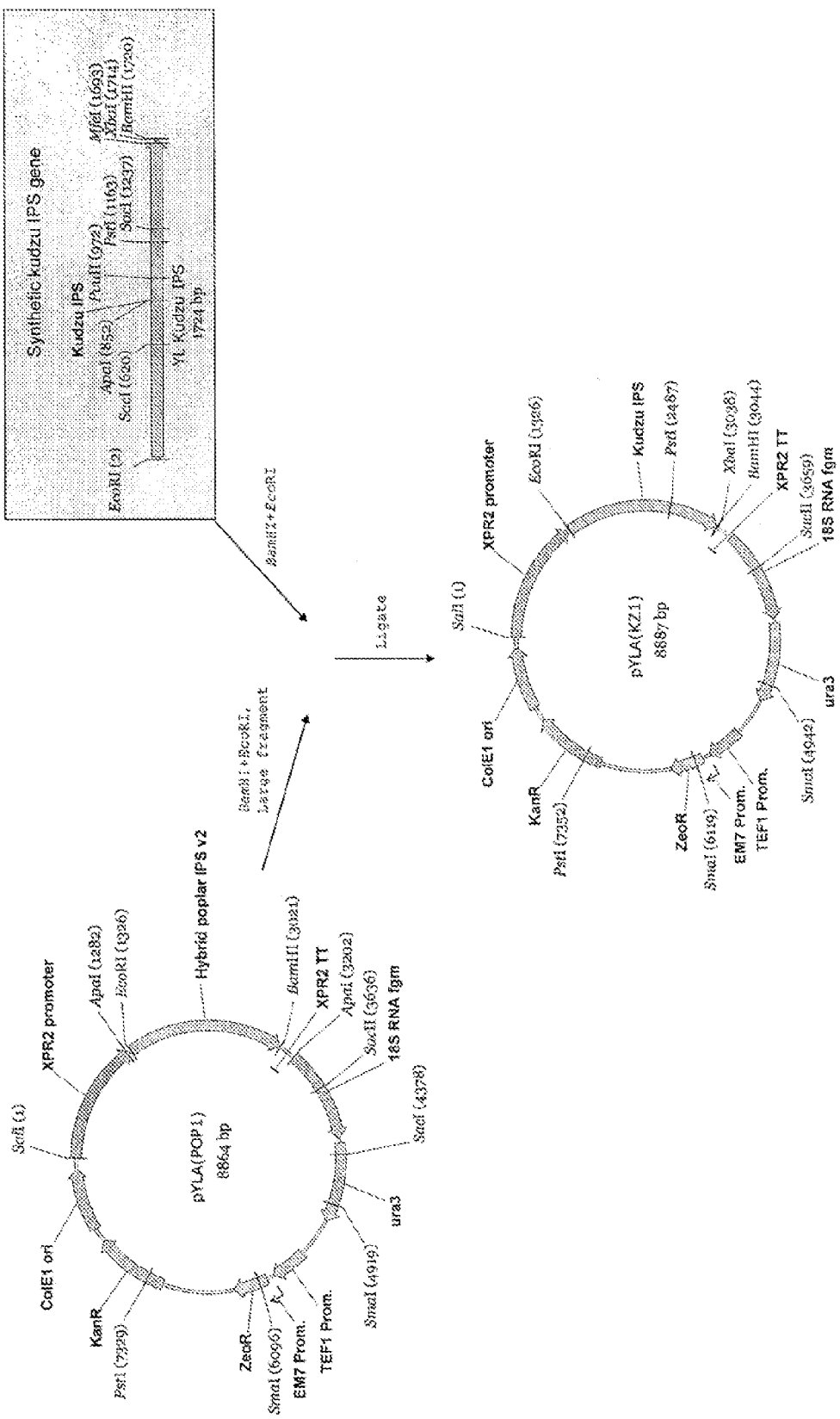
FIG. 18C shows a schematic outlining construction of the vector pYLA(KZ1)
Figure 18D:
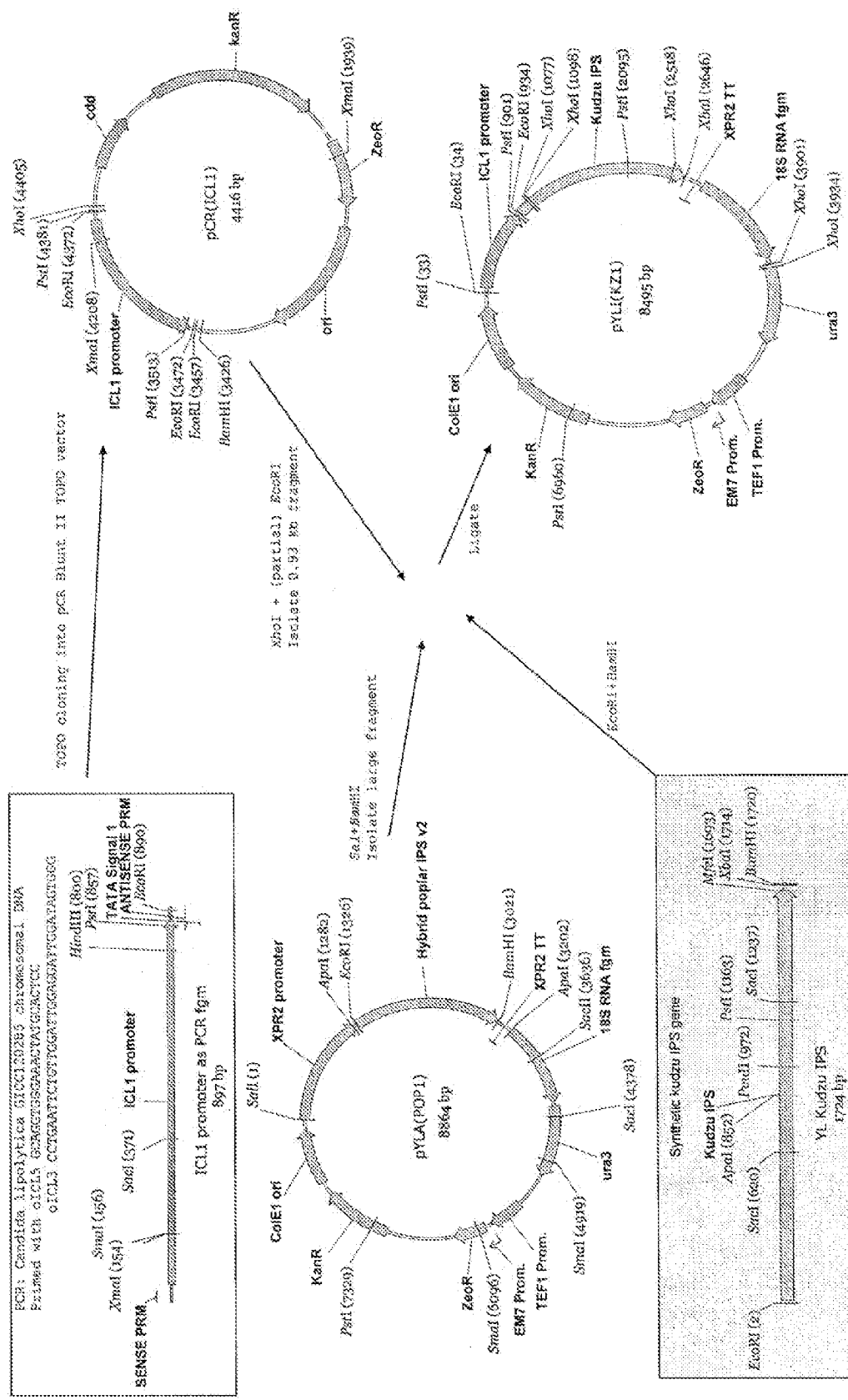
FIG. 18D shows a schematic outlining construction of the vector pYLI(KZ1)
Figure 18E:
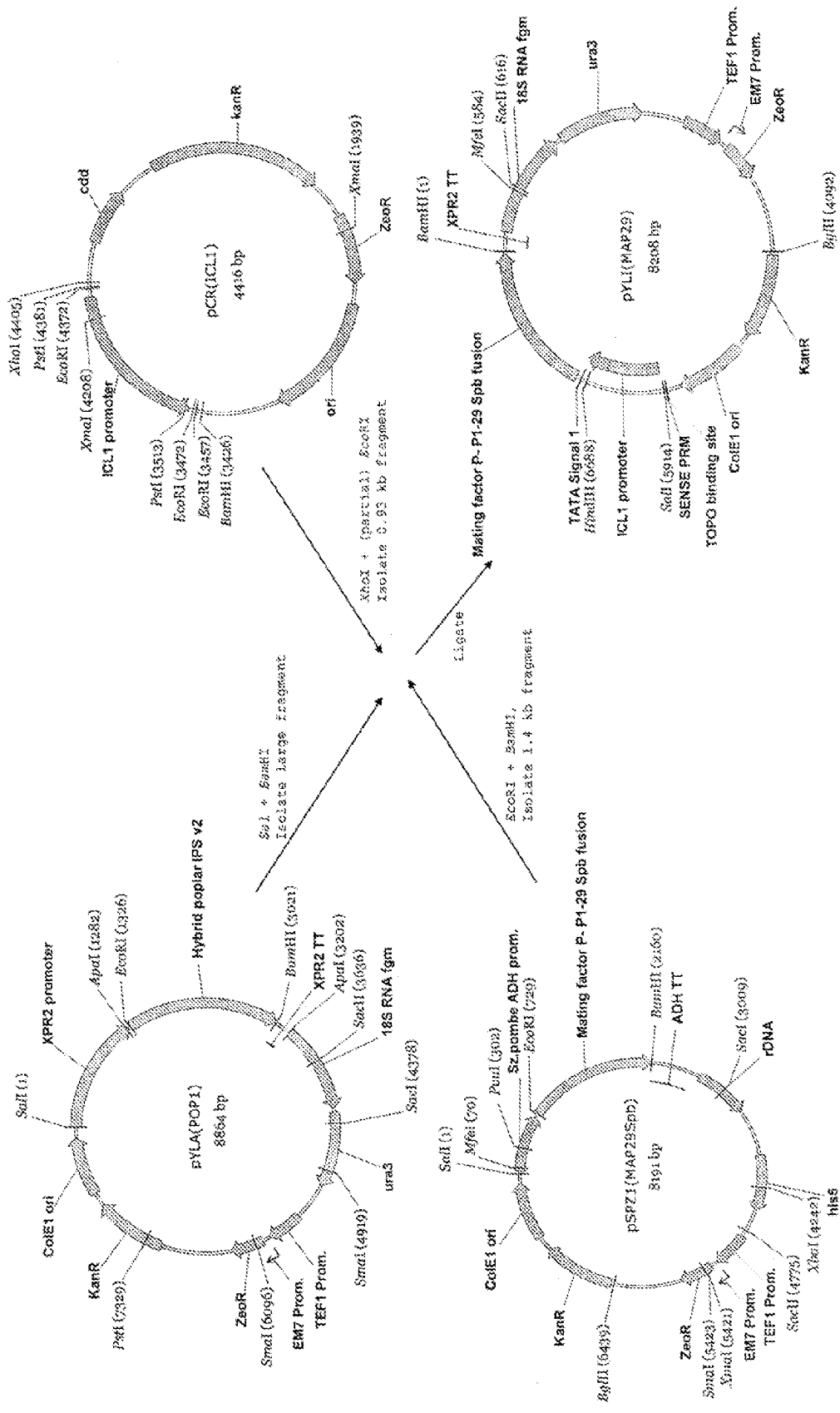
FIG. 18E shows a schematic outlining construction of the vector pYLI(MAP29)
Figure 18F:
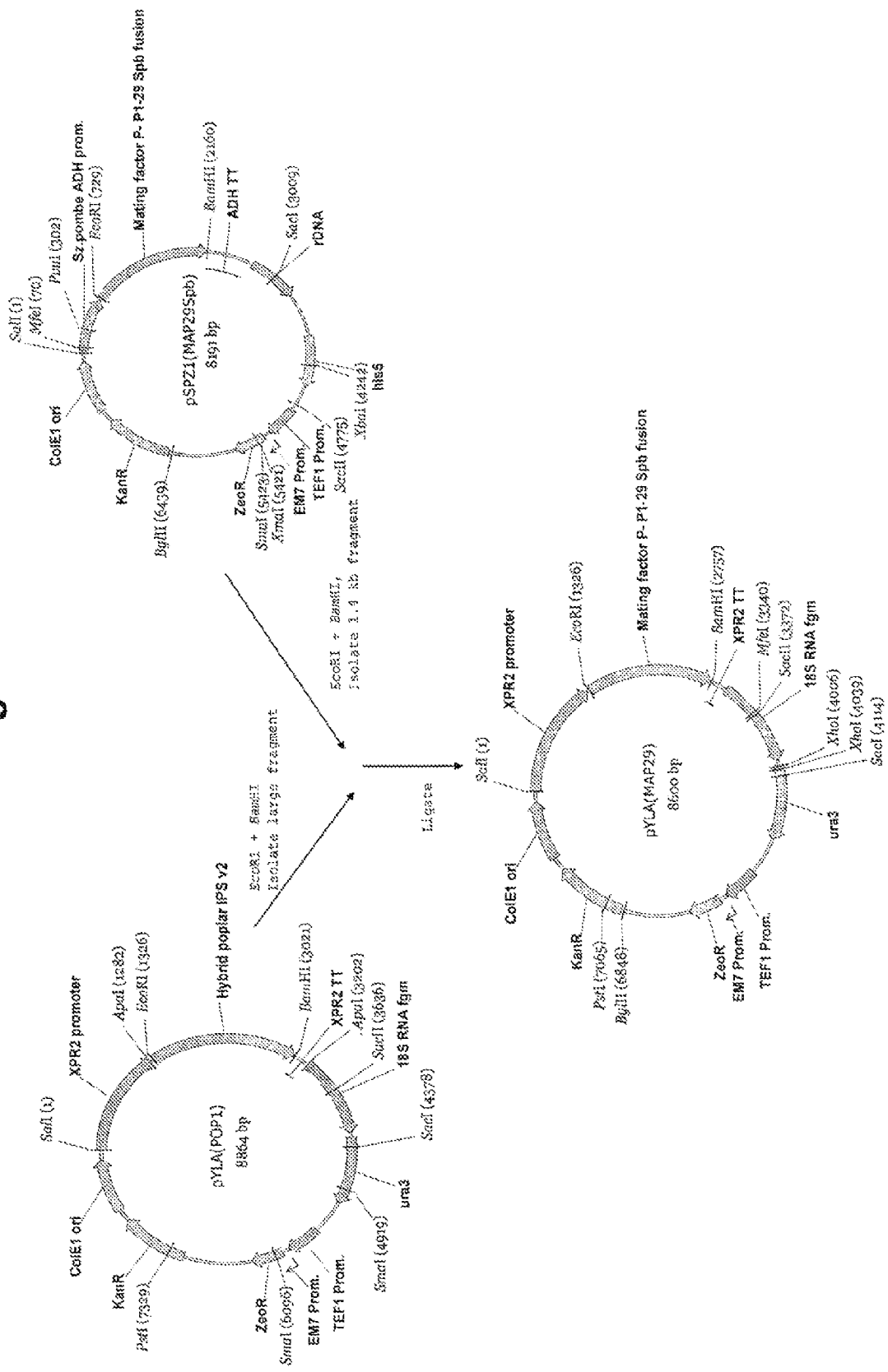
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred µl aliquots of the cell suspension were mixed with linearized plasmid DNA solution (10-20 µg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Figure 20:
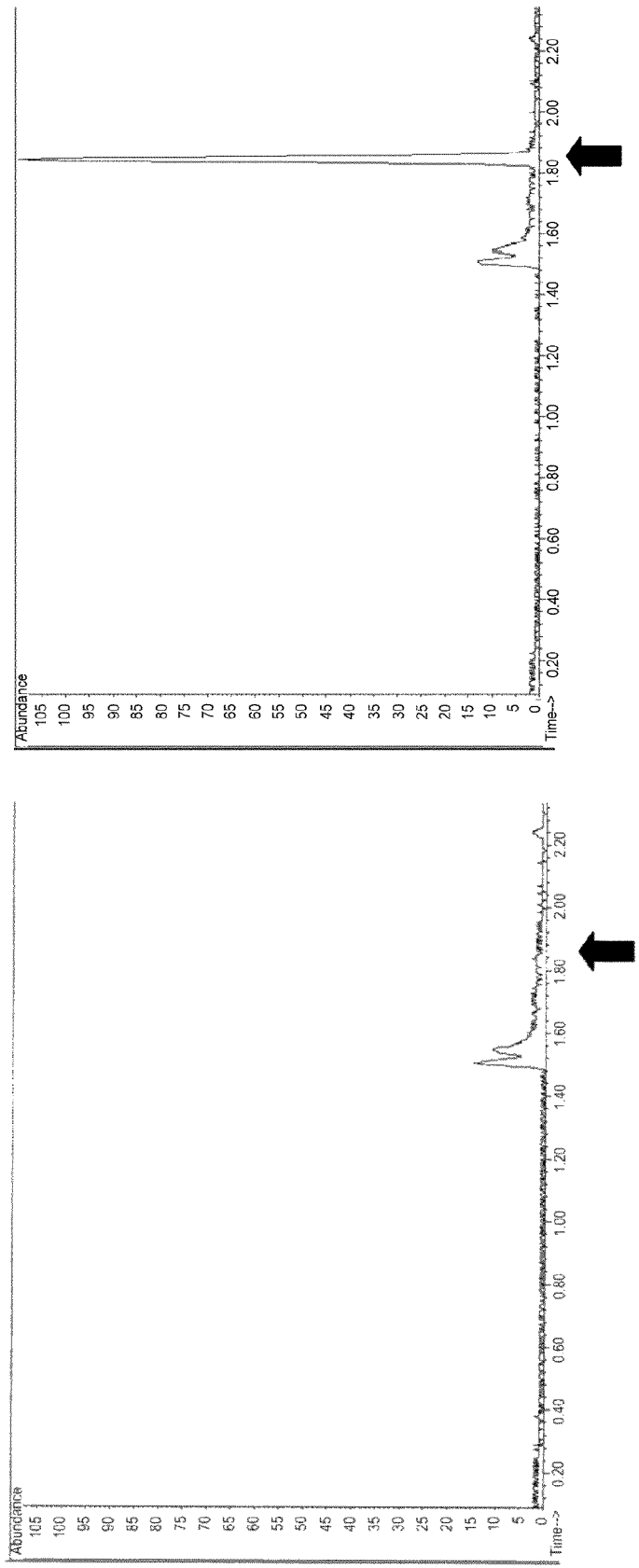
FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 µg/L to 1 µg/L, FIG. 20). No isoprene was detected in the headspace of the control strains carrying phytase gene instead of an isoprene synthase gene.

Example 7

Figure 21:
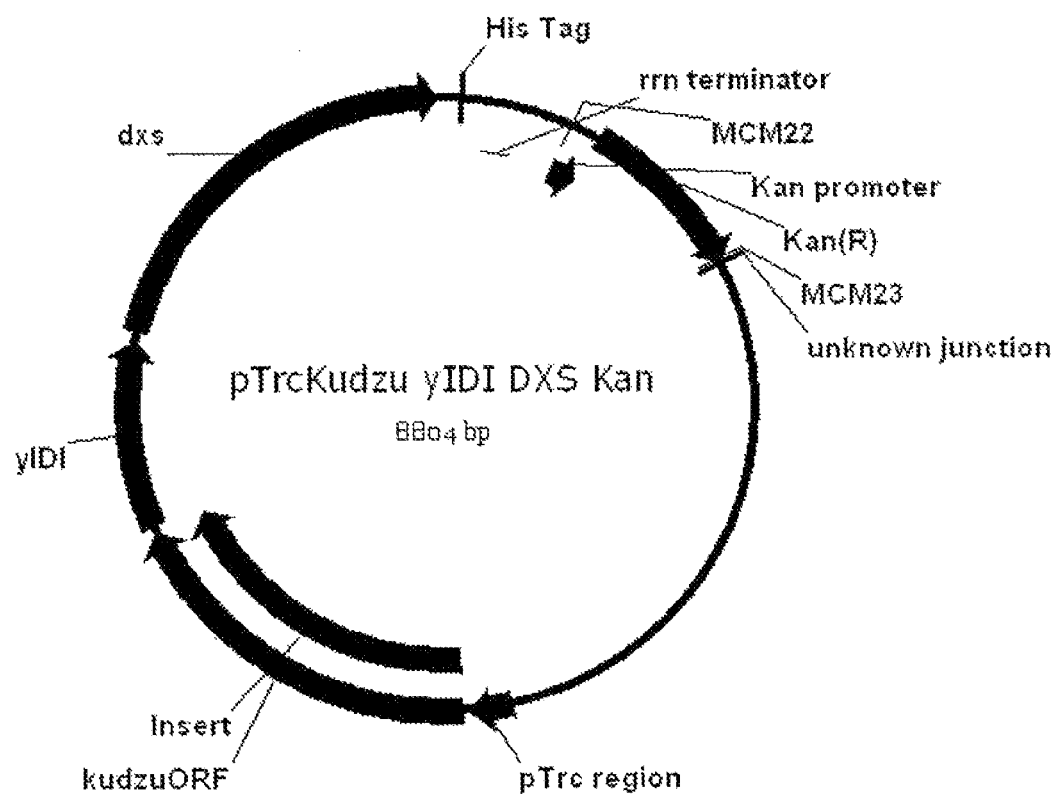
FIG. 21 is a map of pTrcKudzu yIDI DXS Kan.
Figure 34:
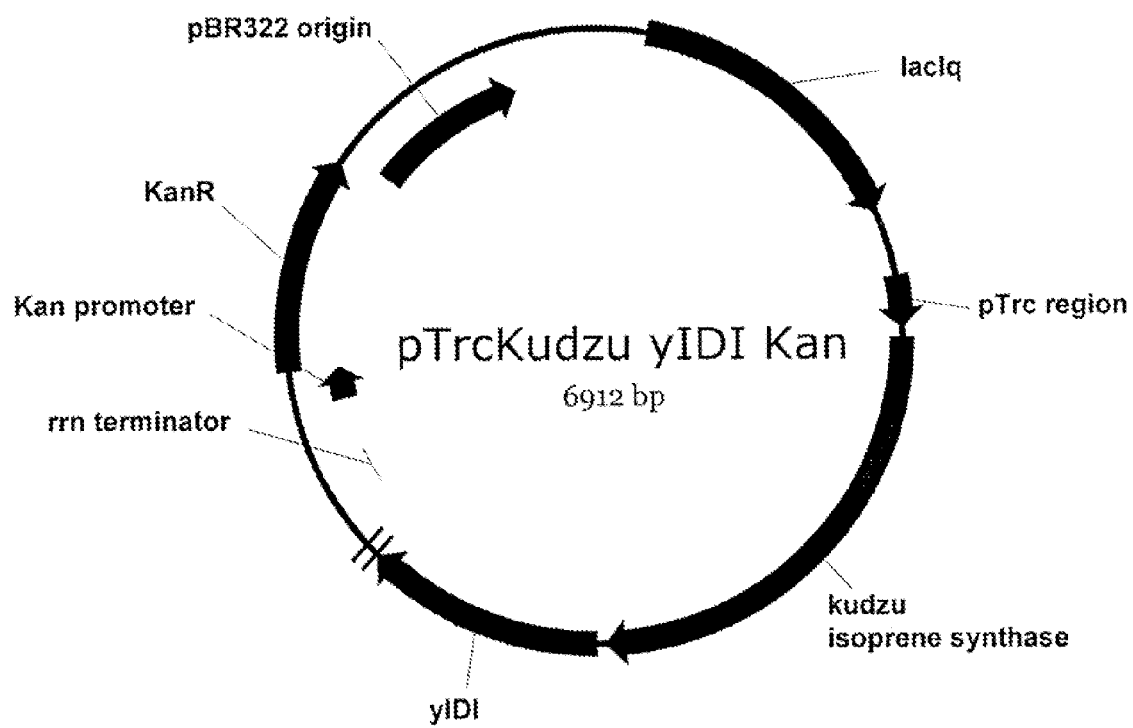
FIG. 34 is a map of pTrcKudzu yIDI Kan.
Figure 36:
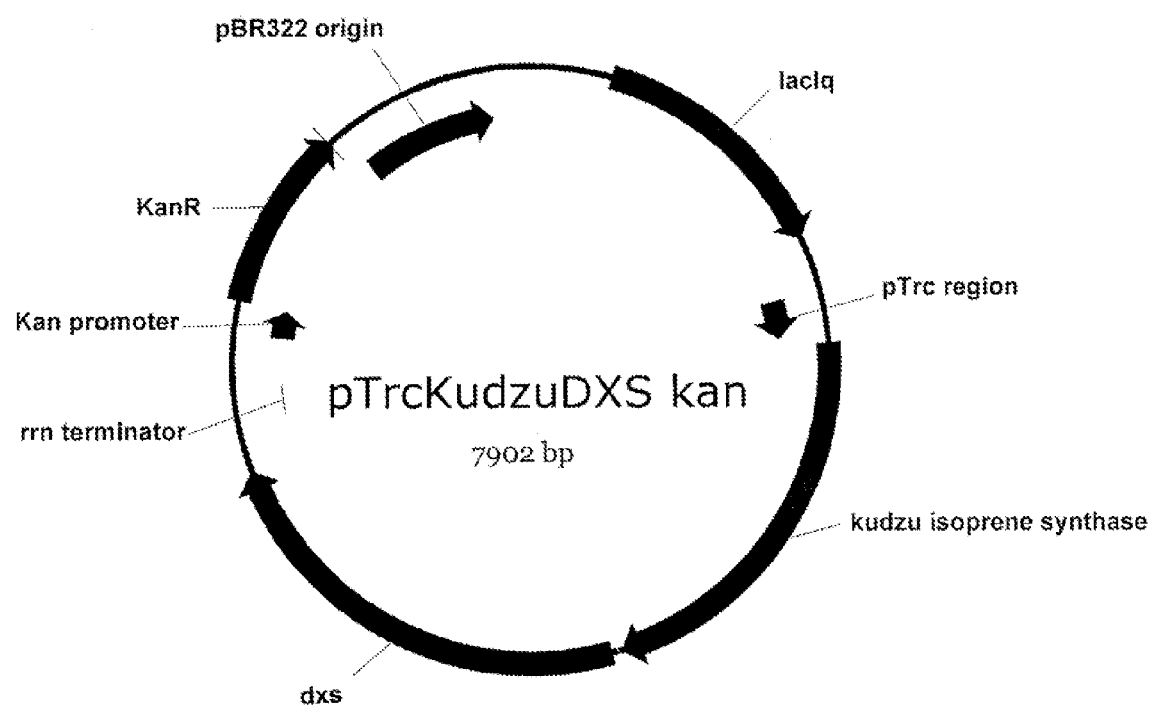
FIG. 36 is a map of pTrcKudzuDXS Kan.
Figure 38:
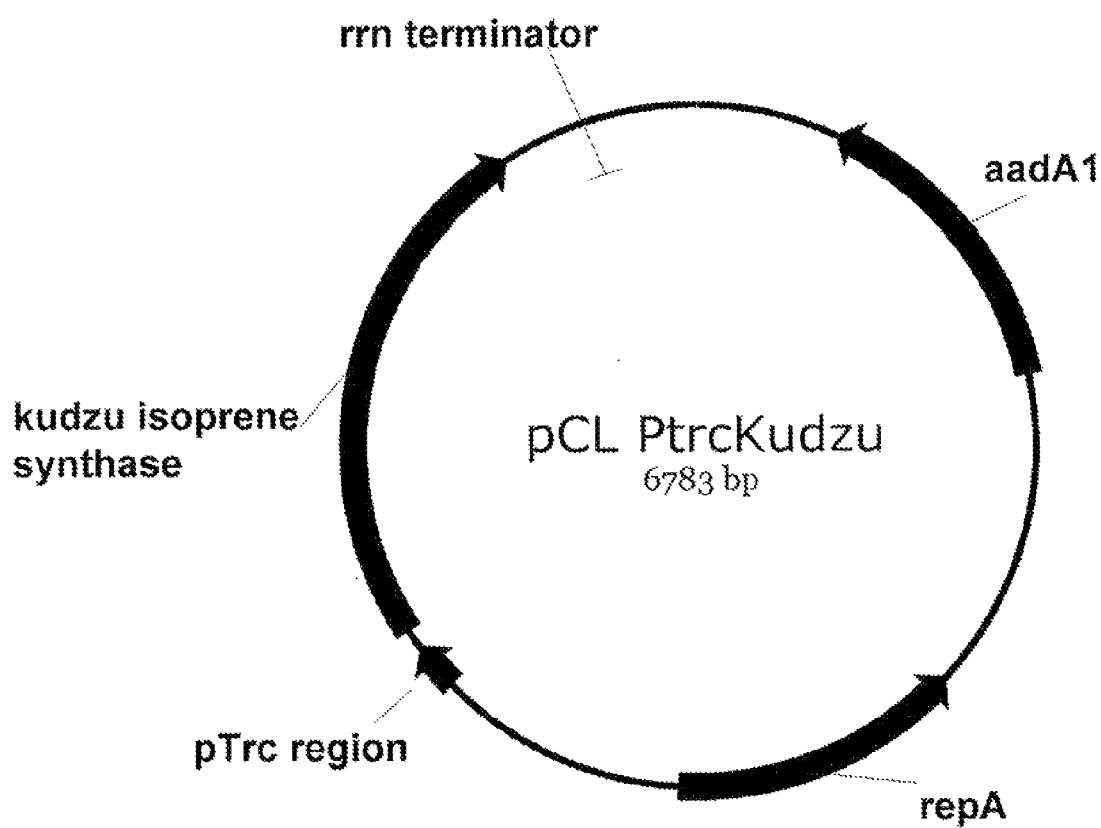
FIG. 38 is a map of pCL PtrcKudzu.
Figure 40:
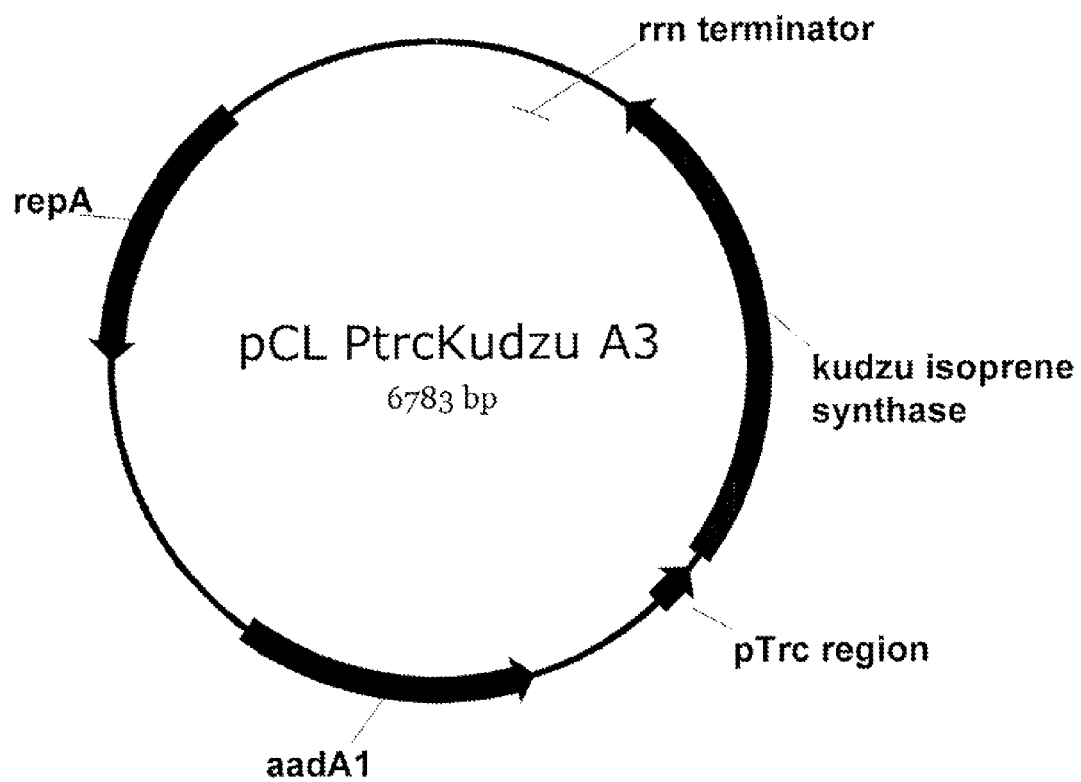
FIG. 40 is a map of pCL PtrcKudzu A3.
Figure 42:
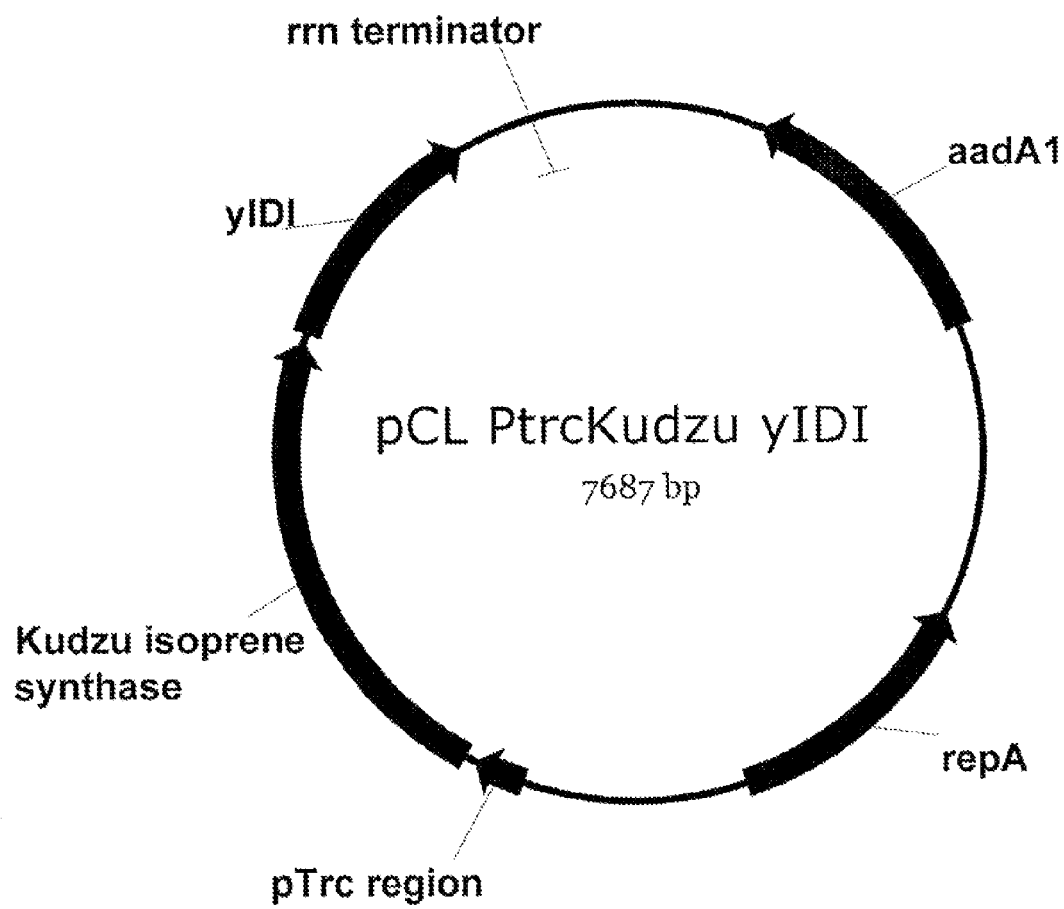
FIG. 42 is a map of pCL PtrcKudzu yIDI.
Figure 44:
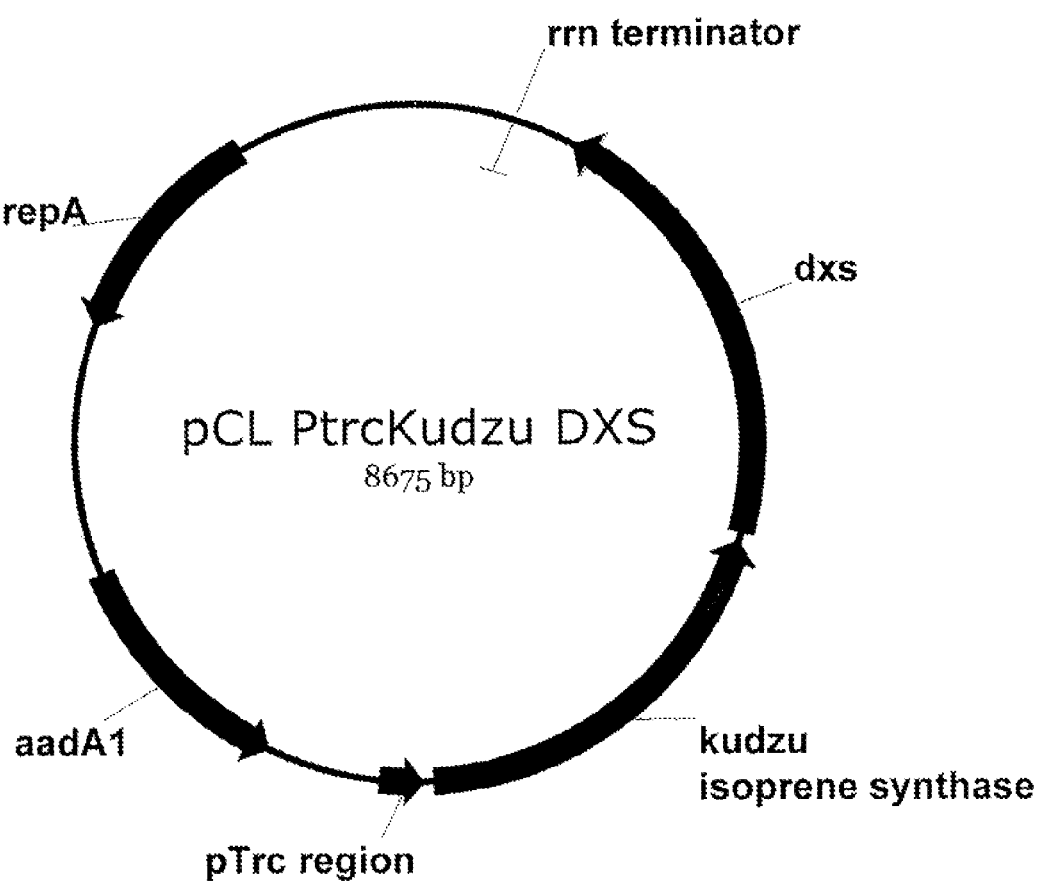
FIG. 44 is a map of pCL PtrcKudzu DXS.
Figure 46A:
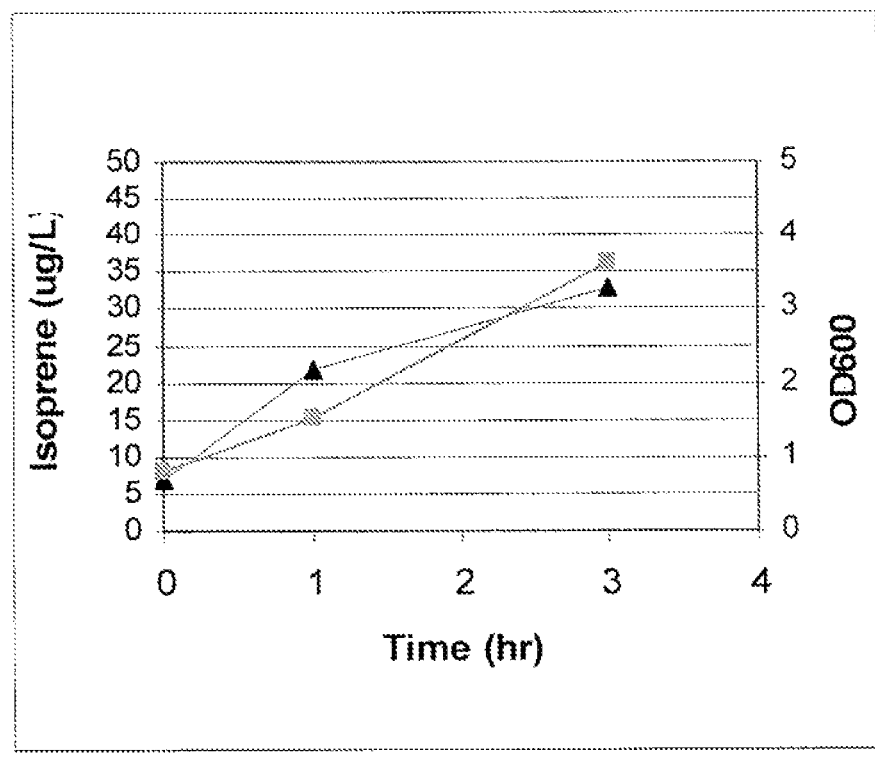
FIG. 46 shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.
Figure 46B:
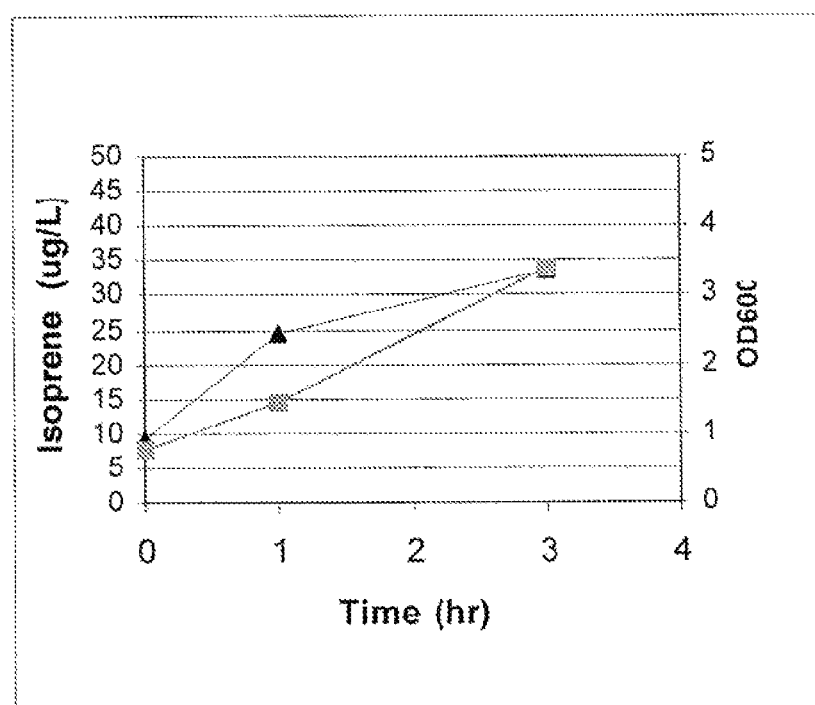
Figure 46C:
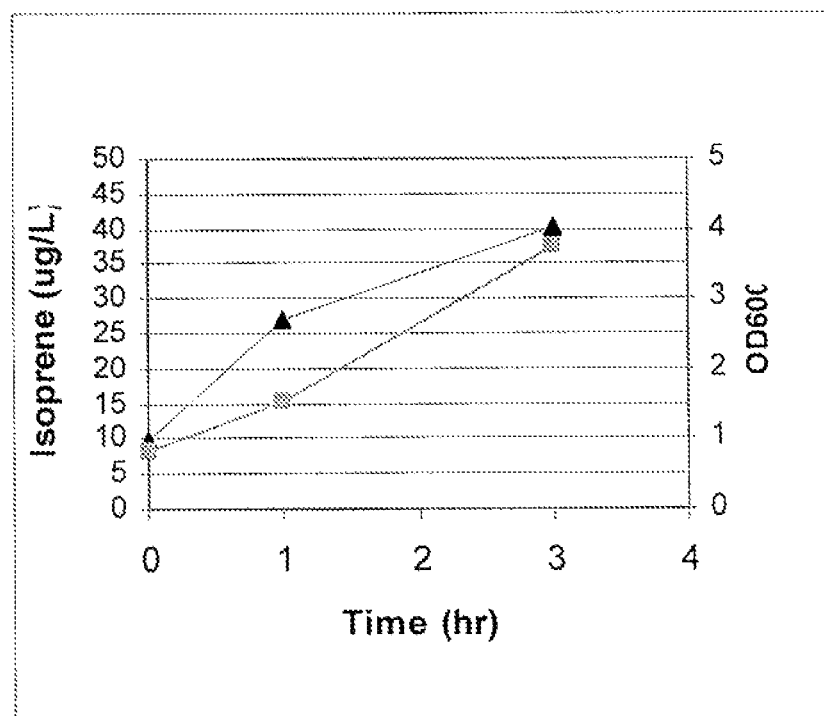
Figure 46D:
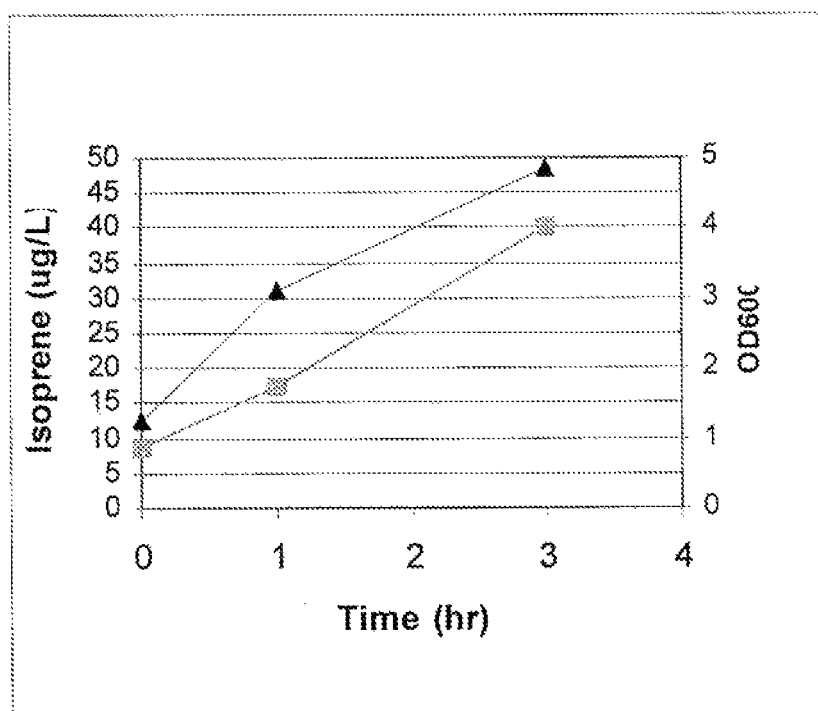
Figure 46E:
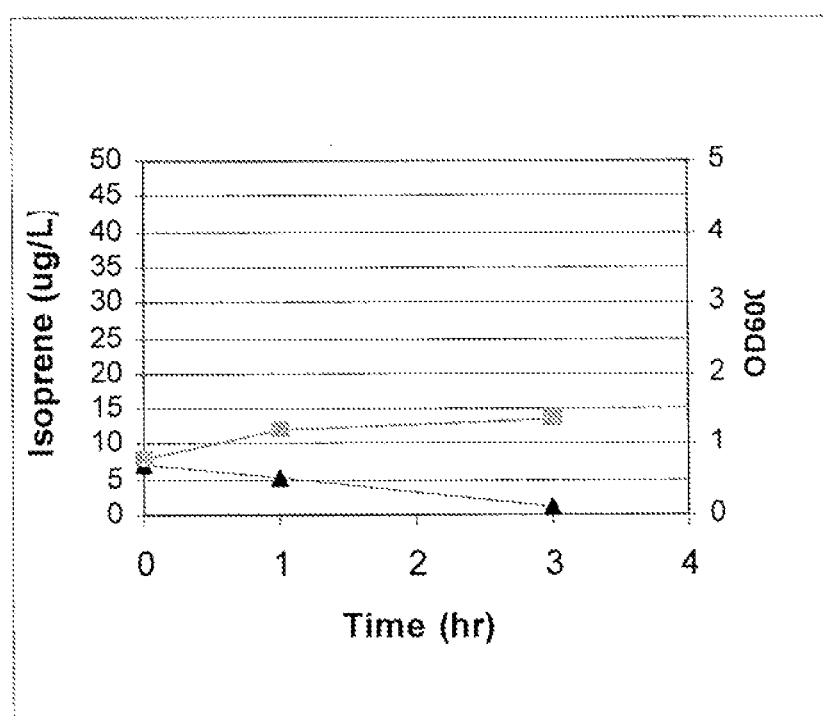

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli*
i) Construction of pTrcKudzuKan The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GAT-CAAGCTTAACCGGAATTGCCAGCTG (SEQ ID NO:14) and MCM23 5'-GATCCGATCGTCAGAAGAACTCGT-CAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 µg/ml.
ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATG-CATCGCCCTTAGGAGGTAAAAAAAAATGAC (SEQ ID NO:16) and PstI-YIDI 1 R 5'-CCTTCTGCAGGACGCGT-TGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 µg/ml kanamycin. Several transformants were isolated and sequenced and the resulting plasmid was called pTrcKudzu-yIDI(kan) (FIGS. 34 and 35).
iii) Construction of pTrcKudzu DXS Kan Plasmid pTrcKudzuKan was digested with PstI, treated with SAP, heat killed and gel purified. It was ligated to a PCR product encoding dxs from *E. coli* with a synthetic RBS. The primers for PCR were MCM 13 5'-GATCATGCATTCGC-CCTTAGGAGGTAAAAAAACAT-GAGTTTTGATATTGCCAAATACCCG (SEQ ID NO:18) and MCM14 5'-CATGCTGCAGTTATGCCAGCCAGGC-CTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 µg/ml. Several transformants were isolated and sequenced and the resulting plasmid was called pTrcKudzu-DXS(kan) (FIGS. 36 and 37).
iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGG-TAAAAAAACATGAGTTTTGATATTGCCAAATACCCG (SEQ ID NO:18) and MCM14 5'-CATGCTGCAGTTATGC-CAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).
v) Construction of pCL PtrcKudzu A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 µg/ml. Several clones were isolated and sequenced and two were selected. pCL PtrcKudzu and pCL PtrcKudzu (A3) have the insert in opposite orientations (FIGS. 38-41).
vi) Construction of pCL PtrcKudzu yIDI The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu yIDI (FIGS. 42 and 43).
vii) Construction of pCL PtrcKudzu DXS The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu DXS (FIGS. 44 and 45).
II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 µg/mL. Cultures of pCL PtrcKudzu (E), pCL PtrcKudzu, pCL PtrcKudzu-yIDI (F) and pCL PtrcKudzu-DXS (G) were grown in LB spectinomycin 50 µg/mL. Cultures were induced with 400 µM IPTG at time 0 ($OD_{600}$ approximately 0.5) and samples taken for isoprene headspace measurement (see Example 1). Results are shown in FIG. 23A-23G.

Figure 23A:
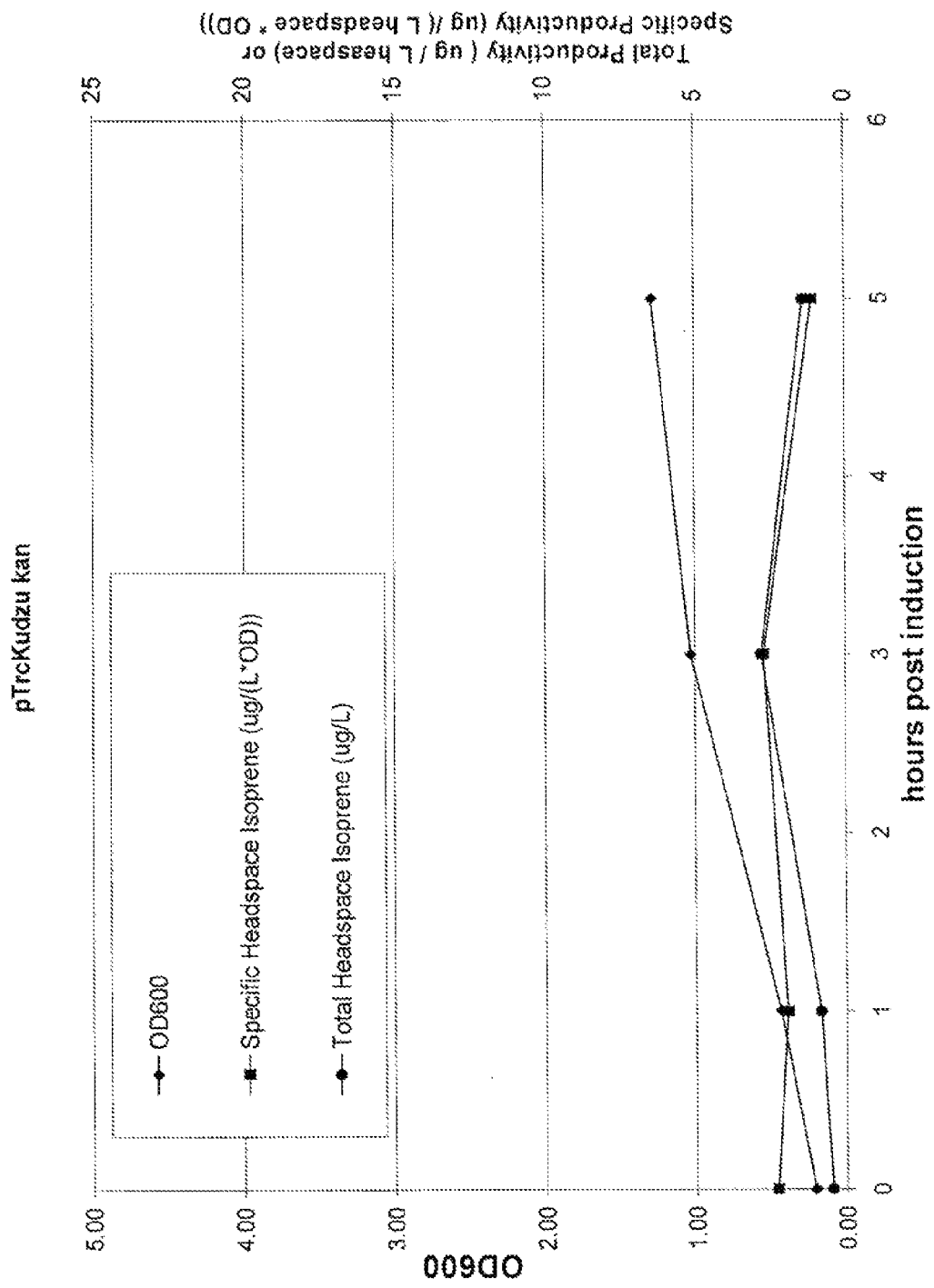
FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23B:
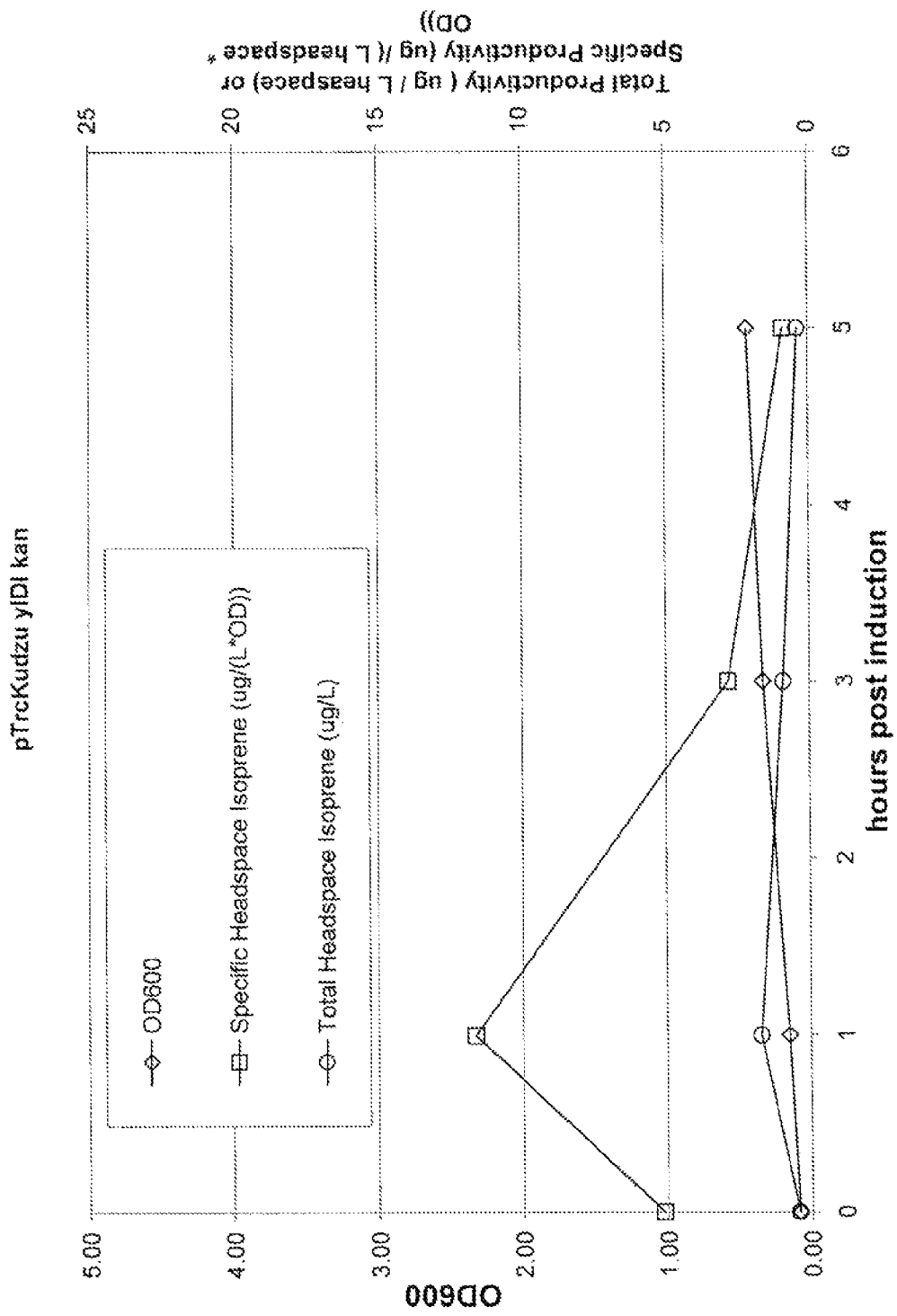
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
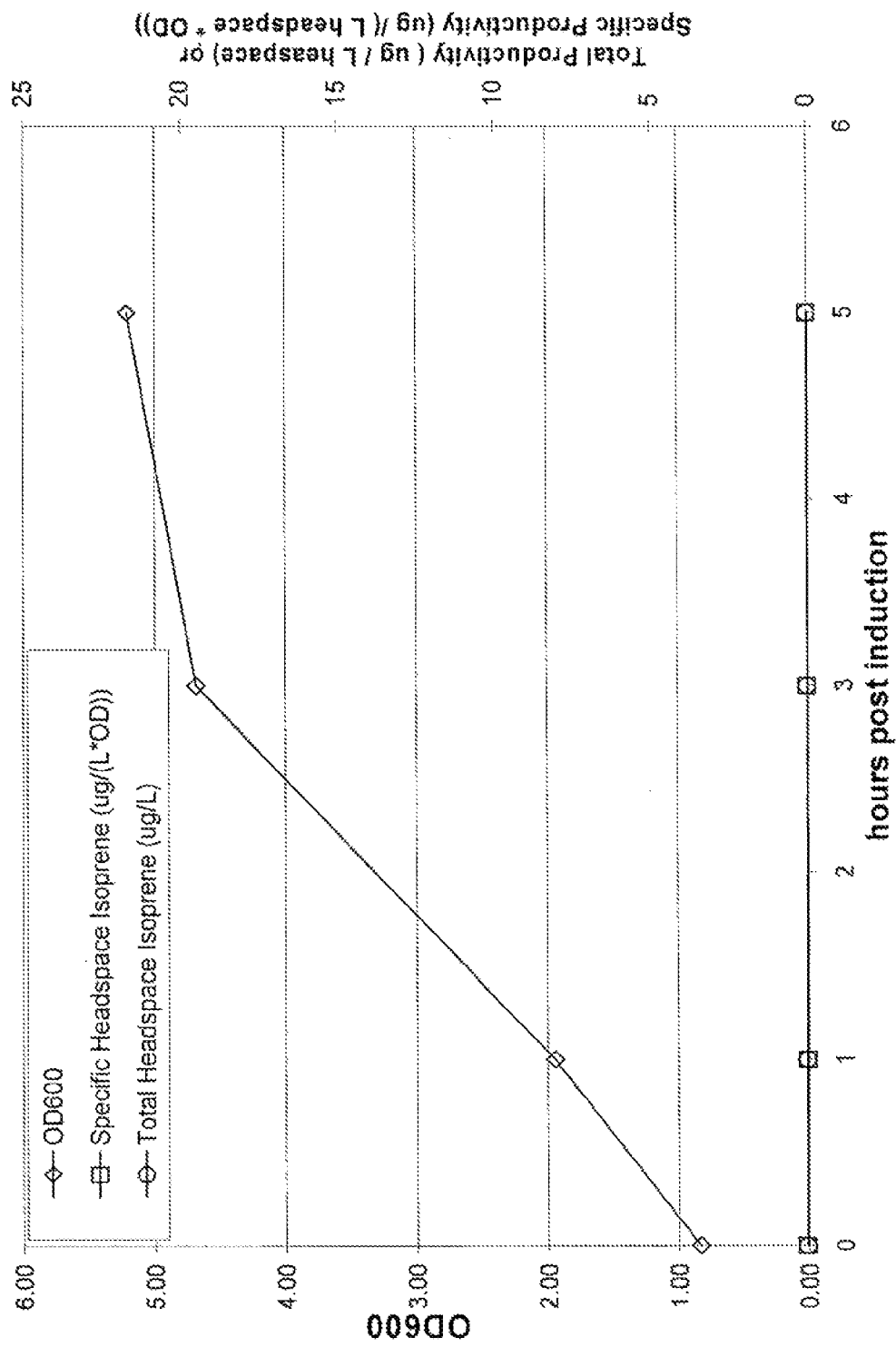
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23D:
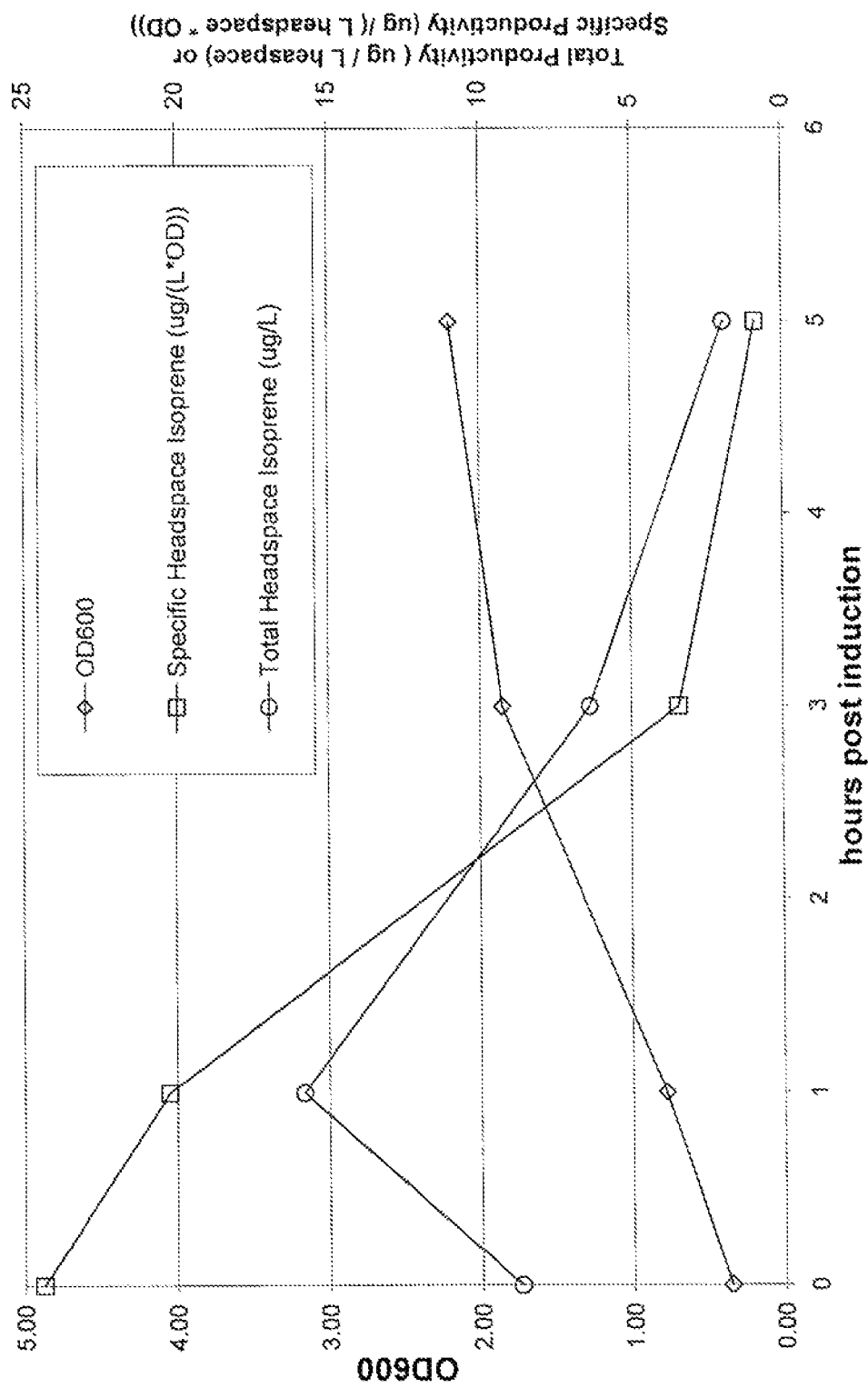
FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23E:
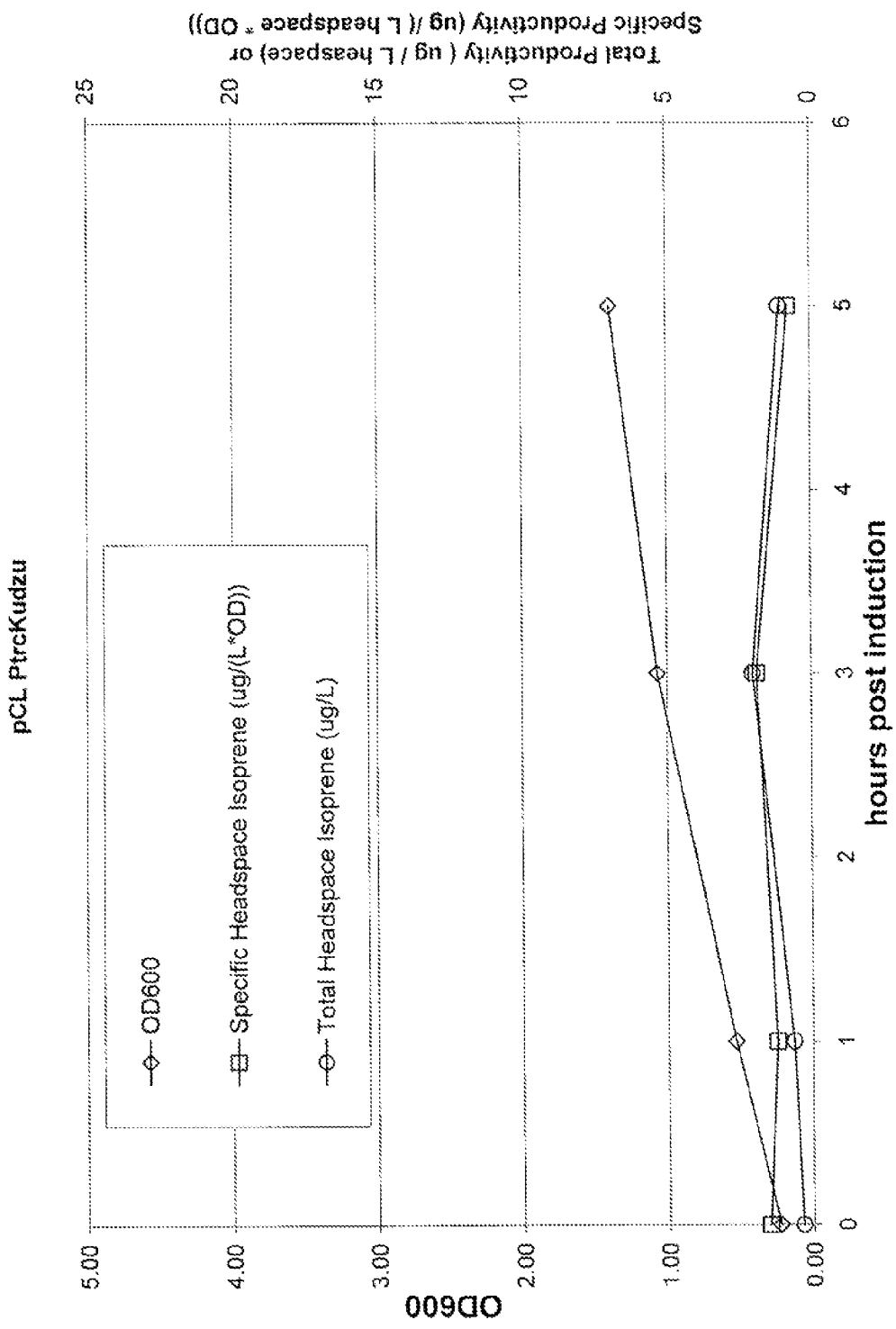
FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23F:
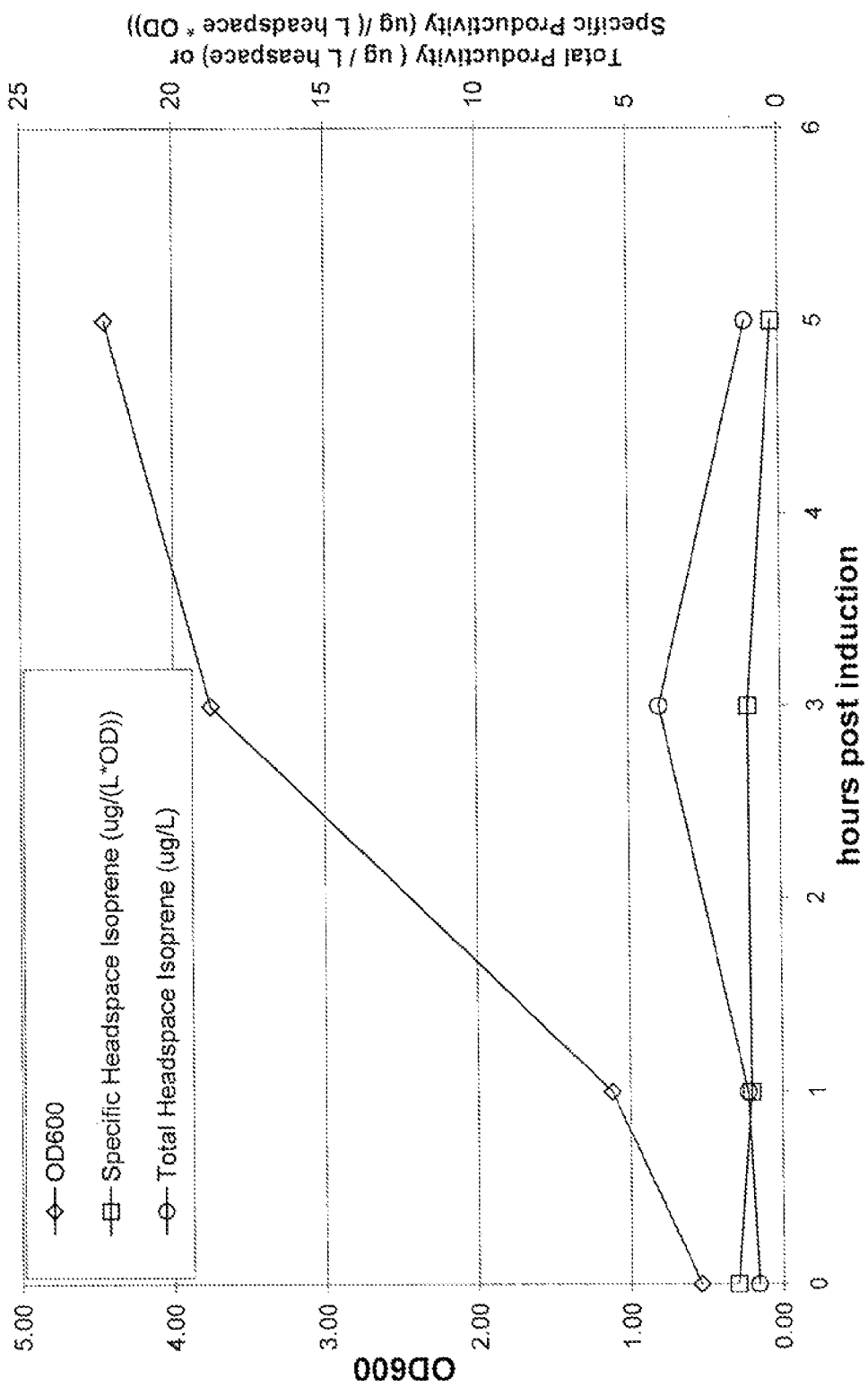
FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23G:
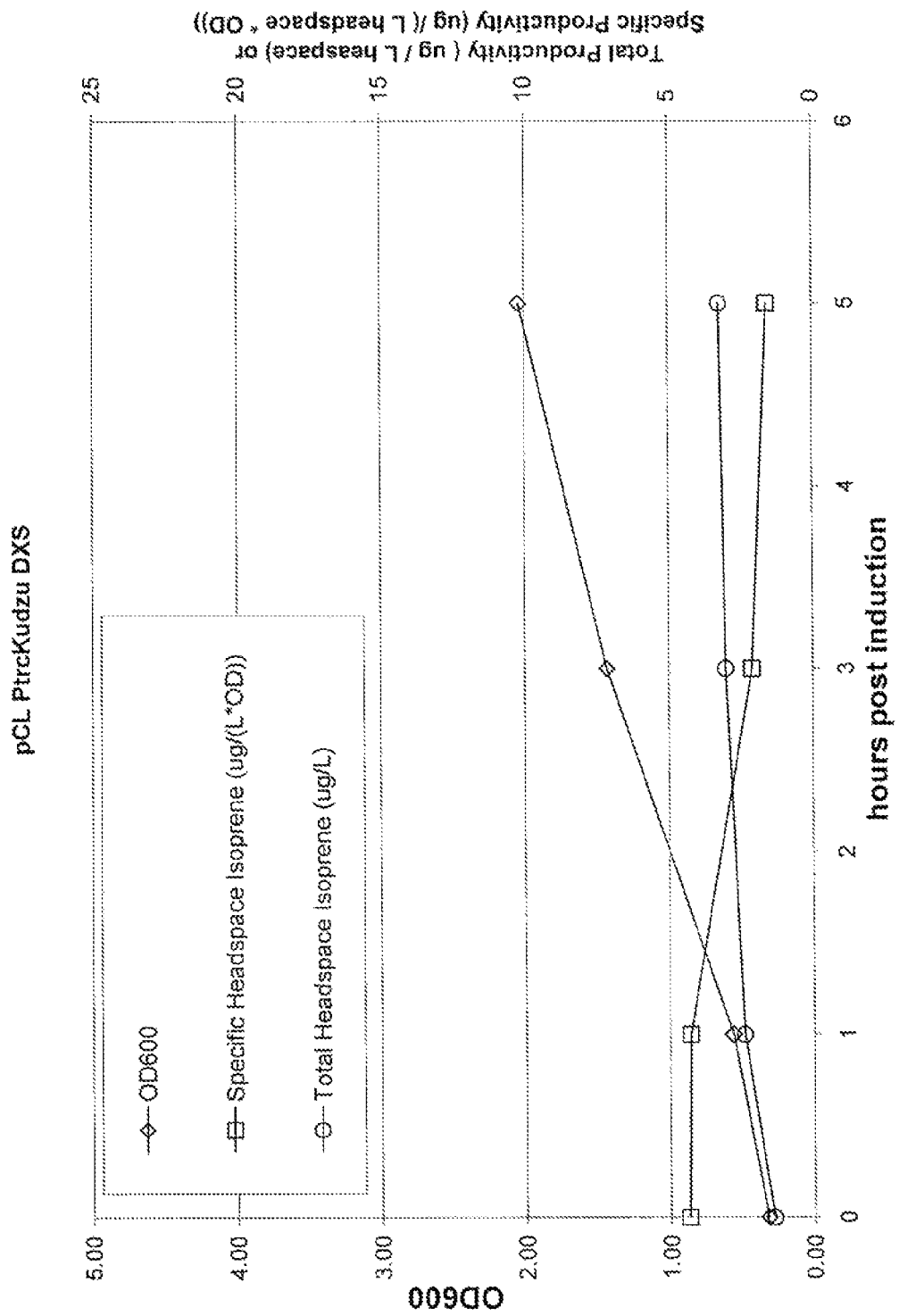
FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23H:
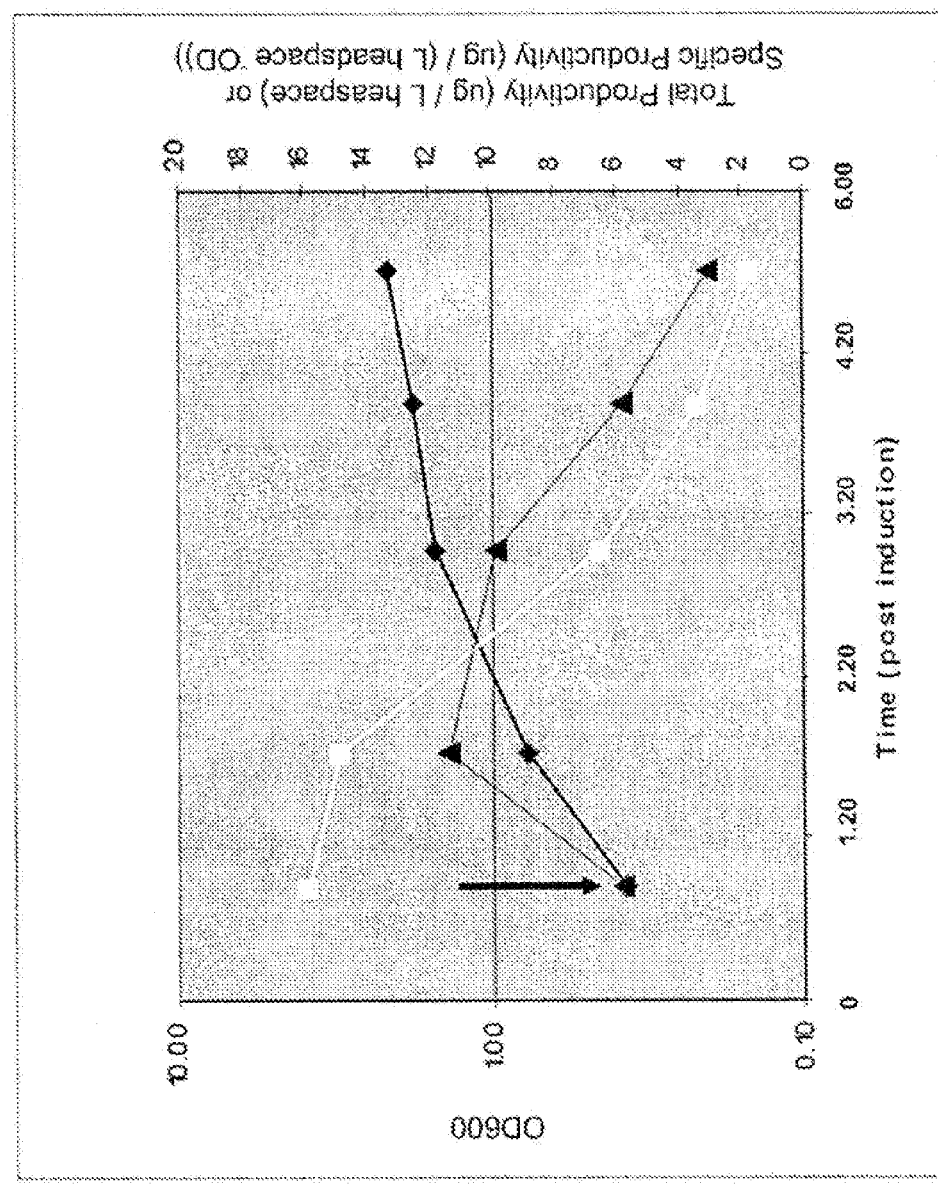
FIG. 23H is a graph showing production of isoprene from glucose in BL21/pTrcKudzuIDIDXSkan. The arrow indicates the time of induction with IPTG (400 μmol). The x-axis is time after induction; the y-axis is $OD_{600}$ and the y2-axis is total productivity of isoprene (μg/L headspace or specific productivity (μg/L headspace/OD). Black diamonds represent $OD_{600}$, black triangles represent isoprene productivity (μg/L) and white squares represent specific productivity of isoprene (μg/L/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 µM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 µg/ml). The culture was incubated overnight at 25° C. with shaking. The following day the overnight culture was diluted to an $OD_{600}$ of 0.05 in 25 ml of TM3 and 0.2% YE and 1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB and kanamycin (50 µg/ml). The culture was incubated overnight at 25° C. with shaking. The following day the overnight culture was diluted to an $OD_{600}$ of 0.05 in 25 ml of TM3 and 0.2% YE and 1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (XDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. coli* Grown in Fed-Batch Culture Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonia gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
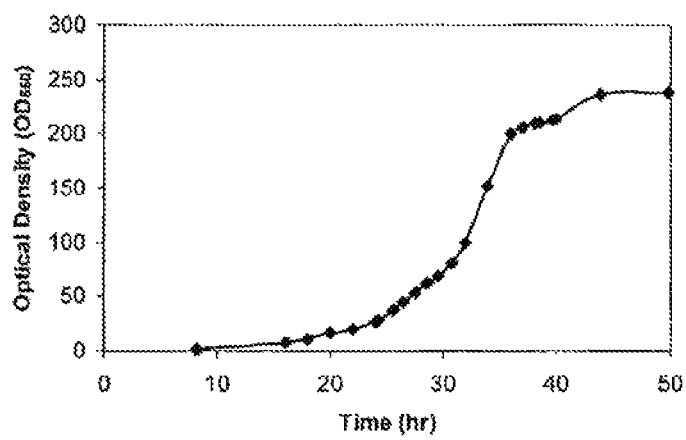
FIG. 49 shows graphs demonstrating isoprene production from a 500 L bioreactor with *E. coli* cells containing the pTrcKudzu and yIDI and DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
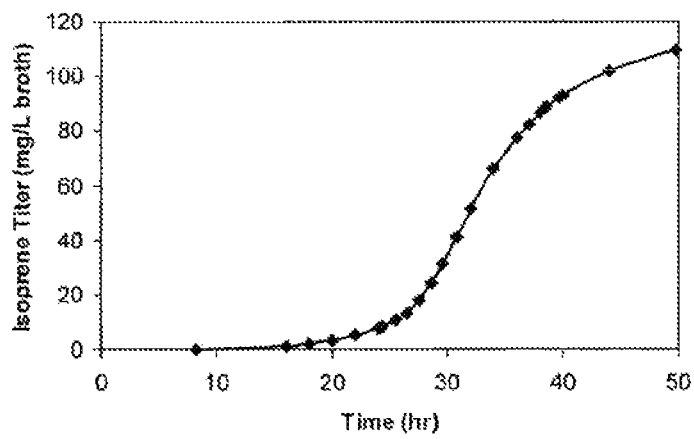
Figure 49C:
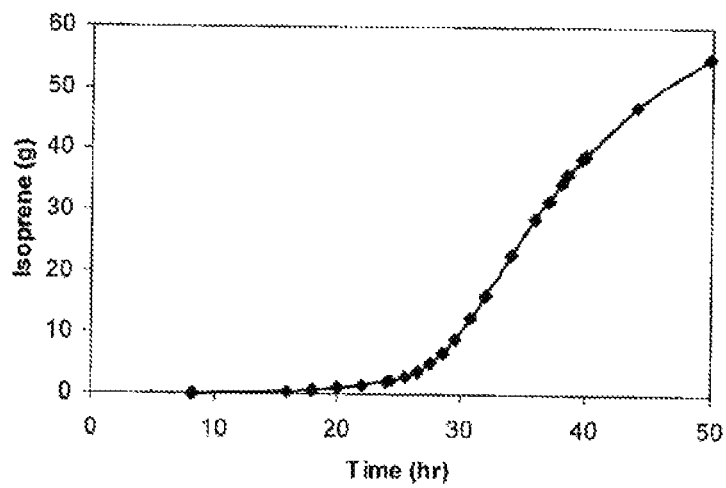

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in *E. coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTAC-CGTTCTTAACTTCTGC, SEQ ID NO:21) and MVK-Pst1-R (5'-ATGGCTGCAGGCCTATCGCAAATTAGCT-TATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and Taq1 restriction endonucleases and the fragment was gel purified and ligated into pTrcHis2B digested with SacI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTG-GAATTCGCCCTTCTGCAGC, SEQ ID NO:25) and NsiI-MVD 1 F (5'-GTAGATGCATGCAGAATTCGCCCTTAAG-GAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATG-CATCGCCCTTAGGAGGTAAAAAAAATGAC, SEQ ID NO:28) to amplify the yIDI gene. In some cases the IPP isomerase gene, idi from *E. coli* was used. To amplify idi from *E. coli* chromosomal DNA, the following primer set was used: PstI-CIDI 1 R (5'-GTGTGATGGATATCTGCAGAAT-TCG, SEQ ID NO:29) and NsiI-CIDI 1 F (5'-CATCAATG-CATCGCCCTTAGGAGGTAAAAAAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and transformants were grown at 37° C. overnight with selection on LA containing kanamycin (50 µg/ml). The transformants were verified by restriction enzyme digestion and one was frozen as a stock. The plasmid was designated pTrcK-anKKDIy.

II. Cloning a Kudzu Isoprene Synthase Gene into pTrcK-anKKDIy

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTTACT (SEQ ID NO:31) and MCM53 5'-CGGTCGACGGATCCCT-GCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 µg/ml). The correct insertion of the fragment was verified by sequencing and this strain was designated MCM93.

Figure 24:
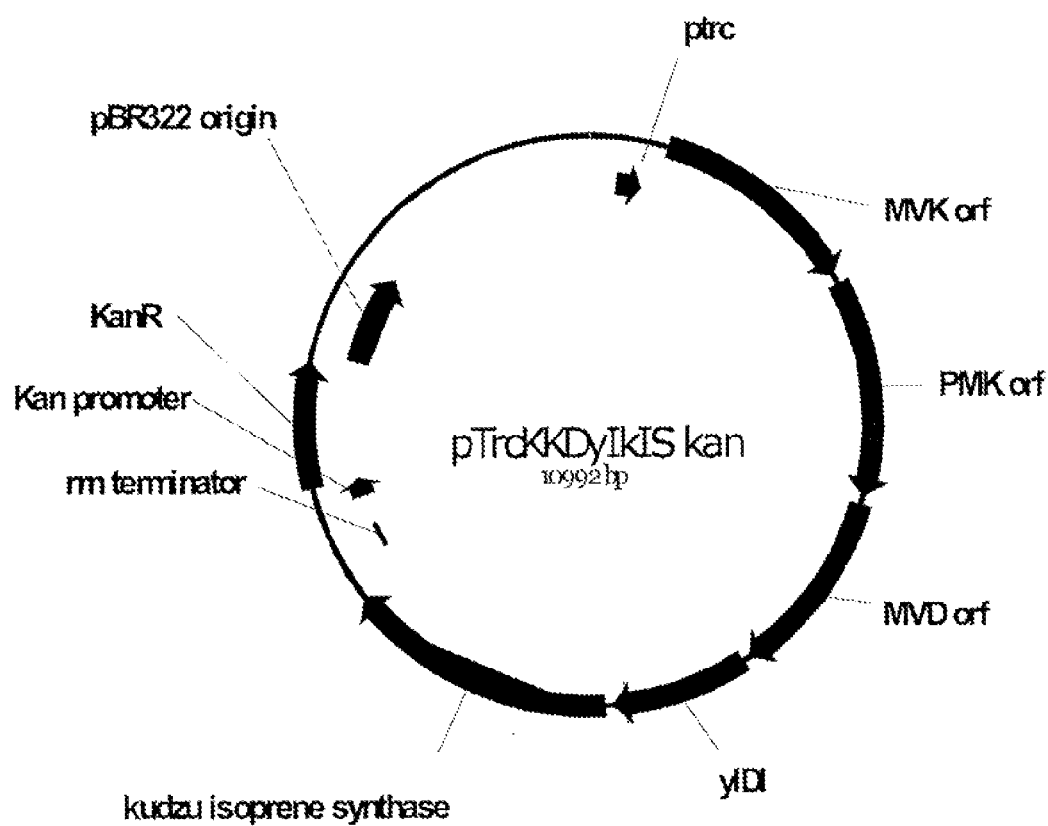
FIG. 24 is a map of pTrcKKDyIkIS kan.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 µg/ml. The correct transformant was verified by restriction digestion and the plasmid was designated pTrcKKDyIkISKan (FIGS. 24 and 25). This plasmid was transformed into BL21(λDE3) cells (Invitrogen).

III. Isoprene Production from Mevalonate in *E. coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 µM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67 \times 10^4$ nmol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

```
CF 07-60 (+) Start of mvaE w/RBS + ATG start codon
SacI
                                        (SEQ ID NO: 34)
5'-GAGACATGAGCTCAGGAGGTAAAAAAACATGAAAACAGTAGTTATT
ATTG CF 07-62 (-) Fuse mvaE to mvaS with RBS in between
                                        (SEQ ID NO: 35)
5'-TTTATCAATCCCAATTGTCATGTTTTTTTACCTCCTTTATTGTTTT
CTTAAATC
```

The mvaS gene was amplified from *E. faecalis* genomic DNA (ATCC 700802D-5) with a RBS and spacer from *E. coli* in front using the following primers:

```
CF 07-61 (+) Fuse mvaE to mvaS with RBS in between
                                        (SEQ ID NO: 36)
5'-GATTTAAGAAAACAATAAAGGAGGTAAAAAAACATGACAATTGGGA
TTGATAAA CF 07-102 (-) End of mvaS gene BglII
                                        (SEQ ID NO: 37)
5'-GACATGACATAGATCTTTAGTTTCGATAAGAACGGT
```

The PCR fragments were fused together with PCR using the following primers:

```
CF 07-60 (+) Start of mvaE w/RBS + ATG start codon
SacI
                                        (SEQ ID NO: 34)
5'-GAGACATGAGCTCAGGAGGTAAAAAAACATGAAAACAGTAGTTATT
ATTG CF 07-102 (-) End of mvaS gene BglII
                                        (SEQ ID NO: 37)
5'-GACATGACATAGATCTTTAGTTTCGATAAGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA and 50 µg/ml carbenicillin plates. A total of six colonies were chosen and grown overnight in LB and 50 µg/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                        (SEQ ID NO: 38)
5'-ATGAAAACAGTAGTTATTATTGATGC CF 07-59 (-) End of mvaE gene
                                        (SEQ ID NO: 39)
5'-ATGTTATTGTTTTCTTAAATCATTTAAAATAGC CF 07-82 (+) Start of mvaS gene
                                        (SEQ ID NO: 40)
5'-ATGACAATTGGGATTGATAAAATTAG CF 07-83 (-) End of mvaS gene
                                        (SEQ ID NO: 41)
5'-TTAGTTTCGATAAGAACGGT CF 07-86 (+) Sequence in mvaE
                                        (SEQ ID NO: 42)
5'-GAAATAGCCCCATTAGAAGTATC CF 07-87 (+) Sequence in mvaE
                                        (SEQ ID NO: 43)
5'-TTGCCAATCATATGATTGAAAATC CF 07-88 (+) Sequence in mvaE
                                        (SEQ ID NO: 44)
5'-GCTATGCTTCATTAGATCCTTATCG CF 07-89 (+) Sequence mvaS
                                        (SEQ ID NO: 45)
5'-GAAACCTACATCCAATCTTTTGCCC
```

The plasmid called pTrcHis2AUpperPathway#1 was correct by sequencing and was transformed into the commercially available *E. coli* strain BL21. Selection was done on LA and 50 µg/ml carbenicillin. Two transformants were chosen and grown in LB and 50 µg/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

Figure 26:
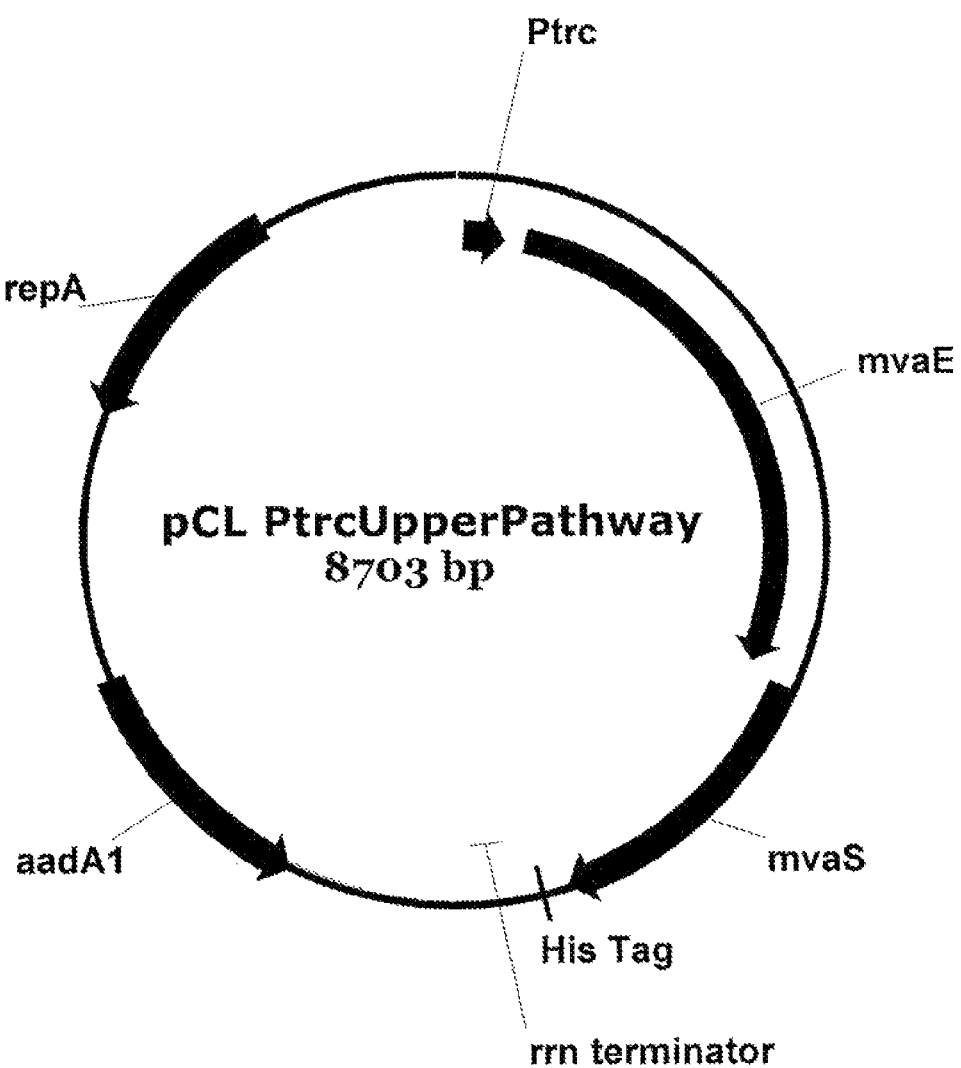
FIG. 26 is a map of pCL PtrcUpperPathway.

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 µg/ml). A correct colony was identified by screening for the presence of the insert by PCR. The plasmid was designated pCL PtrcUpperPathway (FIGS. 26 and 27).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 μg/ml) and Spectinomycin (50 μg/ml). The transformants were checked by plasmid prep to ensure that both plasmids were retained in the host. The strain was designated MCM127.

VII. Production of Mevalonic Acid from Glucose in E. coli/pUpperpathway

Single colonies of the BL21/pTrcHis2A-mvaE/mvaS or FM5/p pTrcHis2A-mvaE/mvaS are inoculated into LB and carbenicillin (100 μg/ml) and are grown overnight at 37° C. with shaking at 200 rpm. These cultures were diluted into 50 ml medium in 250 ml baffled flasks to an $OD_{600}$ of 0.1. The medium was TM3, 1 or 2% glucose, carbenicillin (100 ug/ml) or TM3, 1% glucose, hydrolyzed soy oil, and carbenicillin (100 ug/ml) or TM3 and biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 μM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of E. coli cells with nucleic acids encoding Enterococcus faecalis AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in E. coli.

VIII. Production of Isoprene from E. coli BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21(λDE3) and the transformations were done by standard methods. Transformants were selected on L agar containing kanamycin (50 μg/ml) or kanamycin plus spectinomycin (both at a concentration of 50 μg/ml). Plates were grown at 37° C. The resulting strains were designated as follows:

Grown on Kanamycin Plus Spectinomycin (50 μg/ml Each)
MCM127-pCL Upper MVA and pTrcKKDyIkIS (kan) in BL21(λDE3)
MCM131-pCL1920 and pTrcKKDyIkIS (kan) in BL21(λDE3)
MCM125-pCL Upper MVA and pTrcHis2B (kan) in BL21(λDE3)
Grown on Kanamycin (50 μg/ml)
MCM64-pTrcKudzu yIDI DXS (kan) in BL21(λDE3)
MCM50-pTrcKudzu (kan) in BL21(λDE3)
MCM123-pTrcKudzu yIDI DXS DXR (kan) in BL21(λDE3)

The above strains were streaked from freezer stocks to LA and appropriate antibiotic and grown overnight at 37° C. A single colony from each plate was used to inoculate shake flasks (25 ml LB and the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB and the appropriate antibiotic. The cultures were then diluted into 25 ml LB, % glucose, and the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

| Production of isoprene in E. coli strains | |
| --- | --- |
| Strain | Isoprene ($\mu g/L_{broth}$/hr/OD) |
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS #503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

Example 9

Construction of the Upper and Lower MVA Pathway for Integration into Bacillus subtilis

I. Construction of the Upper MVA Pathway in Bacillus subtilis

The upper pathway from Enterococcus faecalis is integrated into B. subtilis under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

1: PaprE

```
CF 07-134 (+) Start of aprE promotoer PstI
                                            (SEQ ID NO: 82)
5'-GACATCTGCAGCTCCATTTTCTTCTGC CF 07-94 (-) Fuse PaprE to mvaE
                                            (SEQ ID NO: 83)
5'-CAATAATAACTACTGTTTTCACTCTTTACCCTCTCCTTTTAA
```

Template: *Bacillus subtilis* chromosomal DNA 2: mvaE

```
CF 07-93 (+) fuse mvaE to the aprE promoter (GTG
start codon)
                                            (SEQ ID NO: 84)
5'-TTAAAAGGAGAGGGTAAAGAGTGAAAACAGTAGTTATTATTG CF 07-62 (-) Fuse mvaE to mvaS with RBS in between
                                            (SEQ ID NO: 35)
5'-TTTATCAATCCCAATTGTCATGTTTTTTTACCTCCTTTATTGTTTT
CTTAAATC
```

Template: *Enterococcus faecalis* chromosomal DNA (from ATCC)

3. mvaS

```
CF 07-61 (+) Fuse mvaE to mvaS with RBS in between
                                            (SEQ ID NO: 36)
5'-GATTTAAGAAAACAATAAAGGAGGTAAAAAAACATGACAATTGGGA
TTGATAAA CF 07-124 (-) Fuse the end of mvaS to the
terminator
                                            (SEQ ID NO: 85)
5'-CGGGGCCAAGGCCGGTTTTTTTTAGTTTCGATAAGAACGAACGGT
```

Template: *Enterococcus faecalis* chromosomal DNA

4. *B. amyliquefaciens* alkaline serine protease terminator

```
CF 07-123 (+) Fuse the end of mvaS to the
terminator
                                            (SEQ ID NO: 86)
5'-ACCGTTCGTTCTTATCGAAACTAAAAAAAACCGGCCTTGGCCCCG CF 07-46 (-) End if B. amyliquefaciens terminator
BamHI
                                            (SEQ ID NO: 63)
5'-GACATGACGGATCCGATTACGAATGCCGTCTC
```

Template: *Bacillus amyliquefaciens* chromosomal DNA
PCR Fusion Reactions
5. Fuse mvaE to mvaS

```
CF 07-93 (+) fuse mvaE to the aprE promotoer
(GTG start codon)
                                            (SEQ ID NO: 84)
5'-TTAAAAGGAGAGGGTAAAGAGTGAAAACAGTAGTTATTATTG CF 07-124 (-) Fuse the end of mvaS to the
terminator
                                            (SEQ ID NO: 85)
5'-CGGGGCCAAGGCCGGTTTTTTTTAGTTTCGATAAGAACGAACGGT
```

Template: #2 and 3 from above
6. Fuse mvaE-mvaS to aprE promoter

```
CF 07-134 (+) Start of aprE promoter PstI
                                            (SEQ ID NO: 82)
5'-GACATCTGCAGCTCCATTTTCTTCTGC CF 07-124 (-) Fuse the end of mvaS to the
terminator
                                            (SEQ ID NO: 85)
5'-CGGGGCCAAGGCCGGTTTTTTTTAGTTTCGATAAGAACGAACGGT
```

Template #1 and #4 from above
7. Fuse PaprE-mvaE-mvaS to terminator

```
CF 07-134 (+) Start of aprE promoter PstI
                                            (SEQ ID NO: 82)
5'-GACATCTGCAGCTCCATTTTCTTCTGC CF 07-46 (-) End of B. amyliquefaciens terminator
BamHI
                                            (SEQ ID NO: 63)
5'-GACATGACGGATCCGATTACGAATGCCGTCTC
```

Template: #4 and #6

Figure 50:
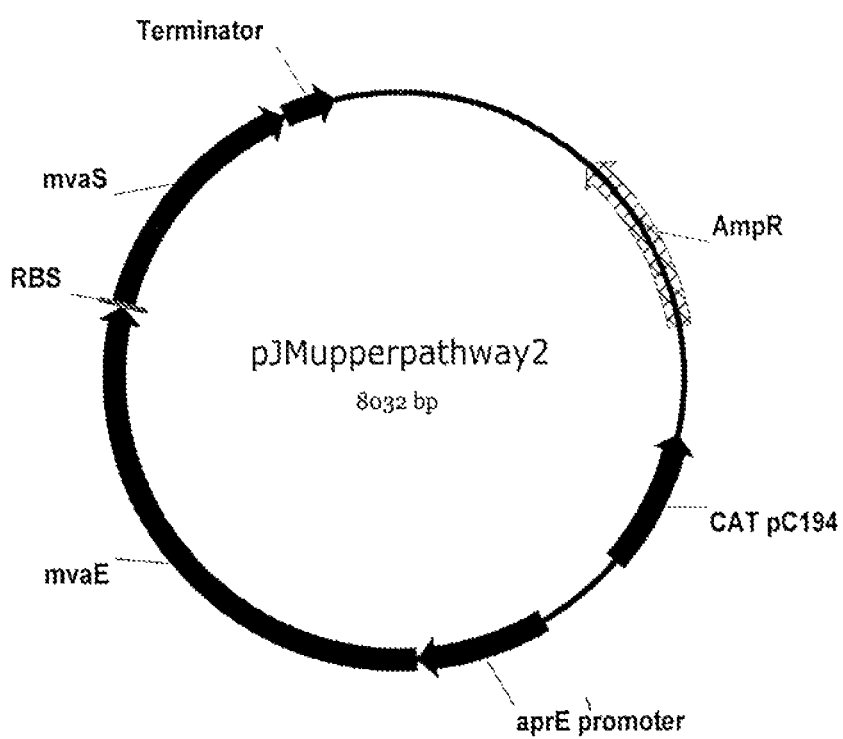
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51). Purified plasmid DNA is transformed into *Bacillus subtilis* aprEnprE PxylcomK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

Sequencing Primers:

```
CF 07-134 (+) Start of aprE promoter PstI
                                            (SEQ ID NO: 82)
5'-GACATCTGCAGCTCCATTTTCTTCTGC CF 07-58 (+) Start of mvaE gene
                                            (SEQ ID NO: 38)
5'-ATGAAAACAGTAGTTATTATTGATGC CF 07-59 (-) End of mvaE gene
                                            (SEQ ID NO: 39)
5'-ATGTTATTGTTTTCTTAAATCATTTAAAATAGC CF 07-82 (+) Start of mvaS gene
                                            (SEQ ID NO: 40)
5'-ATGACAATTGGGATTGATAAAATTAG CF 07-83 (-) End of mvaS gene
                                            (SEQ ID NO: 41)
5'-TTAGTTTCGATAAGAACGAACGGT
```

-continued

CF 07-86 (+) Sequence in mvaE
(SEQ ID NO: 42)
5'-GAAATAGCCCCATTAGAAGTATC

CF 07-87 (+) Sequence in mvaE
(SEQ ID NO: 43)
5'-TTGCCAATCATATGATTGAAAATC

CF 07-88 (+) Sequence in mvaE
(SEQ ID NO: 44)
5'-GCTATGCTTCATTAGATCCTTATCG

CF 07-89 (+) Sequence mvaS
(SEQ ID NO: 45)
5'-GAAACCTACATCCAATCTTTTGCCC

Transformants are selected on LA containing chloramphenicol at a concentration of 5 µg/ml. One colony is confirmed to have the correct integration by sequencing and is plated on LA containing increasing concentrations of chloramphenicol over several days, to a final level of 25 µg/ml. This results in amplification of the cassette containing the genes of interest. The resulting strain is designated CF 455: pJMupperpathway#1 X Bacillus subtilis aprEnprE Pxyl comK (amplified to grow on LA containing chloramphenicol 25 µg/ml).

II. Construction of the Lower MVA Pathway in Bacillus subtilis

Figure 28:
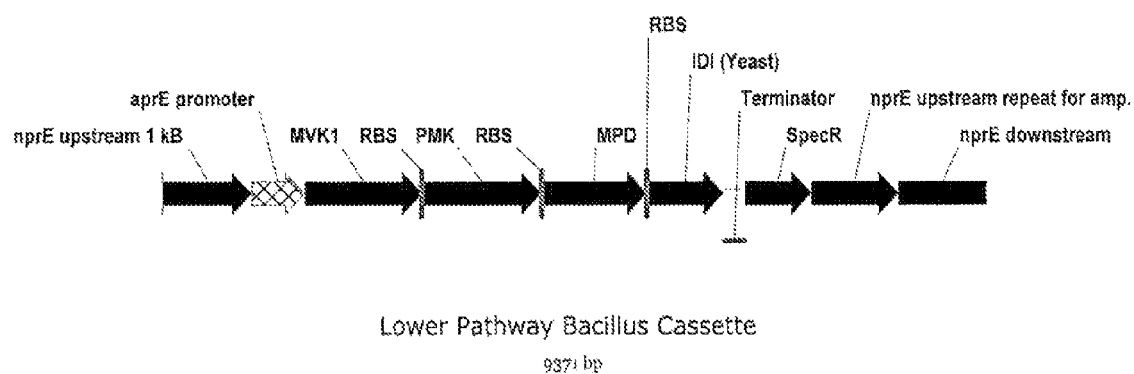
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvk1, pmk, mpd and idi are combined in a cassette consisting of flanking DNA regions from the nprE region of the B. subtilis chromosome (site of integration), the aprE promoter, and the spectinomycin resistance marker (see FIGS. 28 and 29). This cassette is synthesized by DNA2.0 and is integrated into the chromosome of B. subtilis containing the upper MVA pathway integrated at the aprE locus. The kudzu isoprene synthase gene is expressed from the replicating plasmid described in Example 4 and is transformed into the strain with both upper and lower pathways integrated.

Example 10

Production of Isoprene in E. coli Expressing M. mazei Mevalonate Kinase and P. alba Isoprene Synthase I. Construction of Vectors and Strains Encoding M. mazei Mevalonate Kinase (MVK) and P. alba Isoprene Synthase
(i) Construction of Strain EWL201 (BL21, Cm-GI1.2-KKDyI)

E. coli BL21 (Novagen brand, EMD Biosciences, Inc.) was a recipient strain, transduced with MCM331 P1 lysate (lysate prepared according to the method described in Ausubel, et al., Current Protocols in Molecular Biology. John Wiley and Sons, Inc.). Transductants were selected for by spreading cells onto L Agar and 20 µg/µl chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 µg/µl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 µl Resuspension Buffer (20 mM Tris, 1 mM EDTA, 50 mM NaCl, pH 7.5) and 4 µl RNase, DNase-free (Roche) was added. The tubes were incubated at 37° C. for 30 minutes followed by the addition of 4 µl 10% SDS and 4 µl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 µl each of saturated phenol pH7.9 (Ambion Inc.) and chloroform were added. The tubes were mixed well and microcentrifuged for 5 minutes. A second extraction was done with 400 µl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 µl TE.

Using Pfu Ultra II DNA polymerase (Stratagene) and 200 ng/µl of genomic DNA as template, 2 different sets of PCR reaction tubes were prepared according to manufacturer's protocol. For set 1, primers MCM130 and GB Cm-Rev (Table 4) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 4) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct (picked one and designated as strain EWL201).

ii) Construction of Strain EWL204 (BL21, Loopout-GI1.2-KKDyI)

The chloramphenicol marker was looped out of strain EWL201 using plasmid pCP20 as described by Datsenko and Wanner (2000) (Datsenko et al., Proc Natl. Acad. Sci USA 97:6640-6645, 2000). One-step inactivation of chromosomal genes in Escherichia coli K-12 using PCR products. (Datsenko et al., PNAS, 97: 6640-6645, 2000). EWL201 cells were grown in L Broth to midlog phase and then washed three times in ice-cold, sterile water. An aliquot of 50 µl of cell suspension was mixed with 1 µl of pCP20 and the cell suspension mixture was electroporated in a 2 mm cuvette (Invitrogen Corp.) at 2.5 Volts and 25 uFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 µg/µl chloramphenicol and 50 µg/µl carbenicillin and incubated at 30° C. overnight. The next day, a single clone was grown in 10 ml L Broth and 50 µg/µl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 µg/µl chloramphenicol plates. Plates were then incubated overnight at 30° C. Cells able to grow on LA plates, but not LA and 20 µg/µl chloramphenicol plates, were deemed to have the chloramphenicol marker looped out (picked one and designated as strain EWL204).

iii) Construction of Plasmid pEWL230 (pTrc P. alba)

Figure 54:
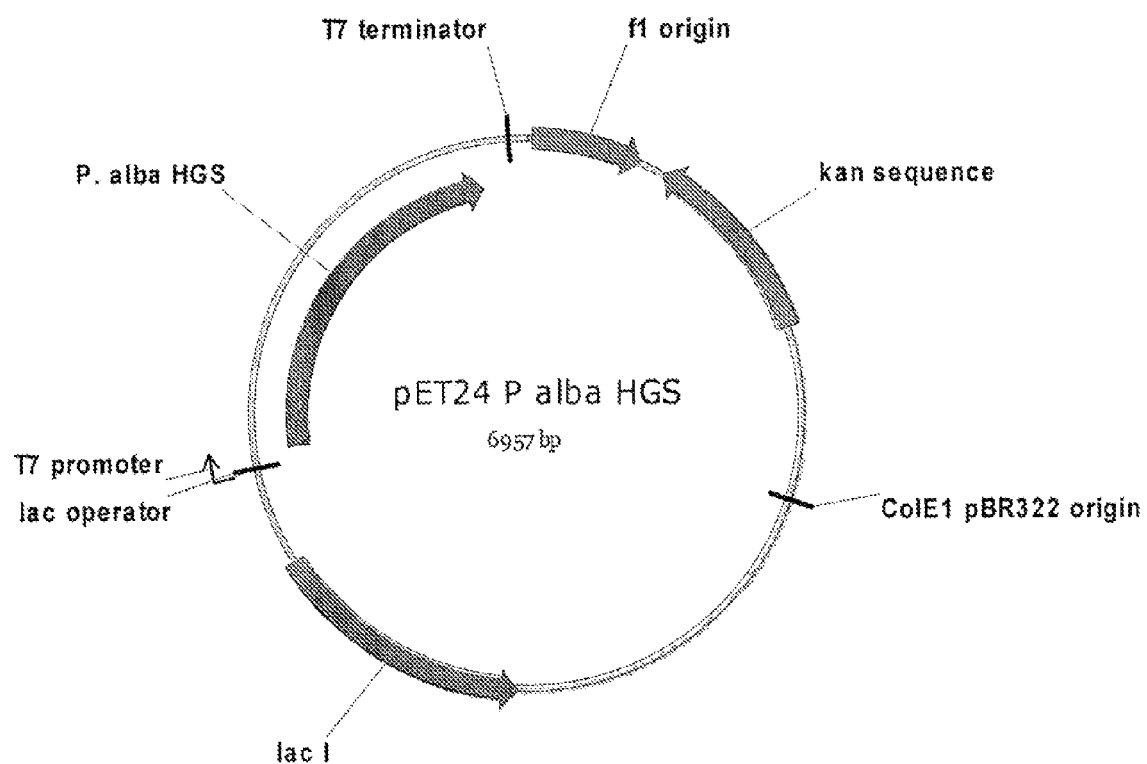
FIG. 54 is a map of plasmid pET24 *P. alba* HGS.

Generation of a synthetic gene encoding Populus alba isoprene synthase (P. alba HGS) was outsourced to DNA2.0 Inc. (Menlo Park, Calif.) based on their codon optimization method for E. coli expression. The synthetic gene was custom cloned into plasmid pET24a (Novagen brand, EMD Biosciences, Inc.) and delivered lyophilized (FIGS. 54, 55A and 55B).

A PCR reaction was performed to amplify the *P. alba* isoprene synthase (*P. alba* HGS) gene using pET24 *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

Figure 56:
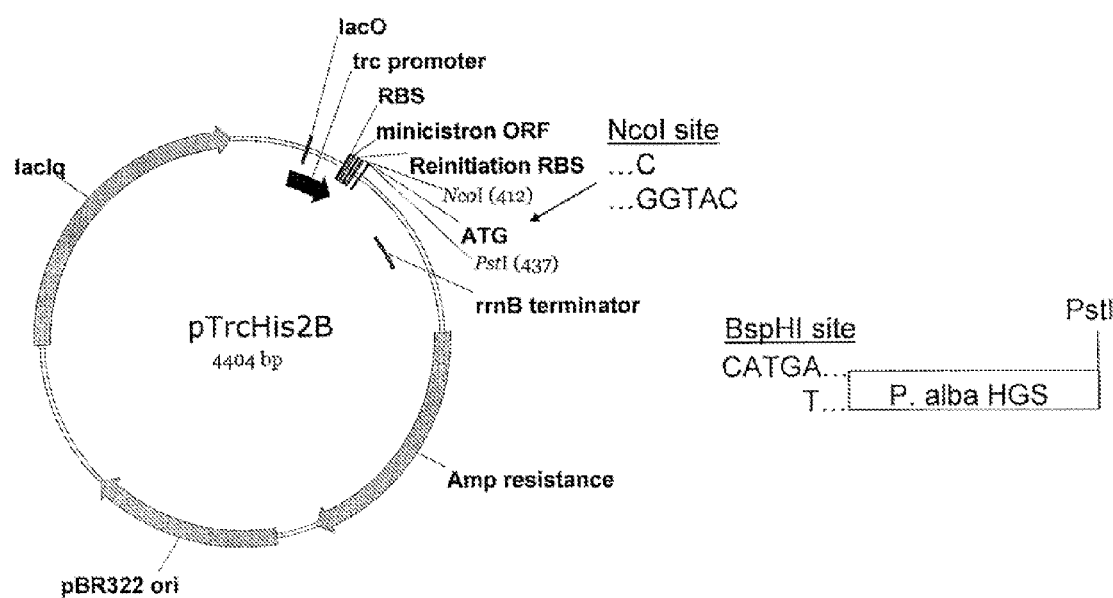
FIG. 56 is a schematic diagram showing restriction sites used for endonuclease digestion to construct plasmid EWL230 and compatible cohesive ends between BspHI and NcoI sites.
Figure 57:
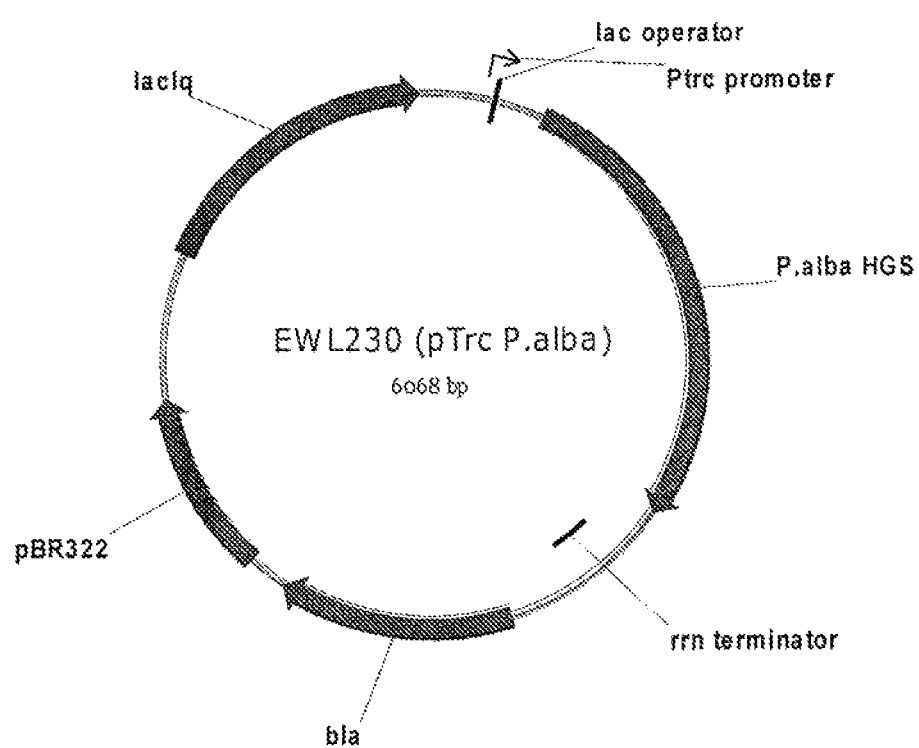
FIG. 57 is a map of plasmid EWL230.

*P. alba* isoprene synthase PCR product was then digested in a 20 µl reaction containing 1 µl BspHI endonuclease (New England Biolabs) with 2 µl 10×NEB Buffer 4. The reaction was incubated for 2 hours at 37° C. The digested PCR fragment was then purified using the QIAquick PCR Purification Kit. A secondary restriction digest was performed in a 20 µl reaction containing 1 µl PstI endonuclease (Roche) with 2 µl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 µl reaction containing 1 µl NcoI endonuclease (Roche), 1 µl PstI endonuclease, and 2 µl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 56). Using the compatible cohesive ends of BspHI and NcoI sites, a 20 µl ligation reaction was prepared containing 5 µl *P. alba* isoprene synthase insert, 2 µl pTrc vector, 1 µl T4 DNA ligase (New England Biolabs), 2 µl 10× ligase buffer, and 10 µl ddH$_2$O. The ligation mixture was incubated at room temperature for 40 minutes. The ligation mixture was desalted by floating a 0.025 µm nitrocellulose membrane filter (Millipore) in a petri dish of ddH$_2$O and applying the ligation mixture gently on top of the nitrocellulose membrane filter for 30 minutes at room temperature. MCM446 cells (See section II) were grown in LB to midlog phase and then washed three times in ice-cold, sterile water. An aliquot of 50 µl of cell suspension was mixed with 5 µl of desalted pTrc *P. alba* HGS ligation mix. The cell suspension mixture was electroporated in a 2 mm cuvette at 2.5 Volts and 25 uFd using a Gene Pulser Electroporator. 1 ml of LB is immediately added to the cells, then transferred to a 14 ml polypropylene tube (Sarstedt) with a metal cap. Cells were allowed to recover by growing for 2 hour at 30° C. Transformants were selected on L Agar and 50 µg/µl carbenicillin and 10 mM mevalonic acid and incubated at 30° C. The next day, 6 transformants were picked and grown in 5 ml L Broth and 50 µg/µl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. All 6 plasmids were the correct size and shipped to Quintara Biosciences (Berkeley, Calif.) for sequencing with primers MCM65, MCM66, EL1000 (Table 4). DNA sequencing results showed all 6 plasmids were correct. Picked one and designated plasmid as EWL230 (FIGS. 57, 58A and 58B).

iv) Construction of Plasmid pEWL244 (pTrc *P. alba*-mMVK)

A PCR reaction was performed to amplify the *Methanosarcina mazei* (*M. mazei*) MVK gene using MCM376 as the template (see section v), primers MCM165 and MCM177 (see Table 4), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The *M. mazei* MVK PCR product was purified using QIAquick PCR Purification Kit (Qiagen Inc.)

Figure 59:
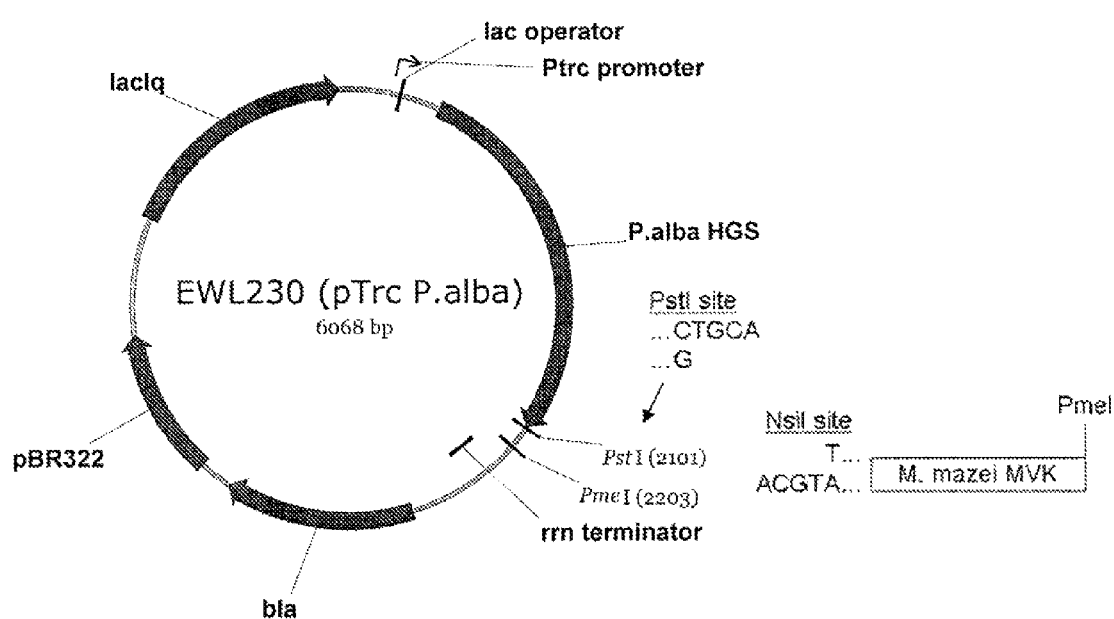
FIG. 59 is a schematic diagram showing restriction sites used for endonuclease digestion to construct plasmid EWL244 and compatible cohesive ends between NsiI and PstI sites.
Figure 60:
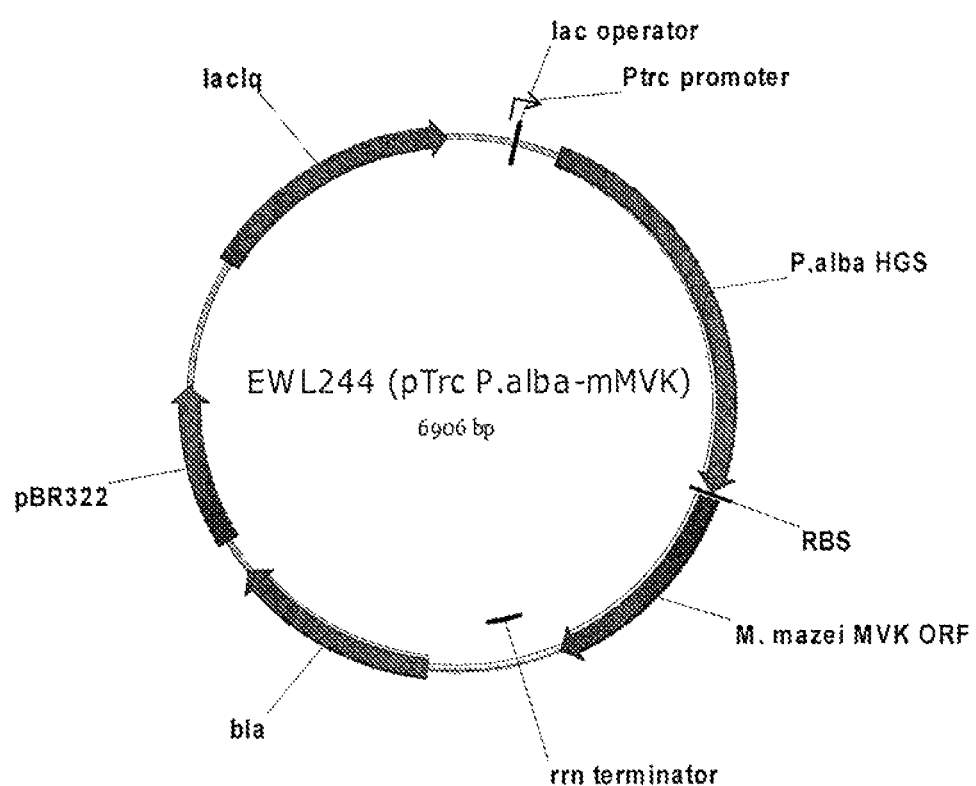
FIG. 60 is a map of EWL244.
Figure 62:
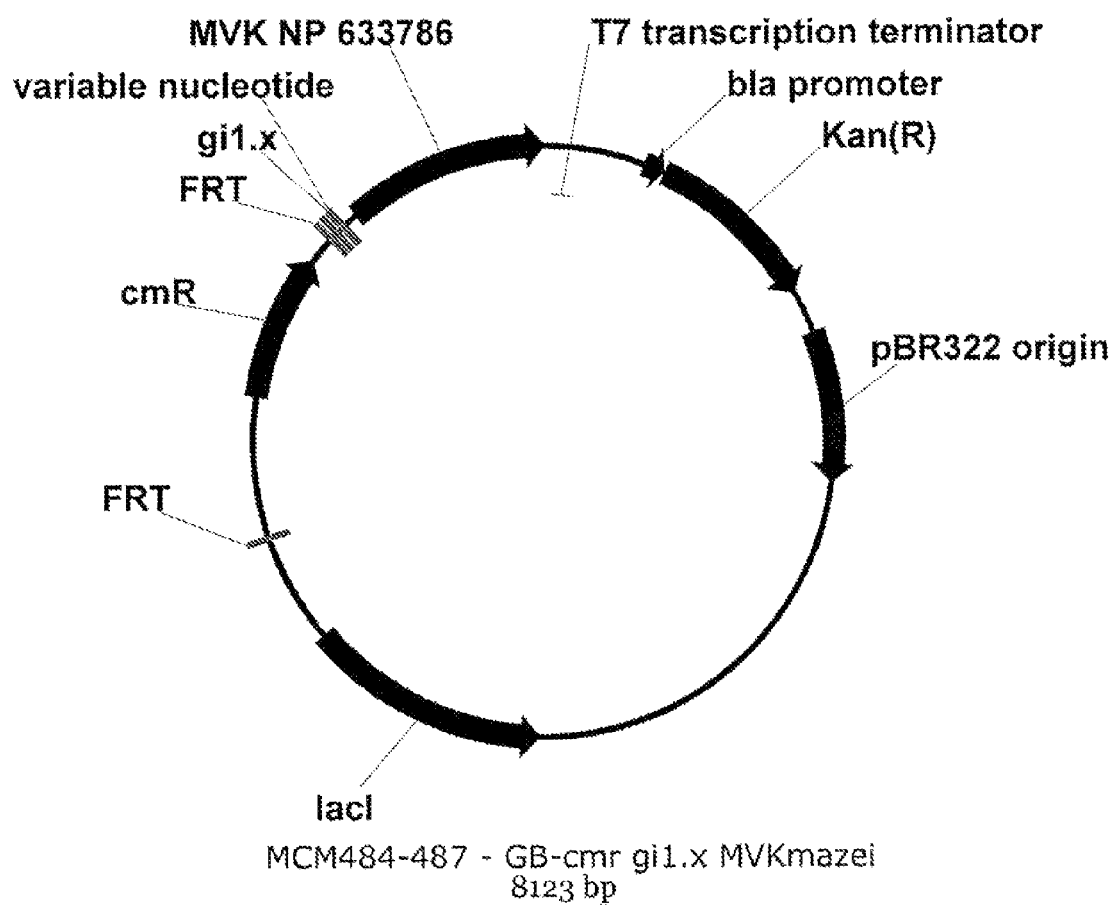
FIG. 62 is a map of plasmids MCM484-487.

The *M. mazei* MVK PCR product was then digested in a 40 µl reaction containing 8 µl PCR product, 2 µl PmeI endonuclease (New England Biolabs), 4 µl 10×NEB Buffer 4, 4 µl 10×NEB BSA, and 22 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl NsiI endonuclease (Roche), 4.7 µl 10× Buffer H, and 40 µl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 µl reaction containing 10 µl plasmid, 2 µl PmeI endonuclease, 4 µl 10×NEB Buffer 4, 4 µl 10×NEB BSA, and 20 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl PstI endonuclease, 4.7 µl 10× Buffer H, and 40 µl of PmeI digested EWL230 linear fragment. The reaction was incubated for 3 hours at 37° C. The digested PCR fragment was then gel purified using a 1.2% E-gel and extracted using the QIAquick Gel Extraction Kit (FIG. 59). Using the compatible cohesive ends of NsiI and PstI sites, a 20 µl ligation reaction was prepared containing 8 µl *M. mazei* MVK insert, 3 µl EWL230 plasmid, 1 µl T4 DNA ligase, 2 µl 10× ligase buffer, and 6 µl ddH$_2$O. The ligation mixture was incubated at overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. An aliquot of 50 µl of cell suspension was mixed with 5 µl of desalted pTrc *P. alba*-mMVK ligation mix. The cell suspension mixture was electroporated in a 2 mm cuvette at 2.5 Volts and 25 uFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 µg/µl carbenicillin and 5 mM mevalonic acid plates and incubated at 30° C. The next day, 6 transformants were picked and grown in 5 ml LB and 50 µg/µl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. Three of the 6 plasmids were the correct size and shipped to Quintara Biosciences for sequencing with primers MCM65, MCM66, EL1000, EL1003, and EL1006 (Table 4). DNA sequencing results showed all 3 plasmids were correct. Picked one and designated plasmid as EWL244 (FIGS. 60 and 61A-B).

v) Construction of Plasmid MCM376-MVK from *M. mazei* Archaeal Lower in pET200D.

Figure 73A:
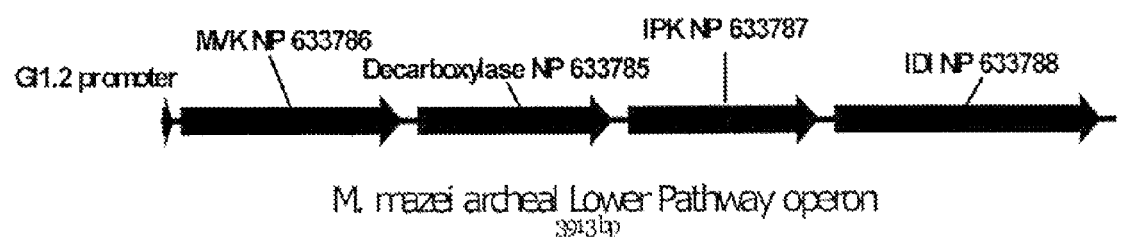
FIG. 73A is a map of the *M. mazei* archaeal Lower Pathway operon.
Figure 74A:
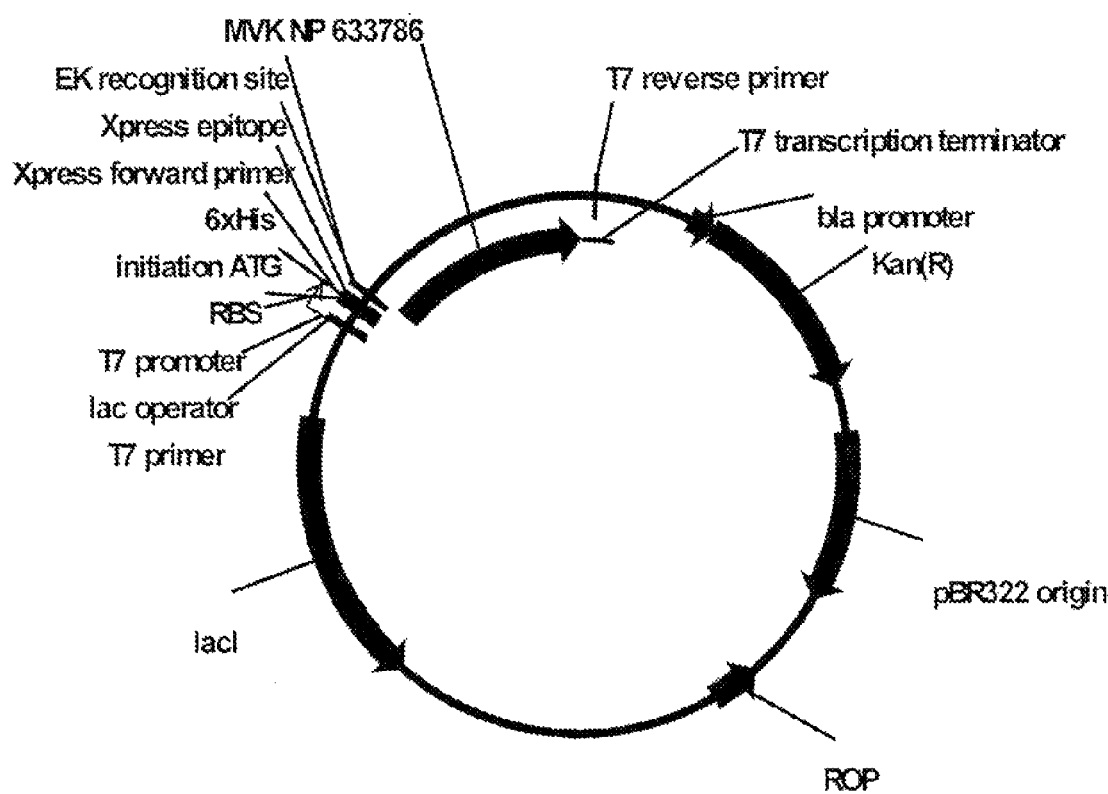
FIG. 74A is a map of MCM376-MVK from *M. mazei* archaeal Lowerin pET200D.
Figure 75A:
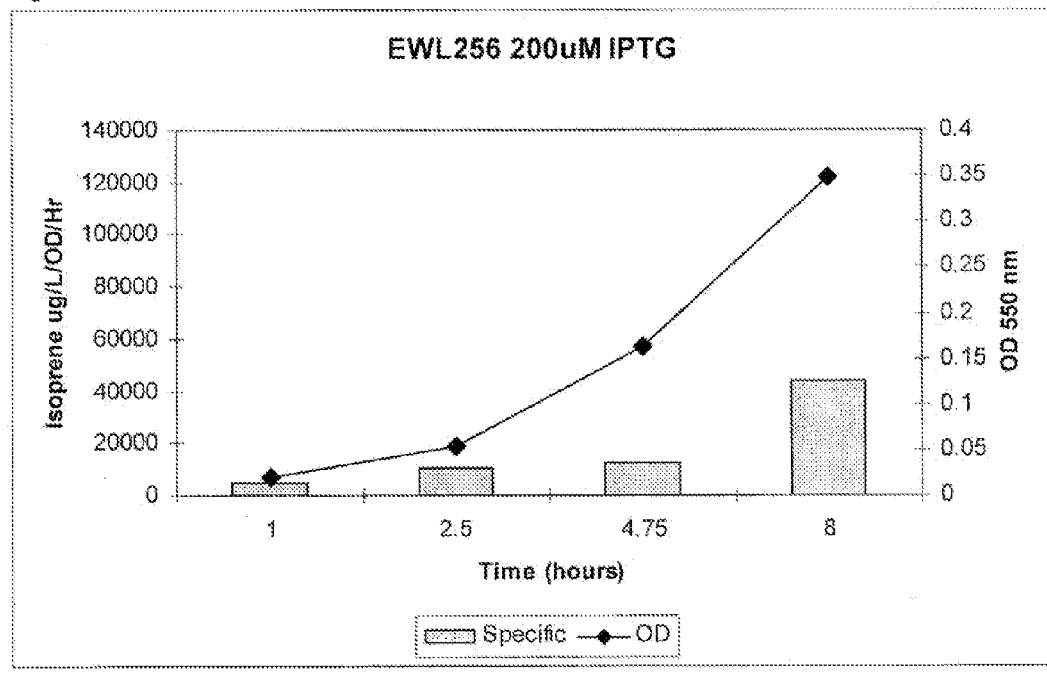
FIGS. 75A-75D show growth and specific productivity of isoprene production for EWL256 compared to RM11608-2. Growth (OD550) is represented by the white diamonds; specific productivity of isoprene is represented by the solid bars. The x-axis is time (hours) post-induction with either 200 (FIGS. 75A and 75B) or 400 (FIGS. 75C and 75D) uM IPTG. Y-1 axis is productivity of isoprene (ug/L/OD/hr) and Y-2 is arbitrary units of optical density at a wavelength of 550.
Figure 75B:
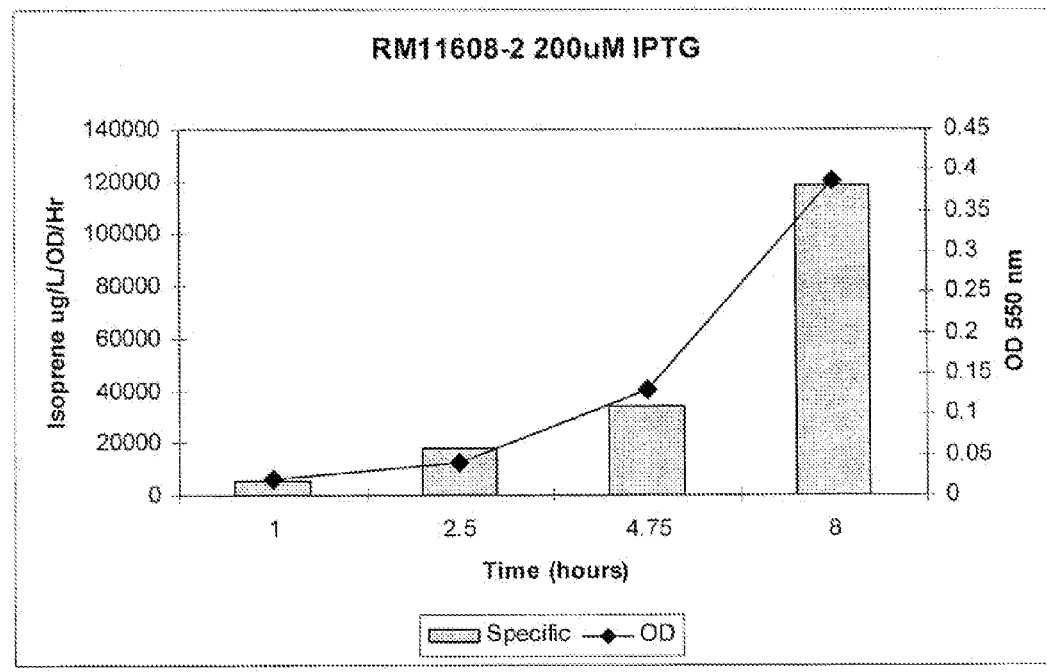
Figure 75C:
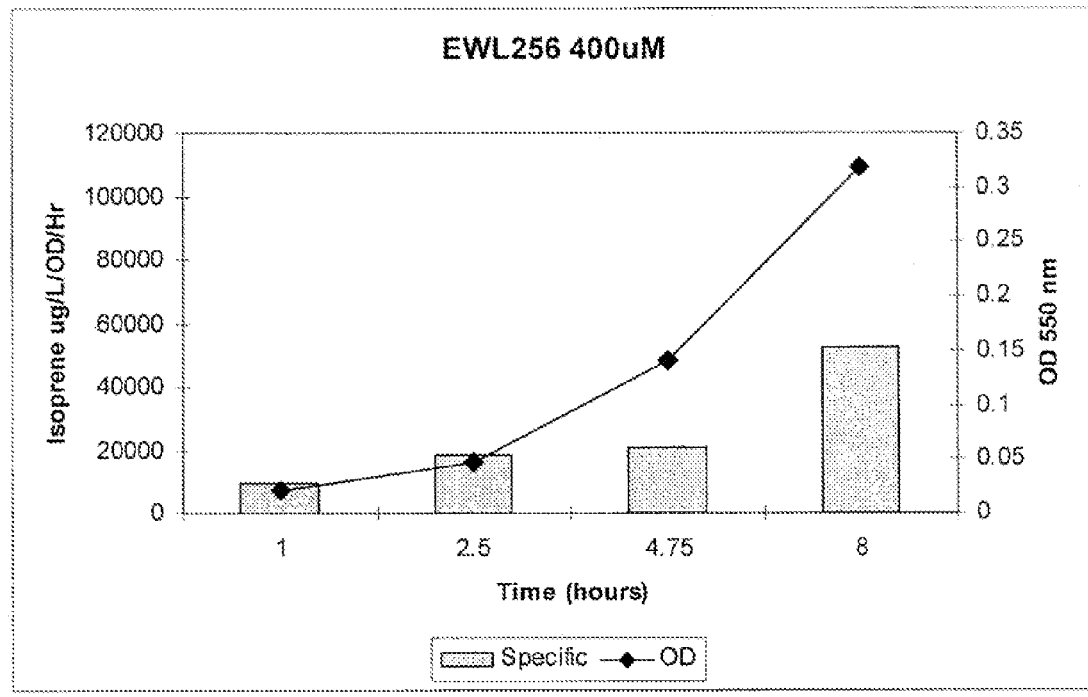
Figure 75D:
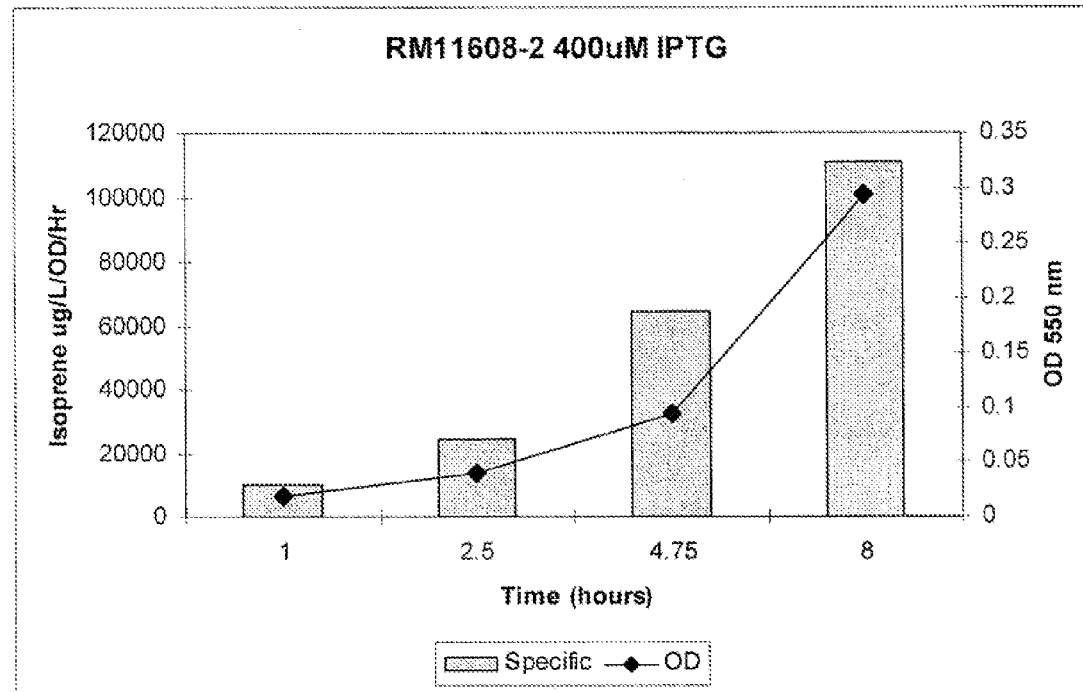

The MVK ORF from the *M. mazei* archaeal Lower Pathway operon (FIGS. 73A-C) was PCR amplified using primers MCM161 and MCM162 (Table 4) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 74A-C).

vi) Construction of Strain EWL251 (BL21(DE3), Cm-GI1.2-KKDyI, pTrc *P.alba*-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 µl of cell suspension with 1 µl of plasmid EWL244. The cell suspension mixture was electroporated in a 2 mm cuvette at 2.5 Volts and 25 uFd using a Gene Pulser Electroporator. 1 ml of LB is immediately added to the cells, then the cells were transferred to a 14 ml polypropylene tube with a metal cap. Cells were allowed to recover by growing for 2 hours at 30° C. Transformants were selected on LA and 50 µg/µl carbenicillin and 5 mM mevalonic acid plates and incubated at 37° C. One colony was selected and designated as strain EWL251.

vii) Construction of Strain EWL256 (BL21(DE3), Cm-GI1.2-KKDyI, pTrc *P. alba*-mMVK, pCL Upper MVA)

EWL251 cells were grown in LB to midlog phase and then washed three times in ice-cold, sterile water. Mixed 50 µl of cell suspension with 1 µl of plasmid MCM82 (which is pCL PtrcUpperPathway encoding *E. faecalis* mvaE and mvaS). The cell suspension mixture was electroporated in a 2 mm cuvette at 2.5 Volts and 25 uFd using a Gene Pulser Electroporator. 1 ml of LB was immediately added to the cells, then transferred to a 14 ml polypropylene tube with a metal cap. Cells were allowed to recover by growing for 2 hour at 30° C. Transformants were selected on LA and 50 µg/µl carbenicillin and 50 µg/µl spectinomycin plates and incubated at 37° C. Picked one colony and designated as strain EWL256.

TABLE 4

Primer Sequences

| Primer name | Primer sequence |
|---|---|
| MCM130 | ACCAATTGCACCCGGCAGA (SEQ ID NO: 94) |
| GB Cm Rev | GCTAAAGCGCATGCTCCAGAC (SEQ ID NO: 95) |
| MVD For | GACTGGCCTCAGATGAAAGC (SEQ ID NO: 96) |
| MVD Rev | CAAACATGTGGCATGGAAAG (SEQ ID NO: 97) |
| MCM182 | GGGCCCGTTTAAACTTTAACTAGACTCTGCAGTTAGCGTTCAAA CGGCAGAA (SEQ ID NO: 98) |

TABLE 4-continued

Primer Sequences

| Primer name | Primer sequence |
|---|---|
| MCM192 | CGCATGCATGTCATGAGATGTAGCGTGTCCACCGAAAA (SEQ ID NO: 99) |
| MCM65 | ACAATTTCACACAGGAAACAGC (SEQ ID NO: 100) |
| MCM66 | CCAGGCAAATTCTGTTTTATCAG (SEQ ID NO: 101) |
| EL1000 | GCACTGTCTTTCCGTCTGCTGC (SEQ ID NO: 102) |
| MCM165 | GCGAACGATGCATAAAGGAGGTAAAAAAACATGGTATCCTGTTC TGCGCCGGGTAAGATTTACCTG (SEQ ID NO: 103) |
| MCM177 | GGGCCCGTTTAAACTTTAACTAGACTTTAATCTACTTTCAGACC TTGC (SEQ ID NO: 104) |
| EL1003 | GATAGTAACGGCTGCGCTGCTACC (SEQ ID NO: 105) |
| EL1006 | GACAGCTTATCATCGACTGCACG (SEQ ID NO: 106) |
| MCM161 | CACCATGGTATCCTGTTCTGCG (SEQ ID NO: 107) |
| MCM162 | TTAATCTACTTTCAGACCTTGC (SEQ ID NO: 108) |

II. Construction of MCM442-449: BL21 and BL21(DE3) with FRT-cmR-FRT-gi1.x-mKKDyI i) Construction of Template for Recombination FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers MCM193 and MCM195 were used to amplify the resistance cassette from the FRT-gb2-Cm-FRT template using Stratagene Herculase II Fusion kit according to the manufacturer's protocol. The 50 uL reaction was cycled as follows: 95° C., 2 minutes; (95° C., 20 seconds, 55° C., 20 seconds, 72° C., 1 minute)×5, (95° C., 20 seconds, 60° C., 20 seconds, 72° C., 1 minute)×25; 72° C., 3 minutes; 4° C. until cool. The amplicon was purified by a Qiagen PCR column according to the manufacturer's protocol and eluted in 30 uL EB (Elution Buffer). DNA was digested with NdeI and PciI in a 20 uL reaction with 1× Roche H buffer and 0.5 uL BSA. Plasmid MCM376 was digested in a 10 uL reaction containing 1 uL each of NdeI, NcoI, and Roche H buffer. Reactions proceeded overnight at 37° C., and then cut DNA was purified on Qiagen PCR columns and eluted in 30 uL EB. The PCR product was ligated into MCM376 in a reaction containing 1 uL vector, 3 uL PCR product, 1 uL Roche Quick Ligase Buffer 2, 5 uL Buffer 1, and 1 uL Ligase. The reaction proceeded at room temperature for 3 hours and then 5 uL was transformed into Invitrogen TOP10 cells according to the manufacturer's protocol. Transformants were selected on L agar (LA) and chloramphenicol (10 ug/mLO) at 37° C. overnight.

Transformant colonies were patched onto LA containing chloramphenicol (30 ug/mL) and kanamycin (50 ug/ml) for storage and sent to Quintara (Berkeley, Calif.) for sequencing. Four clones, one each with the four different nucleotides at the "N" in primer MCM195, were found to have the correct sequence for the inserted promoter. Clones were grown in 5 mL LB containing chloramphenicol (30 ug/mL) and kanamycin (50 ug/mL) and used for the preparation of plasmid DNA. This plasmid was retransformed into TOP10 cells and strains were frozen as:

TABLE 5

| | MCM484-487 |
|---|---|
| MCM484 | cmR-gi1.6-MVK(mazei) in pET (clone A1-3, variable nt A) |
| MCM485 | cmR-gi1.0-MVK(mazei) in pET (clone B4-6, variable nt C) |
| MCM486 | cmR-gi1.2-MVK(mazei) in pET (clone C1-5, variable nt G) |
| MCM487 | cmR-gi1.5-MVK(mazei) in pET (clone C3-3, variable nt T) | ii) Creation of Recombination Target Strains MCM349 and MCM441

The chloramphenicol resistance (cmR) marker was looped out of strain MCM331 using plasmid pGB706 (GeneBridges) according to Manufacturer's instructions. MCM331 cells were grown to mid-log in LB and washed three times in iced, sterile water. A 1 uL aliquot of pGB706 DNA was added to 50 uL of cell suspension and this mixture was electroporated in a 2 mm cuvette at 2.5 volts, 25 uFd followed immediately by recovery in 500 uL LB for one hour at 30 C. Transformants were selected on LB containing tetracycline (5 ug/ml) at 30° C. The following day, a clone was grown up at 30° C. in LB containing tetracycline (5 ug/ml) until visibly turbid ($OD_{600}$-0.5-0.8). This culture was streaked onto LB and grown overnight at 37° C. A clone that was unable to grow on LB containing chloramphenicol (10 ug/mL) or LB containing tetracycline (5 ug/mL) was frozen as MCM348. Plasmid MCM356 (pRedET carbencillin; GeneBridges) was electroporated in as described above and transformants were selected on LB containing carbenicillin (50 ug/mL) at 30° C. A clone was grown in LB carbenicillin (50 ug/mL) at 30° C. and frozen as MCM349.

Strain MCM441 was created by electrotransforming plasmid MCM356 into EWL204 as above.

iii) Recombination of FRT-cmR-FRT-gi1.x-mMVK into MCM349 and MCM441

Plasmids MCM484-487 were used as template for PCR amplification with primers MCM120 and MCM196 and Herculase II Fusion kit, according to the manufacturer's protocol. Three reactions per template were carried out, with 0, 1, or 3 uL DMSO. The 50 uL reactions were cycled as follows: 95° C., 2 minutes; (95° C., 20 seconds; 55° C. 20 seconds; 72° C., 1.5 minutes) for five cycles; (95° C., 20 seconds; 60° C. 20 seconds; 72° C., 1.5 minutes) for 25 cycles; 72° C. for 3 minutes; 4° C., overnight.] The three reactions from a given template were pooled and purified on Qiagen PCR columns and eluted with 30 uL EB at 60° C. 5 uL DNA was digested with 1 uL DpnI in 1× Roche Buffer A for 3 hours at 37° C. This DNA was then microdialyzed against excess water for 30 minutes.

Strains were grown in 5 mL LB containing carbenicillin (50 ug/mL) from fresh streaks at 30 C to an OD600 of ~0.5. 40 mM L-arabinose was added and cultures were incubated at 37 C for 1.5 hours. Cells were harvested and electroporated with 3 uL dialyzed amplicons above, and then recovered in 500 uL SOC at 37 C for 1.5-3 hours. Transformants were selected on LA plates containing chloramphenicol (5 ug/mL) at 37° C.

Kanamycin sensitive clones were screened by PCR for insertion of the amplicon. PCR products from positive clones were sequenced to verify the sequence of inserted DNA. Amplicons were consistent with the FRT-gi1.2-yKKDyI at attTn7 in MCM441 and 348 being replaced by FRT-cmR-FRT-gi1.x-mKKDyI (The yK and mK designations refer to the mevalonate kinase from Saccharomyces cerevisiae and Methanosarcina mazei respectively).

TABLE 6A

The following strains were grown in LB containing chloramphenicol (5 ug/mL) and frozen.

| Strain ID | Name | Parent | Recombination Amplicon Template |
|---|---|---|---|
| MCM442 | BL21(DE3) cmR-gi1.6mKKDyI A1, clone37 (A) | MCM349 | MCM484 |
| MCM443 | BL21(DE3) cmR-gi1.0mKKDyI B4, clone27 (C) | MCM349 | MCM485 |
| MCM444 | BL21(DE3) cmR-gi1.2mKKDyI C1, clone16 (G) | MCM349 | MCM486 |
| MCM445 | BL21(DE3) cmR-gi1.5mKKDyI C3, clone7 (T) | MCM349 | MCM487 |
| MCM446 | BL21 cmR-gi1.6mKKDyI A1-3 (A) | MCM441 | MCM484 |
| MCM447 | BL21 cmR-gi1.0mKKDyI B4-6 (C) | MCM441 | MCM485 |
| MCM448 | BL21 cmR-gi1.2mKKDyI C1-5 (G) | MCM441 | MCM486 |
| MCM449 | BL21 cmR-gi1.5mKKDyI C3-3 (T) | MCM441 | MCM487 |

TABLE 6B

| | Primers |
|---|---|
| MCM120 | AAAGTAGCCGAAGATGACGGTTTGTCACATGGAGTTGGCAGGAT GTTTGATTAAAAGCAATTAACCCTCACTAAAGGGCGG (SEQ ID NO: 109) |
| MCM193 | GATATACATATGAATTAACCCTCACTAAAGG (SEQ ID NO: 110) |
| MCM195 | GCATGCATGACATGTTTTTTTACCTCCTTTGTTATCCGCTCACA ATTAGTGGTTGAATTATTTGCTCAGGATGTGGCATNGTCAAGGG CGCGGCCGCGATCTAATACGACTCACTATAGGGCTCG (SEQ ID NO: 111) |
| MCM196 | AGGCTCTCAACTCTGACATGTTTTTTTCCTCCTTAAGGGTGCAG GCCTATCGCAAATTAGCTTAATCTACTTTCAGACCTTGCTCGG (SEQ ID NO: 112) |

III. The Effect of Yeast Extract on Isoprene Production in E. coli Expressing Genes from the Mevalonic Acid Pathway and Grown in Fed-Batch Culture at the 15-L Scale Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Figure 67A:
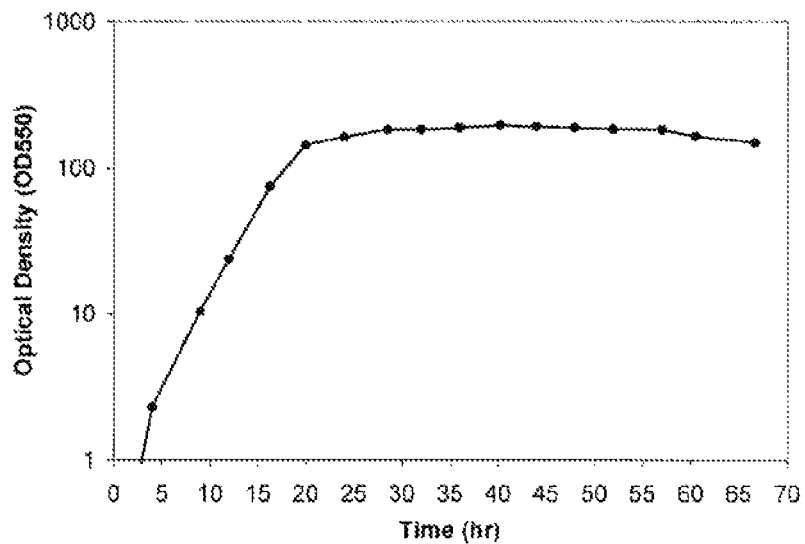
FIGS. 67A-67D are graphs of isoprene production by *E. coli* strain (EWL256) expressing genes from the MVA pathway and grown in fed-batch culture at the 15-L scale without yeast extract feeding.
Figure 67B:
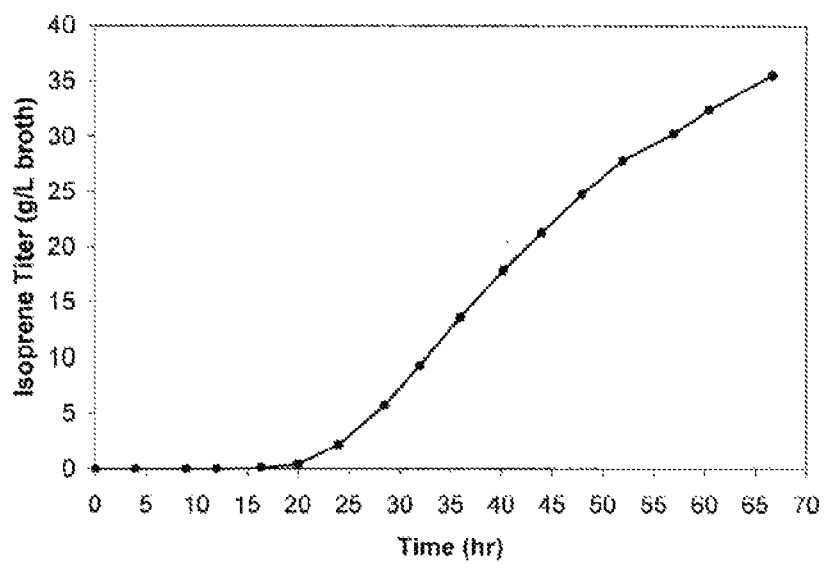
Figure 67C:
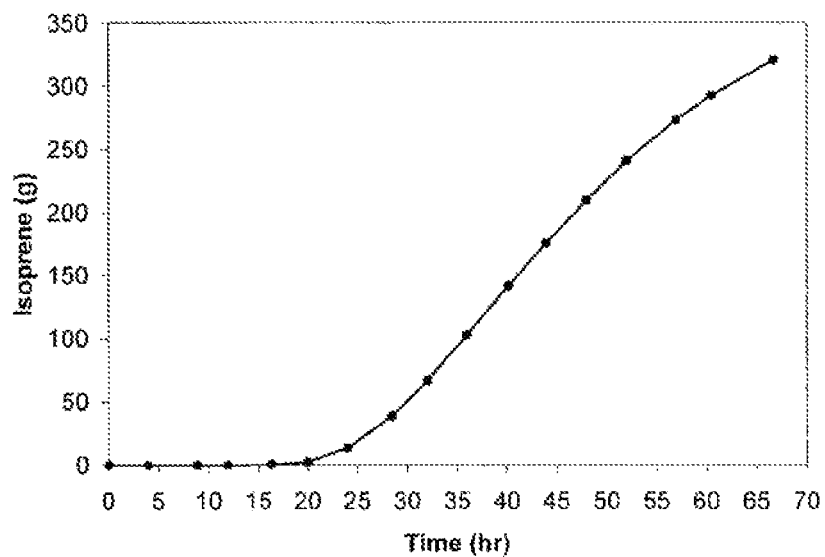
Figure 67D:
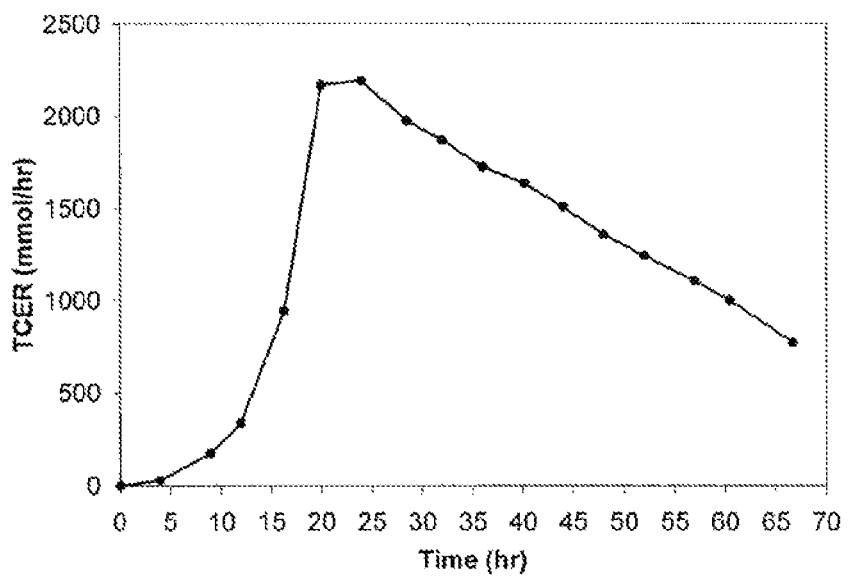

Fermentation was performed in a 15-L bioreactor with BL21 (DE3) E. coli cells containing the upper mevalonic acid (MVA) pathway (pCL Upper), the integrated lower MVA pathway (gi1.2KKDyI), and high expression of mevalonate kinase from M. mazei and isoprene synthase from P. alba (pTrcAlba-mMVK). This experiment was carried out to monitor isoprene formation from glucose at the desired fermentation pH 7.0 and temperature 30° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

i) Production of Isoprene in *E. coli* Cells (EL256) Grown in Fed-Batch Culture Without Yeast Extract Feeding Glucose was fed at an exponential rate until cells reached the stationary phase. After this time the glucose feed was decreased to meet metabolic demands. The total amount of glucose delivered to the bioreactor during the 67 hour fermentation was 3.9 kg. Induction was achieved by adding isopropyl-beta-D-1-thiogalactopyranoside (IPTG). The IPTG concentration was brought to 102 uM when the optical density at 550 nm ($OD_{550}$) reached a value of 9. The IPTG concentration was raised to 192 uM when $OD_{550}$ reached 140. The $OD_{550}$ profile within the bioreactor over time is shown in FIG. 67A. The isoprene level in the off gas from the bioreactor was determined using a Hiden mass spectrometer. The isoprene titer increased over the course of the fermentation to a final value of 35.6 g/L (FIG. 67B). The total amount of isoprene produced during the 67 hour fermentation was 320.6 g and the time course of production is shown in FIG. 67C. The metabolic activity profile, as measured by TCER, is shown in FIG. 67D. The molar yield of utilized carbon that went into producing isoprene during fermentation was 17.9%. The weight percent yield of isoprene from glucose was 8.1%.

Figure 68A:
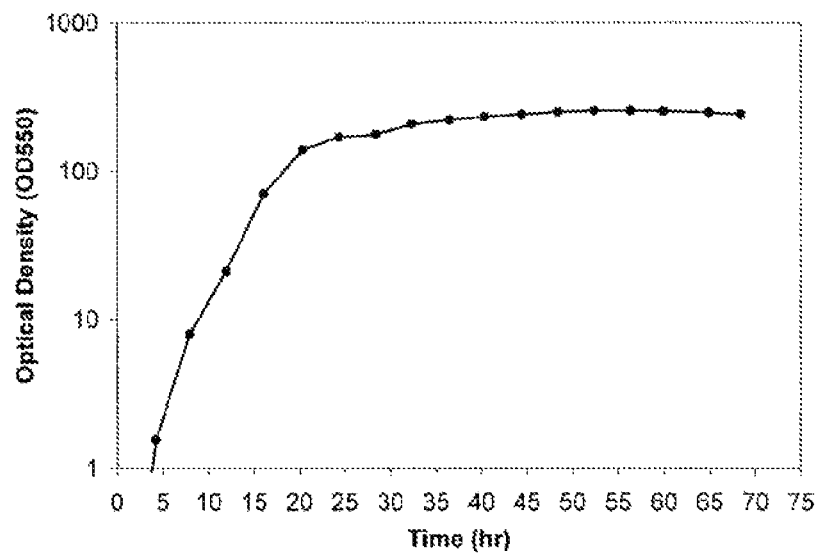
FIGS. 68A-68E are graphs of isoprene production by *E. coli* strain (EWL256) expressing genes from the MVA pathway and grown in fed-batch culture at the 15-L scale with yeast extract feeding.
Figure 68B:
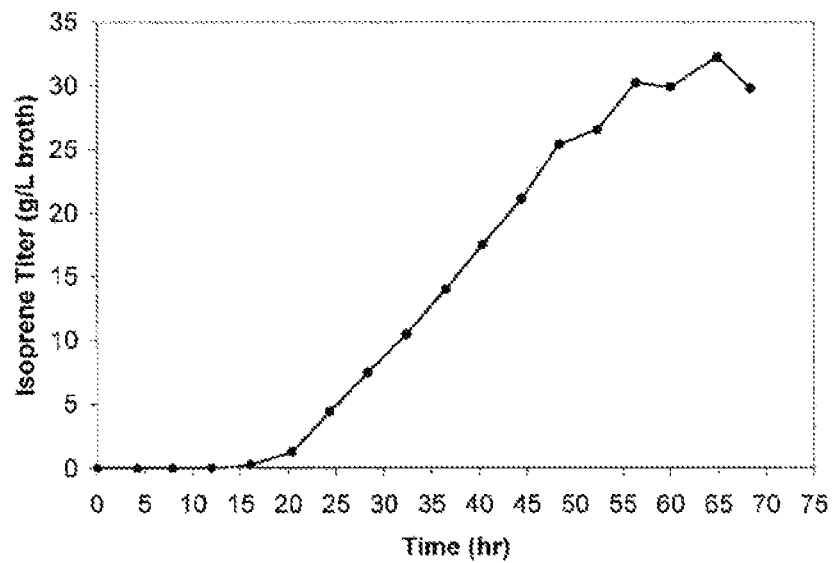
Figure 68C:
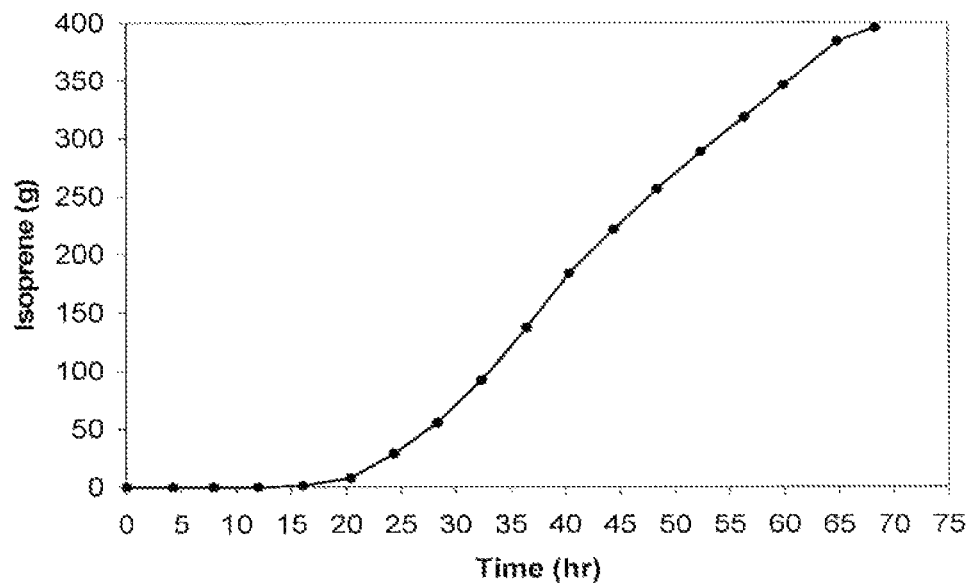
Figure 68D:
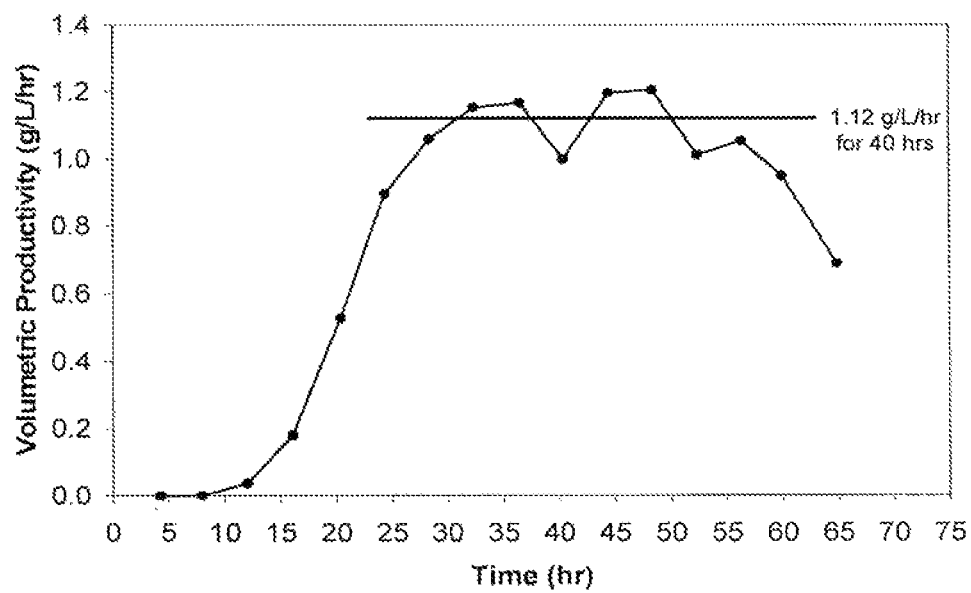
Figure 68E:
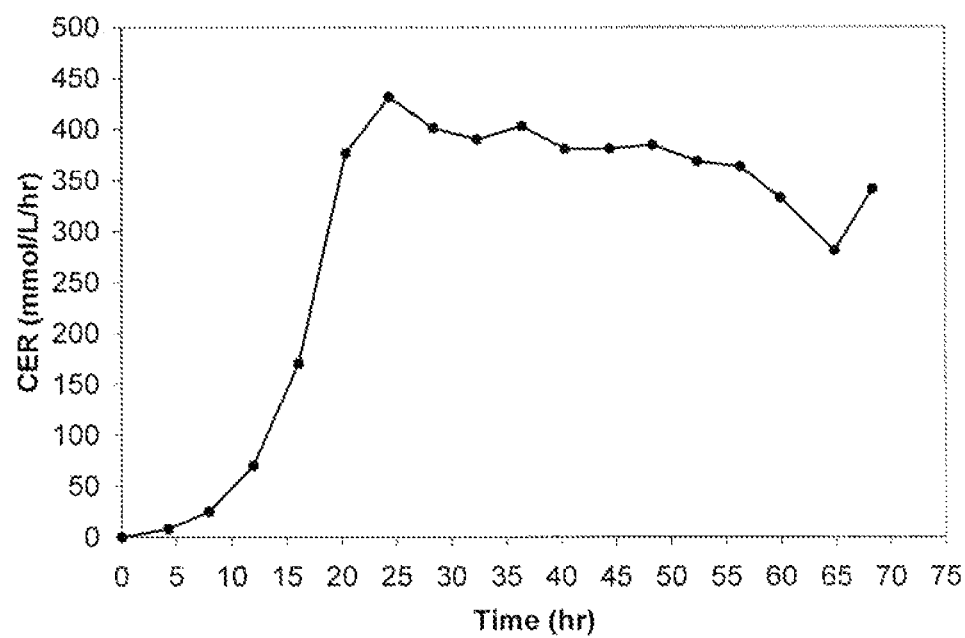

Production of Isoprene in *E. coli* Cells (EL256) Grown in Fed-Batch Culture with Yeast Extract Feeding Glucose was fed at an exponential rate until cells reached the stationary phase. After this time the glucose feed was decreased to meet metabolic demands. The total amount of glucose delivered to the bioreactor during the 68 hour fermentation was 7.1 kg. A total of 1.06 kg of yeast extract was also fed during the fermentation. Induction was achieved by adding IPTG. The IPTG concentration was brought to 208 uM when the optical density at 550 nm ($OD_{550}$) reached a value of 7. The IPTG concentration was raised to 193 uM when $OD_{550}$ reached 180. The $OD_{550}$ profile within the bioreactor over time is shown in FIG. 68A. The isoprene level in the off gas from the bioreactor was determined using a Hiden mass spectrometer. The isoprene titer increased over the course of the fermentation to a maximum value of 32.2 g/L (FIG. 68B). The total amount of isoprene produced during the 68 hour fermentation was 395.5 g and the time course of production is shown in FIG. 68C. The time course of volumetric productivity is shown in FIG. 68D and shows that an average rate of 1.1 g/L/hr was maintained for between 23 and 63 hours. The metabolic activity profile, as measured by CER, is shown in FIG. 68E The molar yield of utilized carbon that went into producing isoprene during fermentation was 10.3%. The weight percent yield of isoprene from glucose was 5.2%.

IV. Production of Isoprene from Different Carbon Sources in *E. coli* Harboring the Mevalonic Acid (MVA) Pathway and Isoprene Synthase (EWL256)

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Modified Trace Metal Solution 1 ml. All of the components were dissolved sequentially in $diH_2O$. The pH was adjusted to 6.8 with ammonium hydroxide (30%) and brought to volume. Media was filter sterilized with a 0.22 micron filter. Carbon source was added to a final concentration of 1%. Required antibiotics were added after sterilization and pH adjustment.

1000× Trace Metal Solution (Per Liter Fermentation Media):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in $diH_2O$, pH to 3.0 with HCl/NaOH, and then brought to volume and filter sterilized with a 0.22 micron filter.

i) Preparation of AFEX Biomass Hydrolysate

AFEX pretreated corn stover was hydrolyzed to prepare biomass hydrolysate containing both xylose, glucose and acetate.

AFEX pretreated corn stover, received from Michigan Biotechnology Institute, was used. The pretreatment conditions were, 60% moisture, 1:1 ammonia loading, and 90° C. for 30 minutes, then air dried. The moisture content in the AFEX pretreated corn stover was 21.27%. Content of glucan and xylan in the AFEX pretreated corn stover were 31.7% and 19.1% (dry basis) respectively. The enzyme used was accellerase 1000, Grindamyl H121 (Danisco xylanase product from *Aspergillus niger* for bread-making industry).

For saccharification, 20 g of AFEX pretreated corn stover was added into a 500 ml flask, together with 5 ml of 1 M pH 4.8 sodium citrate buffer, 2.25 ml of Accellerase 1000, 0.1 ml of Grindamyl H121, and 72.65 ml of DI water. The flask was put in an orbital shaker, and incubated at 50° C. for 96 hours.

For analysis, one sample was taken from the shaker, and analyzed using HPLC. The hydrolysate contained 37.2 g/l of glucose and 24.3 g/L of xylose, and 7.6 g/L of oligomers of glucose and/or xylose. Additionally, the hydrolysate also contains 1.17 g/L acetate.

ii) Experimental Procedure

An inoculum of the *E. coli* strain EWL256 containing the MVA pathway and isoprene synthase was taken from a frozen vial and streaked onto an LB broth agar plate containing spectinomycin (50 ug/mL) and carbinicllin (50 ug/mL) and incubated at 30° C. overnight. A single colony was inoculated into TM3 media containing glucose, xylose, glycerol, acetate or biomass as only carbon source and grown overnight at 30° C. Cells grow on acetate reached a significantly lower optical density. Cells grown on glucose, glycerol, biomass hydrolysate or acetate were diluted into 20 mL of TM3 media containing the respective carbon sources to reach an optical density of between 0.1 measured at 600 nM. A negative control not containing any carbon source was prepared from the glucose overnight culture. A separate experiment was performed with glucose and xylose, where the cultures were diluted to an optical density of 0.05. All culture conditions (except for acetate and glycerol) were tested in duplicates and the presented results are averaged between these cultures. Production of isoprene was induced with 200 μM IPTG from the beginning of the experiment. The flasks were incubated at 30° C. in an orbital shaker (200 rpm) and growth was followed by measuring optical density. After the glucose fed cultures had reached an optical density of approximately 0.4, samples were analyzed for isoprene production from all the tested carbon sources every hour for three hours. Samples of 100 μL were transferred in duplicates to 2 mL glass vials, sealed and incubated for 30 min at 30° C. The bacteria were then heat killed by incubation at 80° C. for 8 minutes. The amount of produced isoprene was measured using GC-MS and specific productivity (μg/L*hr) was calculated.

iii) Results

Significant production of isoprene could be demonstrated during growth on all the tested carbon sources. These carbon sources are examples of common alcohols, organic acids, sugars containing 5 or 6 carbon units (C5 or C6), and biomass hydrolysate.

Figure 69D:
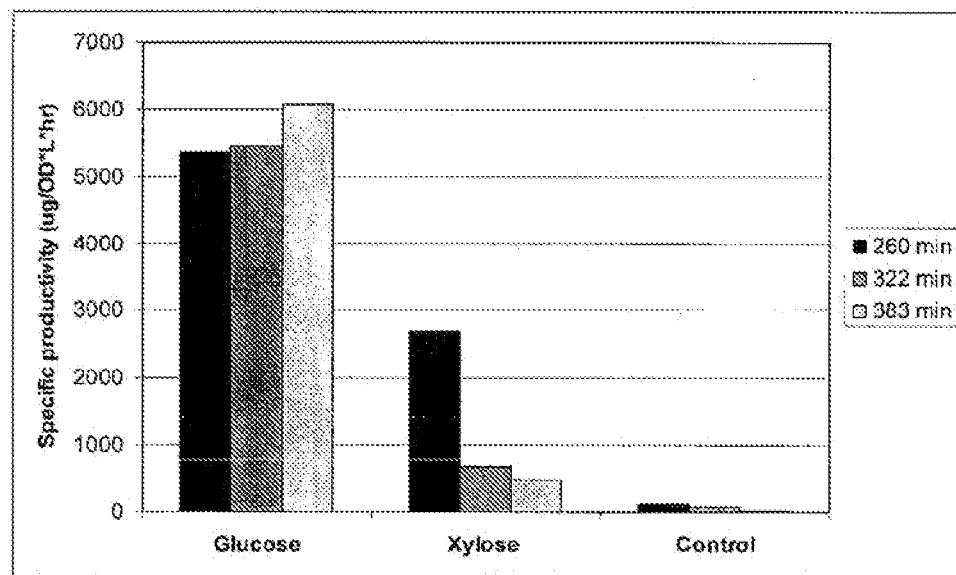

The initial growth rate on biomass hydrolysate was comparable to the growth rate on glucose (FIG. 69A). The initial specific productivity during growth on biomass hydrolysate was significantly higher than during growth on glucose. This demonstrates that biomass hydrolysate can be used as an efficient source of carbon for the production of isoprene. The specific productivity declined after 255 minutes of growth on biomass hydrolysate (FIG. 69B). The bacteria had a slower growth rate with xylose as only carbon source when compared to glucose (FIG. 69C), but a significant specific isoprene productivity was measured (FIG. 69D). This shows that both C5 and C6 sugars can be utilized for the production of isoprene via the mevalonate acid pathway.

Surprisingly, bacteria grown on acetate as the only carbon source had a specific productivity of isoprene approximately twice as high as during growth on glucose (FIG. 69A). The bacteria grew slower on acetate when compared to glucose (FIG. 69B), but the performed experiment demonstrates that acetate can also be used as a carbon source for the production of isoprene. Acetate was also present in the biomass hydrolysate as measured by HPLC.

The bacteria grew well with glycerol as only carbon source (FIG. 69A) and significant production of isoprene was demonstrated (FIG. 69B). This shows that common alcohols may also be used as carbon sources for production of isoprene via the mevalonate acid pathway.

Example 11

Expression of Isoprene-Synthase from Plant in *Streptomyces* sp.

Figure 71:
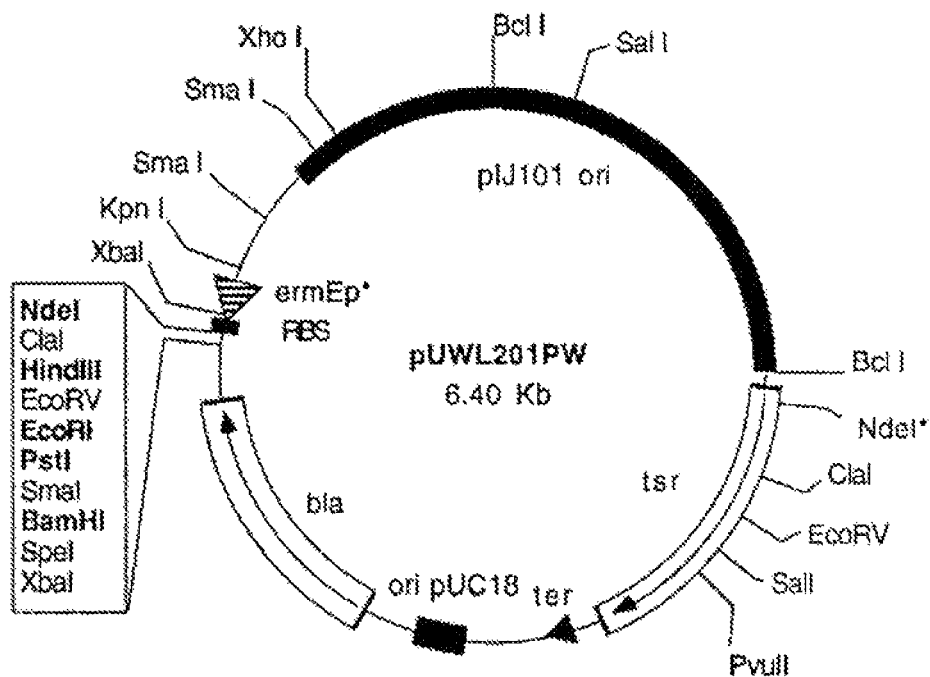
FIG. 71 is a map of the *E. coli-Streptomyces* shuttle vector pUWL201PW (6400 bp) used for cloning isoprene synthase from Kudzu. Tsr, thiostrepton resistance gene. Picture is taken from Doumith et al., *Mol. Gen. Genet.* 264: 477-485, 2000.

The gene for isoprene synthase Kudzu was obtained from plasmid pJ201:19813. Plasmid pJ201:19813 encodes isoprene synthase from *Pueraia lobata* (Kudzu plant) and was codon-optimized for *Pseudomonas fluorescens*, *Pseudomonas putida*, *Rhodopseudomonas palustris* and *Corynebacterium* (FIGS. 79A-79C (SEQ ID NO:123)). Digestion of plasmid pJ201:19813 with restriction enzymes NdeI and BamHI liberated gene iso19813 that was ligated into the *Streptomyces-E. coli* shuttle vector pUWL201PW (Doumith et al., *Mol. Gen. Genet.* 264: 477-485, 2000; FIG. 71) to generate pUWL201_iso. Successful cloning was verified by restriction analysis of pUWL201_iso. Expression of isoprene synthase iso19813 was under control of the erm-promoter which allows for constitutive expression in *Streptomycetes* species, but not for expression in *E. coli*.

PUWL201PW (no insert) and pUWL201_iso were introduced in *Streptomyces albus* J1074 (Sanchez et al., *Chem. Biol.* 9:519-531, 2002) by transformation of protoplasts as described by Hopwood et al., *The John innes foundation, Norwich*, 1985.

A 200 µl aliquot of protoplast suspensions was transformed with 1.9 µg pUWL201PW or 2.9 µg pUWL201_iso. After incubation overnight at 28° C. on non-selective R5-agar-plates, positive transformants were selected by further incubation for 4 days in R3-overlay agar containing thiostrepton (250 µg/ml). Thiostrepton resistant transformants were examined for presence of the pUWL-plasmids by plasmid preparation using Plasmid Mini Kit (Qiagen). Prepared plasmid DNA was reintroduced in *E. coli* DH5α to generate sufficient amounts of plasmid DNA to be analyzed by restriction analysis. Positive transformants were selected on ampicillin-containing L-agar plates and insert analysis was done by digestion of plasmid DNA with NdeI and BamHI endonucleases. Isoprene synthase was identified as a 1.7 kb fragment in positive pUWL201 iso clones while in the control strains (pUWL201PW) no such fragment was observed.

Figure 72:
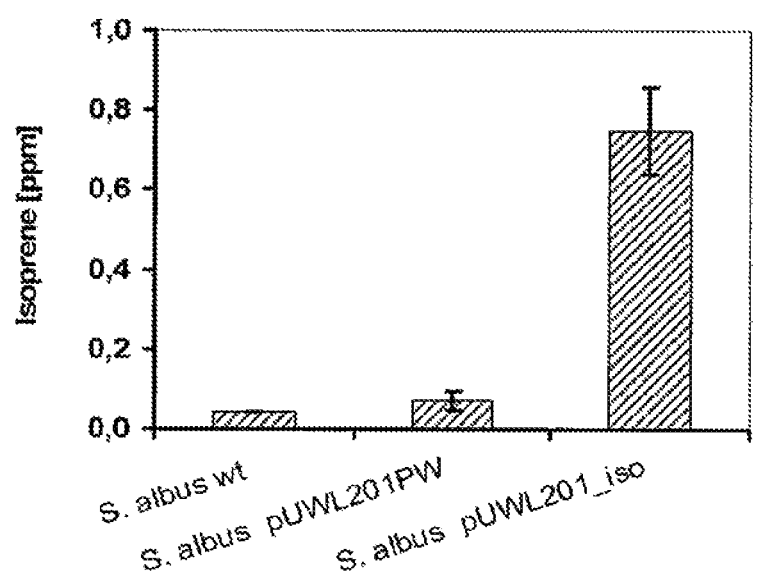
FIG. 72 shows isoprene formation by *Streptomyces albus* wild type strain ("wt") and strains harboring plasmid pUWL201PW (negative control) or pUWL201_iso (encoding isoprene synthase from Kudzu).

Wild type strain and transformants of *S. albus* containing control plasmid pUWL201PW or isoprene synthase encoding pUWL201_iso were analyzed for isoprene formation. Strains were cultivated in duplicate on solid media (tryptic soy broth agar, TSB; 2.5 ml) in presence or absence of thiostrepton (200 µg/ml) and incubated for 4 days at 28° C. in sealed head-space vials (total volume 20 ml). 500 µl head-space samples (end point measurements) were analyzed by GC-MS in SIM-mode and isoprene was identified according to reference retention times and molecular masses (67 m/z). Isoprene present in head-space samples was quantified by previously generated calibration curves. While wild-type *S. albus* and control strains harboring pUWL201PW produced isoprene in concentrations slightly higher than the detection limit (0.04-0.07 ppm), *S. albus* harboring pUWL201_iso produced isoprene in at least tenfold excess compared to controls (0.75 ppm; FIG. 72). The results demonstrate successful expression of plant-derived isoprene synthase in a prokaryotic organism of the Actinomycetes group.

Example 12

Production of Isoprene or Mevalonate from Fatty Acid or Palm Oil in *E. coli* fadR atoC LS5218 Containing the Upper or Upper and Lower Mevalonic Acid Pathway Plus Kudzu Isoprene Synthase

*Escherichia coli* fadR atoC strain LS5218 (#6966) was obtained from the Coli Genetic Stock Center. FadR encodes a transcription repressor that negatively regulates expression of the genes encoding fatty acid degradation enzymes (Campbell et al., *J. Bacteriol.* 183: 5982-5990, 2001). AtoC is a response regulator in a two-component regulatory system with AtoS, regulates acetolactate metabolism. The fadR atoC strain allows constitutive expression of the fatty acid degradation genes and incorporates long chain fatty acids into long-chain-length polyhydroxyalkanoates. When palm oil is used as a carbon source for either mevalonate or isoprene production, the palm oil was converted to glycerol plus fatty acid. Methods for this are well known in the art, and it can be done either enzymatically by incubation with a lipase (for example Porcine pancreatic lipase, *Candida rugosa* lipase, or other similar lipases) or chemically by saponification with a base such as sodium hydroxide.

i) *E. coli* fadR atoC Strain Expressing the Upper Mevalonic Acid Pathway

Figure 70A:
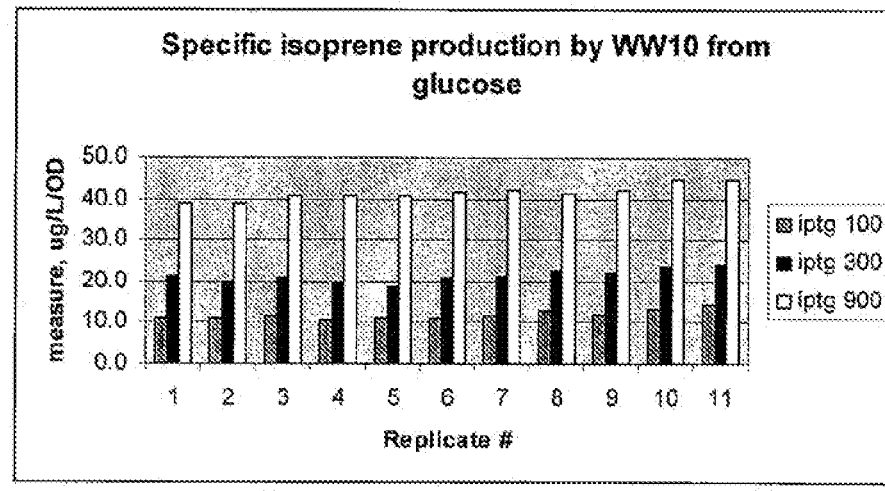
FIGS. 70A and 70B show the production of isoprene by *E. coli* strains from glucose and from fatty acid, respectively. For FIG. 70A, eleven colonies from the transformation of WW4 with pMCM118, the plasmid bearing the lower mevalonic acid pathway, were picked to verify the presence of the lower pathway. Cell from the colonies were cultured in TM3 medium containing 0.1% yeast extract and 2% glucose. Aliquots of induced culture were assayed for isoprene production after 4 hours of induction. All colonies showed the production of isoprene. The inducer IPTG had a strong growth inhibitory effect as was evident from the 3 to 4.6-fold reduced cell density in going from 50 to 900 uM concentration of the inducer (data not shown). The graph shows that higher induction, yields a higher specific titer of isoprene. For FIG. 70B, the production culture was inoculated from a washed overnight culture at 1 to 10 dilution. The culture was grown for several hours and induced with 50 uM IPTG. The left bar shows isoprene assay results four hours after induction followed by a one hour isoprene accumulation assay. The middle bar shows the one hour normalized value for the same culture with the same induction period but analyzed by a 12 hour isoprene accumulation assay. The right bar shows the value for a one hour isoprene accumulation assay of the culture that was induced for 13 hours.

Strain WW4 was created by electroporating pCLPtrcUpperPathway into LS5218 using standard methods (Sambrooke et al., Molecular Cloning: A Laboratory Manual, 2$^{nd}$ ed., Cold Spring Harbor, 1989). Incorporation of the plasmid was demonstrated by the production of mevalonic acid (MVA) when cells were cultured in TM3 medium supplemented with either C12 fatty acid (FA) or palm oil as the carbon source. To demonstrate production of MVA by WW4 from fatty acid, cells from an overnight culture were diluted 1 to 100 into 5 mL of modified TM3 medium (TM3 without yeast extract) supplemented with 0.25% C12 FA (Sigma cat #L9755). The first sign of MVA production (24 mg/L) was apparent after overnight incubation at 30° C. of the IPTG induced culture. Production increased over three days with the final level of 194 mg/L of MVA produced. To demonstrate production of MVA by WW4 from oil, cells from an overnight culture were diluted 1 to 100 into modified TM3 medium supplemented with 200 mg of digested palm oil per 5 mL of TM3 medium. The first sign of MVA production (50 mg/L) was apparent after overnight incubation of the IPTG induced culture at 30° C. Production increased over three days with a final level of 500 mg/L of MVA produced.

ii) E. coli fadR atoC Strain Expressing the Upper and Lower MVA Pathway Plus Kudzu Isoprene Synthase Escherichia coli strain WW4 (LS5218 fadR atoC pCLPtr-cUpperPathway) was transformed with pMCM118 [pTrcK-KDyIkIS] to yield WW10. The incorporation of the plasmid was demonstrated by evidence of production of isoprene when the strain was cultured in TM3 and glucose and induced with IPTG (100, 300, or 900 uM). The strain was relatively sensitive to IPTG and showed a significant growth defect even at 100 uM IPTG. These results are shown in FIG. 70A.

To test isoprene production from dodecanoic acid, WW10 was cultured overnight in L broth containing spectinomycin (50 ug/ml), and kanamycin (50 ug/ml) at 37 C with shaking at 200 rpm. The cells were washed with modified TM3 medium by centrifugation and resuspension in their original culture volume with this medium. The washed and resuspended cells from this starter culture were diluted 1 to 100 and 1 to 10 into 5 mL of modified TM3 medium containing 0.125% C12 Fatty Acid (Sigma cat #L9755).

To demonstrate production of mevalonate from palm oil, the oil was predigested with lipase at 37° C. and 250 rpm for several days to release the fatty acids (evidence of hydrolysis was judged by the foam formed when tubes were shaken).

Figure 70B:
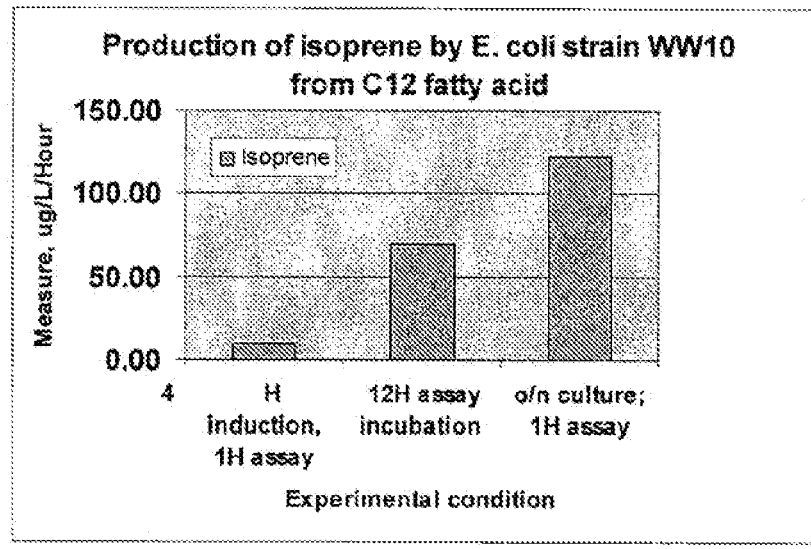

In addition, a culture was set up by diluting the washed cells at 1 to 10 into modified TM3 medium contained in test tubes with palm oil. A further tube was set up by the addition of 0.125% C12FA to the remainder (2.5 mL) of the washed cells without further dilution (bioconversion). After 3.75 hours of growth at 30° C. with shaking at 250 rpm all of the cultures were induced by the addition of 50 uM IPTG. Incubation was continued for 4 hours after which time 200 uL of each of the cultures was assayed for isoprene accumulation with a modified head space assay (1 hour accumulation at 30° C. with shaking at 500 rpm). An additional isoprene assay was conducted by a 12 hour incubation of the assay glass block prior to GCMS analysis. Incubation of the induced cultures was continued overnight and 200 uL aliquots were again assayed for isoprene production (1 hour, 30 deg, 500 rpm Shel-Lab shaker) the following morning. Analysis of these cultures showed the production of significant levels of isoprene. The highest levels of isoprene were observed in the culture which was seeded at 1/10 dilution from the overnight starter culture after it had been incubated and induced overnight. This result suggests that this culture continued to grow and increase in cell density. These results are shown in FIG. 70B. Cell density could not be measured directly because the fatty acid suspension had a turbid appearance. Cell density of this culture was therefore determined by plating an aliquot of the culture and showed $8 \times 10^7$ colony forming units. This corresponds approximately to an $OD_{600}$ of 0.1. Nevertheless, this culture provided significant isoprene production; no isoprene is observed for similar strains without the pathway described in this example.

Example 13

Improvement of Isoprene Production by Constitutive Expression of ybhE in E. coli This example shows production of isoprene in a strain constitutively expressing ybhE (pgl) compared to a control strain with wild type ybhE. The gene ybhE (pgl) encodes a 6-phosphogluconolactonase that suppresses posttranslational gluconylation of heterologously expressed proteins and improves product solubility and yield while also improving biomass yield and flux through the pentose phosphate pathway (Aon et al. *Applied and Environmental Microbiology*, 74(4): 950-958, 2008).

The BL21 strain of E. coli producing isoprene (EWL256) was constructed with constitutive expression of the ybhE gene on a replicating plasmid pBBR1MCS5 (Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F and PglGI1.5-R were used to amplify the resistance cassette from the FRT-gb2-Cm-FRT template using Stratagene Herculase II Fusion kit according to the manufacturer's protocol. The PCR reaction (50 uL final volume) contained: 5 uL buffer, 1 uL template DNA (FRT-gb2-Cm-F from Gene Bridges), 10 pmols of each primer, and 1.5 uL 25 mM dNTP mix, made to 50 uL with dH$_2$O. The reaction was cycled as follows: 1×2 minutes, 95° C. then 30 cycles of (30 seconds at 95° C.; 30 seconds at 63° C.; 3 minutes at 72° C.).

The resulting PCR product was purified using the QiaQick PCR purification kit (Qiagen) and electroporated into electrocompetent MG1655 cells harboring the pRed-ET recombinase-containing plasmid as follows. Cells were prepared by growing in 5 mLs of L broth to and OD600~0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold dH$_2$O. The final cell pellet was resuspended in 40 uL of ice cold dH$_2$O and 2-5 uL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 ug/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

The chromosomal DNA of MG1655 GI1.5-pgl::CMP was used as template to generate a PCR fragment containing the FRT-CMP-FRT-GI1.5-ybhE construct. This construct was cloned into pBBR1MCS5(Gentamycin) as follows. The fragment, here on referred to as CMP-GI1.5-pgl, was amplified using the 5' primer Pglconfirm-F and 3' primer 3' EcoRV-pglstop. The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5(Gentamycin). A 20 µl ligation reaction was prepared containing 5 µl CMP-GI1.5-pgl insert, 2 µl pBBR1MCS5 (Gentamycin) vector, 1 µl T4 DNA ligase (New England Biolabs), 2 µl 10× ligase buffer, and 10 µl ddH$_2$O. The ligation mixture was incubated at room temperature for 40 minutes then 2-4 uL were electroporated into electrocompetent Top10 cells (Invitrogen) using the parameters disclosed above. Transformants were selected on L agar containing 10 ug/ml chloramphenicol and 5 ug/ml Gentamycin. The sequence of the selected clone was determined using a number of the primers described above as well as with the in-house T3 and Reverse primers provided by Sequetech, CA. This plasmid was designated pBBRC-MPGI1.5-pgl (FIGS. 77A-B and SEQ ID NO:122).

Plasmid pBBRCMPGI1.5-pgl was electroporated into EWL256, as described above in Example 10 and transformants were plated on L agar containing Chloramphenicol (10 ug/mL), Gentamycin (5 ug/mL), spectinomycin (50 ug/mL), and carbenicillin (50 ug/mL). One transformant was selected and designated RM11608-2.

Primers:

```
Pgl-F
                                            (SEQ ID NO: 115)
5'-
ACCGCCAAAAGCGACTAATTTTAGCTGTTACAGTCAGTTGAATTAACCCT
CACTAAAGGGCGGCCGC-3'

PglGI1.5-R
                                            (SEQ ID NO: 116)
5'-
GCTGGCGATATAAACTGTTTGCTTCATGAATGCTCCTTTGGGTTACCTCC
GGGAAACGCGGTTGATTTGTTTAGTGGTTGAATTATTTGCTCAGGATGTG
GCATAGTCAAGGGCGTGACGGCTCGCTAATACGACTCACTATAGGGCTCG
AG-3'

3' EcoRV-pglstop:
                                            (SEQ ID NO: 117)
5'-CTT GAT ATC TTA GTG TGC GTT AAC CAC CAC pgl +49 rev:
                                            (SEQ ID NO: 118)
CGTGAATTTGCTGGCTCTCAG Bottom Pgb2:
                                            (SEQ ID NO: 119)
GGTTTAGTTCCTCACCTTGTC Top GB's CMP (946):
                                            (SEQ ID NO: 120)
ACTGAAACGTTTTCATCGCTC Pglconfirm-F
                                            (SEQ ID NO: 121)
5'-ACCGCCAAAAGCGACTAATTTTAGCT-3'
``` i) Small Scale Analysis

Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of *E. coli* strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 μL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (μg/L) by the OD reading and the time (hour).

The two strains EWL256 and RM11608-2 were assessed at 200 and 400 uM IPTG induction levels. Samples were analyzed for isoprene production and cell growth (OD550) at 1, 2.5, 4.75, and 8 hours post-induction. Samples were done in duplicate.

b) Results

The experiment demonstrated that at 2 different concentrations of IPTG the strain expressing the ybhE (pgl) had a dramatic 2-3 fold increase in specific productivity of isoprene compared to the control strain.

ii) Isoprene Fermentation from *E. coli* Expressing *M. mazei* Mevalonate Kinase, *P. alba* Isoprene Synthase, and pgl Over-Expression (RHM111608-2) and Grown in Fed-Batch Culture at the 15-L Scale Medium Recipe (Per Liter Fermentation Medium)

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in Di $H_2O$, pH to 3.0 with HCl/NaOH, then q.s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi1.2KKDyI), high expression of mevalonate kinase from *M. mazei* and isoprene synthase from *P. alba* (pTrcAlba-mMVK), and high expression of pgl (pBBR-pgl). This experiment was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 uM when the optical density at 550 nm ($OD_{550}$) reached a value of 4. The IPTG concentration was raised to 192 uM when OD$_{550}$ reached 150. The OD$_{550}$ profile within the bioreactor over time is shown in FIG. 78A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 78B). The isoprene titer increased over the course of the fermentation to a maximum value of 40.0 g/L at 40 hours (60.5 g/L at 59 hours) (FIG. 78C). The total amount of isoprene produced during the 40-hour (59-hour) fermentation was 281.3 g (451.0 g at 59 hours) and the time course of production is shown in FIG. 78D. The time course of volumetric productivity is shown in FIG. 78E and shows that an average rate of 1.0 g/L/hr was maintained between 0 and 40 hours (1.4 g/L/hour between 19 and 59 hour). The metabolic activity profile, as measured by CER, is shown in FIG. 78F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

Appendix 1

Exemplary 1-deoxy-D-xylulose-5-phosphate Synthase Nucleic Acids and Polypeptides
ATH: AT3G21500(DXPS1) AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YP03177(dxs)
YPK: y1008(dxs)
YPM: YP_0754(dxs)
YPA: YPA 2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)

SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NG00036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331

NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068

SIL: SPO0247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730
MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194

ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001
Exemplary Acetyl-CoA-Acetyltransferase Nucleic Acids and Polypeptides
HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639(MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165c
PIC: PICST_31707(ERG10)
CAL: CaO19.1591(erg10)
CGR: CAGLOL12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOO_1778(XOO1778)
VCH: VCA0690
VCO: VC0395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH_0850(phbA1) PSPPH_2209(phbA2)
PFL: PFL_1478(atoB-2) PFL_2321 PFL_3066 PFL_4330(atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011
ACI: ACIAD0694 ACIAD1612 ACIAD2516(atoB)
SON: SO_1677(atoB)
SDN: Sden_1943
SFR: Sfri_1338 Sfri_2063
SAZ: Sama_1375
SBL: Sbal_1495
SBM: Shew185_1489
SBN: Sbal195_1525
SLO: Shew_1667 Shew_2858
SPC: Sputcn32_1397
SSE: Ssed_1473 Ssed_3533

SPL: Spea_2783
SHE: Shewmr4_2597
SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping_0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp1788
NOC: Noc_1891
AEH: Mlg_0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(atoB) CV_2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810(phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330(phbA) BURPS1710b_2453(atoB-2)
BPL: BURPS1106A_2197(bktB) BURPS1106A_2202(phbA)
BPD: BURPS668_2160(bktB) BURPS668_2165(phbA)
BTE: BTH_12144 BTH_12256 BTH_12261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(th1A)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C 05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748

RPC: RPC_0504 RPC_0636 RPC_0641 RPC_0832 RPC_1050 RPC_2005 RPC_2194 RPC_2228
RPD: RPD_0306 RPD_0320 RPD 3105 RPD_3306
RPE: RPE 0168 RPE_0248 RPE_3827
NWI: Nwi_3060
XAU: Xaut_3108 Xaut_4665
CCR: CC 0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP 3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE 3133
NAR: Saro_0809 Saro_1069 Saro_1222 Saro_2306 Saro_2349
SAL: Sala_0781 Sala_1244 Sala_2896 Sala 3158
SWI: Swit_0632 Swit_0752 Swit_2893 Swit_3602 Swit_4887 Swit_5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044(atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAM_022450
BPU: BPUM_2374(yhfS) BPUM_2941 BPUM_3373
OIH: OB06760B06890B26320B3013
GKA: GK1658 GK3397
SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300_0355 SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: LJ1609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CBO3200(thl)
CBE: Cbei_0411 Cbei_3630
CKL: CKL_3696(thlA1) CKL_3697(thlA2) CKL_3698(thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260 MTU: Rv1135A Rv1323(fadA4) Rv3546(fadA5)
MTC: MT1365(phbA)

MBO: Mb1167 Mb1358(fadA4) Mb3576(fadA5) Mb3586c (fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159
Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941
Exemplary HMG-CoA Synthase Nucleic Acids and Polypeptides
HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(L00578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG_01026
ANI: AN4923.2
AFM: AFUA_3G10660 AFUA_8G07210
AOR: AO090003000611 AO090010000487
CNE: CNC05080 CNG02670
UMA: UM05362.1
ECU: ECU10_0510
DDI: DDBDRAFT_0217522 DDB_0219924(hgsA)
TET: TTHERM_00691190
TBR: Tb927.8.6110
YPE: YPO1457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799

BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005—Spy_0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363
LCA: LSEI_1785
LGA: LGAS_1372
LRE: Lreu_0676
PPE: PEPE_0868
EFA: EF1363
OOE: OEOE_0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)
HMA: rrnAC1740(mvaS)
HWA: HQ2868A(mvaB)
NPH: NP2608A(mvaB_1) NP4836A(mvaB_2)
Exemplary Hydroxymethylglutaryl-CoA Reductase Nucleic Acids and Polypeptides
HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dmel_CG10367 (Hmgcr)
CEL: F08F8.2
OSA: 4347443
SCE: YLR450W(HMG2) YML075C(HMG1)
AGO: AGOS_AER152W
CGR: CAGLOL11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)

SPG: SpyM3_0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PTO1143
PAB: PAB2106(mvaA)
PFU: PF1848
TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pisl_0814
PCL: Pcal_1085
PAS: Pars_0796
Exemplary Mevalonate Kinase Nucleic Acids and Polypeptides
HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(LOC585785)
DME: Dmel_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lpl2017
LPP: lpp 2022
BBA: Bd1027(1 mbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)

SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PT01352
PHO: PH1625
PAB: PAB0372(mvk)
PFU: PF1637(mvk)
TKO: TK1474
RCI: LRC399(mvk)
APE: APE_2439
HBU: Hbut_0877
SSO: SS00383
STO: ST2185
SAI: Saci_2365(mvk)
MSE: Msed_1602
PAI: PAE3108
PIS: Pisl_0467
PCL: Pcal_1835
Exemplary Phosphomevalonate Kinase Nucleic Acids and Polypeptides
HSA: 10654(PMVK)
PTR: 457350(PMVK)
MCC: 717014(Pmvk)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGLOF03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO_0241
LPL: lp_1733(mvaK2)

LJO: LJ1207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244
Exemplary Diphosphomevalonate Decarboxylase Nucleic Acids and Polypeptides
HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvdl)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PT00478 PT01356
SSO: SSO2989
STO: ST0977
SAI: Saci_1245(mvd)
MSE: Msed_1576

Exemplary Isopentenyl Phosphate Kinases (IPK) Nucleic Acids and Polypeptides
*Methanobacterium thermoautotrophicum* gi|2621082
*Methanococcus jannaschii* DSM 2661 gi|1590842;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231

Exemplary Isopentenyl-Diphosphate Delta-Isomerase (IDI) Nucleic Acids and Polypeptides
HSA: 3422(IDI1) 91734(ID12)
PTR: 450262(ID12) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(L00586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042 SSON_3489(yhfK)
SBO: SBO_3103
SDY: SDY_3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RR1: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)

SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCgl2223(cgl2305)
CGB: cg2531(idi)
CEF: CE2207
CDI: DIP1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G(crt_2) VNG7060 VNG7149

HMA: rrnAC3484(idi)
HWA: HQ2772A(idiA) HQ2847A(idiB)
NPH: NP0360A(idiB_1) NP4826A(idiA) NP5124A(idiB_2)
TAC: Ta0102
TVO: TVN0179
PTO: PT00496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SS00063
STO: ST2059
SAI: Saci_0091
MSE: Msed_2136
PAI: PAE0801
PIS: Pisl_1093
PCL: Pcal_0017
PAS: Pars 0051
TPE: Tpen_0272

Exemplary Isoprene Synthase Nucleic Acids and Polypeptides
Genbank Accession Nos.
AY341431
AY316691
AY279379
AJ457070
AY182241

What is claimed as new and desired to be protected by Letters Patent of the United States is:

1. A method of producing isoprene, the method comprising:
   (a) culturing recombinant cells under suitable culture conditions for the production of isoprene, wherein the cells comprise nucleic acids encoding
      (i) a heterologous isoprene synthase polypeptide,
      (ii) an isopentenyl-diphosphate delta-isomerase (DI) polypeptide, and
      (iii) at least one of a 1-Deoxyxylulose-5-phosphate synthase (DXS) polypeptide and/or one or more mevalonate (MVA) pathway polypeptides and wherein the cells
         (1) produce greater than about 400 nmole/gwcm/hr of isoprene,
         (2) convert more than about 0.002 molar percent of the carbon that the cells consume from a cell culture medium into isoprene,
         (3) have an average volumetric productivity of isoprene greaterthan about 0.1mg/Lbroth/hr of isoprene, or
         (4) produce at least 0.0037 grams of isoprene per gram of dry cell mass (gdcm); and
   (b) producing isoprene.
2. The method of claim 1, further comprising recovering the isoprene produced by the cells.
3. The method of claim 1, wherein the cells further comprise an endogenous nucleic acid encoding an isoprene synthase polypeptide.
4. The method of claim 1, wherein the isoprene synthase polypeptide is a plant isoprene synthase polypeptide.
5. The method of claim 4, wherein the plant isoprene synthase polypeptide is a poplar isoprene synthase polypeptide.
6. The method of claim 4, wherein the plant isoprene synthase polypeptide is a kudzu isoprene synthase polypeptide.
7. The method of claim 1, wherein the nucleic acid encoding an IDI polypeptide of (a)(ii) is a heterologous nucleic acid encoding an IDI polypeptide.
8. The method of claim 1, wherein the nucleic acid encoding an IDI polypeptide of (a)(ii) is a copy of an endogenous nucleic acid encoding an IDI polypeptide.
9. The method of claim 1, wherein the nucleic acid encoding a DXS polypeptide of (a)(iii) is a heterologous nucleic acid encoding a DXS polypeptide.
10. The method of claim 1, wherein the nucleic acid encoding a DXS polypeptide of (a)(iii) is a copy of an endogenous nucleic acid encoding a DXS polypeptide.
11. The method of claim 1, wherein at least one of the nucleic acids encoding one or more MVA pathway polypeptides of (a)(iii) is a heterologous nucleic acid.
12. The method of claim 1, wherein at least one of the nucleic acids encoding one or more MVA pathway polypeptides of (a)(iii) is a copy of an endogenous nucleic acid.

13. The method of claim 1, wherein the cells comprise two or more polypeptides of the MVA pathway.

14. The method of claim 1, wherein the cells comprise three or more polypeptides of the MVA pathway.

15. The method of claim 1, wherein the cells comprise four or more polypeptides of the MVA pathway.

16. The method of claim 1, wherein the cells comprise polypeptides of the entire MVA pathway.

17. The method of claim 1, wherein at least one of the nucleic acids encoding a polypeptide of (a)(i)-(a)(iii) is in a vector.

18. The method of claim 1, wherein at least one of the nucleic acids encoding a polypeptide of (a)(i)-(a)(iii) is integrated into a chromosome of the cells.

19. The method of claim 1, wherein at least one of the nucleic acids encoding a polypeptide of (a)(i)-(a)(iii) is over-expressed.

20. The method of claim 19, wherein the over-expressed nucleic acid is cloned into a multicopy plasmid.

21. The method of claim 20, wherein the over-expressed nucleic acid is placed under an inducible promoter or a constitutive promoter.

22. The method of claim 1, wherein the cells are fungal, bacterial, plant, or algal cells.

23. The method of claim 22, wherein the cells are fungal cells.

24. The method of claim 23, wherein the cells are *Aspergillus*, yeast, or *Trichoderma*, cells.

25. The method of claim 24, wherein the yeast cells are *Saccharomyces* sp., *Schizosaccharomyces* sp., *Pichia* sp., *Yarrowia* sp. or *Candida* sp. cells.

26. The method cells of claim 23, where the cells are selected from the group consisting of *A. oryzae, A. niger, S. cerevisiae, S. pombe, T. reesei, H. insolens, H. lanuginose, H. grisea, C. lucknowense, A. sojae, A. japonicus, A. nidulans, A. aculeatus, A. awamori, F. roseum, F. graminum , F. cerealis, F. oxysporuim, F. venenatum, N. crassa, M. miehei, T. viride, F. oxysporum*, and *F. solan* cells.

27. The method of claim 22, wherein the cells are bacterial cells.

28. The method of claim 27, wherein the cells are gram-positive bacterial cells or gram-negative bacterial cells.

29. The method of claim 27, wherein the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B.megaterium, B. coagulans, B. circulans, B. lautus, B. thuringiensis, S. albus, S. lividans, S. coelicolor, S. griseus, Pseudomonas* sp., *Corynebacteria* sp., and *P. alcaligenes* cells.

30. The method of claim 22, wherein the cells are plant cells.

31. The method of claim 30, wherein the plant cells are selected from the group consisting of: the family Fabaceae, the Faboideae subfamily, kudzu, poplar, *Populus alba× tremula, Populus alba*, aspen, *Populus tremuloides*, and *Quercus robur* cells.

32. The method of claim 22, wherein the cells are algal cells.

33. The method of claim 32, wherein the algal cells are selected from the group consisting of: green algae, red algae, glaucophytes, chlorarachniophytes, euglenids, chromista, and dinoflagellates.

* * * * *